United States Patent
Hudkins et al.

(10) Patent No.: US 9,914,731 B2
(45) Date of Patent: Mar. 13, 2018

(54) PYRAZOLO[1,5-A]PYRIDINE DERIVATIVES AND METHODS OF THEIR USE

(71) Applicant: Ignyta, Inc., San Diego, CA (US)

(72) Inventors: Robert L Hudkins, Chester Springs, PA (US); Allison L Zulli, Wayne, PA (US)

(73) Assignee: IGNYTA, INC., San Diego, CA (US)

( * ) Notice: Subject to any disclaimer, the term of this patent is extended or adjusted under 35 U.S.C. 154(b) by 0 days.

(21) Appl. No.: 15/108,400

(22) PCT Filed: Dec. 18, 2014

(86) PCT No.: PCT/US2014/071040
§ 371 (c)(1),
(2) Date: Jun. 27, 2016

(87) PCT Pub. No.: WO2015/100117
PCT Pub. Date: Jul. 2, 2015

(65) Prior Publication Data
US 2016/0318929 A1    Nov. 3, 2016

Related U.S. Application Data

(60) Provisional application No. 61/920,819, filed on Dec. 26, 2013.

(51) Int. Cl.
*C07D 471/04* (2006.01)

(52) U.S. Cl.
CPC .................. *C07D 471/04* (2013.01)

(58) Field of Classification Search
CPC .... C07D 471/04; A61K 8/494; A61K 8/4953; A61K 31/407; A61K 31/437
See application file for complete search history.

(56) References Cited

FOREIGN PATENT DOCUMENTS

| CN | 102827186 A | 12/2012 |
|---|---|---|
| EP | 2 103 620 A1 | 9/2009 |
| WO | WO-2008/113559 A2 | 9/2008 |
| WO | WO-2010/017047 A1 | 2/2010 |
| WO | WO 2013/180949 A1 | 12/2013 |

OTHER PUBLICATIONS

International Search Report and Written Opinion dated Mar. 6, 2015 in related application PCT/US2014/0710040.
PCT International Search Report and Written Opinion for Application No. PCT/US2014/071040 dated Mar. 6, 2015. (10 pages).

*Primary Examiner* — Kendra D Carter
(74) *Attorney, Agent, or Firm* — Foley & Lardner LLP

(57) ABSTRACT

The invention is directed to pyrazolo[1,5-a]pyridine derivatives and their use as AXL and c-MET kinase inhibitors.

18 Claims, No Drawings

PYRAZOLO[1,5-A]PYRIDINE DERIVATIVES AND METHODS OF THEIR USE

CROSS REFERENCE TO RELATED APPLICATION

This application is a National Stage Entry of PCT International Application No. PCT/US2014/071040, filed Dec. 18, 2014, which claims the benefit of U.S. Provisional Application No. 61/920,819, filed Dec. 26, 2013, the entirety of each of which is incorporated by reference herein.

TECHNICAL FIELD

The invention is directed to pyrazolo[1,5-a]pyridine derivatives and their use as AXL and c-MET kinase inhibitors.

BACKGROUND

The present invention is directed to compounds that have activity as inhibitors of protein kinases. Protein kinases participate in the signaling events that control the activation, growth, and differentiation of cells in response to extracellular mediators and to changes in the environment. Inappropriately high protein kinase activity has been implicated, directly or indirectly, in many diseases. For example, high protein kinase activity can result in the failure of control mechanisms for the kinase, those related to, e.g., mutation, over-expression or inappropriate activation of the enzyme; or by over- or underproduction of cytokines or growth factors upstream or downstream of the kinase. In all of these instances, selective inhibition of the action of the kinase would be expected to have a beneficial effect.

Receptor tyrosine kinases (RTK) are generally activated by ligands that promote receptor dimerization and, in turn, autophosphorylation of tyrosine residues within the cytosolic domain. The binding of signaling proteins to these phosphorylated tyrosine residues leads to further downstream signaling. AXL family RTKs are unique in that they are activated by GAS6, a member of the vitamin K-dependent protein family that resembles blood coagulation factors rather than typical growth factors. The receptor tyrosine kinase AXL (also known as Ufo and Tyrol) belongs to a family of tyrosine receptors that includes Tyro3 (Sky) and Mer (Tyro12). Human AXL is a 2,682-bp open reading frame capable of directing the synthesis of an 894-amino acid polypeptide. Important cellular functions of GAS6/AXL include cell adhesion, migration, phagocytosis, and inhibition of apoptosis. GAS6 and AXL family receptors are highly regulated in a tissue and disease specific manner.

AXL is characterized by a unique molecular structure, in that the intracellular region has the typical structure of a receptor tyrosine kinase and the extracellular domain contains fibronectin III and Ig motifs similar to cadherin-type adhesion molecules. During development, AXL is expressed in various organs, including the brain, suggesting that this RTK is involved in mesenchymal and neural development. In the adult, AXL expression is low but returns to high expression levels in a variety of tumors. GAS6 is, so far, the single, activating ligand for AXL.

The oncogenic potential of AXL was first discovered in chronic myelogenous leukemia, but it has been demonstrated to play a role in the progression and metastasis of other cancer types. The increased expression of AXL and/or AXL ligand, Gash, has been shown in a number of human malignancies, including ovarian, melanoma, renal cell carcinoma, uterine leiomyoma, uterine endometrial cancer, thyroid carcinoma, gastric cancer, breast cancer, NSCLC, CML, AML, colorectal carcinoma, prostate cancer, various lymphomas, and esophageal cancer. The biochemical effects of increased expression of AXL are associated with increased oncogenic transformation, cell survival, proliferation, migration, angiogenesis, and cellular adhesion. Target validation studies of in vivo cancer models show that inhibition of Axl expression by RNAi blocked tumor growth in those models (see, e.g., Li, Y. et al. Oncogene 2009, 28:3442-3455).

In addition to the association with cancer and tumorigenesis, RTKs are implicated in a number of other cell and physiological functions. These include regulation of vascular smooth muscle homeostasis, platelet function, thrombus stabilization, innate immunity, and inflammation.

cMET kinase is also a receptor tyrosine kinase. HGF (hepatocyte growth factor, also known as scatter factor), the ligand for cMET, is secreted by cells of mesodermal origin whereas cMET is predominantly expressed on cells of epithelial/endothelial origin resulting in paracrine epithelial-mesenchymal cell signaling. Binding of HGF to the extracellular region of cMET activates the intracellular cMET tyrosine kinase activity.

cMET is believed to be involved in protein phosphorylation events that regulate cell proliferation, apoptosis, motility, and dissociation of cell-cell interactions, morphogenesis, angiogenesis, and epithelial-mesenchymal transition. Misregulation of cMET can lead to unregulated cell proliferation and survival. cMET is thought to be a key regulator of invasive growth, cancer tumorgenesis, and progression to metastasis. cMET gene amplification, alteration, mutation, and protein over expression or activation of cMET through autocrine or paracrine mechanisms have been detected in a wide variety of carcinomas. For example, in human gastric cancer tissue, cMET has been found to be over-expressed and amplified. In human glioblastomas and carcinomas of lung, thyroid and breast, cMET has been found to be activated as a result of increased HGF levels and autocrine signaling. In human lung cancer tissue, cMET signaling has been found to be upregulated as a mechanism of drug resistance. Activating mutations in cMET, although not as common, have been reported in sporadic and hereditary papillary renal carcinomas, head and neck squamous carcinomas as well as gastric and lung cancers. Furthermore, increased expression, the most common cMET alteration found in a wide variety of human tumors (including but not limited to renal, ovarian, hepatocellular, non-small cell lung, bone, liver metastasis of colon, oral squamous cell, esophageal, gastric, pancreatic, and prostatic cancers) correlates with poor prognosis In summary, the AXL and cMET proteins appear to have a key role in a number of human disorders, including cancer. Thus, these proteins are an attractive and valuable target for the discovery and development of new therapeutic agents to treat cancer and other conditions. There is a need for the design of specific and selective inhibitors for the treatment of disorders mediated and/or associated with AXL and cMET.

SUMMARY

The invention is directed to compounds of Formula I:

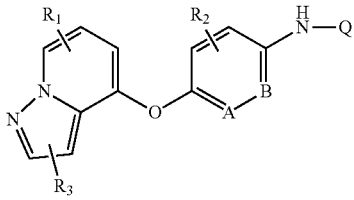

wherein A, B, $R_1$, $R_2$, $R_3$, and Q are as defined herein. Methods of using the compounds of Formula I to treat cancer are also described.

DETAILED DESCRIPTION OF ILLUSTRATIVE EMBODIMENTS

The invention is directed to compounds of Formula I:

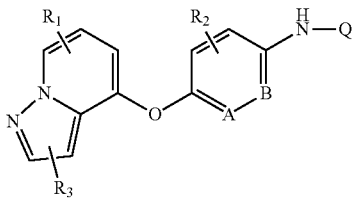

wherein $R_1$ is H; halo; —$C_{1-6}$alkyl; —$C_{1-6}$alkoxy; optionally substituted pyridyl; optionally substituted pyrimidinyl; optionally substituted pyrazinyl; optionally substituted pyrazolyl; optionally substituted imidazolyl; optionally substituted isoxazolyl; optionally substituted oxazolyl; optionally substituted thiazolyl; optionally substituted isothiazolyl; optionally substituted morpholinyl; optionally substituted piperazinyl, optionally substituted piperidinyl; optionally substituted tetrahydropyranyl; optionally substituted pyrrolidinyl; tetrahydrothiopyranyl 1,1-dioxide; thiomorpholinyl 1,1-dioxide; pyrrolidinyl-one; piperidinyl-one; optionally substituted —NH-aryl; optionally substituted —NH-pyridyl; optionally substituted —NH-pyrimidinyl; —C(O)NH$C_{1-6}$alkyl; —C(O)N($C_{1-6}$alkyl)$_2$; —NHS(O)$_2C_{1-6}$alkyl; —N($C_{1-6}$alkyl)S(O)$_2C_{1-6}$alkyl; —NHC(O)$C_{1-6}$alkyl; —N$C_{1-6}$alkylC(O)$C_{1-6}$alkyl; —NHC(O)O$C_{1-6}$alkyl; —N$C_{1-6}$alkylC(O)O$C_{1-6}$alkyl; —NHC(O)NH$C_{1-6}$alkyl; —N$C_{1-6}$alkylC(O)N($C_{1-6}$alkyl)$_2$; optionally substituted —NHC(O)-piperazinyl; or optionally substituted —N$C_{1-6}$alkylC(O)-piperazinyl;

$R_2$ is H, halo, —$C_{1-6}$alkyl, —$C_{1-6}$alkoxy, —OH, —O-alkaryl, or trihaloalkyl;

$R_3$ is H or halo;

A is $CR_2$ or N;

B is $CR_2$ or N;

Q is —S(O)$_2$aryl optionally substituted with halo or $C_{1-6}$alkyl; pyridyl optionally substituted with halo or —C(O)NHphenyl; pyrimidinyl; pyrazinyl; —C(O)—NHC(O)-alkaryl optionally substituted with halo or $C_{1-6}$alkyl; —C(S)—NHC(O)-alkyl optionally substituted with halo or $C_{1-6}$alkyl; —C(O)-alkyl optionally substituted with halo or $C_{1-6}$alkyl; —C(O)NH-aryl optionally substituted with halo, $C_{1-6}$alkyl, or $C_{1-6}$alkoxy; —C(O)—O-aryl optionally substituted with halo, $C_{1-6}$alkyl, or $C_{1-6}$alkoxy; or

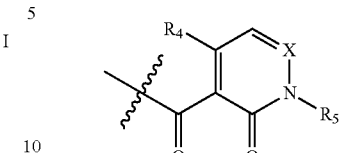

wherein X is $CR_6$, wherein $R_6$ is H or $C_{1-6}$alkyl; or N; $R_4$ is H; $C_{1-6}$alkoxy; halo; —$OC_{1-6}$alkylene-$C_{1-6}$alkoxy; —NH$C_{1-6}$alkyl; or —N($C_{1-6}$alkyl)$_2$;

$R_5$ is aryl optionally substituted with halo or $C_{1-6}$alkyl; or alkaryl optionally substituted with halo or $C_{1-6}$alkyl; or

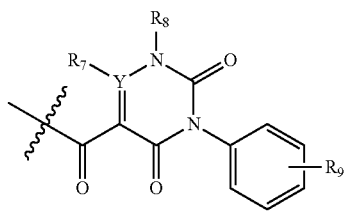

wherein Y is C or N;

$R_7$ is H or $C_{1-6}$alkyl;

$R_8$ is H; $C_{1-6}$alkylene-O—$C_{1-6}$alkyl; $C_{1-6}$alkyl; $C_{1-6}$alkylene-O—$C_{1-6}$alkaryl; or $C_{1-6}$alkylene-OH;

$R_9$ is H, $C_{1-6}$alkyl; or halo;

or

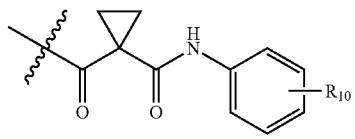

wherein $R_{10}$ is H; halo; or $C_{1-6}$alkyl;

or

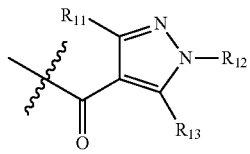

wherein $R_{11}$ is H or $C_{1-6}$alkyl;

$R_{12}$ is H; $C_{1-6}$alkyl; or aryl optionally substituted with halo $R_{13}$ is H; $C_{1-6}$alkyl; or trihalo$C_{1-6}$alkyl;

or

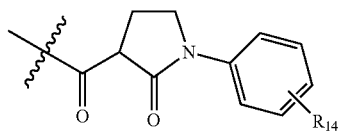

wherein

R$_{14}$ is H; C$_{1-6}$alkyl; or halo;

and pharmaceutically acceptable salts thereof.

Compounds of the invention can also include tautomeric forms, such as keto-enol tautomers. Tautomeric forms can be in equilibrium or sterically locked into one form by appropriate substitution.

In preferred embodiments of the invention, A is CR$_2$. In other embodiments, A is N. In some embodiments of the invention, B is CR$_2$. In yet other embodiments, B is N. In preferred embodiments, A is CR$_2$ and B is CR$_2$. In other embodiments, A is N and B is CR$_2$. In other embodiments, A is CR$_2$ and B is N. In yet other embodiments, A is N and B is N.

In those embodiments wherein A and/or B are CR$_2$, each R$_2$ is independently H, halo, —C$_{1-6}$alkyl, —C$_{1-6}$alkoxy, —OH, —O-alkaryl, or trihaloalkyl. Preferably, R$_2$ is H or halo, preferably F. In other embodiments, each R$_2$ is independently —C$_{1-6}$alkyl, for example, methyl, ethyl, propyl, isopropyl, butyl, sec-butyl, and tert-butyl. In other embodiments, each R$_2$ is independently —C$_{1-6}$alkoxy, for example, methoxy, ethoxy, propoxy, isopropoxy, butoxy, sec-butoxy, and tert-butoxy. In yet other embodiments, R$_2$ is —OH. In still other embodiments, each R$_2$ is independently —O-alkaryl, for example, benzyl. Alternatively, each R$_2$ is independently trihaloalkyl, for example, trifluoromethyl.

In preferred embodiments of the invention, each R$_2$ is independently H, halo, —C$_{1-6}$alkyl, —C$_{1-6}$alkoxy, —OH, —O-alkaryl, or trihaloalkyl. Preferably, R$_2$ is H or halo, preferably F. In other embodiments, each R$_2$ is independently —C$_{1-6}$alkyl, for example, methyl, ethyl, propyl, isopropyl, butyl, sec-butyl, and tert-butyl. In other embodiments, each R$_2$ is independently —C$_{1-6}$alkoxy, for example, methoxy, ethoxy, propoxy, isopropoxy, butoxy, sec-butoxy, and tert-butoxy. In yet other embodiments, R$_2$ is —OH. In still other embodiments, each R$_2$ is independently —O-alkaryl, for example, benzyl. Alternatively, each R$_2$ is independently trihaloalkyl, for example, trifluoromethyl.

In some embodiments, R$_3$ is H. In other embodiments, R$_3$ is halo, for example, F, Cl, or Br.

In preferred embodiments of the invention, Q is

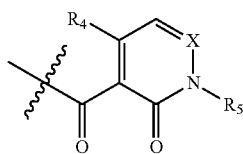

wherein X is CR$_6$ or N. Preferably, X is CR$_6$. In certain embodiments, R$_6$ is H. In other embodiments, R$_6$ is C$_{1-6}$alkyl, for example, methyl, ethyl, propyl, isopropyl, butyl, sec-butyl, and tert-butyl. In other embodiments of the invention X is N.

In these embodiments, R$_4$ is preferably H. In other embodiments, R$_4$ is C$_{1-6}$alkoxy, for example, methoxy, ethoxy, propoxy, tert-butoxy, and the like. In other embodiments, R$_4$ is halo, for example, F, Cl, or Br. In yet other embodiments, R$_4$ is —OC$_{1-6}$alkylene-O—C$_{1-6}$alkyl. In these embodiments, the alkylene preferably includes 1, 2, or 3 carbons and the O—C$_{1-6}$alkyl is, for example, methoxy, ethoxy, propoxy, tert-butoxy, and the like. Preferred —OC$_{1-6}$alkylene-O—C$_{1-6}$alkyl moieties include, for example —CH$_2$CH$_2$—O—CH$_2$CH$_3$. In other embodiments, R$_4$ is —NHC$_{1-6}$alkyl, for example, —NHCH$_3$ or —NHCH$_2$CH$_3$. In still other embodiments, R$_4$ is —N(C$_{1-6}$alkyl)$_2$, for example, —N(CH$_3$)$_2$.

Also in these embodiments, R$_5$ is aryl, preferably phenyl or naphthyl. Alternatively, R$_5$ is aryl, such as phenyl or naphthyl, substituted with halo, for example, F, Cl, or Br. In other embodiments, R$_5$ is aryl, such as phenyl or naphthyl, substituted with C$_{1-6}$alkyl, for example, methyl, ethyl, propyl, butyl, and the like. In other embodiments, R$_5$ is alkaryl, for example, benzyl. In yet other embodiments, R$_5$ is alkaryl, for example benzyl, substituted with halo, for example F, Cl, or Br. In still other embodiments, R$_5$ is alkaryl, for example benzyl, substituted with C$_{1-6}$alkyl, for example, methyl, ethyl, propyl, isopropyl, butyl, sec-butyl, or tert-butyl.

In some embodiments of the invention, Q is

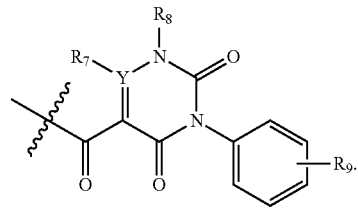

In some embodiments, Y is C. In other embodiments, Y is N.

In preferred embodiments, R$_7$ is H. In other embodiments, R$_7$ is C$_{1-6}$alkyl, for example, methyl, ethyl, propyl, isopropyl, butyl, sec-butyl, or tert-butyl.

In yet other embodiments, R$_8$ is H. In other embodiments, R$_8$ is C$_{1-6}$alkylene-O—C$_{1-6}$alkyl. In these embodiments, the alkylene preferably includes 1, 2, or 3 carbons and the O—C$_{1-6}$alkyl is, for example, methoxy, ethoxy, propoxy, tert-butoxy, and the like. Preferred —OC$_{1-6}$alkylene-C$_{1-6}$alkoxy moieties include, for example, —CH$_2$CH$_2$—O—CH$_2$CH$_3$. In other embodiments, R$_8$ is C$_{1-6}$alkyl, for example, methyl, ethyl, propyl, isopropyl, butyl, sec-butyl, or tert-butyl. In yet other embodiments, R$_8$ is C$_{1-6}$alkylene-O—C$_{1-6}$alkaryl. In these embodiments, the alkylene preferably includes 1, 2, or 3 carbons and the O—C$_{1-6}$alkaryl is, for example —O-benzyl. In still other embodiments, R$_8$ is C$_{1-6}$ alkylene-OH. In these embodiments, the alkylene preferably includes 1, 2, or 4 carbons.

In some embodiments, R$_9$ is H. In still other embodiments, R$_9$ is C$_{1-6}$alkyl, for example, methyl, ethyl, propyl, isopropyl, butyl, sec-butyl, or tert-butyl. In yet other embodiments, R$_9$ is halo, for example, F, Cl, or Br.

In some embodiments of the invention, Q is

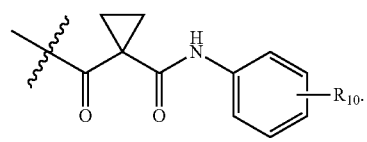

In these embodiments, R$_{10}$ can be H. In other embodiments, R$_{10}$ is halo, for example, F, Cl, or Br. In yet other embodiments, R$_{10}$ is C$_{1-6}$alkyl, for example, methyl, ethyl, propyl, isopropyl, butyl, sec-butyl, or tert-butyl.

In some other embodiments of the invention, Q is

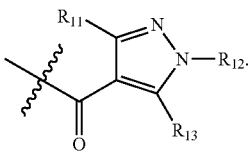

In such embodiments, $R_{11}$ can be H. In other embodiments, $R_{11}$ is $C_{1-6}$alkyl, for example, methyl, ethyl, propyl, isopropyl, butyl, sec-butyl, or tert-butyl.

In yet other embodiments, $R_{12}$ is H. In other embodiments, $R_{12}$ is $C_{1-6}$alkyl, for example, methyl, ethyl, propyl, isopropyl, butyl, sec-butyl, or tert-butyl. In other embodiments, $R_{12}$ is aryl, for example, phenyl or naphthyl. In yet other embodiments, $R_{12}$ is aryl, for example, phenyl or naphthyl, substituted with halo, for example, F, Cl, or Br.

In other embodiments, $R_{13}$ is H. In other embodiments, $R_{13}$ is $C_{1-6}$alkyl, for example, methyl, ethyl, propyl, isopropyl, butyl, sec-butyl, and tert-butyl. In yet other embodiments, $R_{13}$ is trihalo$C_{1-6}$alkyl, for example trifluoromethyl.

In other embodiments of the invention, Q is

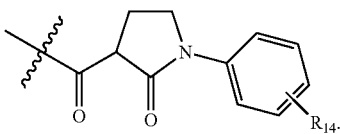

In these embodiments, $R_{14}$ can be H. In other embodiments, $R_{14}$ is $C_{1-6}$alkyl, for example, methyl, ethyl, propyl, isopropyl, butyl, sec-butyl, or tert-butyl. In still other embodiments, $R_{14}$ halo, for example F, Cl, or Br.

In other embodiments of the invention, Q is —S(O)$_2$aryl, for example, —S(O)$_2$phenyl or —S(O)$_2$naphthyl. In other embodiments, Q is —S(O)$_2$aryl for example, —S(O)$_2$phenyl or —S(O)$_2$naphthyl, wherein the aryl is substituted with halo, for example, F, Cl, or Br. In other embodiments, Q is —S(O)$_2$aryl for example, —S(O)$_2$phenyl or —S(O)$_2$naphthyl, wherein the aryl is substituted with $C_{1-6}$alkyl, for example, methyl, ethyl, propyl, isopropyl, butyl, sec-butyl, or tert-butyl.

In other embodiments, Q is pyridyl. In yet other embodiments, Q is pyridyl substituted with halo, for example, F, Cl, or Br. In still other embodiments, Q is pyridyl substituted with —C(O)NHphenyl.

In other embodiments, Q is pyrimidyl. The pyrimidyl can be optionally substituted.

In other embodiments, Q is pyrazinyl. The pyrazinyl can be optionally substituted.

In yet other embodiments, Q is —C(O)—NHC(O)-alkaryl, wherein the alkaryl is, for example, benzyl. In other embodiments, Q is —C(O)—NHC(O)-alkaryl, wherein the alkaryl, for example benzyl, is substituted with halo, for example, F, Cl, or Br. In still other embodiments, Q is —C(O)—NHC(O)-alkaryl, wherein the alkaryl, for example benzyl, is substituted with $C_{1-6}$alkyl, for example, methyl, ethyl, propyl, isopropyl, butyl, sec-butyl, or tert-butyl.

In yet other embodiments, Q is —C(S)—NHC(O)-alkaryl, wherein the alkaryl is, for example, benzyl. In other embodiments, Q is —C(S)—NHC(O)-alkaryl, wherein the alkaryl, for example benzyl, is substituted with halo, for example, F, Cl, or Br. In still other embodiments, Q is —C(S)—NHC(O)-alkaryl, wherein the alkaryl, for example benzyl, is substituted with $C_{1-6}$alkyl, for example, methyl, ethyl, propyl, isopropyl, butyl, sec-butyl, or tert-butyl.

In other embodiments, Q is —C(O)-alkaryl, wherein the alkaryl is, for example, benzyl. In yet other embodiments, Q is C(O)-alkaryl, wherein the alkaryl is, for example, benzyl, substituted with halo, for example, F, Cl, or Br. In other embodiments, Q is C(O)-alkaryl, wherein the alkaryl is, for example, benzyl, substituted with $C_{1-6}$alkyl, for example, methyl, ethyl, propyl, isopropyl, butyl, sec-butyl, or tert-butyl.

In other embodiments, Q is —C(O)NH-aryl, wherein the aryl is, for example, phenyl or naphthyl. In yet other embodiments, Q is C(O)NH-aryl, wherein the aryl is, for example, phenyl or naphthyl, substituted with halo, for example F, Cl, or Br. In yet other embodiments, Q is C(O)NH-aryl, wherein the aryl is, for example, phenyl or naphthyl, substituted with $C_{1-6}$alkyl, for example, methyl, ethyl, propyl, isopropyl, butyl, sec-butyl, and tert-butyl. In yet other embodiments, Q is C(O)NH-aryl, wherein the aryl is, for example, phenyl or naphthyl, substituted with $C_{1-6}$alkoxy, for example, methoxy, ethoxy, propoxy, and the like.

In other embodiments, Q is —C(O)—O-aryl, wherein the aryl is, for example, phenyl or naphthyl. In yet other embodiments, Q is —C(O)—O-aryl, wherein the aryl is, for example, phenyl or naphthyl, substituted with halo, for example F, Cl, or Br. In yet other embodiments, Q is C(O)—O-aryl, wherein the aryl is, for example, phenyl or naphthyl, substituted with $C_{1-6}$alkyl, for example, methyl, ethyl, propyl, isopropyl, butyl, sec-butyl, and tert-butyl. In yet other embodiments, Q is C(O)—O-aryl, wherein the aryl is, for example, phenyl or naphthyl, substituted with $C_{1-6}$alkoxy, for example, methoxy, ethoxy, propoxy, and the like.

In some embodiments, $R_1$ is H.

In other embodiments, $R_1$ is halo, for example, F, Cl, or Br.

In still other embodiments, $R_1$ is with $C_{1-6}$alkyl, for example, methyl, ethyl, propyl, isopropyl, butyl, sec-butyl, or tert-butyl.

In other embodiments, $R_1$ is —$C_{1-6}$alkoxy, for example methoxy, ethoxy, propoxy, butoxy, ter-butoxy, and the like.

In some embodiments, $R_1$ is pyridyl. In other embodiments, $R_1$ is optionally substituted pyridyl.

In some embodiments, $R_1$ is pyrimidinyl. In other embodiments, $R_1$ is optionally substituted pyrimidinyl.

In some embodiments, $R_1$ is pyrazinyl. In other embodiments, $R_1$ is optionally substituted pyrazinyl.

In some embodiments, $R_1$ is pyrazolyl. In other embodiments, $R_1$ is optionally substituted pyrazolyl.

In some embodiments, $R_1$ is imidazolyl. In other embodiments, $R_1$ is optionally substituted imidazolyl.

In some embodiments, $R_1$ is isoxazolyl. In other embodiments, $R_1$ is optionally substituted isoxazolyl.

In some embodiments, $R_1$ is oxazolyl. In other embodiments, $R_1$ is optionally substituted oxazolyl.

In some embodiments, $R_1$ is thiazolyl. In other embodiments, $R_1$ is optionally substituted thiazolyl.

In some embodiments, $R_1$ is isothiazolyl. In other embodiments, $R_1$ is optionally substituted isothiazolyl.

In some embodiments, $R_1$ is morpholinyl. In other embodiments, $R_1$ is optionally substituted morpholinyl.

In some embodiments, $R_1$ is piperazinyl. In other embodiments, $R_1$ is optionally substituted piperazinyl.

In some embodiments, $R_1$ is piperidinyl. In other embodiments, $R_1$ is optionally substituted piperidinyl.

In some embodiments, $R_1$ is tetrahydropyranyl. In other embodiments, $R_1$ is optionally substituted tetrahydropyranyl.

In some embodiments, $R_1$ is pyrrolidinyl. In other embodiments, $R_1$ is optionally substituted pyrrolidinyl.

In some embodiments, $R_1$ is tetrahydrothiopyranyl 1,1-dioxide. The tetrahydrothiopyranyl 1,1-dioxide can be optionally substituted.

In some embodiments, $R_1$ is thiomorpholinyl 1,1-dioxide. The thiomorpholinyl 1,1-dioxide can be optionally substituted In some embodiments, $R_1$ is pyrrolidinyl-one. The pyrrolidinyl-one can be optionally substituted.

In some embodiments, $R_1$ is piperidinyl-one. The piperidinyl-one can be optionally substituted.

In some embodiments, $R_1$ is —NH-aryl, for example, —NH-phenyl or —NH-naphthyl. In other embodiments, $R_1$ is optionally substituted —NH-aryl.

In some embodiments, $R_1$ is —NH-pyridyl. In other embodiments, $R_1$ is optionally substituted —NH-pyridyl.

In some embodiments, $R_1$ is —NH-pyrimidinyl. In other embodiments, $R_1$ is optionally substituted —NH— pyrimidinyl.

In some embodiments, $R_1$ is $C(O)NHC_{1-6}alkyl$. In other embodiments, $R_1$ is
—$C(O)N(C_{1-6}alkyl)_2$.

In some embodiments, $R_1$ is —$NHS(O)_2C_{1-6}alkyl$.

In some embodiments, $R_1$ is —$N(C_{1-6}alkyl)S(O)_2 C_{1-6}alkyl$.

In some embodiments, $R_1$ is —$NHC(O)C_{1-6}alkyl$.

In some embodiments, $R_1$ is —$NC_{1-6}alkylC(O)C_{1-6}alkyl$.

In some embodiments, $R_1$ is —$NHC(O)OC_{1-6}alkyl$.

In some embodiments, $R_1$ is —$NC_{1-6}alkylC(O)OC_{1-6}alkyl$.

In some embodiments, $R_1$ is —$NHC(O)NHC_{1-6}alkyl$.

In some embodiments, $R_1$ is —$NC_{1-6}alkylC(O)N(C_{1-6}alkyl)_2$.

In some embodiments, $R_1$ is —NHC(O)-piperazinyl. In other embodiments, $R_1$ is optionally substituted —NHC(O)-piperazinyl In some embodiments, $R_1$ is —$NC_{1-6}alkylC(O)$-piperazinyl. In other embodiments, $R_1$ is optionally substituted —$NC_{1-6}alkylC(O)$-piperazinyl.

As used herein, "alkyl" refers to saturated hydrocarbon group which is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. An alkyl group can contain from 1 to about 20, from 2 to about 20, from 1 to about 10, from 1 to about 8, from 1 to about 6, from 1 to about 4, or from 1 to about 3 carbon atoms. By way of example, "$C_{1-6}alkyl$" refers to an alkyl group having from 1 to 6 carbon atoms.

As used herein, "alkoxy" refers to an —O-alkyl group. Example alkoxy groups include methoxy, ethoxy, propoxy (e.g., n-propoxy and isopropoxy), t-butoxy, and the like. "$C_{1-6}alkoxy$" refers to an alkoxy group having from 1 to 6 carbon atoms.

As used herein, "alkylene" refers to the divalent radical of an alkyl group. Examples includes —$CH_2$—, —$CH_2CH_2$—, —$CH_2$—$CH_2$—$CH_2$—, —$CH_2$—$CH_2$—$CH_2$—$CH_2$—, and the like. Alkylene groups can be optionally substituted.

As used herein, "aryl" refers to refers to aromatic carbocyclyl groups including monocyclic or polycyclic aromatic hydrocarbons such as, for example, phenyl, naphthyl, anthracenyl, phenanthrenyl, indanyl, indenyl, and the like. In some embodiments, aryl groups have from 6 to about 18 carbon atoms.

As used herein, "alkaryl" refers to an alkyl moiety substituted by an aryl group. Example aralkyl groups include benzyl and naphthylmethyl groups. In some embodiments, aralkyl groups have from 7 to 11 carbon atoms.

As used herein, "halo" refers to F, Cl, Br, and I.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like. An alkyl group in which three of the hydrogen atoms are replaced with halogen atoms can be referred to as "trihaloalkyl." An exemplary trihaloalkyl group is $CF_3$.

As used herein, "substituted" refers to where at least one hydrogen atom of a chemical group is replaced by a non-hydrogen moiety. Example substituents include —OH, oxo (=O), $C_{1-6}alkyl$, $C_{1-6}alkoxy$, aryl, $C_{1-6}alkaryl$, halo, $haloC_{1-6}alkyl$, morpholinyl, piperazinyl, $N$—$C_{1-6}alkyl$-piperazinyl, or dioxolanyl.

As used herein, "tetrahydrothiopyranyl 1,1-dioxide" refers to the moiety,

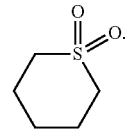

As used herein, "thiomorpholinyl 1,1-dioxide" refers to the moiety

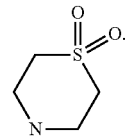

The above chemical terms can be combined to refer to moieties containing a combination of chemical groups.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

Compounds of the invention are useful for inhibiting AXL and/or cMet kinases. Inhibition of one or both of these kinases has been associated with the treatment of cancer, for example, leukemia, colon cancer, melanoma, kidney cancer, liver cancer, stomach cancer, breast cancer, and brain cancer. As such, compounds of the invention, or compositions comprising one or more compounds of the invention, are useful for the treatment of cancer.

When employed as pharmaceuticals, the compounds of Formula (I) can be administered in the form of pharmaceutical compositions. These compositions can be administered by a variety of routes including oral, rectal, transdermal, subcutaneous, intravenous, intramuscular, and intranasal, and can be prepared in a manner well known in the pharmaceutical art.

This invention also includes pharmaceutical compositions which contain, as the active ingredient, one or more of the compounds of Formula (I) above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing an appropriate amount of active ingredient. For example, the unit dosage form can include from about 5 to about 500 mg or about 5 to about 100 mg of active ingredient. Alternatively, the unit dosage form can include about 10 to about 30 mg, of the active ingredient.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. For example, the compounds utilized in the pharmaceutical methods of the invention can be administered at the initial dosage of about 0.001 mg/kg to about 100 mg/kg daily. In another embodiment, the daily dose range is from about 0.1 mg/kg to about 10 mg/kg. The compounds of the invention can be administered one, two, three, or four times daily. It will be understood, however, that the amount and timing of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. An amount adequate to accomplish this is referred to as "therapeutically effective amount." Effective doses will depend on the disease condition being treated as well as by the judgement of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present invention also includes pharmaceutical kits useful, for example, in the treatment or prevention of inflammatory diseases, which comprise one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The compounds of the invention can be prepared according to methods known to those skilled in the art and in view of the following description and schemes.

The synthesis of intermediate 6-bromo-pyrazolo[1,5-a]pyridin-4-ol (see, e.g., WO10/017047), and the general route to 6-substituted pyrazolo[1,5-a]pyridin-4-ol intermediates is outlined in Scheme 1 below. 1,3 Dipolar addition of acetylene methyl ester to 1-amino-3-bromo-5-methoxy-pyridinium gave 6-bromo-4-methoxy-pyrazolo[1,5-a]pyridine-3-carboxylic acid methyl ester as the major product. The minor 4-bromo-6-methoxy-pyrazolo[1,5-a]pyridine-3-carboxylic acid methyl ester was separated by column chromatography. 6-Bromo-4-methoxy-pyrazolo[1,5-a]pyridine-3-carboxylic acid methyl ester was hydrolyzed, decarboxylation and O-demethylation in a one-pot reaction at 48% HBr reflux to produce 6-bromo-pyrazolo[1,5-a]pyridin-4-ol. Pyrazolo[1,5-a]pyridin-4-ol was synthesized starting with 3-benzyloxypyridine using literature procedure (Heterocycles, 1996, 43, 2249).

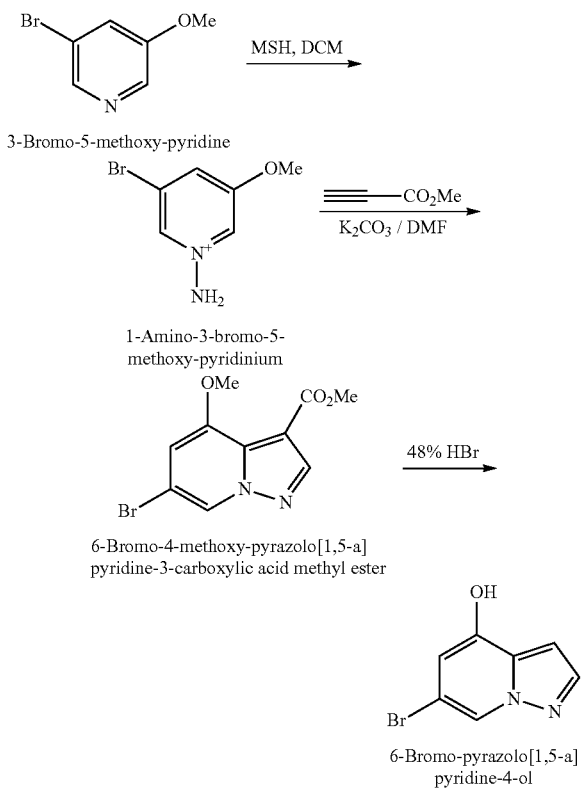

Scheme 1. Synthesis of pyrazolo[1,5-a]pyridin-4-ol intermediates.

Schemes 2-7 summarize the synthesis of 6-substituted pyrazolopyridine compounds of the invention. Scheme 2 describes a general route to 6-aryl and heteroaryl pyrazolo[1,5-a]pyridine targets via Suzuki- or Stille-coupling chemistry. Alkylation of 6-bromo-pyrazolo[1,5-a]pyridin-4-ol with 1,2-difluoro4-nitrobenzene with sodium hydride in DMF produced 6-bromo-4-(2-fluoro-4-nitro-phenoxy)-pyrazolo[1,5-a]pyridine. Starting with other substituted 4-fluoronitrobenzenes (for example 4-fluoro-3-methoxy-1-nitro-benzene, 4-fluoro-2-methoxy-1-nitro-benzene, 4-fluoro-1-nitro-2-trifluoromethyl-benzene, 4-fluoro-2-methyl-1-nitro-benzene etc) gives entry to central ring substituted examples. Coupling the nitro-bromo intermediate with an aryl or heteroaryl tin or boronic acid under Stille or Suzuki coupling conditions produces the nitro intermediate 1. The intermediate nitro can be reduced to the aniline intermediate 2 using standard procedures such as catalytic hydrogenation (Pd/C or palladium hydroxide/C), tin (II) chloride dihydrate or zinc and ammonium chloride. Final amide examples of the invention can be synthesized coupling aniline intermediates with carboxylic acids, in the presence of a coupling agent such as HATU, DCC, EDCI, TBTU, HOBT, BOP, PyBOP and DIEA to yield the target examples. Additional standard amide formation methods such as via the anilines with an acid anhydrides or acid chloride would produce the target examples.

Scheme 2

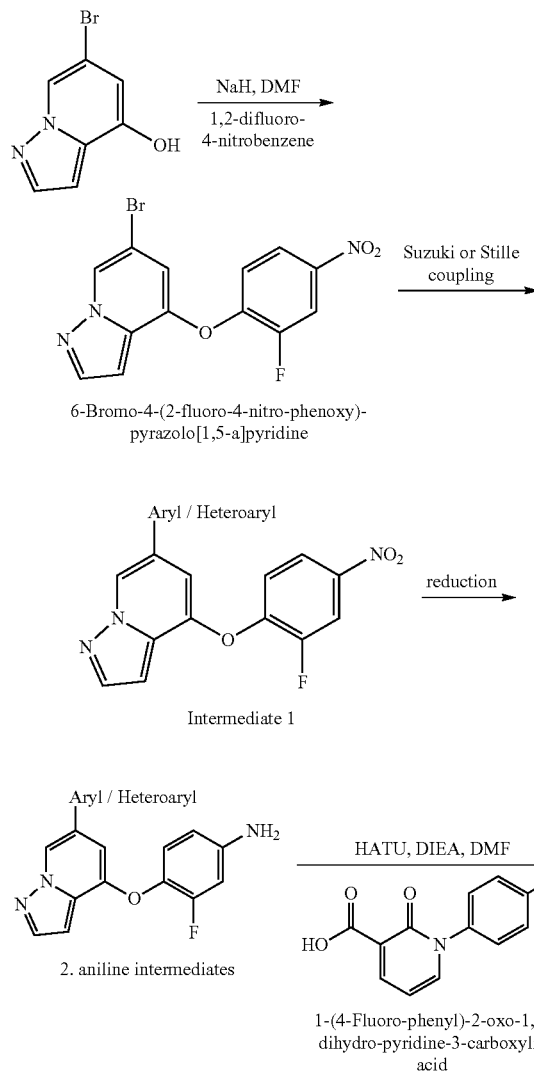

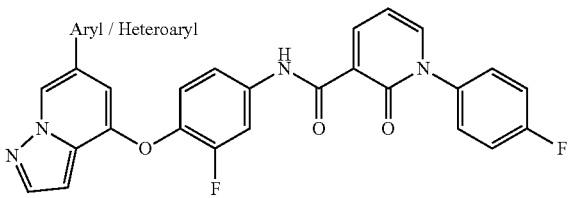

Scheme 3 outlines a general route to 6-heterocylic examples using Buchwald coupling chemistry as demonstrated with morpholine example 56. Buchwald coupling 6-bromo-4-(2-fluoro-4-nitro-phenoxy)-pyrazolo[1,5-a]pyridine and morpholine produced 4-(2-fluoro-4-nitro-phenoxy)-6-morpholin-4-yl-pyrazolo[1,5-a]pyridine. Reduction of the nitro to the aniline intermediate and amide formation as described previously produced Example 56. Heterocyclic amines in place of morpholine, include, for example, piperidine, pyrrolidine, piperazine, 4,4-difluoropiperidine, 3,3-difluoropyrrolidine, 1,4-dioxa-8-aza-spiro[4.5] decane, thiomorpholine, pyrrolidin-2-one, piperidin-2-one would produce the target examples of the invention. Non-aromatic heterocyclic examples can also be synthesized by coupling the heterocyclic vinyl boronic or tin reagent (Suzuki or Stille reaction); for example 4-(4,4,5,5-tetramethyl-[1,3,2]dioxaborolan-2-yl)-3,6-dihydro-2H-pyridine-1-carboxylic acid tert butyl ester or 4-(4,4,5,5-Tetramethyl-[1,3,2]dioxaborolan-2-yl)-3,6-dihydro-2H-pyran.

Scheme 3

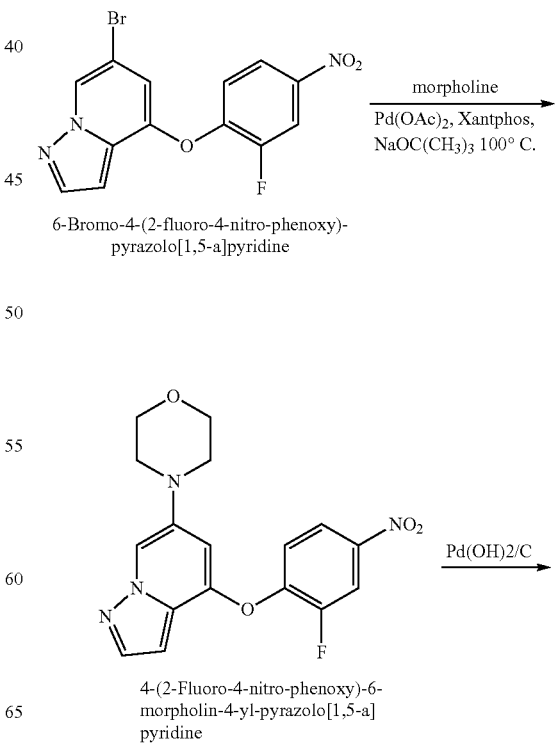

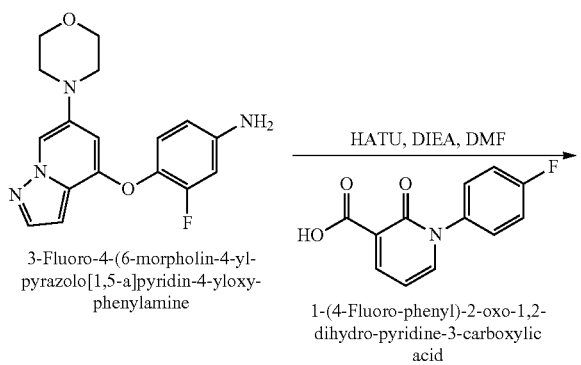

3-Fluoro-4-(6-morpholin-4-yl-pyrazolo[1,5-a]pyridin-4-yloxy-phenylamine 1-(4-Fluoro-phenyl)-2-oxo-1,2-dihydro-pyridine-3-carboxylic acid

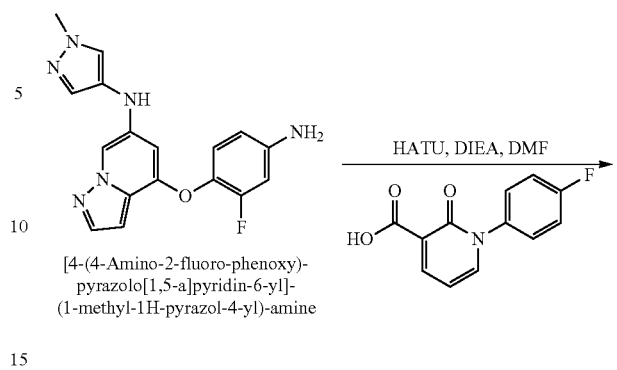

[4-(4-Amino-2-fluoro-phenoxy)-pyrazolo[1,5-a]pyridin-6-yl]-(1-methyl-1H-pyrazol-4-yl)-amine

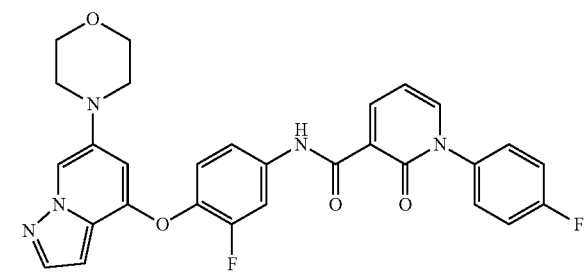

Example 56

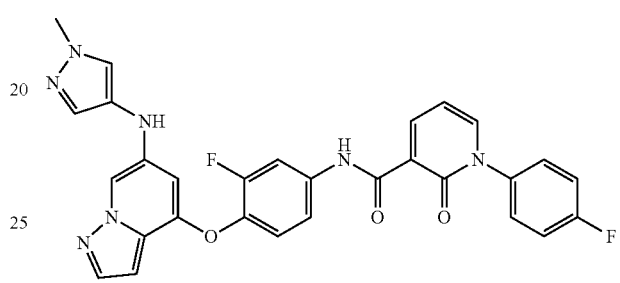

Example 79

Scheme 4 outlines the general procedure to arylamines or heteroarylamine examples using Buchwald conditions starting with a 6-bromo-4-(4-nitro-phenoxy)-pyrazolo[1,5-a]pyridine intermediate. Anilines, substituted anilines or heteroaryl amines are suitable substrates demonstrated in the examples.

Scheme 4

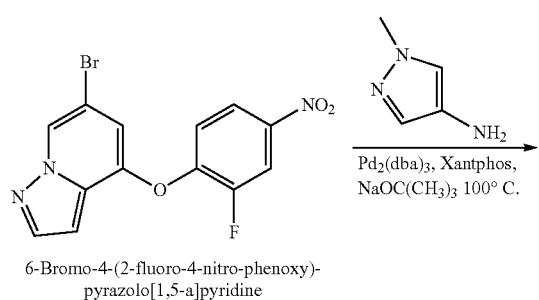

6-Bromo-4-(2-fluoro-4-nitro-phenoxy)-pyrazolo[1,5-a]pyridine

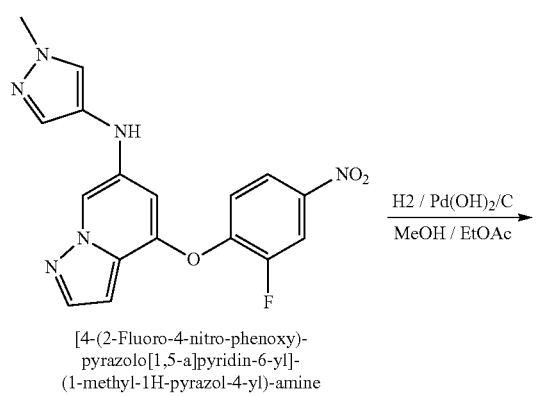

[4-(2-Fluoro-4-nitro-phenoxy)-pyrazolo[1,5-a]pyridin-6-yl]-(1-methyl-1H-pyrazol-4-yl)-amine Scheme 5 outlines routes to 6-urea substituted examples as exemplified by example 147. Buchwald coupling reaction with a 6-bromo-4-(4-nitro-phenoxy)-pyrazolo[1,5-a]pyridine intermediate and benzophenone imine, followed by acid hydrolysis produces the 6-amino intermediate. Reaction of the amine with a carbamoyl chloride, for example N,N-dimethylcarbamoyl chloride or isocyanates, yields nitro urea compounds of the invention. Reduction of the nitro group followed by amide coupling as described previously yields compounds of the invention. As shown in Scheme 6, in similar manners, intermediate 6-amides, carbamates, sulfonamide, and sulfamides can also be synthesized using the described procedure.

Scheme 5

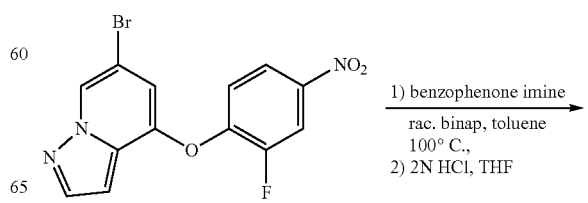

19
-continued
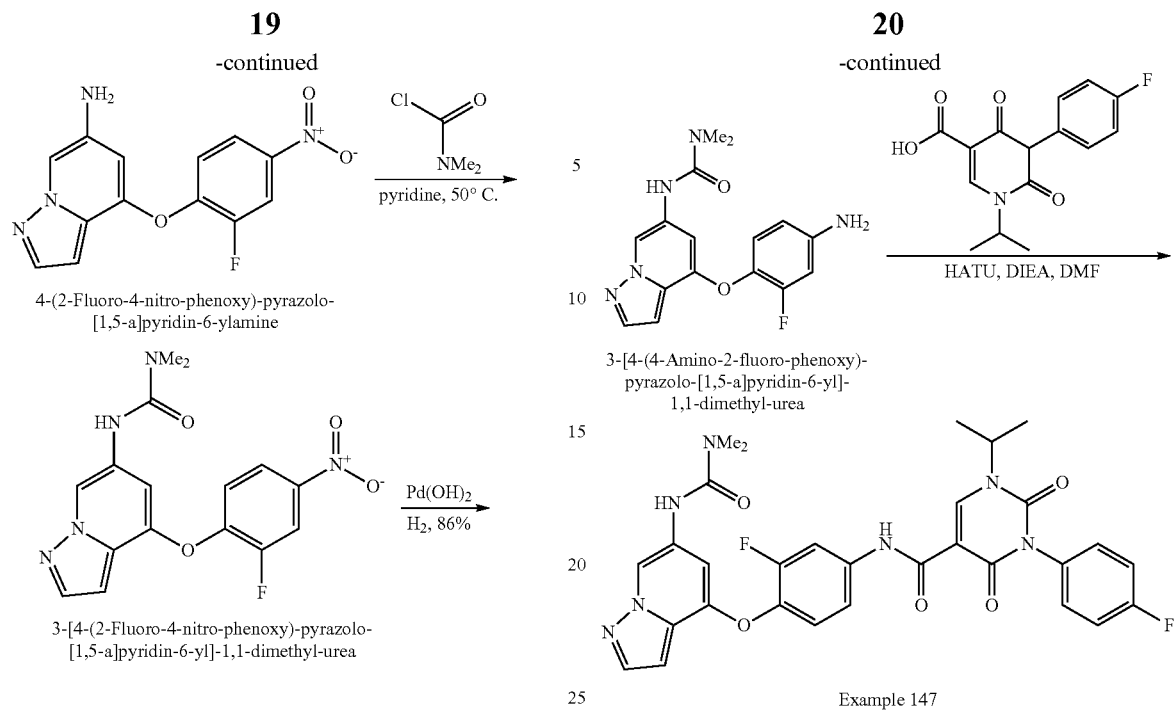
Example 147
Scheme 6
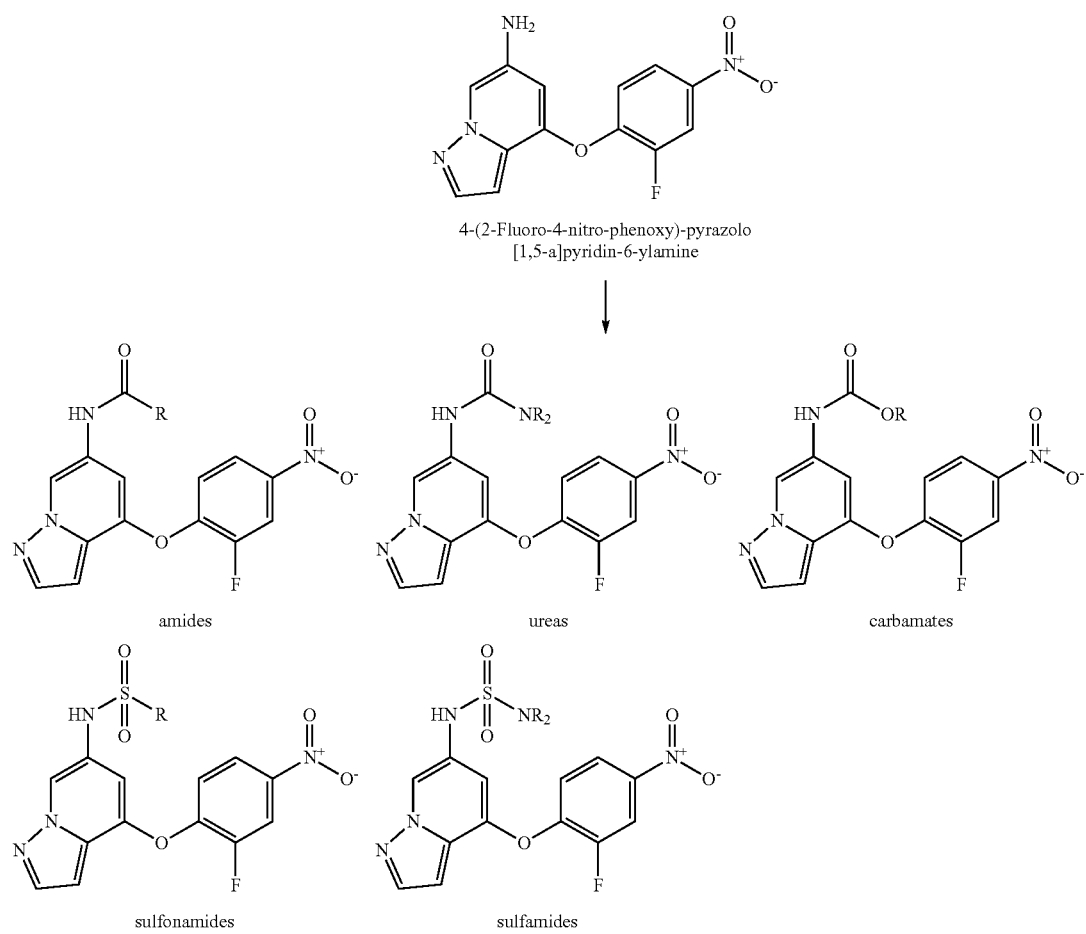

Scheme 7 outlines suggested routes to central ring pyridyl compounds of the invention. Alkylation of 6-bromo-pyrazolo[1,5-a]pyridin-4-ol with 2-fluoro-5-nitro-pyridine produces the 6-bromo-4-(5-nitro-pyridin-2-yloxy)-pyrazolo[1,5-a]pyridine isomer. Copper-mediated coupling of 6-bromo-pyrazolo[1,5-a]pyridin-4-ol and 5-bromo-2-nitro-pyridine produces the 6-bromo-4-(6-nitro-pyridin-3-yloxy)-pyrazolo[1,5-a]pyridine isomer. Nitro reduction to the aniline intermediate and amide coupling produces, for example, pyridine regioisomers example 116 and example 124.

2,4-Dioxo-1,2,3,4-tetrahydro-pyrimidine-5-carboxylic acids for amide coupling can be synthesized as outlined in scheme 8. Starting with a 2-aminomethylene malonate and reacting with any appropriate aryl, heteroaryl or alkyl isocyanate produces ureidomethylene-malonic acid esters. The ureidomethylene-malonic acid esters can be cyclized using a base such as KOH, NaOH or Na ethoxide in ethanol to produce the N1-H 2,4-dioxo-1,2,3,4-tetrahydro-pyrimidine-5-carboxylic acid esters. Starting with an N-substituted 2-aminomethylene malonate would produce an N1 substituted 2,4-dioxo-1,2,3,4-tetrahydro-pyrimidine-5-carboxylic acid ester. Starting with substitution on the methylene malonate, for example 2-(1-aminoethylidene)-malonic acid ester or 2-(1-amino-2-cyclopropyl-ethylidene)-malonic acid

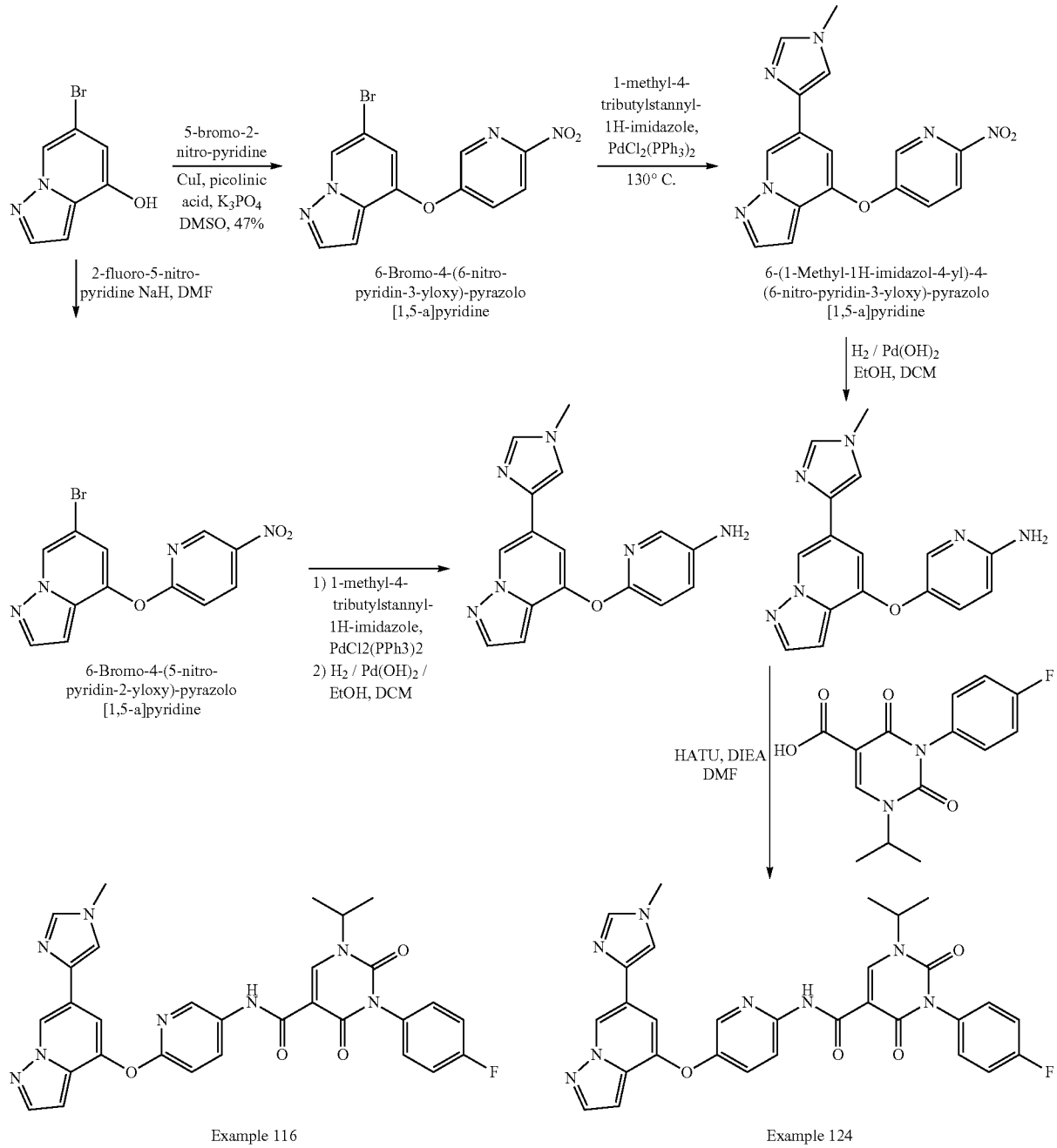

Scheme 7 ester would produce the corresponding C6 substituted 2,4-dioxo-1,2,3,4-tetrahydro-pyrimidine-6-methyl-5-carboxylic acid ester or 2,4-dioxo-1,2,3,4-tetrahydro-pyrimidine-6-cyclopropylmethyl-5-carboxylic acid ester. The N1-H intermediate may be alkylated under standard conditions using a based, for example K$_2$CO$_3$ in a solvent such as DMSO or DMF to produce the N1-substituted-2,4-dioxo-1,2,3,4-tetrahydro-pyrimidine-5-carboxylic acid ester.

Examples where 2,4-dioxo-1,2,3,4-tetrahydro-pyrimidine-5-carboxylic acid amides are N1 aryl or heteroaryl may be synthesized as outlined in Scheme 9. The sequential reaction of 4-fluoroaniline with ethyl isocyanate then diethyl ethoxymethylenemalonate produced 1-ethyl-3-(4-fluoro-phenyl)-2,4-dioxo-1,2,3,4-tetrahydro-pyrimidine-5-carboxylic acid ethyl ester and 3-ethyl-1-(4-fluoro-phenyl)-2,4-dioxo-1,2,3,4-tetrahydro-pyrimidine-5-carboxylic acid ethyl ester. The 1-(4-fluorophenyl) isomer can be separated from the mixture by crystallization. The 2,4-dioxo-1,2,3,4-tetrahydro-pyrimidine-5-carboxylic acid can be produced under basic hydrolysis or acid conditions. Examples where 2,4-dioxo-1,2,3,4-tetrahydro-pyrimidine-5-carboxylic acid ester are N1 and N3 unsubstituted maybe mono- or dialkylated from the di-H compound using standard conditions.

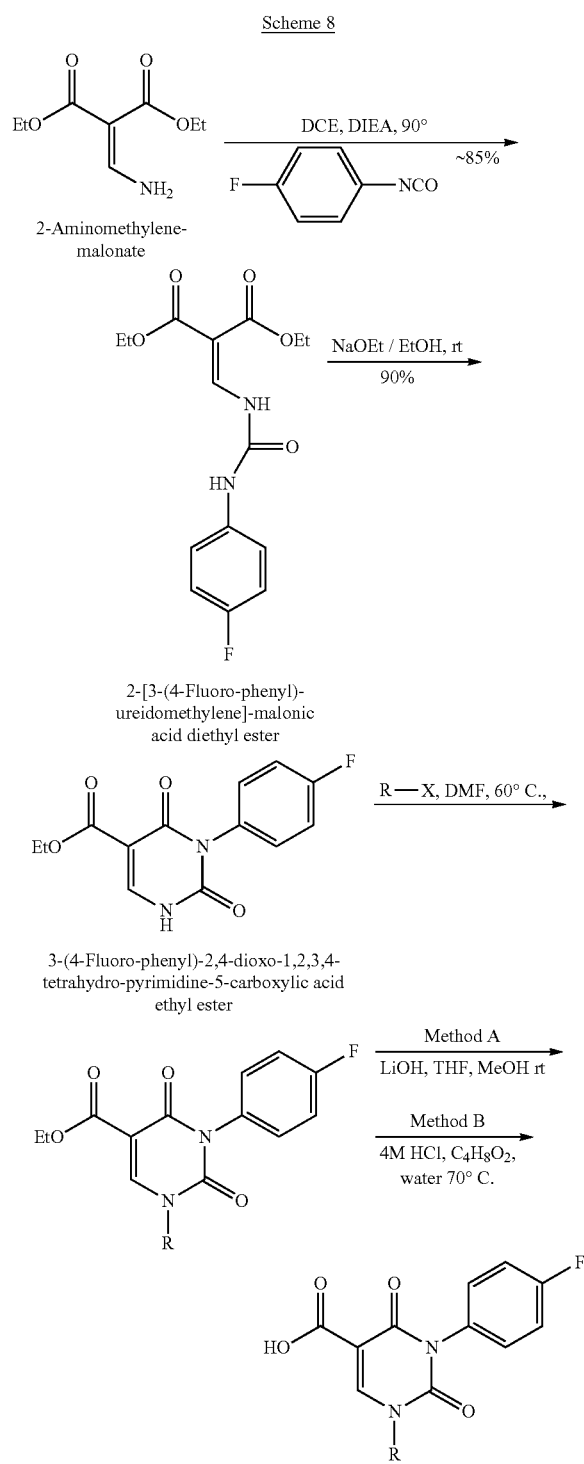

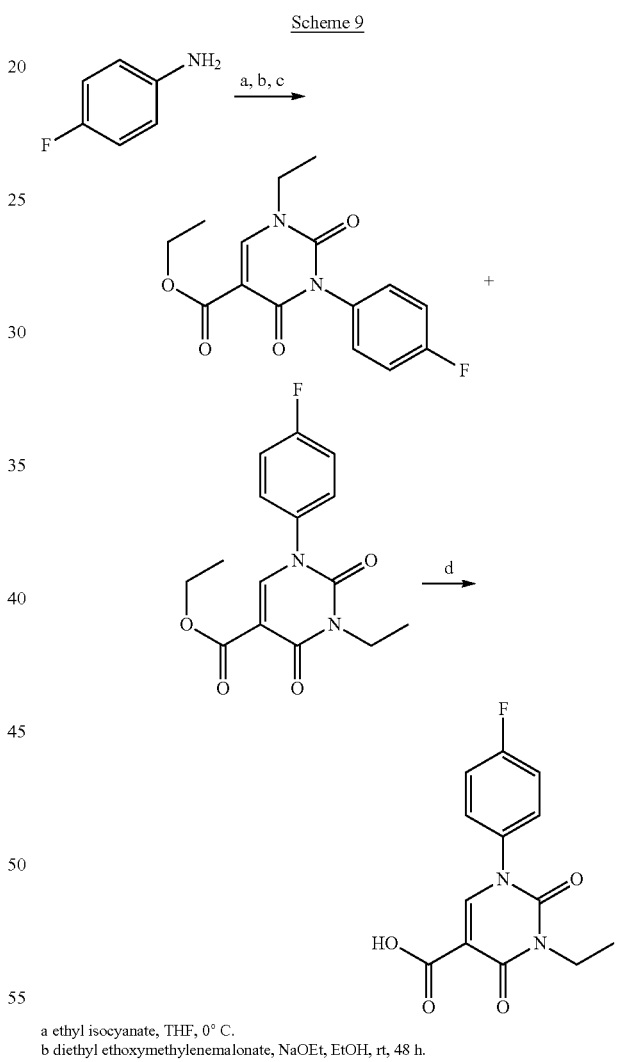

a ethyl isocyanate, THF, 0° C.
b diethyl ethoxymethylenemalonate, NaOEt, EtOH, rt, 48 h.
c ethyl acetate / hexanes.
d 1N LiOH, MeOH, THF, 60° C., 18 h.

Dioxo-2,3,4,5-tetrahydro-[1,2,4]triazine-6-carboxylic acid esters may be synthesized as outlined in Scheme 10. 2-Oxo-malonic acid diethyl ester and 4-fluorophenyl thiosemicarbazide condensation produced 4-(4-fluorophenyl)-5-oxo-3-thioxo-2,3,4,5-tetrahydro-[1,2,4]triazine-6-carboxylic acid ethyl ester. Oxidation with, for example hydrogen peroxide and acetic acid produces 4-(4-fluorophenyl)-3,5- dioxo-2,3,4,5-tetrahydro-[1,2,4]triazine-6-carboxylic acid ethyl ester. Alkylation under conditions described for 2,4-dioxo-1,2,3,4-tetrahydro-pyrimidine-5-carboxylic acid esters produced 2-substituted 4-(4-fluorophenyl)-3,5-dioxo-2,3,4,5-tetrahydro-[1,2,4]triazine-6-carboxylic acid ethyl esters. N1 and/or N4 unsubstituted 3,5-dioxo-2,3,4,5-tetrahydro-[1,2,4]triazine-6-carboxylic acid ethyl esters may be alkylated to produce the corresponding substituted 3,5-dioxo-2,3,4,5-tetrahydro-[1,2,4]triazine-6-carboxylic acid ethyl esters.

tific, Waltham, Mass.). The final concentrations were 0.3 μM TK substrate-biotin, and 1.3 μM ATP. Compounds (100 nL), diluted in 100% DMSO on the Biomek FX, (Beckman Coulter, Inc., Brea, Calif.), were transferred to the assay plates using the Biomek FX pintool (2.5% final DMSO in assay). A 2× concentration (final=12 ng/mL) of GST-AXL (diluted in assay buffer) was added to plates at 10 uL/well using the Multidrop Combi. Plates were sealed, briefly shaken and incubated at 25° C. for 30 minutes. A 4× stock of Streptavidin-XL665 (final=18.8 nM) and a 1:100 diluted

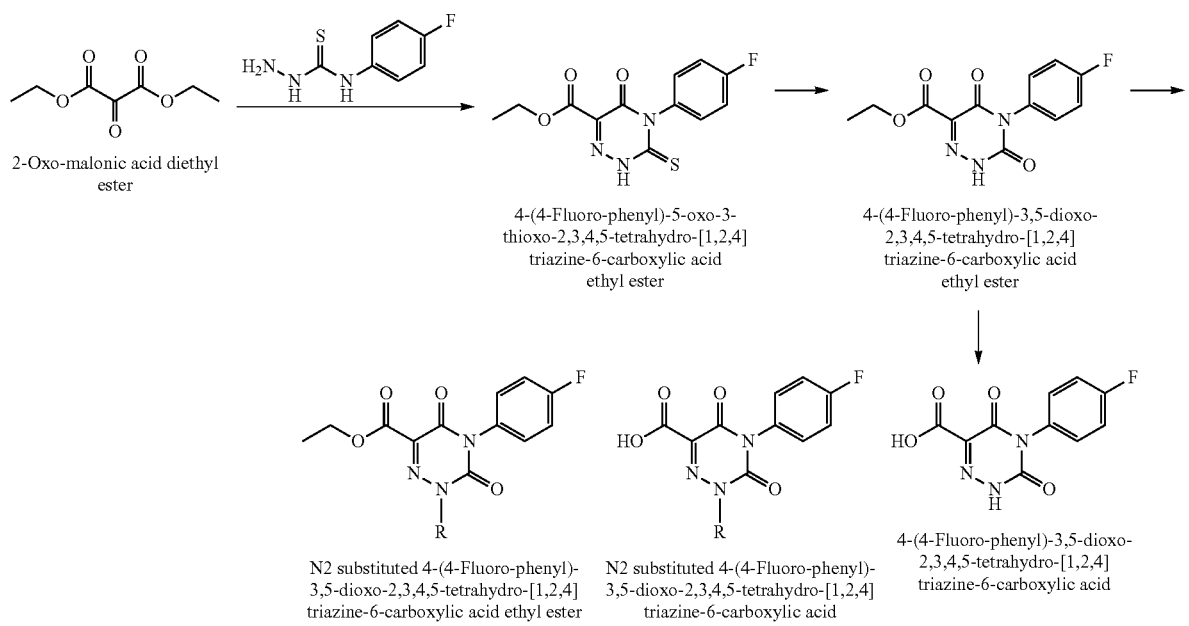

Scheme 10.
General synthesis of 3,5-dioxo-2,3,4,5-tetrahydro-[1,2,4]triazine-6-carboxylic acids Compounds of the invention inhibit AXL tyrosine kinase and/or MET kinase. As such, the compounds of the invention are useful for treating cancer in a patient. Examples of cancers that can be treated with compounds of the invention include, for example, leukemia, colon cancer, melanoma, kidney cancer, liver cancer, stomach cancer, breast cancer, or brain cancer.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

EXAMPLES

AXL Kinase Assay

The ability of compounds to inhibit the kinase activity of recombinant human baculovirus-expressed AXL was measured by homogeneous TRF (HTRF) using Cisbio's Kin-EASE™ assay system in white 384-well Optiplates. Assay buffer contained 1 mM DTT, 2 mM $MnCl_2$, 2% DMSO, 50 nM supplement enzymatic buffer, and 1× enzymatic buffer. A 2× concentration of tyrosine kinase (TK) substrate-biotin/ATP mixture made in assay buffer was added to plates at 10 μL/well using the Multidrop Combi (Thermo Fisher Scienstock of TK antibody-cryptate were made in HTRF detection buffer and mixed together just prior to adding 20 μL/well on the Multidrop Combi. Plates were sealed, briefly shaken and incubated at 25° C. for 1 hour. The fluorescence of the resulting solution was measured using the Perki-nElmer EnVision™ 2102 multi-label plate reader (Perki-nElmer, Waltham, Mass.) with an excitation wavelength of 337 nm (laser) and emission wavelengths of 590 and 665 nm. Raw data was expressed as the ratio of 665/590×10,000.

C-MET Kinase Assay

The cMET kinase assay was performed in 384-well Fluotrac™ 200 HiBase microplates using the HTRF Kin-EASE™ assay described above for AXL except that the assay volume was reduced to half. Enzyme concentration was 8 ng/mL of recombinant human baculovirus-expressed cMET while the substrate concentrations were 0.1 μM and 0.02 μM for the biotinylated peptide and ATP, respectively. Instead of the Multidrop Combi, the BioRAPTR® FRD microfluidic workstation (Beckman Coulter, Brea, Calif.) was utilized for reagent additions.

Data Analysis

Inhibition curves for compounds were generated by plotting percent control activity versus log 10 of the concentration of compound. $IC_{50}$ values were calculated by nonlinear regression using the sigmoidal dose-response (variable slope) equation in GraphPad Prism as follows:

$y=\text{bottom}+(\text{top}-\text{bottom})/(1+10(\log \text{IC}_{50}-x)*\text{Hill Slope})$ where y is the % kinase activity at a given concentration of compound, x is the logarithm of the concentration of compound, bottom is the % of control kinase activity at the highest compound concentration tested, and top is the % of control kinase activity at the lowest compound concentration examined. The values for bottom and top were fixed at 0 and 100, respectively.

General Synthesis Methods for 2,4-dioxo-1,2,3,4-tetrahydropyrimidine-5-carboxylic acids Method A: 1-cyclopropylmethyl-3-(4-fluorophenyl)-2,4-dioxo-1,2,3,4-tetrahydropyrimidine-5-carboxylic acid a) 2-Aminomethylene-malonic acid diethyl ester (16.7 g, 89.2 mmol) and 4-fluorophenyl isocyanate (10.6 mL, 93.7 mmol) in 1,2-dichloroethane (25 mL, 320 mmol) was added N,N-diisopropylethylamine (17.1 mL, 98.1 mmol) and heated at 100° C. for 6 h. The mixture was cooled on an ice bath and the solid collected and washed with ether to give the urea (24.5 g, 85%). mp=198-200° C.; LCMS m/z=347 (M+23); $^1$H NMR (DMSO) δ: 10.57 (d, 1H, J=12.3 Hz), 10.41 (s, 1H, J=12.45 Hz), 8.45 (d, 1H, J=12.5 Hz), 7.48-7.53 (m, 2H), 7.16-7.21 (m, 2H), 4.24 (q, 2H, J=7 Hz), 4.15 (q, 2H, J=7 Hz), 1.22-1.28 (m, 6H).

b) 2-[3-(4-Fluorophenyl)ureidomethylene]malonic acid diethyl ester (24 g; 70 mmol) was suspended in Ethanol (100 mL) and added 21% NaOEt in EtOH (41.7 mL, 112 mmol) drop wise at rt. The mixture was stirred 4 h, upon which time the mixture became thick slurry. The mixture was concentrated and the residue partitioned between EtOAc and 1M citric acid. The EtOAc layer was washed with water and brine, dried over MgSO$_4$ and was concentrated. The solid was triturated with ether-hexanes (1/3) to give 3-(4-fluorophenyl)-2,4-dioxo-1,2,3,4-tetrahydropyrimidine-5-carboxylic acid ethyl ester as a white solid. mp 206-8° C.; LCMS m/z=279 (M+1); $^1$H NMR (DMSO) δ: 12.0 (s, 1H), 8.25 (s, 1H), 7.31 (bs, 2H), 7.29 (d, 2H, J=3 Hz), 4.17 (q, 2H, J=7 Hz), 1.23 (t, 3H, J=7 Hz).

c) 3-(4-Fluorophenyl)-2,4-dioxo-1,2,3,4-tetrahydropyrimidine-5-carboxylic acid ethyl ester (3.50 g, 11.6 mmol), potassium carbonate (3.22 g, 23.3 mmol) and cyclopropylmethyl bromide (3.39 mL, 35.0 mmol) in N,N-dimethylformamide (10 mL) was heated at 65° C. for 12 h. The mixture was cooled to rt, partitioned between EtOAc and 1N Na$_2$CO$_3$, water and brine and then dried over MgSO$_4$. LCMS m/z=333 (M+1); $^1$H NMR (CDCL$_3$): 8.42 (s, 1H), 7.16-7.19 (m, 4H), 4.35 (q, 2H, J=7 Hz), 3.74 (d, 2H, J=7 Hz), 1.35 (t, 3H, J=7 Hz), 1.25 (m, 1H), 0.72 (m, 2H), 0.42 (m, 2H).

d) The oil from step c was dissolved in methanol (10 mL) and tetrahydrofuran (10 mL) and 1 M of lithium hydroxide (10.6 mL) was added. After stirring at rt for 6 h the mixture was concentrated and extracted with 1N Na$_2$CO$_3$ (2×). The basic layer was acidified with 1N HCl on an ice bath and the product collected and dried to give 1-cyclopropylmethyl-3-(4-fluorophenyl)-2,4-dioxo-1,2,3,4-tetrahydropyrimidine-5-carboxylic acid as a white solid. LCMS m/z=305 (M+1); $^1$H NMR (DMSO) δ: 12.62 (s, 1H), 8.82 (s, 1H), 7.30-7.39 (m, 4H), 3.79 (d, 2H, J=7.2 Hz), 1.20 (m, 1H), 0.50-0.55 (m, 2H), 0.38-0.42 (m, 2H).

Method B: 3-(4-Fluorophenyl)-1-isopropyl-2,4-dioxo-1,2,3,4-tetrahydropyrimidine-5-carboxylic acid a) 3-(4-Fluorophenyl)-2,4-dioxo-1,2,3,4-tetrahydropyrimidine-5-carboxylic acid ethyl ester (15 g, 54 mmol), potassium carbonate (14.9 g, 108 mmol) and isopropyl iodide (10.8 mL, 108 mmol) in N,N-dimethylformamide (35 mL) was heated at 70° C. for 12 h. The mixture was concentrated, dissolved in EtOAc and was filtered. The EtOAc layer was washed with 1N Na$_2$CO$_3$, water and brine and was concentrated. The product was crystallized from EtOAc-ether-hexanes to give [3-(4-fluorophenyl)-1-isopropyl-2,4-dioxo-1,2,3,4-tetrahydropyrimidine-5-carboxylic acid ethyl ester as a white solid (15.5 g, 90%). mp 142-4° C.; LCMS m/z=321 (M+1), $^1$H NMR (CDCl$_3$) δ: 8.35 (s, 1H), 7.14-7.19 (m, 4H), (4.91 (h, 1H, J=6.8 Hz), 4.35 (q, 2, J=7.2 Hz), 1.44 (d, 6H, J=7 Hz), 1.36 (t, 3H, J=7.2 Hz).

b) [3-(4-Fluorophenyl)-1-isopropyl-2,4-dioxo-1,2,3,4-tetrahydropyrimidine-5-carboxylic acid ethyl ester (15 g, 47 mmol) was added 4M HCl in dioxane (18.7 mL, 216 mmol) and water (5 mL) and heated at 70° C. overnight. The product upon cooling precipitated, additional water (~10 mL) was added and the product collected and dried to give 3-(4-fluorophenyl)-1-isopropyl-2,4-dioxo-1,2,3,4-tetrahydropyrimidine-5-carboxylic acid as a white solid. mp 168-9° C.; LCMS m/z=293 (M+1); $^1$H NMR (DMSO) δ: 12.67 (s, 1H), 8.58 (s, 1H), 7.29-7.39 (M, 4H), 4.72 (h, 1H, J=6.8 Hz), 1.38 (d, 6H, J=6.8 Hz).

c)

The following 2,4-dioxo-1,2,3,4-tetrahydropyrimidine-5-carboxylic acids demonstrate the synthesis.

3-(4-Fluorophenyl)-2,4-dioxo-1,2,3,4-tetrahydropyrimidine-5-carboxylic acid. LCMS m/z=251 (M+1); $^1$H NMR (DMSO) δ: 12.56 (b, 1H), 12.39 (s, 1H), 8.36 (s, 1H), 7.29-7.38 (M, 4H).

1-Ethyl-3-(4-fluorophenyl)-2,4-dioxo-1,2,3,4-tetrahydropyrimidine-5-carboxylic acid. mp=166-8° C.; LCMS m/z=279 (M+1); $^1$H NNR (DMSO) δ: 12.6 (bs, 1H), 8.82 (s, 1H), 7.29-7.38 (m, 4H), 3.94 (q, 2H, J=7.3 Hz), 1.25 t, 3H, J=7 Hz).

3-(4-Fluorophenyl)-1-methyl-2,4-dioxo-1,2,3,4-tetrahydropyrimidine-5-carboxylic acid LCMS m/z=265 (M+1); $^1$HNMR (DMSO) δ: 12.59 (s, 1H), 8.80 (s, 1H), 7.3 (m, 4H), 3.56 (s, 3H).

1-Allyl-3-(4-fluorophenyl)-2,4-dioxo-1,2,3,4-tetrahydropyrimidine-5-carboxylic acid. LCMS m/z=291 (M+1); $^1$H NMR (DMSO) δ: 1H NMR (DMSO) δ: 12.66 (s, 1H), 8.72 (s, 1H), 7.27-7.41 (m, 4H), 5.89-5.99 (m, 1H), 5.24-5.35 (m, 2H), 4.53 (m, 2H).

3-(4-Fluorophenyl)-2,4-dioxo-1-pentyl-1,2,3,4-tetrahydropyrimidine-5-carboxylic acid. LCMS m/z=321 (M+1); $^1$H NMR (DMSO) δ: 12.62 (s, 1H), 8.78 (s, 1H), 7.30-7.38 (m, 4H), 3.89 (m, 2H), 1.65 (m, 2H), 1.28 (m, 4H), 0.87 (t, 3H, J=7.4 Hz).

1-(2-Ethoxyethyl)-3-(4-fluorophenyl)-2,4-dioxo-1,2,3,4-tetrahydro-pyrimidine-5-carboxylic acid. LCMS m/z=323 (M+1); $^1$H NMR (DMSO) δ: 12.509 (s, 1H), 8.66 (s, 1H), 7.39-7.39 (m, 4H), 4.09 (t, 2H, J=5 Hz), 3.61 (t, 2H, J=5 Hz), 3.47 (q, 2H, J=7.2 Hz), 1.11 (t, 3H, J=7.2 Hz).

1-(2-Benzyloxyethyl)-3-(4-fluorophenyl)-2,4-dioxo-1,2,3,4-tetrahydropyrimidine-5-carboxylic acid. LCMS m/z=385 (M+1); $^1$H NMR (DMSO) δ: 12.59 (s, 1H), 8.72 (s, 1H), 7.31-7.34 (m, 9H), 4.52 (s, 2H), 4.15 (t, 2H, J=5 Hz), 3.68 (t, 2H, J=5 Hz).

General Synthesis of 3,5-dioxo-2,3,4,5-tetrahydro-[1,2,4]triazine-6-carboxylic acids 4-(4-Fluorophenyl)-2-isopropyl-3,5-dioxo-2,3,4,5-tetrahydro[1,2,4]triazine-6-carboxylic acid Step a. 4-(4-fluorophenyl)-5-oxo-3-thioxo-2,3,4,5-tetrahydro-[1,2,4]triazine-6-carboxylic acid ethyl ester. A mixture of 2-oxo-malonic acid diethyl ester (2.5 mL, 16 mmol) and 4-fluorophenyl thiosemicarbazide (3.0 g, 16 mmol) in ethanol (60 mL, 1000 mmol) was heated at reflux for 3 days. The mixture was cooled to rt and the separated solid was filtered, washed with cold ethanol and dried to give 3.44 g (71%). LCMS m/z=296 (M+1); $^1$H NMR (DMSO) δ: 7.35 (m, 4H), 4.30 (q, 2H, J=7.1 Hz), 1.27 (t, 3H, J=7.1 Hz).

Step b. 4-(4-Fluorophenyl)-3,5-dioxo-2,3,4,5-tetrahydro-[1,2,4]triazine-6-carboxylic acid ethyl ester. To a solution of 4-(4-fluorophenyl)-5-oxo-3-thioxo-2,3,4,5-tetrahydro-1,2,4-triazine-6-carboxylic acid ethyl ester (11 g, 37 mmol) in N,N-dimethylformamide (100 mL) and acetic acid (40 mL, 700 mmol) was added 50% aq. hydrogen peroxide (11 mL, 190 mmol). The mixture was stirred at rt 2 days, the solvent was removed and the product was taken up in ethylacetate and washed successively with water and brine. After drying, the solvent was evaporated. The solid obtained was triturated with ether, filtered and washed with cold ether to yield 9.85 g (95%). LCMS m/z=280 (M+1); $^1$H NMR (DMSO) δ: 13.1 (s, 1H), 7.42-7.28 (2m, 4H), 4.29 (q, 2H, J=7.1 Hz), 1.27 (t, 3H, J=7.1 Hz).

Step c. 4-(4-Fluorophenyl)-2-isopropyl-3,5-dioxo-2,3,4,5-tetrahydro-[1,2,4]triazine-6-carboxylic acid ethyl ester. 4-(4-Fluorophenyl)-3,5-dioxo-2,3,4,5-tetrahydro-1,2,4-triazine-6-carboxylic acid ethyl ester (1000 mg, 4 mmol), isopropyl iodide (0.72 mL, 7.16 mmol) and potassium carbonate (544 mg, 3.94 mmol) in N,N-dimethylformamide (20 mL) was heated at 65° C. for 60 min. The reaction mixture was cooled to rt and was concentrated, diluted with EtOAc and was filtered through a pad of celite. The filtrate was concentrated and the product purified by flash chromatography (hexane: EtOAc 3:1) to give a white solid (1.1 g, 96%). LCMS m/z=322 (M+1); $^1$H NMR (DMSO) δ: 7.41-7.31 (m, 4H), 4.86 (m, 1H), 4.31 (q, 2H, J=7.0 Hz), 1.31-1.26 (overlapping t and d, 9H).

Step d. 4-(4-Fluorophenyl)-2-isopropyl-3,5-dioxo-2,3,4,5-tetrahydro[1,2,4]triazine-6-carboxylic acid. Sulfuric acid (10 mL, 200 mmol) was carefully added to a mixture of 4-(4-fluorophenyl)-2-isopropyl-3,5-dioxo-2,3,4,5-tetrahydro-1,2,4-triazine-6-carboxylic acid ethyl ester (1100 mg, 3.4 mmol) and water (2 mL). The mixture became homogenous after a few minutes. The reaction mixture was stirred at 40° C. overnight, was cooled to rt and was carefully added to ice. The mixture was saturated with solid NaCl and was extracted repeatedly from EtOAc (3×). The combined EtOAc layer was washed with brine, dried over magnesium sulfate, and concentrated to give the product as foam (100%). LCMS m/z=294 (M+1); $^1$H NMR (Methanol d4) δ: 7.35-7.31 (2m, 4H), 4.95 (m, 1H), 4.31 (q, 2H, J=7.0 Hz), 1.41 (d, 6H, J=6.6 Hz).

Using the method for 4-(4-Fluorophenyl)-2-isopropyl-3,5-dioxo-2,3,4,5-tetrahydro[1,2,4]triazine-6-carboxylic acid 2-Ethyl-4-(4-fluorophenyl)-3,5-dioxo-2,3,4,5-tetrahydro-[1,2,4]triazine-6-carboxylic acid was synthesized. LCMS m/z=280 (M+1); 1H NMR (Methanol-d4) δ: 7.34-7.18 (m, 4H), 4.10 (q, 2H, J=7.2 Hz), 1.38 (t, 3H, J=7.2 Hz).

Example 1

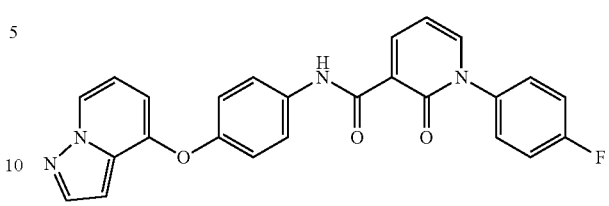

Step 1. 4-(Pyrazolo[1,5-a]pyridin-4-yloxy)-phenylamine.
Pyrazolo[1,5-a]pyridin-4-ol (1.00 g, 7.46 mmol) in N,N-dimethylformamide (20 mL) was added sodium hydride, (60% disp. in mineral oil, 0.447 g, 11.2 mmol) at 0° C. After 0.5 h 4-fluoronitrobenzene (1.16 g, 8.20 mmol) was added and the mixture stirred at rt overnight. Then 1 mL of water was added and the mixture was concentrated, dissolved in EtOAc and washed with 1 M of sodium carbonate solution (25 mL), water and brine then dried over MgSO$_4$. The product was purified by ISCO chromatography (EtOAc/hexanes 25% to 60%). The nitro intermediate was dissolved in EtOAc and MeOH (1:1, 25 mL) and hydrogenated with 20% Pd(OH)$_2$/C, 50% wet (0.1 g, 0.09 mmol) on a Parr apparatus overnight. The catalyst was filtered off, and the solvent concentrated to give a white solid. 1H NMR (CDCl3) δ: 8.21 (d, 1H, J=6.5 Hz), 7.93 (s, 1H), 6.97 (d, 2H, J=7.2 Hz), 6.73 (d, 2H, J=7.2 Hz), LCMS m/z=226 (M+1). 6.66 (s, 1H), 6.60 (t, 1H, J=7.2 Hz), 6.31 (d, 1H, J=7 Hz), 3.67 (bs, 2H).

Step 2. 1-(4-Fluoro-phenyl)-2-oxo-1,2-dihydro-pyridine-3-carboxylic acid [4-(pyrazolo[1, 5-a]pyridin-4-yloxy)-phenyl]-amide. N,N,N',N'-Tetramethyl-O-(7-azabenzotriazol-1-yl)uronium hexafluorophosphate (HATU) (162 mg, 0.36 mmol) and 1-(4-fluoro-phenyl)-2-oxo-1,2-dihydro-pyridine-3-carboxylic acid (0.0994 g, 0.426 mmol) in N,N-dimethylformamide (4 mL) was added N,N-diisopropylethylamine (0.21 mL, 1.98 mmol). After 0.5 h 4-(pyrazolo[1, 5-a]pyridin-4-yloxy)-phenylamine (0.080 g, 0.36 mmol) was added and the reaction stirred at rt for 20 h and was concentrated. The solid was dissolved in EtOAc and washed with 2N Na$_2$CO$_3$ solution, water and brine, and dried (MgSO$_4$). The product was triturated with MeOH-ether to give a white solid. mp=172-4° C.; LCMS m/z=441 (M+1); $^1$H NMR (DMSO) δ: 11.94 (s, 1H), 8.58 (d, 1H, J=6.7 Hz), 8.48 (d, 1H, J=6.8 Hz), 8.10 (d, 1H, J=6.8 Hz), 8.0 (s, 1H), 9.76 (d, 2H, J=9.6 Hz), 7.59-7.62 (m, 2H), 7.4-7.44 (t, 1H, J=9.2 Hz), 7.16 (d, 2H, J=9.2 Hz), 6.81 (t, 1H, J=7.2 Hz), 6.71 (t, 1H, J=7.6 Hz), 6.58 (m, 2H).

Example 2

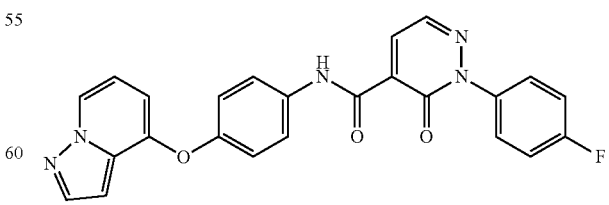

Step 1. 3-Fluoro-4-(pyrazolo[1,5-a]pyridin-4-yloxy)-phenylamine was synthesized using the methods for 4-(pyrazolo[1,5-a]pyridin-4-yloxy)-phenylamine. LC/MS m/z=244 (M+1).

Step 2. 2-(4-Fluoro-phenyl)-3-oxo-2,3-dihydro-pyridazine-4-carboxylic acid [4-(pyrazolo[1,5-a]pyridin-4-yloxy)-phenyl]-amide. This example was synthesized using 4-(pyrazolo[1,5-a]pyridin-4-yloxy)-phenylamine and 2-(4-fluoro-phenyl)-3-oxo-2,3-dihydro-pyridazine-4-carboxylic acid by the methods for example 1. mp=220-2° C.; LCMS m/z=442 (M+1); ¹H NMR (DMSO) δ: 11.55 (s, 1H), 8.50 (d, 1H, J=6.8 Hz), 8.37 (m, 1H), 8.26 (m, 1H), 7.99 (s, 1H), 7.79 (d, 2H, J=8.2 Hz), 7.66-7.69 (m, 2H), 7.38-7.42 (t, 2H, J=8.6 Hz), 7.19 (d, 2H, J=8.2 Hz), 6.82 (t, 1H, J=6.6 Hz), 6.67 (d, 1H, J=7.8 Hz), 6.56 (s, 1H).

Example 3

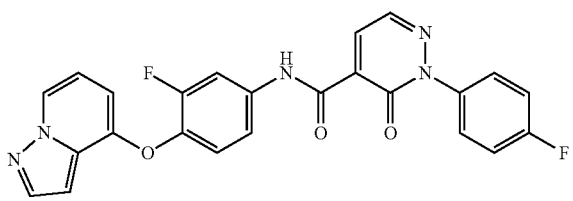 [SMILES: O=C(Nc1ccc(Oc2cccn3nccc23)c(F)c1)c1ccnn(-c2ccc(F)cc2)c1=O]

2-(4-Fluoro-phenyl)-3-oxo-2,3-dihydro-pyridazine-4-carboxylic acid [3-fluoro-4-(pyrazolo[1,5-a]pyridin-4-yloxy)-phenyl]-amide. This example was synthesized using 3-fluoro-4-(pyrazolo[1,5-a]pyridin-4-yloxy)-phenylamine and 2-(4-fluoro-phenyl)-3-oxo-2,3-dihydro-pyridazine-4-carboxylic acid by the methods for example 1. mp=209-10° C.; LCMS m/z=460 (M+1); ¹H NMR (DMSO) δ: 11.66 (s, 1H), 8.49 (d, 1H, J=7.2 Hz); 8.38 (d, 1H, J=3 Hz), 8.26 (d, 1H, J=3 Hz), 8.0 (m, 2H), 7.66-7.69 (m, 2H), 7.52 (d, 1H, J=8.6 Hz), 7.35-7.43 (m, 3H), 6.79 (t, 1H, J=6.8 Hz), 6.69 (s, 1H), 6.49 (d, 1H, J=7.6 Hz).

Example 4

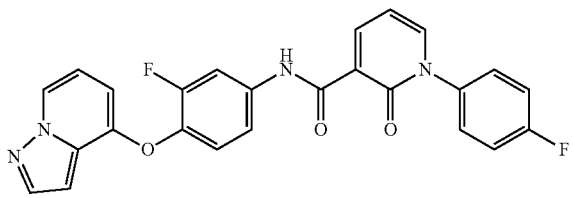 [SMILES: O=C(Nc1ccc(Oc2cccn3nccc23)c(F)c1)c1cccn(-c2ccc(F)cc2)c1=O]

1-(4-Fluoro-phenyl)-2-oxo-1,2-dihydro-pyridine-3-carboxylic acid [3-fluoro-4-(pyrazolo[1,5-a]pyridin-4-yloxy)-phenyl]-amide. This example was synthesized using 3-fluoro-4-(pyrazolo[1,5-a]pyridin-4-yloxy)-phenylamine and 1-(4-fluoro-phenyl)-2-oxo-1,2-dihydro-pyridine-3-carboxylic acid by the methods for example 1. mp=214-5° C.; LCMS m/z 459 (M+1); ¹H NMR (DMSO) δ: 12.08 (s, 1H), 8.59 (d, 1H, J=7.2 Hz), 8.48 (d, 1H, J=7.2 Hz), 8.13 (d, 1H, J=7.2 Hz), 8.0-8.03 (m, 2H), 7.59-7.62 (m, 2H), 7.4-7.47 (m, 3H), 7.31-7.36 (m, 1H), 6.7-6.8 (m, 3H), 7.46 (d, 1H, J=7.2 Hz).

Example 5

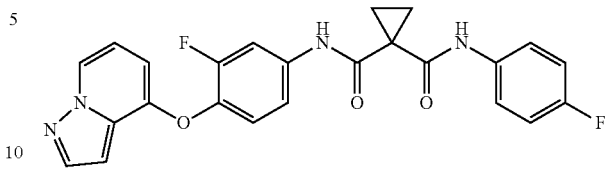

Cyclopropane-1,1-dicarboxylic acid (4-fluoro-phenyl)-amide [3-fluoro-4-(pyrazolo[1,5-a]pyridin-4-yloxy)-phenyl]-amide. This example was synthesized using 3-fluoro-4-(pyrazolo[1,5-a]pyridin-4-yloxy)-phenylamine and 1-(4-fluoro-phenylcarbamoyl)-cyclopropanecarboxylic acid by the methods for example 1. The product was crystallized from ether-hexanes to give a white solid. mp=78-80° C.; LCMS m/z=449 (M+1); ¹H NMR (DMSO) δ: 10.3 (s, 1H), 10.0 (s, 1H), 8.42 (d, 1H, J=8.2 Hz), 8.0 (s, 1H), 7.46 (d, 1H, J=12 Hz), 7.6 (bs, 2H), 7.45 (m, 1H), 7.32 (m, 1H), 7.15 (m, 2H), 6.78 (m, 1H), 6.69 (s, 1H), 6.42 (m, 1H).

Example 6

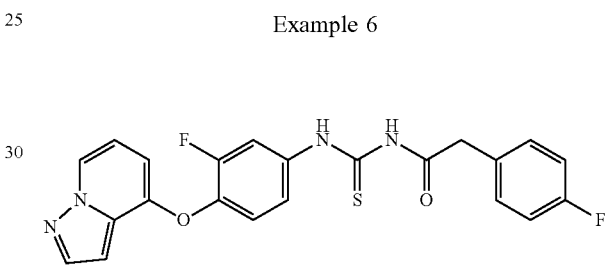

1-[2-(4-Fluoro-phenyl)-acetyl]-3-[3-fluoro-4-(pyrazolo[1,5-a]pyridin-4-yloxy)-phenyl]-thiourea. To a solution of sodium thiocyanate (0.03455 g, 0.4262 mmol) in ethyl acetate (2 mL) was added (4-fluoro-phenyl)acetyl chloride (0.0584 mL, 0.426 mmol). The solution was stirred at rt for 1 h and added to 3-fluoro-4-(pyrazolo[1,5-a]pyridin-4-yloxy)-phenylamine (0.0864 g, 0.355 mmol) in methylene chloride (2 mL). This mixture was stirred 2 h at rt, diluted with EtOAc, washed with 2N Na₂CO₃, water and brince then dried (MgSO₄). The product was purified by ISCO chromatography (25%-50% EtOAc-hexanes) to give example 6 and example 7.

Example 6 data: mp=143-5° C.; LCMS m/z=439 (M+1); ¹H NMR (DMSO) δ: 12.42 (s, 1H), 11.79 (s, 1H), 8.50 (d, 1H, J=6.7 Hz), 8.0 (s, 1H), 7.95 (d, 1H, J=12 Hz), 7.36-7.43 (m, 4H), 7.19 (m, 2H), 6.82 (m, 1H), 6.67 (s, 1H), 6.52 (d, 1H, J=6.7 Hz). 3.8 (s, 2H).

Example 7

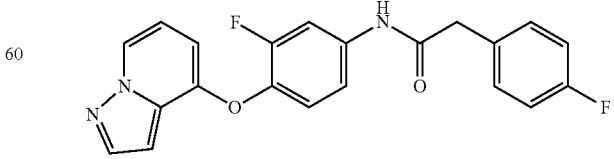

2-(4-Fluoro-phenyl)-N-[3-fluoro-4-(pyrazolo[1,5-a]pyridin-4-yloxy)-phenyl]-acetamide. mp=160-2° C.; ¹H NMR (DMSO) δ: 10.46 (s, 1H), 8.46 (d, 1H, J=8.6 Hz), 8.0 (s, 1H), 7.81 (d, 1H, J=12.8 Hz), 7.32-7.37 (m, 4H), 7.16 (t, 2H, J=7.2 Hz), 6.7 (s, 1H), 6.4 (d, 1H, 7.6 Hz), 3.67 (s, 2H).

Example 8

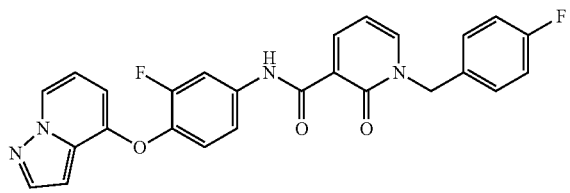 [SMILES: O=C(Nc1ccc(Oc2cccn3nccc23)c(F)c1)c1cccn(Cc2ccc(F)cc2)c1=O]

1-(4-Fluoro-benzyl)-2-oxo-1,2-dihydro-pyridine-3-carboxylic acid [3-fluoro-4-(pyrazolo[1,5-a]pyridin-4-yloxy)-phenyl]-amide. This example was synthesized using 3-fluoro-4-(pyrazolo[1,5-a]pyridin-4-yloxy)-phenylamine and 1-(4-fluoro-benzyl)-2-oxo-1,2-dihydro-pyridine-3-carboxylic acid by the methods for example 1. mp=192-4° C.; LCMs m/z=473 (M+1); ¹H NMR (DMSO) δ: 12.2 (s, 1H), 8.49 (t, 2H, J=8.2 Hz), 8.33 (d, 1H, J=6.6 Hz), 8.0 (m, 2H), 7.43 (m, 3H), 7.34 (t, 1H, J=7.4 Hz), 7.2 (t, 2H, J=8.4 Hz), 6.8 (t, 1H, J=7.2 Hz), 6.7 (m, 2H), 6.5 (d, 1H, J=7.6 Hz), 6.3 (s, 2H).

Example 9

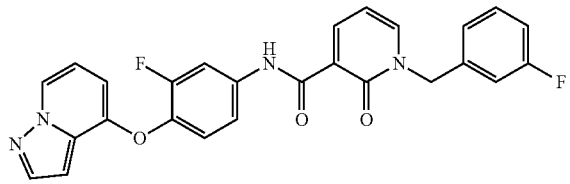 [SMILES: O=C(Nc1ccc(Oc2cccn3nccc23)c(F)c1)c1cccn(Cc2cccc(F)c2)c1=O]

1-(3-Fluoro-benzyl)-2-oxo-1,2-dihydro-pyridine-3-carboxylic acid [3-fluoro-4-(pyrazolo[1,5-a]pyridin-4-yloxy)-phenyl]-amide. This example was synthesized using 3-fluoro-4-(pyrazolo[1,5-a]pyridin-4-yloxy)-phenylamine and 1-(3-fluoro-benzyl)-2-oxo-1,2-dihydro-pyridine-3-carboxylic acid by the methods for example 1. mp 195-7° C.; LCMS m/z=473 (M+1); ¹H NMR (DMSO) δ: 12.17 (s, 1H), 8.47-8.52 (m, 2H), 8.33 (d, 1H, J=6.2 Hz), 8.0-8.02 (m, 2H), 7.40-7.46 (m, 2H), 7.34 (t, 1H, J=9 Hz), 7.14-7.21 (m, 3H), 6.79 (t, 1H, J=7 Hz), 6.69-6.72 (m, 2H), 6.46 (d, 1H, J=7 Hz), 5.34 (s, 2H).

Example 10

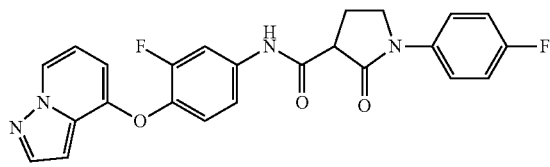 [SMILES: O=C(Nc1ccc(Oc2cccn3nccc23)c(F)c1)C1CCN(c2ccc(F)cc2)C1=O]

1-(4-Fluoro-phenyl)-2-oxo-pyrrolidine-3-carboxylic acid [3-fluoro-4-(pyrazolo[1,5-a]pyridin-4-yloxy)-phenyl]-amide. This example was synthesized using 3-fluoro-4-(pyrazolo[1,5-a]pyridin-4-yloxy)-phenylamine and 1-(4-fluoro-phenyl)-2-oxo-pyrrolidine-3-carboxylic acid by the methods for example 1. mp 162-3° C.; LCMS m/z=449 (M+1); ¹H NMR (DMSO) δ: 10.62 (s, 1H), 8.45 (d, 1H, J=6.6 Hz), 8.02 (s, 1H), 7.87 (d, 1H, J=12 Hz), 7.69-7.72 (m, 2H), 7.38-7.44 (m, 2H), 7.25 (t, 2H, J=8.6 Hz), 6.77 (t, 1H, J=7 Hz), 6.7 (s, 1H), 6.45 (d, 1H, J=7 Hz), 3.89-3.93 (m, 2H), 3.77 (t, 1H, J=7.7 Hz), 2.38-2.44 (m, 2H).

Example 11

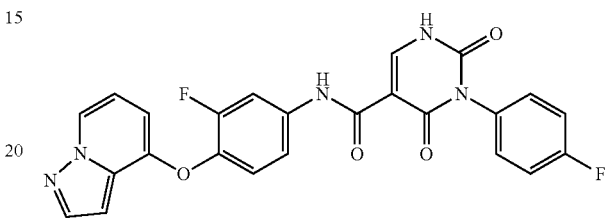

3-(4-Fluoro-phenyl)-2,4-dioxo-1,2,3,4-tetrahydro-pyrimidine-5-carboxylic acid [3-fluoro-4-(pyrazolo[1,5-a]pyridin-4-yloxy)-phenyl]-amide. This example was synthesized using 3-fluoro-4-(pyrazolo[1,5-a]pyridin-4-yloxy)-phenylamine and 3-(4-fluoro-phenyl)-2,4-dioxo-1,2,3,4-tetrahydro-pyrimidine-5-carboxylic acid by the methods for example 1. The product was crystallized from MeOH to give a white solid. mp>300° C.; LCMS m/z=476 (M+1); ¹H NMR (DMSO) δ: 12.4 (bs, 1H), 11.14 (s, 1H), 8.46 (m, 2H), 7.95-8.01 (m, 2H), 7.31-7.39 (m, 6H), 6.78 (t, 1H, J=7.2, 14 Hz), 6.69 (s, 1H), 6.43 (d, 1H, J=7.3 Hz).

Example 12

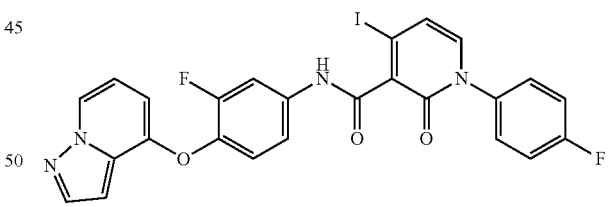

1-(4-Fluoro-phenyl)-4-iodo-2-oxo-1,2-dihydro-pyridine-3-carboxylic acid [3-fluoro-4-(pyrazolo[1,5-a]pyridin-4-yloxy)-phenyl]-amide. This example was synthesized using 3-fluoro-4-(pyrazolo[1,5-a]pyridin-4-yloxy)-phenylamine and 1-(4-fluoro-phenyl)-4-iodo-2-oxo-1,2-dihydro-pyridine-3-carboxylic acid by the methods for example 1. mp=90-2° C.; LCMS m/z=585 (M+1); ¹H NMR (DMSO) δ: 10.1 (s, 1H), 8.46 (d, 1H, J=6.2 Hz), 8.0 (s, 1H), 7.84 (d, 1H, J=12 Hz), 7.4-7.6 (m, 3H), 7.38-7.48 (m, 4H), 6.86 (d, 1H, J=7.2 Hz), 6.75-6.79 (m, 1H), 7.2 (bs, 1H), 6.46 (d, 1H, J=7.4 Hz).

Example 13

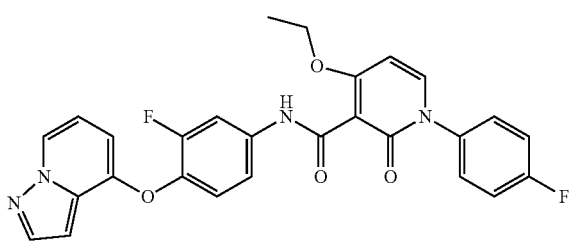 [SMILES: CCOc1ccn(-c2ccc(F)cc2)c(=O)c1C(=O)Nc1ccc(Oc2cccn3nccc23)c(F)c1]

4-Ethoxy-1-(4-fluoro-phenyl)-2-oxo-1,2-dihydro-pyridine-3-carboxylic acid [3-fluoro-4-(pyrazolo[1,5-a]pyridin-4-yloxy)-phenyl]-amide TFA salt. Example 12 (0.05 g, 0.08 mmol) in tetrahydrofuran (3 mL) and ethanol (3 mL) was added 4 M of sodium ethoxide in ethanol (0.043 mL, 0.17 mmol). After stirring at rt for 4 h the mixture was concentrated, dissolved in EtOAc and washed with 2N Na$_2$CO$_3$, water and brine then dried (MgSO$_4$). The product was purified by reverse phase prep HPLC to give a white solid as the TFA salt. mp=230-2° C.; LCMS m/z=503 (M+1); $^1$H NMR (DMSO) δ: 10.5 (s, 1H), 8.46 (d, 1H, J=6.5 Hz), 8.0 (s, 1H), 7.84-7.91 (m, 2H), 7.45 (m, 3H), 7.32-7.39 (m, 3H), 6.76 (t, 1H, J=7.2, 14 Hz), 6.7 (s, 1H), 6.51 (d, 1H, J=7.6 Hz), 6.43 (d, 1H, J=7.6 Hz), 4.26 (q, 2H, J=6.7 Hz), 1.30 (t, 3H, J=6.7, 13.5 Hz).

Example 14

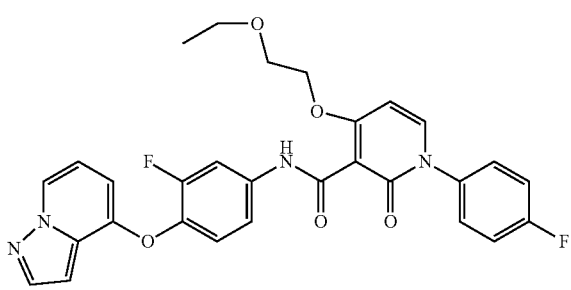 [SMILES: CCOCCOc1ccn(-c2ccc(F)cc2)c(=O)c1C(=O)Nc1ccc(Oc2cccn3nccc23)c(F)c1]

4-(2-Ethoxy-ethoxy)-1-(4-fluoro-phenyl)-2-oxo-1,2-dihydro-pyridine-3-carboxylic acid [3-fluoro-4-(pyrazolo[1,5-a]pyridin-4-yloxy)-phenyl]-amide. This example was synthesized using example 12 and 2-ethoxyethanol by the methods for example 13. mp 76-80° C.; LCMS m/z=547 (M+1); $^1$H NMR (DMSO) δ: 10.55 (s, 1H), 8.46 (d, 1H, J=7.2 Hz), 8.0 (s, 1H), 7.87-7.90 (m, 2H), 7.45 (m, 3H), 7.34-7.39 (m, 3H), 6.77 (t, 1H, J=7.2 Hz), 6.71 (s, 1H), 6.53 (m, 1H), 6.42 (m, 1H), 4.3 (bs, 2H), 3.66 (b, 2H), 3.46 (m, 2H), 1.0 (t, 3H, J=7.4, 14 Hz).

Example 15

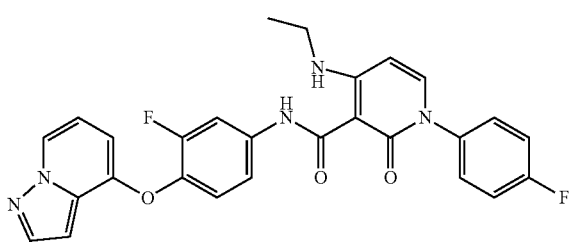 [SMILES: CCNc1ccn(-c2ccc(F)cc2)c(=O)c1C(=O)Nc1ccc(Oc2cccn3nccc23)c(F)c1]

4-Ethylamino-1-(4-fluoro-phenyl)-2-oxo-1,2-dihydro-pyridine-3-carboxylic acid [3-fluoro-4-(pyrazolo[1,5-a]pyridin-4-yloxy)-phenyl]-amide. This example was synthesized using example 12 and ethylamine by the method for example 13. white solid mp=114-118° C.; LCMS m/z=502 (M+1); $^1$H NMR (DMSO) δ: 13.0 (s, 1H), 10.5 (s, 1H), 8.47 (m, 1H), 8.0 (m, 1H), 7.93 (d, 1H, J=12 Hz), 7.7 (d, 1H, j=8.6 Hz), 7.47 (m, 2H), 7.30-7.37 (m, 3H), 6.78 (m, 1H), 6.69 (m, 1H), 6.43 (d, 1H, J=7.45 Hz), 6.27 (d, 1H, J=7.45 Hz), 3.42 (m, 2H), 1.25 (m, 3H).

Example 16

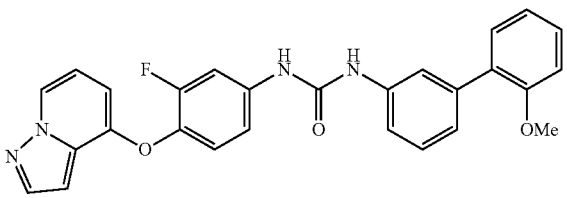 [SMILES: COc1ccccc1-c1cccc(NC(=O)Nc2ccc(Oc3cccn4nccc34)c(F)c2)c1]

1-[3-Fluoro-4-(pyrazolo[1,5-a]pyridin-4-yloxy)-phenyl]-3-(2'-methoxy-biphenyl-3-yl)-urea. 3-fluoro-4-(pyrazolo[1,5-a]pyridin-4-yloxy)-phenylamine (0.05 g, 0.2 mmol) and 3'-isocyanato-2-methoxy-biphenyl (0.056 g, 0.25 mmol) in methylene chloride (3 mL) was stirred at rt for 48 h. The solid precipitate was collected and dried to give a white solid. mp=193-4° C.; LCMS mz=469 (M+1); $^1$H NMR (DMSO) δ: 9.67 (s, 1H), 8.38-8.5 (m, 3H), 8.0 (s, 1H), 7.74 (m, 1H), 7.58 (b, 2H), 7.45 (b, 2H), 7.32 (bm, 3H), 7.14 (m, 2H), 6.72-6.78 (m, 2H), 6.41 (s, 1H), 3.95 (s, 3H).

Example 17

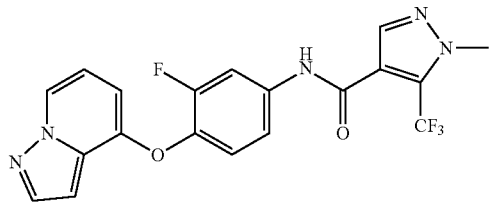 [SMILES: Cn1ncc(C(=O)Nc2ccc(Oc3cccn4nccc34)c(F)c2)c1C(F)(F)F]

1-Methyl-5-trifluoromethyl-1H-pyrazole-4-carboxylic acid [4-(pyrazolo[1, 5-a]pyridin-4-yloxy)-phenyl]-amide. This example was synthesized using 3-fluoro-4-(pyrazolo[1,5-a]pyridin-4-yloxy)-phenylamine and 1-methyl-5-trifluoromethyl-1H-pyrazole-4-carboxylic acid by the methods for example 1. mp 92-3° C.; LCMS m/z=402 (M+1); $^1$H NMR (DMSO) δ: 10.4 (s, 1H), 8.48 (d, 1H, J=6.98 Hz), 8.04 (s, 1H), 7.99 (s, 1H), 7.77 (d, 1H, J=9.8 Hz), 7.17 (d, 1H, J=7.4 Hz), 6.81 (t, 1H, J=8, 14 Hz), 6.54-6.58 (m, 2H), 4.05 (s, 3H).

The following examples 18-21 were synthesized using methods for example 17 and the appropriate pyrazole acid.

Example 18

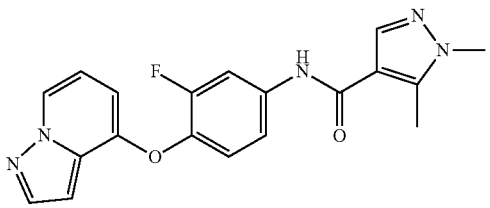 [SMILES: Cc1c(C(=O)Nc2ccc(Oc3cccn4nccc34)c(F)c2)cnn1C]

1-(4-Fluoro-phenyl)-5-methyl-1H-pyrazole-4-carboxylic acid [4-(pyrazolo[1, 5-a]pyridin-4-yloxy)-phenyl]-amide. mp=172-3° C.; LCMS m/z=428 (M+1); $^1$H NMR (DMSO) δ: 9.94 (s, 1H), 8.48 (d, 1H, J=8.4 Hz), 8.31 (s, 1H), 8.00 (s, 1H), 7.79 (d, 1H, J=7.8 Hz), 7.60-7.63 (m, 2H), 7.41 (t, 1H, J=8.4, 16 Hz), 7.17 (d, 1H, J=7.4 Hz), 6.82 (t, 1H, J=7.3, 14.6 Hz), 6.59 (s, 1H), 6.55 (d, 1H, J=7.3 Hz), 2.5 (s, 3H).

Example 19

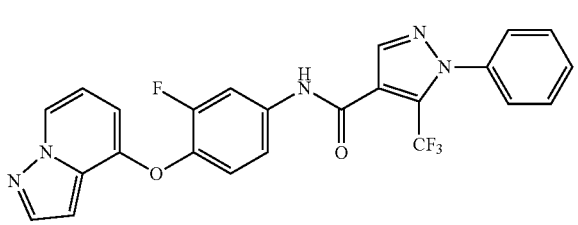 [SMILES: O=C(Nc1ccc(Oc2cccn3nccc23)c(F)c1)c1cnn(-c2ccccc2)c1C(F)(F)F]

1-Phenyl-5-trifluoromethyl-1H-pyrazole-4-carboxylic acid [4-(pyrazolo[1, 5-a]pyridin-4-yloxy)-phenyl]-amide. mp=195-6° C.; LCMS m/z=464 (M+1); $^1$H NMR (DMSO) δ: 10.6 (s, 1H), 8.49 (d, 1H, J=7.4 Hz), 8.32 (s, 1H), 8.00 (s, 1H), 7.78 (d, 2H, J=8 Hz), 7.62 (m, 3H), 7.55 (m, 2H), 7.20 (d, 2H, J=8 Hz), 6.82 (t, 1H, J=7, 14 Hz), 6.56-6.59 (m, 2H).

Example 20

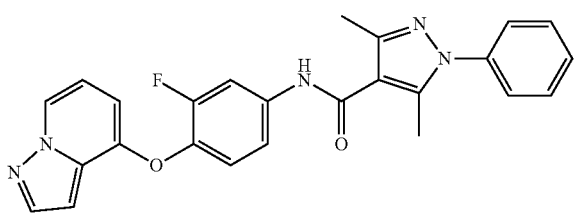 [SMILES: Cc1nn(-c2ccccc2)cc1C(=O)Nc1ccc(Oc2cccn3nccc23)c(F)c1]

3,5-Dimethyl-1-phenyl-1H-pyrazole-4-carboxylic acid [4-(pyrazolo[1,5-a]pyridin-4-yloxy)-phenyl]-amide. mp=206-7° C.; LCMS m/z=424 (M+1); $^1$H NMR (DMSO) δ: 9.92 (s, 1H), 8.47 (d, 1H, J=6.6 Hz), 8.00 (s, 1H), 7.77 (d, 2H, J=7.2 Hz), 7.47-7.56 (m, 5H), 7.18 (d, 2H, J=7.2 Hz), 6.81 (t, 1H, J=7, 14 Hz), 6.61 (s, 1H), 6.53 (d, 1H, J=8.2 Hz), 2.42 (s, 3H), 2.37 (s, 3H).

Example 21

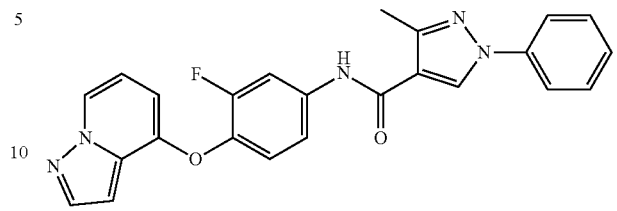

5-Methyl-1-phenyl-1H-pyrazole-4-carboxylic acid [4-(pyrazolo[1,5-a]pyridin-4-yloxy)-phenyl]-amide. mp=204-5° C.; LCMS m/z=410 (M+1); $^1$H NMR (DMSO) δ: 9.95 (s, 1H), 8.48 (d, 1H, J=6.8 Hz), 8.32 (s, 1H), 8.00 (s, 1H), 7.80 (d, 2H, J=8.2 Hz), 7.51-7.58 (m, 5H), 7.17 (d, 2H, J=8.2 Hz), 6.82 (t, 1H, J=7.2, 14 Hz), 6.60 (s, 1H), 6.55 (d, 1H, J=8.3 Hz), 2.50 (s, 3H).

Example 22

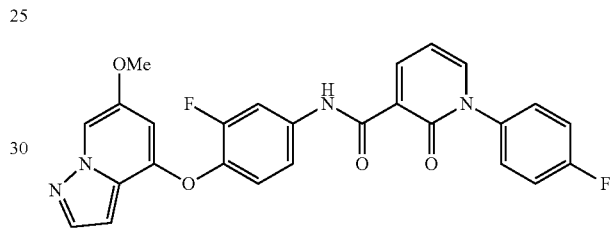

1-(4-Fluoro-phenyl)-2-oxo-1,2-dihydro-pyridine-3-carboxylic acid [3-fluoro-4-(6-methoxy-pyrazolo[1,5-a]pyridin-4-yloxy)-phenyl]-amide. This example was synthesized using 3-fluoro-4-(6-methoxy-pyrazolo[1,5-a]pyridin-4-yloxy)-phenylamine and 1-(4-fluoro-phenyl)-2-oxo-1,2-dihydro-pyridine-3-carboxylic acid by the methods for example 1. mp=174-8° C.; LCMS m/z=489 (M+1); $^1$H NMR (DMSO) δ: 12.03 (s, 1H), 8.57 (d, 1H, J=8.2 Hz), 8.12 (d, 1H, J=6.6 Hz), 8.07 (s, 1H), 7.97 (m, 1H), 7.90 (s, 1H), 7.60 (m, 2H), 7.37-7.44 (m, 2H), 7.20 (t, 1H, J=7 Hz), 6.72 (t, 1H, J=7 Hz), 6.67 (s, 1H), 6.70 (s, 1H), 3.93 (s, 3H).

Example 23

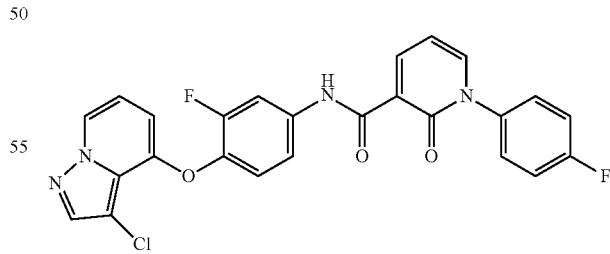

Step 1. 3-Chloro-pyrazolo[1,5-a]pyridin-4-ol. Pyrazolo[1,5-a]pyridin-4-ol (1.0 g, 7.4 mmol) in acetonitrile (10 mL, 200 mmol) was added N-chlorosuccinimide (1.99 g, 14.9 mmol) and stirred at rt for 48 h. The solid that precipitated was collected to give 900 mg as a grey solid. The solvent was concentrated and the solid triturated with ACN and collected to give 300 mg. The material was combined (1.2 g, 90% yield). LCMS m/z=169 (M+1); ¹H NMR (DMSO) δ: 10.68 (s, 1H), 8.16 (d, 1H, J=6.4 Hz), 7.95 (s, 1H), 6.73 (m, 1H), 6.49 (d, 1H, J=7 Hz).

Step 2. 3-Chloro-4-(2-fluoro-4-nitro-phenoxy)-pyrazolo[1,5-a]pyridine. 3-Chloro-pyrazolo[1,5-a]pyridin-4-ol (1.2 g, 7.1 mmol) in N,N-dimethylformamide (10 mL) was added sodium hydride, 60% disp. in mineral oil (0.43 g, 11 mmol) at 0° C. After 0.5 h, 1,2-difluoro-4-nitro-benzene (1.2 g, 7.8 mmol) was added dropwise. The reaction was stirred at rt 14 h, concentrated, dissolved in EtOAc and washed with 1N Na₂CO₃, water and brine and dried (MgSO₄). The product was purified by ISCO chromatography (25 to 60% EtOAc/hexanes, silica gel column). LCMS m/z=308 (M+1); ¹H NMR (DMSO) δ: 8.70 (d, 1H), 8.39 (d, 1H), 8.19 (s, 1H), 8.04 (d, 1H), 7.16-7.24 (m, 2H), 7.00 (t, 1H).

Step 3. 4-(3-Chloro-pyrazolo[1,5-a]pyridin-4-yloxy)-3-fluoro-phenylamine. 3-Chloro-4-(2-fluoro-4-nitro-phenoxy)-pyrazolo[1,5-a]pyridine (0.800 g, 2.60 mmol) in methanol (20 mL) and tetrahydrofuran (20 mL) at 0° C. was added zinc (1.7 g, 26 mmol) and ammonium chloride (0.695 g, 13 mmol) simultaneously. The ice bath was removed and the reaction stirred at rt for 8 h, diluted with EtOAc and washed with 1N Na₂CO₃ solution water and brine, then dried (MgSO4) and concentrated to give a tan solid. LCMS m/z=278 (M+1).

1-(4-Fluoro-phenyl)-2-oxo-1,2-dihydro-pyridine-3-carboxylic acid [4-(3-chloro-pyrazolo[1,5-a]pyridin-4-yloxy)-3-fluoro-phenyl]-amide. 4-(3-Chloro-pyrazolo[1,5-a]pyridin-4-yloxy)-3-fluoro-phenylamine and 1-(4-fluoro-phenyl)-2-oxo-1,2-dihydro-pyridine-3-carboxylic acid were coupled using methods for Example 1. mp=139-140° C.; LCMS m/z=493 (M+1); ¹H NMR (DMSO) δ: 12.01 (s, 1H), 8.58 (d, 1H, J=7.4 Hz), 8.48 (d, 1H, J=7.4 Hz), 8.15 (m, 2H), 8.02 (d, 1H, J=14 Hz), 7.6 (m, 2H), 7.42 (m, 3H), 7.28 (t, 1H, J=7 Hz), 6.84 (t, 1H, 7 Hz), 6.73 (t, 1H, J=7, 14 Hz), 6.56 (d, 1H, J=7.4 Hz).

Example 24

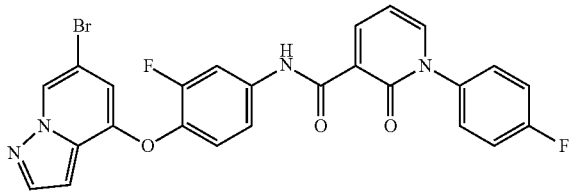 [SMILES: O=C(Nc1ccc(Oc2cc(Br)cn3nccc23)c(F)c1)c1cccn(-c2ccc(F)cc2)c1=O]

Step 1-6-Bromo-4-(2-fluoro-4-nitro-phenoxy)-pyrazolo[1,5-a]pyridine. 6-Bromo-pyrazolo[1,5-a]pyridin-4-ol (2.0 g, 9.4 mmol) in N,N-dimethylformamide (32 mL) at 0° C. was added sodium hydride (0.564 g, 23.5 mmol). After stirring 0.5 h at rt, 1,2-difluoro-4-nitro-benzene (1.14 mL, 10.3 mmol) was added dropwise. After stirring 20 h at rt, the reaction was diluted with EtOAc and washed with 1 M sodium carbonate solution, water, and brine, dried over magnesium sulfate. The product was purified by ISCO chromatography (20% EtOAc/hexanes) to yield 6-bromo-4-(2-fluoro-4-nitro-phenoxy)-pyrazolo[1,5-a]pyridine (2.02 g, 61%) as a yellow solid, mp=132-133° C., LCMS m/z=353 (M+1); ¹H NMR (DMSO-d6) δ: 9.05 (t, 1H), 8.43 (d, 1H), 8.11 (q, 1H), 8.07 (d, 1H), 7.49 (t, 1H), 7.16 (d, 1H), 6.68 (dd, 1H)

Step 2. 4-(6-Bromo-pyrazolo[1,5-a]pyridin-4-yloxy)-3-fluoro-phenylamine. 6-Bromo-4-(2-fluoro-4-nitro-phenoxy)-pyrazolo[1,5-a]pyridine (0.200 g, 0.568 mmol) in tetrahydrofuran (4 mL) and methanol (4 mL) was added zinc (0.3714 g, 5.680 mmol) and ammonium chloride (0.152 g, 2.84 mmol). After stirring at rt overnight, the mixture was filtered, diluted with EtOAc, and washed with water and brine and concentrated to produce 4-(6-bromo-pyrazolo[1,5-a]pyridin-4-yloxy)-3-fluoro-phenylamine (0.075 g; 41%) as a yellow solid. mp 132-133° C.; LCMS m/z=323 (M+1), ¹HNMR (DMSO-d6) δ: 9.05 (t, 1H), 8.43 (dd, 1H), 8.11 (q, 1H), 8.07 (d, 1H), 7.49 (t, 1H) 7.16 (d, 1H), 6.68 (dd, 1H).

Step 3. (4-Fluoro-phenyl)-2-oxo-1,2-dihydro-pyridine-3-carboxylic acid [4-(6-bromo-pyrazolo[1,5-a]pyridin-4-yloxy)-3-fluoro-phenyl]-amide. This example was synthesized using 4-(6-bromo-pyrazolo[1,5-a]pyridin-4-yloxy)-3-fluoro-phenylamine and 1-(4-fluoro-phenyl)-2-oxo-1,2-dihydro-pyridine-3-carboxylic acid by the methods for example 1. mp 265-266° C., LCMS m/z=538 (M+1). ¹H NMR (DMSO-d6) δ: 12.01 (s, 1H), 8.89 (m, 1H), 8.57, 8.59 (dd, 1H, J=2.1, 7.2 Hz), 8.12, 8.14 (dd, 1H, J=2.2, 6.6 Hz), 8.02-8.06 (m, 2H), 7.59-7.63 (m, 2H), 7.47-7.50 (m, 1H), 7.39-7.44 (m, 3H), 6.78 (dd, 1H, J=0.9, 2.4 Hz), 6.74 (m, 1H), 6.53 (s, 1H).

Example 25

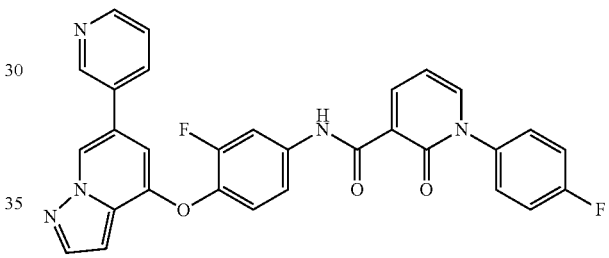

Step 1. 3-Fluoro-4-(6-pyridin-3-yl-pyrazolo[1,5-a]pyridin-4-yloxy)-phenylamine. Into a Schlenk flask under an atmosphere of nitrogen was added palladium acetate (0.0128 g, 0.0568 mmol) and triphenylphosphine (0.0596 g, 0.227 mmol) in 1,4-dioxane (4 mL). After 5 min, 6-bromo-4-(2-fluoro-4-nitro-phenoxy)-pyrazolo[1,5-a]pyridine (Example 24, intermediate from step 1; 0.200 g, 0.568 mmol), 3-pyridylboronic acid (0.0873 g, 0.710 mmol), N,N-dimethylformamide (6 mL) and 1.0 M of sodium carbonate (1.70 mL, 1.70 mmol) were added successively. The reaction was heated at 70° C. 18 h, cooled to rt, diluted with DCM and filtered through celite. The DCM layer was washed with water and brine, the dried over MgSO₄ and concentrated. The product was purified by ISCO chromatography (30% to 70% EtOAc in hexanes) to give 4-(2-fluoro-4-nitro-phenoxy)-6-pyridin-3-yl-pyrazolo[1,5-a]pyridine (0.180 g, 91%). The nitro intermediate was dissolved in EtOAc (15 mL) and hydrogenated under an atmosphere of hydrogen with 20% Pd(OH)₂/C, 50% wet (50 mg) at 40 psi overnight. The catalyst was filtered off and the solvent concentrated to produce 3-fluoro-4-(6-pyridin-3-yl-pyrazolo[1,5-a]pyridin-4-yloxy)-phenylamine (0.160 g; 88%) as a yellow solid. LCMS m/z=321 (M+1). This material was used in the next step.

Step 2. 1-(4-Fluoro-phenyl)-2-oxo-1,2-dihydro-pyridine-3-carboxylic acid 3-fluoro-4-(6-pyridin-3-yl-pyrazolo[1,5-a]pyridin-4-yloxy)-phenyl-amide. This example was synthesized using 3-fluoro-4-(6-pyridin-3-yl-pyrazolo[1,5-a]pyridin-4-yloxy)-phenylamine and 1-(4-fluoro-phenyl)-2- oxo-1,2-dihydro-pyridine-3-carboxylic acid by the methods for example 1. white solid, mp 223-225° C., LCMS m/z=536 (M+1); ¹H NMR (DMSO-d6) δ: 12.10 (s, 1H), 9.03 (s, 1H), 8.93 (d, 1H), 8.59 (m, 2H), 8.15 (dd, 1H, J=2.12, 6.49 Hz), 8.12 (d, 1H), 8.09 (m, 1H), 8.05 (m, 1H), 7.63 (m, 2H) 7.49-7.41 (m, 5H) 6.94 (s, 1H), 6.75 (t, 1H, J=7.2 Hz), 6.72 (dd, 1H).

Example 26

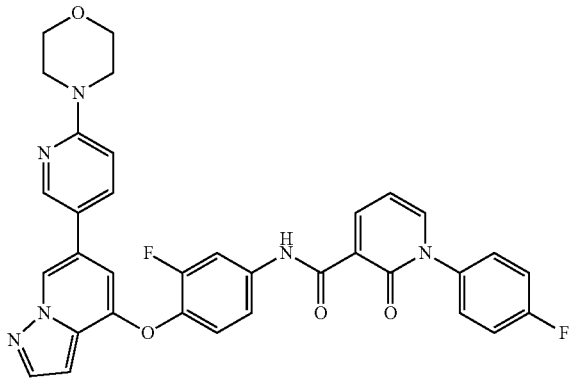 [SMILES: O=C(Nc1ccc(Oc2cc(-c3ccc(N4CCOCC4)nc3)cn3nccc23)c(F)c1)c1cccn(-c2ccc(F)cc2)c1=O]

Step 1. 3-Fluoro-4-[6-(6-morpholin-4-yl-pyridin-3-yl)-pyrazolo[1,5-a]pyridin-4-yloxy]-phenylamine. This intermediate was synthesized using 4-[5-(4,4,5,5-tetramethyl-1,3,2-dioxaborolan-2-yl)-pyridin-2-yl]-morpholine and 6-bromo-4-(2-fluoro-4-nitro-phenoxy)-pyrazolo[1,5-a]pyridine (Example 24, intermediate from step 1) by the procedure for example 25 step 1. LCMS m/z=406 (M+1). ¹H NMR (DMSO) δ: 8.74 (s, 1H), 8.36 (d, 1H, J=2.4 Hz), 8.01 (d, 1H, J=2.4 hz), 7.76-7.79 (m, 1H), 7.08 (t, 1H, J=9.8 Hz), 6.89 (d, 1H, J=9.8 Hz), 6.67 (m, 1H), 6.49-6.54 (m, 2H), 6.41-6.44 (m, 1H), 5.45 (s, 2H), 3.69 (m, 4H), 3.47 (m, 4H).

Step 2. 1-(4-Fluoro-phenyl)-2-oxo-1,2-dihydro-pyridine-3-carboxylic acid {3-fluoro-4-[6-(6-morpholin-4-yl-pyridin-3-yl)-pyrazolo[1,5-a]pyridin-4-yloxy]-phenyl}-amide. This example was synthesized using 3-fluoro-4-[6-(6-morpholin-4-yl-pyridin-3-yl)-pyrazolo[1,5-a]pyridin-4-yloxy]-phenylamine and 1-(4-fluoro-phenyl)-2-oxo-1,2-dihydro-pyridine-3-carboxylic acid by the methods for example 1. White solid, mp 265-266° C. LCMS m/z=621 (M+1); ¹H NMR (DMSO-d6) δ: 12.07 (s, 1H), 8.84 (s, 1H), 8.58 (dd, 1H, J=2.1, 7.3 Hz), 8.43 (d, 1H, J=2.3 Hz), 8.12 (dd, 1H, J=2.1, 6.3 Hz), 8.02 (d, 1H), 8.00 (dd, 1H, J=2.50, 12.9 Hz), 7.86 (dd, 1H, J=2.50, 9.3 Hz), 7.60 (m, 2H), 7.39 (m, 4H), 6.88 (d, 1H, J=8.8 Hz), 6.83 (s, 1H), 6.72 (t, 1H, J=6.95 Hz), 6.63 (d, 1H, J=2.3 Hz), 3.69 (t, 4H, J=9.8 Hz) 3.47 (t, 4H, J=5.09, 9.8 Hz).

Example 27

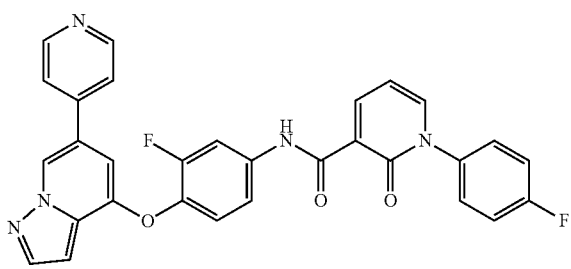 [SMILES: O=C(Nc1ccc(Oc2cc(-c3ccncc3)cn3nccc23)c(F)c1)c1cccn(-c2ccc(F)cc2)c1=O]

Step 1. 3-Fluoro-4-(6-pyridin-4-yl-pyrazolo[1,5-a]pyridin-4-yloxy)-phenylamine. This intermediate was synthesized using 4-Pyridylboronic acid and 6-bromo-4-(2-fluoro-4-nitro-phenoxy)-pyrazolo[1,5-a]pyridine (Example 24, intermediate from step 1) by the procedure for example 25 step 1. tan solid, LCMS m/z=321 (M+1); ¹H NMR (DMSO-d6) δ: 9.04 (t, 1H, J=2.2 Hz), 8.60 (dd, 2H, J=1.84, 4.15 Hz), 8.11 (d, 1H, J=2.20 Hz), 7.10 (t, 1H, 9.9 Hz), 6.76 (dd, 1H, J=0.9, 2.2 Hz), 6.62 (s, 1H), 6.53 (dd, 1H, J=2.7, 13.3 Hz), 6.44 (dd, 1H, 2.7, 8.8 Hz), 5.47 (s, 2H).

Step 2. 1-(4-Fluoro-phenyl)-2-oxo-1,2-dihydro-pyridine-3-carboxylic acid [3-fluoro-4-(6-pyridin-4-yl-pyrazolo[1,5-a]pyridin-4-yloxy)-phenyl]-amide. This example was synthesized using 3-Fluoro-4-(6-pyridin-4-yl-pyrazolo[1,5-a]pyridin-4-yloxy)-phenylamine and 1-(4-fluoro-phenyl)-2-oxo-1,2-dihydro-pyridine-3-carboxylic acid by the methods for example 1. tan solid, mp 209-210° C., LCMS m/z=536 (M+1); HNMR (DMSO-d6) δ: 12.09 (s, 1H), 9.14 (s, 1H), 8.59 (m, 3H), 8.13 (m, 2H) 8.04 (dd, 1H, J=2.30, 12.96 Hz), 7.73 (dd, 2H, J=1.50, 4.43 Hz), 2.60 (m, 2H), 7.42 (m, 4H), 6.94 (s, 1H), 6.73 (m, 2H).

Example 28

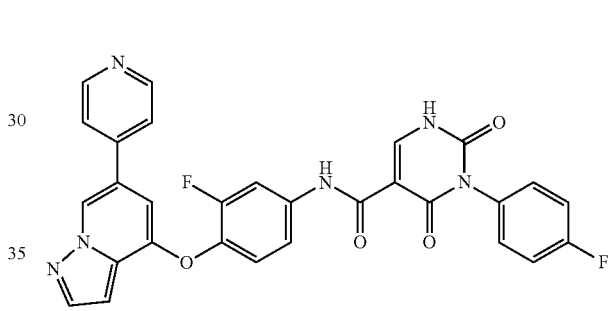

3-(4-Fluoro-phenyl)-2,4-dioxo-1,2,3,4-tetrahydro-pyrimidine-5-carboxylic acid [3-fluoro-4-(6-pyridin-4-yl-pyrazolo[1,5-a]pyridin-4-yloxy)-phenyl]-amide. This example was synthesized using 3-Fluoro-4-(6-pyridin-4-yl-pyrazolo[1,5-a]pyridin-4-yloxy)-phenylamine and 3-(4-fluoro-phenyl)-2,4-dioxo-1,2,3,4-tetrahydro-pyrimidine-5-carboxylic acid by the methods for example 1. white solid, mp 357-358° C., LCMS m/z=553 (M+1); ¹H NMR (DMSO-d6) δ: 12.39 (s, 1H) 11.00 (s, 1H) 9.13 (m, 1H) 8.59 (dd, 2H, J=1.8, 4.9 Hz) 8.45 (s, 1H) 8.12 (d, 1H, J=2.4 Hz) 7.98 (dd, 1H, J=2.7, 13.1 Hz), 7.72 (dd, 2H, J=1.6, 4.5 Hz), 7.31-7.47 (m, 6H), 6.93 (s, 1H), 6.71 (dd, 1H, J=0.9, 2.3 Hz).

Example 29

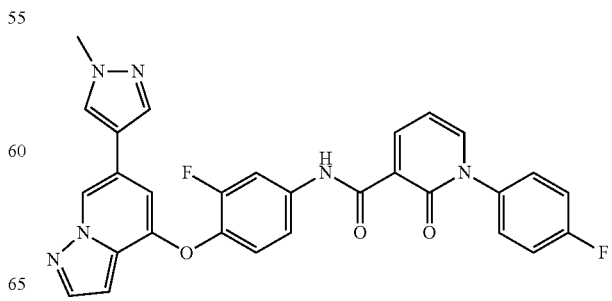

Step 1. 3-Fluoro-4-[6-(1-methyl-1H-pyrazol-4-yl)-pyrazolo[1,5-a]pyridin-4-yloxy]-phenylamine. Into a Schlenk flask, under an atmosphere of nitrogen, was added palladium acetate (0.0159 g, 0.0710 mmol) and triphenylphosphine (0.0745 g, 0.284 mmol) in 1,4-dioxane (5 mL). After 5 min, 6-bromo-4-(2-fluoro-4-nitro-phenoxy)-pyrazolo[1,5-a]pyridine (0.25 g, 0.71 mmol), 1-methyl-4-(4,4,5,5-tetramethyl-[1,3,2]dioxaborolan-2-yl)-1H-pyrazole (0.185 g, 0.887 mmol), N,N-dimethylformamide (8 mL, 100 mmol) and 1.0 M of sodium carbonate solution (2.13 mL) were added successively. The reaction was heated at 70° C. 18 h, cooled to rt, diluted with DCM, filtered through celite and was concentrated. The product was purified by ISCO chromatography (30 to 70% EtOAc in hexanes) to give 4-(2-fluoro-4-nitro-phenoxy)-6-(1-methyl-1H-pyrazol-4-yl)-pyrazolo[1,5-a]pyridine (0.20 g; 80%). LCMS m/z=354 (M+1). The nitro intermediate and 20% Pd(OH)$_2$/C, 50% wet (10:40:50), (50 mg) in EtOAc and MeOH (1:1; 30 mL) was hydrogenated on a Parr at 40 psi under a nitrogen atmosphere overnight. The catalyst was filtered off and the solvent concentrated to give an oil. LCMS m/z=324 (M+1). This material was used in the next step.

Step 2. 1-(4-Fluoro-phenyl)-2-oxo-1,2-dihydro-pyridine-3-carboxylic acid {3-fluoro-4-[6-(1-methyl-1H-pyrazol-4-yl)-pyrazolo[1,5-a]pyridin-4-yloxy]-phenyl}-amide. This example was synthesized using 3-fluoro-4-[6-(1-methyl-1H-pyrazol-4-yl)-pyrazolo[1,5-a]pyridin-4-yloxy]-phenylamine and 1-(4-fluoro-phenyl)-2-oxo-1,2-dihydro-pyridine-3-carboxylic acid by the methods for example 1. mp=204-6° C.; LCMS m/z=539 (M+1). $^1$H NMR (DMSO) δ: 12.09 (s, 1H), 8.83 (s, 1H), 8.57, 8.60 (dd, 1H, J=2.2, 7.3 Hz), 8.12-8.14 (m, 2H), 8.01, 8.04 (dd, 1H, J=2.2, 12.6 Hz), 7.98 (d, 1H, J=2.3 Hz), 7.92 (s, 1H), 7.59-7.62 (m, 2H), 7.31-7.46 (m, 4H), 7.71-7.76 (m, 2H), 6.60 (d, 1H, J=2 Hz), 3.81 (s, 3H).

Example 30

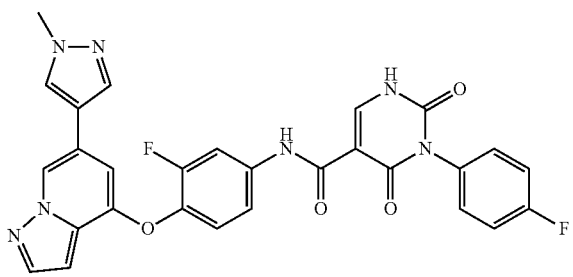 [SMILES: Cn1cc(-c2cc(Oc3ccc(NC(=O)c4c[nH]c(=O)n(-c5ccc(F)cc5)c4=O)cc3F)c3ccnn3c2)cn1]

3-(4-Fluoro-phenyl)-2,4-dioxo-1,2,3,4-tetrahydro-pyrimidine-5-carboxylic acid {3-fluoro-4-[6-(1-methyl-1H-pyrazol-4-yl)-pyrazolo[1,5-a]pyridin-4-yloxy]-phenyl}-amide. This example was synthesized using 3-fluoro-4-[6-(1-methyl-1H-pyrazol-4-yl)-pyrazolo[1,5-a]pyridin-4-yloxy]-phenylamine and 3-(4-fluoro-phenyl)-2,4-dioxo-1,2,3,4-tetrahydro-pyrimidine-5-carboxylic acid by the methods for example 1. mp (HCl salt) 248-250° C.; LCMS m/z=556 (M+1); $^1$H NMR (DMSO) δ: 12.54 (d, 1H), 10.97 (s, 1H), 8.82 (s, 1H), 8.43 (d, 1H), 8.13 (s, 1H), 7.92-7.99 (m, 3H), 7.29-7.46 (m, 6H), 7.74 (s, 1H), 6.6 (s, 1H), 3.8 (s, 3H).

Example 31

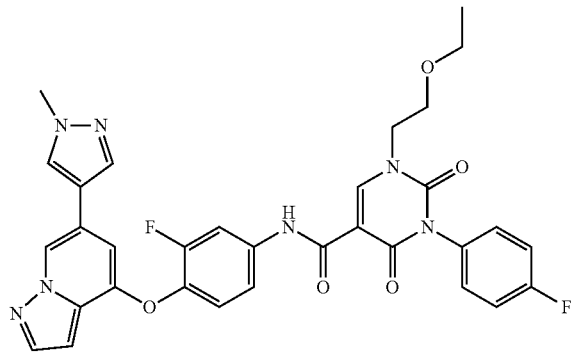 [SMILES: CCOCCn1cc(C(=O)Nc2ccc(Oc3cc(-c4cnn(C)c4)cn4nccc34)c(F)c2)c(=O)n(-c2ccc(F)cc2)c1=O]

1-(2-Ethoxy-ethyl)-3-(4-fluoro-phenyl)-2,4-dioxo-1,2,3,4-tetrahydro-pyrimidine-5-carboxylic acid {3-fluoro-4-[6-(1-methyl-1H-pyrazol-4-yl)-pyrazolo[1,5-a]pyridin-4-yloxy]-phenyl}-amide. This example was synthesized using 3-fluoro-4-[6-(1-methyl-1H-pyrazol-4-yl)-pyrazolo[1,5-a]pyridin-4-yloxy]-phenylamine and 1-(2-ethoxy-ethyl)-3-(4-fluoro-phenyl)-2,4-dioxo-1,2,3,4-tetrahydro-pyrimidine-5-carboxylic acid by the methods for example 1. mp=216-8° C.; LCMS m/z=628 (M+1); 1H NMR (DMSO) δ: 10.97 (s, 1H), 8.82 (s, 1H), 8.76 (s, 1H), 8.13 (s, 1H), 7.96-7.99 (m, 2H), 7.92 (s, 1H), 7.42-7.47 (m, 3H), 7.30-7.37 (m, 3H), 6.75 (s, 1H), 6.60 (m, 1H), 4.15 (t, 2H, J=6 Hz), 3.81 (s, 3H), 3.65 (t, 2H, J=5 Hz), 3.51 (q, 2H, J=7 Hz), 1.13 (t, 3H, J=7 Hz).

Example 32

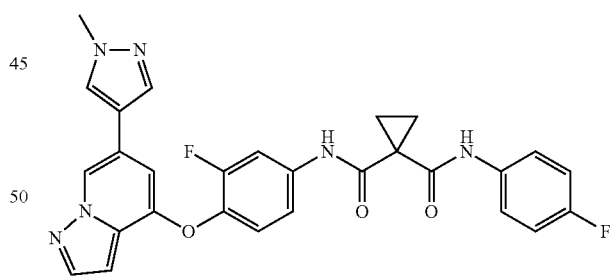

Cyclopropane-1,1-dicarboxylic acid {3-fluoro-4-[6-(1-methyl-1H-pyrazol-4-yl)-pyrazolo[1,5-a]pyridin-4-yloxy]-phenyl}-amide(4-fluoro-phenyl)-amide. This example was synthesized using 3-fluoro-4-[6-(1-methyl-1H-pyrazol-4-yl)-pyrazolo[1,5-a]pyridin-4-yloxy]-phenylamine and 1-(4-fluoro-phenylcarbamoyl)-cyclopropanecarboxylic acid by the methods for example 1. mp>125 (dec) ° C.; LCMS m/z=529 (M+1); $^1$H NMR (DMSO) δ: 10.33 (s, 1H), 9.98 (s, 1H), 8.82 (s, 1H), 8.1 (s, 1H), 7.98 (d, 1H, J=2.3 Hz), 7.86-7.90 (m, 2H), 7.61-7.65 (m, 2H), 7.44 (m, 1H), 7.31 (t, 1H, J=8.6 Hz), 7.15 (t, 1H, J=8.8 Hz), 6.72 (s, 1H), 6.58 (d, 1H, J=2.3 Hz), 3.82 (s, 4H), 1.46 (d, 4H, J=6.1 Hz).

Example 33

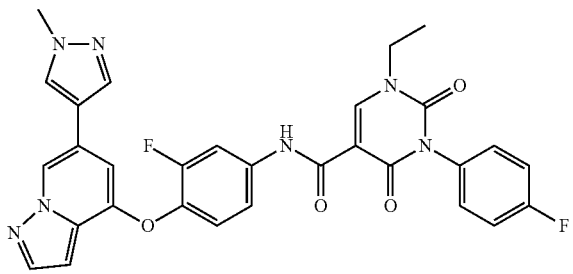 [SMILES: CCn1cc(C(=O)Nc2ccc(Oc3cc(-c4cnn(C)c4)cn4nccc34)c(F)c2)c(=O)n(-c2ccc(F)cc2)c1=O]

1-Ethyl-3-(4-fluoro-phenyl)-2,4-dioxo-1,2,3,4-tetrahydro-pyrimidine-5-carboxylic acid {3-fluoro-4-[6-(1-methyl-1H-pyrazol-4-yl)-pyrazolo[1,5-a]pyridin-4-yloxy]-phenyl}-amide 1-Ethyl-2,4-dioxo-3-phenyl-1,2,3,4-tetrahydro-pyrimidine-5-carboxylic acid (0.044 g, 0.17 mmol) and N,N,N',N'-tetramethyl-O-(7-azabenzotriazol-1-yl)uronium hexafluorophosphate (0.065 g, 0.17 mmol) in N,N-dimethylformamide (2 mL, 20 mmol) was added N,N-diisopropylethylamine (0.054 mL, 0.31 mmol). After stirring at rt for 15 min, 3-fluoro-4-[6-(1-methyl-1H-pyrazol-4-yl)-pyrazolo[1,5-a]pyridin-4-yloxy]-phenylamine (0.05 g, 0.2 mmol) was added. The mixture was stirred at rt overnight then diluted with EtOAc, washed with 1N Na$_2$CO$_3$ solution, water and NaCl solution then dried over MgSO$_4$. The product was purified by MeOH trituration, collected and dried at 65° C. under vacuum to give 60 mg (60%) as a white solid. mp=260-2° C.; LCMS m/z=584 (M+1); $^1$H NMR (DMSO) δ: 11.00 (s, 1H), 8.88 (s, 1H), 8.82 (s, 1H), 8.13 (s, 1H), 7.96-8.00 (m, 2H), 7.92 (s, 1H), 7.40-7.47 (m, 3H), 7.30-7.37 (m, 3H), 6.75 (s, 1H), 6.60 (d, 1H, J=2.2 Hz), 4.01 (q, 2H, J=7 Hz), 3.81 (s, 3H), 1.29 (t, 3H, J=7 Hz).

Example 34

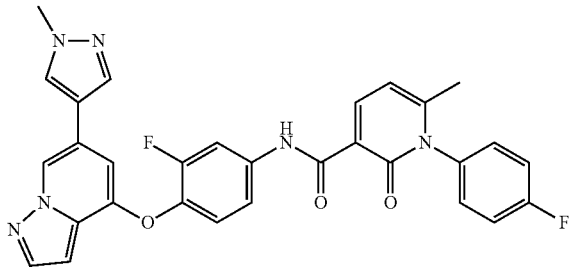 [SMILES: Cc1ccc(C(=O)Nc2ccc(Oc3cc(-c4cnn(C)c4)cn4nccc34)c(F)c2)c(=O)n1-c1ccc(F)cc1]

1-(4-Fluoro-phenyl)-6-methyl-2-oxo-1,2-dihydro-pyridine-3-carboxylic acid {3-fluoro-4-[6-(1-methyl-1H-pyrazol-4-yl)-pyrazolo[1,5-a]pyridin-4-yloxy]-phenyl}-amide. This example was synthesized using 3-fluoro-4-[6-(1-methyl-1H-pyrazol-4-yl)-pyrazolo[1,5-a]pyridin-4-yloxy]-phenylamine and 1-(4-fluoro-phenyl)-6-methyl-2-oxo-1,2-dihydro-pyridine-3-carboxylic acid by the methods for example 33. mp=216-8° C.; LCMS m/z=553 (M+1); $^1$H NMR (DMSO) δ: 12.05 (s, 1H), 8.83 (s, 1H), 8.49 (d, 1H, J=7.2 Hz), 8.13 (s, 1H), 8.02 (d, 1H, J=13.2 Hz), 7.98 (s, 1H), 7.92 (s, 1H), 7.41-7.49 (m, 5H), 7.31 (t, 1H, J=8.6 Hz), 6.71-6.74 (m, 2H), 6.61 (s, 1H), 3.81 (s, 1H), 2.09 (s, 3H).

Example 35

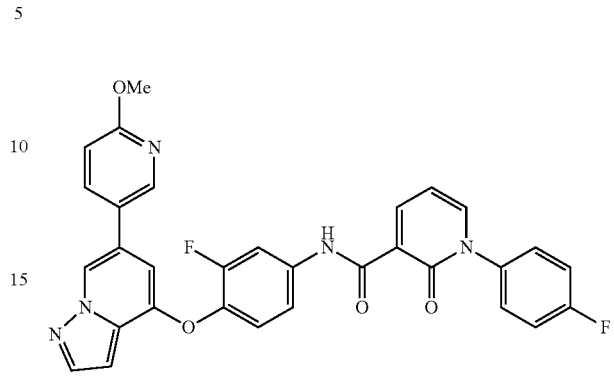

Step 1. 3-Fluoro-4-[6-(6-methoxy-pyridin-3-yl)-pyrazolo[1,5-a]pyridin-4-yloxy]-phenylamine. This intermediate was synthesized using 2-methoxypyridine-5-boronic acid and 6-bromo-4-(2-fluoro-4-nitro-phenoxy)-pyrazolo[1,5-a]pyridine (Example 24, intermediate from step 1) by the procedure for example 29 step 1. LCMS m/z=351 (M+1).

Step 2. 1-(4-Fluoro-phenyl)-2-oxo-1,2-dihydro-pyridine-3-carboxylic acid {3-fluoro-4-[6-(6-methoxy-pyridin-3-yl)-pyrazolo[1,5-a]pyridin-4-yloxy]-phenyl}-amide. This example was synthesized using 3-fluoro-4-[6-(6-methoxy-pyridin-3-yl)-pyrazolo[1,5-a]pyridin-4-yloxy]-phenylamine and 1-(4-fluoro-phenyl)-2-oxo-1,2-dihydro-pyridine-3-carboxylic acid by the methods for example 33. mp=167-9° C.; LCMS m/z=566 (M+1); $^1$H NMR (DMSO) δ: 12.1 (s, 1H), 8.90 (s, 1H), 8.58 (d, 1H, J=6.8 Hz), 8.48 (s, 1H), 8.12 (d, 1H, J=5.2 Hz), 8.01-8.05 (m, 3H), 7.60 (m, 2H), 7.34-7.40 (m, 4H), 6.86 (m, 2H), 6.66-6.72 (m, 2H), 3.9 (s, 3H).

Example 36

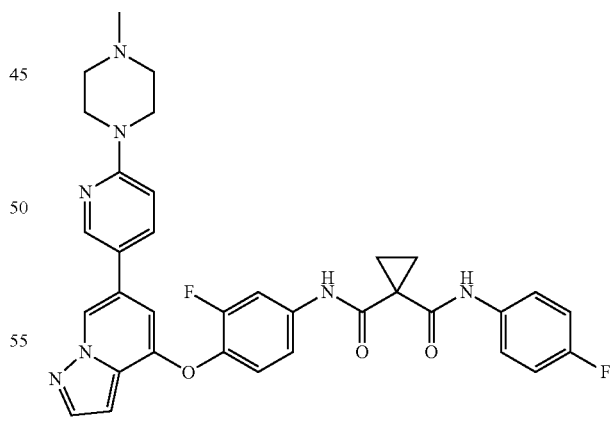

Step 1. 3-Fluoro-4-{6-[6-(4-methyl-piperazin-1-yl)-pyridin-3-yl]-pyrazolo[1,5-a]pyridin-4-yloxy}-phenylamine. This intermediate was synthesized using 1-Methyl-4-[5-(4,4,5,5-tetramethyl-[1,3,2]dioxaborolan-2-yl)-pyridin-2-yl]-piperazine and 6-bromo-4-(2-fluoro-4-nitro-phenoxy)-pyrazolo[1,5-a]pyridine (Example 24, intermediate from step 1) by the procedure for example 29 step 1. LCMS m/z=419 (M+1); 1H NMR (DMSO) δ: 8.82 (s, 1H), 8.33 (m, 1H), 8.00 (m, 1H), 7.72, 7.75 (dd, 1H, J=2.3, 9.8 Hz), 7.08 (t, 1H, J=8.8 Hz), 6.87 (d, 1H, J=8.8 Hz), 6.67 (s, 1H), 6.42-6.54 (m, 3H), 5.45 (s, 2H), 3.51 (m, 4H), 2.38 (m, 4H), 2.20 (s, 3H).

Step 2. Cyclopropane-1,1-dicarboxylic acid (3-fluoro-4-{6-[6-(4-methyl-piperazin-1-yl)-pyridin-3-yl]-pyrazolo[1,5-a]pyridin-4-yloxy}-phenyl)-amide (4-fluoro-phenyl)-amide. This example was synthesized using 3-fluoro-4-{6-[6-(4-methyl-piperazin-1-yl)-pyridin-3-yl]-pyrazolo[1,5-a]pyridin-4-yloxy}-phenylamine and 1-(4-fluoro-phenylcarbamoyl)-cyclopropanecarboxylic acid by the methods for example 33. mp>80° C. (dec); LCMS m/z=624 (M+1). $^1$H NMR (DMSO) δ: 10.39 (bs, 1H), 10.23 (s, 1H), 9.98 (s, 1H), 8.87 (s, 1H), 8.45 (m, 1H), 8.04 (d, 1H, J=2.8 Hz), 7.93, 7.95 (dd, 1H, J=3, 9.4 Hz), 8.85, 8.88 (dd, 1H, J=2.8, 13 z), 7.61-7.64 (m, 2H), 7.45 (m, 1H), 7.34 (t, 1H, J=8.8 Hz), 7.12-7.16 (m, 2H), 7.04 (d, 1H, J=8.8 Hz), 6.76 (s, 1H), 6.64 (d, 1H, J=2 Hz), 4.43 (d, 2H, J=14 Hz), 3.46 (d, 2H, J=8 Hz), 3.23 (t, 2H, J=12 Hz), 3.06 (m, 2H), 2.8 (s, 3H), 1.46 (d, 4H, J=5 Hz).

Example 37

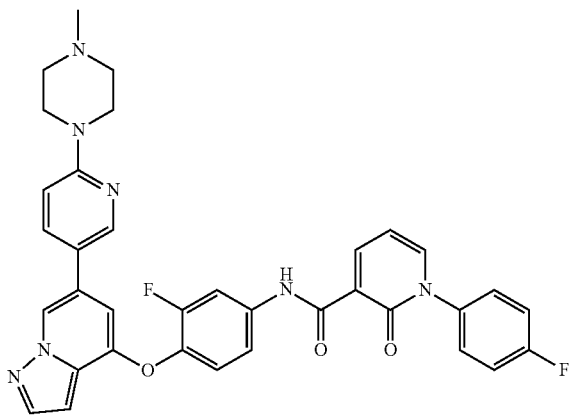 [SMILES: CN1CCN(c2ccc(-c3cc(Oc4ccc(NC(=O)c5cccn(-c6ccc(F)cc6)c5=O)cc4F)c4ccnn4c3)cn2)CC1]

1-(4-Fluoro-phenyl)-2-oxo-1,2-dihydro-pyridine-3-carboxylic acid (3-fluoro-4-{6-[6-(4-methyl-piperazin-1-yl)-pyridin-3-yl]-pyrazolo[1,5-a]pyridin-4-yloxy}-phenyl)-amide. This example was synthesized using 3-fluoro-4-{6-[6-(4-methyl-piperazin-1-yl)-pyridin-3-yl]-pyrazolo[1,5-a]pyridin-4-yloxy}-phenylamine and 1-(4-fluoro-phenyl)-2-oxo-1,2-dihydro-pyridine-3-carboxylic acid by the methods for example 33. mp=228-30° C.; LCMS m/z=634 (M+1); $^1$H NMR (DMSO) δ: 12.0 (s, 1H), 10.84 (s, 1H), 8.89 (s, 1H), 8.56, 8.58 (dd, 1H, J=2.4, 8.6 Hz), 8.48 (d, 1H, J=2.4 Hz), 8.12, 8.14 (dd, 1H, J=2.4, 7 Hz), 7.96-8.04 (m, 3H), 7.58-7.62 (m, 2H), 7.33-7.46 (m, 4H), 7.04 (d, 1H, J=9.2 Hz), 6.85 (s, 1H), 6.73 (t, 1H, J=7.8 Hz), 6.38 (d, 1H, J=1.8 Hz), 4.41 (d, 2H, J=14 Hz), 3.44 (d, 2H, 12 Hz), 3.28 (m, 2H), 3.03 (m, 2H), 2.8 (d, 3H), 1.46 (d, 4H, J=5 Hz).

Example 38

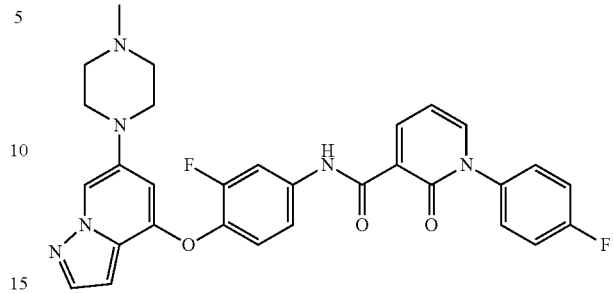

Step 1. 3-Fluoro-4-[6-(4-methyl-piperazin-1-yl)-pyrazolo[1,5-a]pyridin-4-yloxy]-phenylamine. Into a Schlenk flask under an atmosphere of nitrogen was added (2'-dicyclohexylphosphanyl-biphenyl-2-yl)-dimethyl-amine (0.0447 g, 0.114 mmol), 6-bromo-4-(2-fluoro-4-nitro-phenoxy)-pyrazolo[1,5-a]pyridine (0.200 g, 0.568 mmol), 1-methylpiperazine (0.126 mL, 1.14 mmol), palladium acetate (0.0128 g, 0.0568 mmol) and sodium tert-butoxide (0.0819 g, 0.852 mmol) in xylenes (8 mL, 20 mmol). The tube was purged 3× with nitrogen then heated at 120° C. overnight. The mixture was diluted with DCM, filtered was concentrated. The product was dissolved in EtOAc and washed with 1N Na$_2$CO$_3$, water and brine, then was dried over MgSO$_4$. The product was purified by ISCO chromatography (25% to 90% EtOAc in hexanes). The fractions were concentrated and the material used directly in the next step. The nitro intermediate and 20% Pd(OH)$_2$/C, 50% wet (10:40:50), (25 mg) in EtOAc and MeOH (1:1; 30 mL) was hydrogenated on a Parr at 40 psi under a nitrogen atmosphere overnight. The catalyst was filtered off and the solvent concentrated to give an oil. LCMS m/z=342 (M+1).

Step 2. 1-(4-Fluoro-phenyl)-2-oxo-1,2-dihydro-pyridine-3-carboxylic acid {3-fluoro-4-[6-(4-methyl-piperazin-1-yl)-pyrazolo[1,5-a]pyridin-4-yloxy]-phenyl}-amide. This example was synthesized using 3-fluoro-4-[6-(4-methyl-piperazin-1-yl)-pyrazolo[1,5-a]pyridin-4-yloxy]-phenylamine and 1-(4-fluoro-phenyl)-2-oxo-1,2-dihydro-pyridine-3-carboxylic acid by the methods for example 33. LCMS m/z=557 (M+1); $^1$H NMR (DMSO) δ: 12.1 (s, 1H), 9.85 (bs, 1H), 8.58 (d, 1H, J=7.2 Hz), 8.13 (d, 1H, J=6 Hz), 8.09 (s, 1H), 8.02 (d, 1H, J=13 Hz), 7.99 (d, 1H, J=2 Hz), 7.58-7.62 (m, 2H), 7.40-7.46 (m, 3H), 7.29 (m, 1H), 6.73 (t, 1H, J=6.8 Hz), 6.58 (s, 1H), 6.54 (d, 1H, J=2 Hz), 3.62 (d, 2H, J=12 Hz), 3.45 (d, 2H, J=11 Hz), 3.12-3.18 (m, 2H), 2.93 (m, 2H), 2.81 (s, 3H).

Example 39

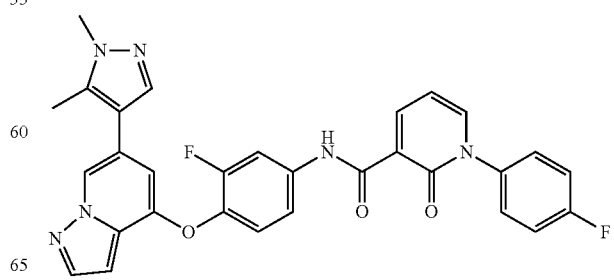

Step 1. 4-[6-(1,5-Dimethyl-1H-pyrazol-4-yl)-pyrazolo[1,5-a]pyridin-4-yloxy]-3-fluoro-phenylamine. This intermediate was synthesized using 1,5-dimethyl-4-(4,4,5,5-tetramethyl-1,3,2-dioxaborolan-2-yl)-1H-pyrazole and 6-bromo-4-(2-fluoro-4-nitro-phenoxy)-pyrazolo[1,5-a]pyridine (Example 24, intermediate from step 1) by the procedure for example 29 step 1. LCMS m/z=338 (M+1).

Step 2. 1-(4-Fluoro-phenyl)-2-oxo-1,2-dihydro-pyridine-3-carboxylic acid {4-[6-(1,5-dimethyl-1H-pyrazol-4-yl)-pyrazolo[1,5-a]pyridin-4-yloxy]-3-fluoro-phenyl}-amide. This example was synthesized using 4-[6-(1,5-dimethyl-1H-pyrazol-4-yl)-pyrazolo[1,5-a]pyridin-4-yloxy]-3-fluoro-phenylamine and 1-(4-fluoro-phenyl)-2-oxo-1,2-dihydro-pyridine-3-carboxylic acid by the methods for example 33. mp 124-6° C.; LCMS m/z=553 (M+1); $^1$H NMR (DMSO) δ: 12.1 (s, 1H), 8.57, 8.59 (dd, 1H, J=2.1, 7.5 Hz), 8.48 (s, 1H), 8.11, 8.13 (dd, 1H, J=2.1, 6.6 Hz), 8.00-8.04 (m, 2H), 7.58-7.62 (m, 2H), 7.56 (s, 1H), 7.34-7.46 (m, 4H), 6.73 (t, 1H, J=7 Hz), 6.65 (d, 1H, J=2 Hz), 6.51 (s, 1H), 3.74 (s, 3H), 2.29 (s, 3H).

Example 40

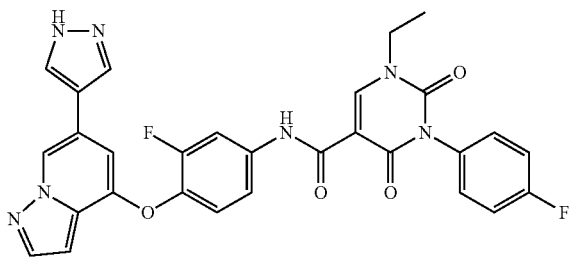 [SMILES: CCn1cc(C(=O)Nc2ccc(Oc3cc(-c4cn[nH]c4)cn4nccc34)c(F)c2)c(=O)n(-c2ccc(F)cc2)c1=O]

Step 1. 3-Fluoro-4-[6-(1H-pyrazol-4-yl)-pyrazolo[1,5-a]pyridin-4-yloxy]-phenylamine. This intermediate was synthesized using 3-1H-pyrazole boronic acid and 6-bromo-4-(2-fluoro-4-nitro-phenoxy)-pyrazolo[1,5-a]pyridine (Example 24, intermediate from step 1) by the procedure for example 29 step 1. LCMS m/z=309 (M+1).

Step 2. 1-Ethyl-3-(4-fluoro-phenyl)-2,4-dioxo-1,2,3,4-tetrahydro-pyrimidine-5-carboxylic acid {3-fluoro-4-[6-(1H-pyrazol-3-yl)-pyrazolo[1,5-a]pyridin-4-yloxy]-phenyl}-amide. This example was synthesized using 3-fluoro-4-[6-(1H-pyrazol-4-yl)-pyrazolo[1,5-a]pyridin-4-yloxy]-phenylamine and 1-ethyl-2,4-dioxo-3-phenyl-1,2,3,4-tetrahydro-pyrimidine-5-carboxylic acid by the methods for example 33. mp>175° C. (dec); LCMS m/z=570 (M+1); $^1$H NMR (DMSO) δ: 12.83 (s, 1H), 11.0 (s, 1H), 8.95 (s, 1H), 8.90 (s, 1H), 8.03 (m, 1H), 7.99 (d, 1H, J=13 Hz), 7.77 (s, 1H), 7.50 (m, 1H), 7.33-7.49 (m, 5H), 6.94 (s, 1H), 6.85 (s, 1H), 6.72 (m, 1H), 4.0 (q, 2H, J=7.4 Hz), 1.29 (t, 3H, J=7.4 Hz).

Example 41

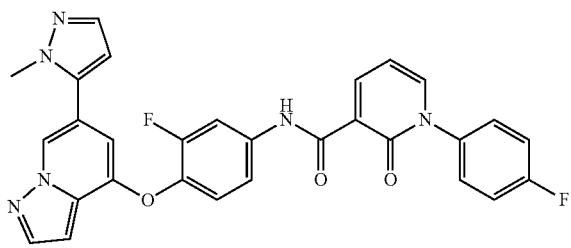 [SMILES: Cn1nccc1-c1cc(Oc2ccc(NC(=O)c3cccn(-c4ccc(F)cc4)c3=O)cc2F)c2ccnn2c1]

Step 1. 6-Bromo-4-(2-fluoro-4-nitro-phenoxy)-pyrazolo[1,5-a]pyridine. To 6-bromo-pyrazolo[1,5-a]pyridin-4-ol (2.0 g, 9.4 mmol) in N,N-dimethylformamide (30 mL) at 0° C. under an atmosphere of nitrogen was added sodium hydride, 60% dispersion in mineral oil (3:2, sodium hydride: mineral oil) (0.94 g, 24 mmol). Stirred 0.5 h at rt, 1,2-difluoro-4-nitro-benzene (1.1 mL, 10.3 mmol) was added drop wise and stirred an additional 4 h at rt. The reaction was diluted with ethyl acetate, washed with water/brine, dried over sodium sulfate, and concentrated. The product was chromatographed on silica gel using a single step column (10-30% ethyl acetate/hexanes) and concentrated to give 2.6 g, 77%. LCMS m/z=353 (M+1).

Step 2. 4-(2-Fluoro-4-nitro-phenoxy)-6-(2-methyl-2H-pyrazol-3-yl)-pyrazolo[1,5-a]pyridine. A Schlenk flask was charged with palladium acetate (0.03 g, 0.11 mmol), triphenylphosphine (0.12 g, 0.45 mmol), and 1,4-dioxane (2 mL) and stirred for 5 min until it turned bright yellow. 6-bromo-4-(2-fluoro-4-nitro-phenoxy)-pyrazolo[1,5-a]pyridine (0.2 g, 0.57 mmol), 5-(1-methyl-1H-pyrazole) boronic acid (0.09 g, 0.68 mmol), N,N-dimethylformamide (5 mL), and 1 M sodium carbonate solution (1.1 mL, 1.14 mmol) were added successively and the reaction was heated at 80° C. overnight under an atmosphere of nitrogen. After cooling to rt, the mixture was diluted with dichloromethane, filtered through celite, and concentrated. The product was chromatographed on silica gel using a single step column (10-50% ethyl acetate/hexanes) and concentrated to give 0.08 g, 41%. LCMS m/z=354 (M+1).

Step 3. 3-Fluoro-4-[6-(2-methyl-2H-pyrazol-3-yl)-[1,5-a]pyridine-4-yloxy]-phenylamine. To 4-(2-fluoro-4-nitro-phenoxy)-6-(2-methyl-2H-pyrazol-3-yl)-pyrazolo[1,5-a]pyridine (0.08 g, 0.23 mmol) in ethyl acetate (10 mL) and methanol (2 mL) under an atmosphere of nitrogen was added 20% Pd(OH)$_2$/C, 50% wet (10:40:50, palladium hydroxide:carbon black:water) (0.07 g, 0.05 mmol) and was hydrogenated at 40 psi on a Parr overnight. The reaction was filtered through a pad of celite, washed with dichloromethane/methanol, and concentrated to give 0.08 g, quant.; LCMS m/z=324 (M+1).

Step 4. 1-(4-Fluoro-phenyl)-2-oxo-1,2-dihydro-pyridine-3-carboxylic acid{3-fluoro-4-[6-(2-methyl-2H-pyrazol-3-yl)-pyrazolo[1,5-a]pyridine-4-yloxy]-phenyl}-amide. To a mixture of 1-(4-fluoro-phenyl)-2-oxo-1,2-dihydro-pyridine-3-carboxylic acid (0.06 g, 0.26 mmol) and N,N,N,N'-tetramethyl-O-(7-azabenzotriazol-1-yl)uronium hexafluorophosphate (0.1 g, 0.26 mmol) in N,N-dimethylformamide (4 mL) was added N,N-diisopropylethylamine (0.08 mL, 0.46 mmol) and stirred at rt. After 0.5 h, 3-fluoro-4-[6-(2-methyl-2H-pyrazole-3-yl)-[1,5-a]pyridine-4-yloxy]-phenylamine (0.08 g, 0.23 mmol) was added and heated at 65-80° C. for 2 h then cooled to rt. The reaction was diluted with ethyl acetate, washed with 1N sodium carbonate solution, water and brine, dried over sodium sulfate, and concentrated. The product was purified using Prep TLC plates (5% methanol/dichloromethane) and concentrated to give 0.04 g, 28%. mp=142-145° C.; LCMS m/z=539 (M+1); $^1$H NMR (DMSO-d$_6$) δ: 12.08 (s, 1H), 8.76 (s, 1H), 8.58 (m, 1H), 8.12 (m, 2H), 8.04 (m, 1H), 7.62 (m, 3H), 7.36-7.46 (bm, 4H), 6.74 (m, 2H), 6.61 (s, 1H), 6.44 (m, 1H), 3.83 (s, 3H).

Example 42

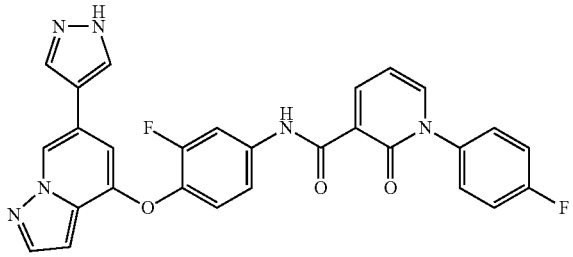 [SMILES: O=C(Nc1ccc(Oc2cc(-c3cn[nH]c3)cn3nccc23)c(F)c1)c1cccn(-c2ccc(F)cc2)c1=O]

Step 1. 4-(2-Fluoro-4-nitro-phenoxy)-6-(1H-pyrazol-4-yl)-pyrazolo[1,5-a]pyridine. The compound was synthesized from 6-bromo-4-(2-fluoro-4-nitro-phenoxy)-pyrazolo[1,5-a]pyridine and 4-(4,4,5,5-tetramethyl-1,3,2-dioxaborolan-2-yl)-pyrazole-1-carboxylic acid tert butyl ester using the susuki method described in example 41 step 2. LCMS m/z=340 (M+1).

Step 2. 4-[4-(2-Fluoro-4-nitro-phenoxy)-pyrazolo[1,5-a]pyridin-6-yl]-pyrazole-1-carboxylic acid tert-butyl ester. To 4-(2-fluoro-4-nitro-phenoxy)-6-(1H-pyrazol-4-yl)-pyrazolo[1,5-a]pyridine (0.14 g, 0.40 mmol) in dichloromethane (10 mL) under an atmosphere of nitrogen was added triethylamine (0.11 mL, 0.81 mmol), di-tert-butyldicarbonate (0.1 g, 0.44 mmol), followed by 4-dimethylaminopyridine (0.01 g, 0.04 mmol) and was stirred at rt overnight. The reaction was washed with 1N sodium carbonate, water and brine, dried over sodium sulfate, and concentrated to give 0.17 g, 97%. LCMS m/z=440 (M+1).

Step 3. 4-[4-(4-Amino-2-fluoro-phenoxy)-pyrazolo[1,5-a]pyridin-6-yl]-pyrazole-1-carboxylic acid tert-butyl ester. The compound was synthesized from 4-[4-(2-fluoro-4-nitro-phenoxy)-pyrazolo[1,5-a]pyridin-6-yl]-pyrazole-1-carboxylic acid tert-butyl ester and 20% Pd(OH)$_2$/C, 50% wet (10:40:50, palladium hydroxide:carbon black:water) using the hydrogenation method described in example 41 step 3. LCMS m/z=410 (M+1).

Step 4. 4-[4-(2-fluoro-4-{[1-(4-fluoro-phenyl)-2-oxo-1,2-dihydro-pyridine-3-carbonyl]-amino}-phenoxy)-pyrazolo[1,5-a]pyridin-6-yl]-pyrazole-1-carboxylic acid tert-butyl ester. The compound was synthesized from 4-[4-(4-amino-2-fluoro-phenoxy)-pyrazolo[1,5-a]pyridin-6-yl]-pyrazole-1-carboxylic acid tert-butyl ester and 1-(4-fluoro-phenyl)-2-oxo-1,2-dihydro-pyridine-3-carboxylic acid using the amide coupling method described in example 41 step 4. LCMS m/z=625 (M+1).

Step 5. 1-(4-Fluoro-phenyl)-2-oxo-1,2-dihydro-pyridine-3-carboxylic acid {3-fluoro-4-[6-(1H-pyrazol-4-yl)-pyrazolo[1,5-a]pyridine-4-yloxy]-phenyl}-amide. 4-[4-(2-fluoro-4-{[1-(4-fluoro-phenyl)-2-oxo-1,2-dihydro-pyridine-3-carbonyl]-amino}-phenoxy)-pyrazolo[1,5-a]pyridin-6-yl]-pyrazole-1-carboxylic acid tert-butyl ester (0.17 g, 0.28 mmol) in dichloromethane (10 mL) was added trifluoroacetic acid (2 mL) and stirred at 25-40° C. for 1 h, concentrated, dissolved in dichloromethane, washed with 1N sodium carbonate, water and brine, dried over sodium sulfate, and concentrated. The product was purified using Prep TLC plates (10% methanol/dichloromethane) and concentrated to give 0.06 g, 42%. mp=210° C.; LCMS m/z=525 (M+1); $^1$H NMR (DMSO-d$_6$) δ: 13.00 (s, 1H), 12.10 (s, 1H), 8.89 (s, 1H), 8.58 (m, 1H), 8.29 (m, 1H), 8.15 (m, 1H), 8.05 (br m, 3H), 7.62 (m, 2H), 7.42 (m, 3H), 7.29 (m, 1H), 6.92 (s, 1H), 6.72 (m, 1H), 6.55 (m, 1H).

Example 43

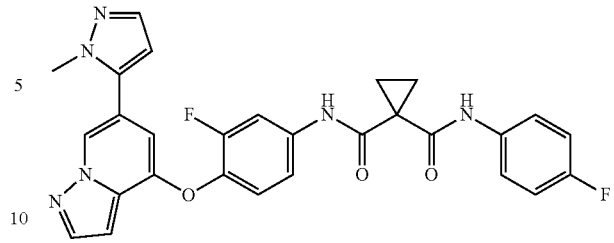

Step 1. 6-Bromo-4-(2-fluoro-4-nitro-phenoxy)-pyrazolo[1,5-a]pyridine. The compound was synthesized from 6-bromo-pyrazolo[1,5-a]pyridin-4-ol and 1,2-difluoro-4-nitro-benzene using the method described in example 41 step 1. LCMS m/z=353 (M+1).

Step 2. 4-(2-Fluoro-4-nitro-phenoxy)-6-(2-methyl-2H-pyrazol-3-yl)-pyrazolo[1,5-a]pyridine. The compound was synthesized from 6-bromo-4-(2-fluoro-4-nitro-phenoxy)-pyrazolo[1,5-a]pyridine and 5-(1-methyl-1H-pyrazole) boronic acid using the susuki method described in example 41 step 2. LCMS m/z=354 (M+1).

Step 3. 3-Fluoro-4-[6-(2-methyl-2H-pyrazol-3-yl)-[1,5-a]pyridine-4-yloxy]-phenylamine. The compound was synthesized from 4-(2-fluoro-4-nitro-phenoxy)-6-(2-methyl-2H-pyrazol-3-yl)-pyrazolo[1,5-a]pyridine and 20% Pd(OH)$_2$/C, 50% wet (10:40:50, palladium hydroxide:carbon black:water) using the reduction method described in example 41 step 3. LCMS m/z=324 (M+1).

Step 4. Cyclopropane-1,1-dicarboxylic acid{3-fluoro-4-[6-(2-methyl-2H-pyrazol-3-yl)-pyrazolo[1,5-a]pyridin-4-yloxy]-phenyl}-amide-(4-fluoro-phenyl)-amide. The compound was synthesized using the amide coupling method described in example 41 step 4. To a mixture of 1-(4-fluorophenylcarbamoyl)-cyclopropanecarboxylic acid (0.07 g, 0.31 mmol) and N,N,N',N'-tetramethyl-O-(7-azabenzotriazol-1-yl)uronium hexafluorophosphate (0.12 g, 0.31 mmol) in N,N-dimethylformamide (3 mL) was added N,N-diisopropylethylamine (0.1 mL, 0.56 mmol) and stirred at rt. After 0.5 h, 3-fluoro-4-[6-(2-methyl-2H-pyrazol-3-yl)-[1,5-a]pyridine-4-yloxy]-phenylamine (0.09 g, 0.28 mmol) was added and was stirred at 80° C. overnight and cooled at rt. The reaction was diluted with ethyl acetate, washed with 1N sodium carbonate, water and brine, dried over sodium sulfate, and concentrated. The product was purified using Prep TLC plates (5% methanol/dichloromethane) and concentrated to give 0.01 g, 7%. mp=70° C.; LCMS m/z=529 (M+1); $^1$H NMR (DMSO-d$_6$) δ: 10.32 (s, 1H), 9.97 (s, 1H), 8.75 (s, 1H), 8.12 (m, 1H), 7.88 (m, 1H), 7.64 (m, 2H), 7.45 (m, 2H), 7.36 (m, 1H), 7.14 (m, 2H), 6.74 (m, 1H), 6.53 (s, 1H), 6.42 (m, 1H), 3.83 (s, 3H), 1.45 (m, 4H).

Example 44

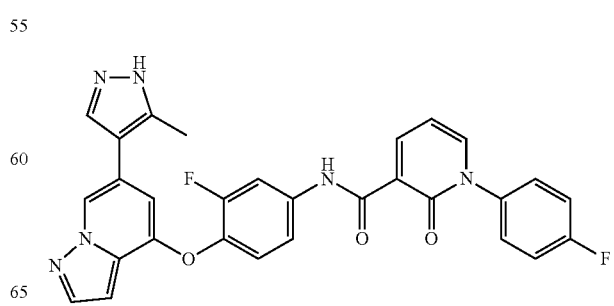

Step 1. 4-(2-Fluoro-4-nitro-phenoxy)-6-(5-methyl-1H-pyrazol-4-yl)-pyrazolo[1,5-a]pyridine. The compound was synthesized from 6-bromo-4-(2-fluoro-4-nitro-phenoxy)-pyrazolo[1,5-a]pyridine and 5-methyl-4-(4,4,5,5-tetramethyl-1,3,2-dioxaborolan-2-yl)-1H-pyrazole using the susuki method described in example 41 step 2. LCMS m/z=354 (M+1).

Step 2. 4-[4-(2-Fluoro-4-nitro-phenoxy)-pyrazolo[1,5-a]pyridin-6-yl]-5-methyl-pyrazole-1-carboxylic acid tert-butyl ester. The compound was synthesized from 4-(2-fluoro-4-nitro-phenoxy)-6-(5-methyl-1H-pyrazol-4-yl)-pyrazolo[1,5-a]pyridine and di-tert-butyldicarbonate using the boc protection method described in example 42 step 2. LCMS m/z=454 (M+1).

Step 3. 4-[4-(4-Amino-2-fluoro-phenoxy)-pyrazolo[1,5-a]pyridin-6-yl]-5-methyl-pyrazole-1-carboxylic acid tert-butyl ester. The compound was synthesized from 4-[4-(2-fluoro-4-nitro-phenoxy)-pyrazolo[1,5-a]pyridin-6-yl]-5-methyl-pyrazole-1-carboxylic acid tert-butyl ester and 20% Pd(OH)$_2$/C, 50% wet (10:40:50, palladium hydroxide:carbon black:water) using the hydrogenation method described in example 41 step 3. LCMS m/z=424 (M+1).

Step 4. 4-[4-(2-fluoro-4{[1-(4-fluoro-phenyl)-2-oxo-1,2-dihydro-pyridine-3-carbon-yl]-amino}-phenoxy)-pyrazolo[1,5-a]pyridin-6-yl]-5-methyl-pyrazole-1-carboxylic acid tert-butyl ester. The compound was synthesized from 4-[4-(4-amino-2-fluoro-phenoxy)-pyrazolo[1,5-a]pyridin-6-yl]-5-methyl-pyrazole-1-carboxylic acid tert-butyl ester and 1-(4-fluoro-phenyl)-2-oxo-1,2-dihydro-pyridine-3-carboxylic acid using the amide coupling method described in example 41 step 4. LCMS m/z=639 (M+1).

Step 5. 1-(4-Fluoro-phenyl)-2-oxo-1,2-dihydro-pyridine-3-carboxylic acid{3-fluoro-4-[6-(5-methyl-1H-pyrazol-4-yl)-pyrazolo[1,5-a]pyridin-4-yloxy]-phenyl}-amide. The compound was synthesized from 4-[4-(4-amino-2-fluoro-phenoxy)-pyrazolo[1,5-a]pyridin-6-yl]-5-methyl-pyrazole-1-carboxylic acid tert-butyl ester and 1-(4-fluoro-phenyl)-2-oxo-1,2-dihydro-pyridine-3-carboxylic acid using the boc-deprotection method described in example 42 step 5. mp=173° C.; LCMS m/z=539 (M+1); $^1$H NMR (DMSO-d$_6$) δ: 12.73 (m, 1H), 12.08 (s, 1H), 8.59 (m, 1H), 8.52 (s, 1H), 8.14 (m, 1H), 8.00 (m, 2H), 7.62 (m, 3H), 7.35-7.45 (m, 4H), 6.76 (m, 1H), 6.63 (m, 2H), 2.31 (m, 3H).

Example 45

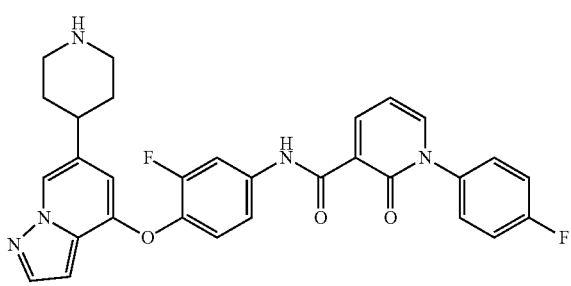 [SMILES: O=C(Nc1ccc(Oc2cc(C3CCNCC3)cn3nccc23)c(F)c1)c1cccn(-c2ccc(F)cc2)c1=O]

Step 1. 4-[4-(2-Fluoro-4-nitro-phenoxy)-pyrazolo[1,5-a]pyridin-6-yl]-3,6-dihydro-2H-pyridine-1-carboxylic acid tert-butyl ester. This compound was synthesized from 6-bromo-4-(2-fluoro-4-nitro-phenoxy)-pyrazolo[1,5-a]pyridine and 4-(4,4,5,5-tetramethyl-[1,3,2]dioxaborolan-2-yl)-3,6-dihydro-2H-pyridine-1-carboxylic acid tert butyl ester using the susuki method described in example 41 step 2. LCMS m/z=455 (M+1).

Step 2. 4-[4-(4-Amino-2-fluoro-phenoxy)-pyrazolo[1,5-a]pyridin-6-yl]-piperidine-1-carboxylic acid tert-butyl ester. This compound was synthesized from 4-[4-(2-fluoro-4-nitro-phenoxy)-pyrazolo[1,5-a]pyridin-6-yl]-3,6-dihydro-2H-pyridine-1-carboxylic acid tert-butyl ester and 20% Pd(OH)$_2$/C, 50% wet (10:40:50, palladium hydroxide:carbon black:water) using the hydrogenation method described in example 41 step 3. LCMS m/z=427 (M+1).

Step 3. 4-[4-(2-Fluoro-4-{[1-(4-fluoro-phenyl)-2-oxo-1,2-dihydro-pyridine-3-carbonyl]-amino}-phenoxy)-pyrazolo[1,5-a]pyridin-6-yl]-piperidine-1-carboxylic acid tert butyl ester. The compound was synthesized from 4-[4-(4-amino-2-fluoro-phenoxy)-pyrazolo[1,5-a]pyridin-6-yl]-piperidine-1-carboxylic acid tert-butyl ester and 1-(4-fluoro-phenyl)-2-oxo-1,2-dihydro-pyridine-3-carboxylic acid using the amide coupling method described in example 41 step 4. LCMS m/z=642 (M+1).

Step 4. 1-(4-Fluoro-phenyl)-2-oxo-1,2-dihydro-pyridine-3-carboxylic acid [3-fluoro-4-(6-piperidin-4-yl-pyrazolo[1,5-a]pyridin-4-yloxy)-phenyl]-amide. This compound was synthesized from 4-[4-(2-fluoro-4-{[1-(4-fluoro-phenyl)-2-oxo-1,2-dihydro-pyridine-3-carbonyl]-amino)-phenoxy)-pyrazolo[1,5-a]pyridin-6-yl]-piperidine-1-carboxylic acid tert butyl ester and trifluoroacetic acid using the boc-deprotection method described in example 42 step 5. mp=94° C.; LCMS m/z=542 (M+1); $^1$H NMR (DMSO-d$_6$) δ: 12.08 (s, 1H), 8.59 (m, 1H), 8.27 (s, 1H), 8.14 (m, 1H), 8.04 (m, 1H), 7.96 (m, 1H), 7.62 (m, 2H), 7.35-7.47 (m, 3H), 7.30 (m, 1H), 6.73 (m, 1H), 6.60 (m, 1H), 6.40 (s, 1H), 2.99 (m, 2H), 2.52 (m, 4H), 1.69 (m, 2H), 1.47 (m, 2H).

Example 46

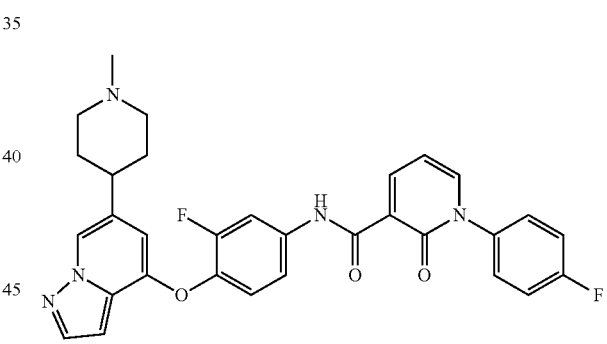

1-(4-Fluoro-phenyl)-2-oxo-1,2-dihydro-pyridine-3-carboxylic acid {3-fluoro-4-[6-(1-methyl-piperidin-4-yl)-pyrazolo[1,5-a]pyridin-4-yloxy]-phenyl}-amide. This compound was synthesized using the methods described in example 45. To 1-(4-fluoro-phenyl)-2-oxo-1,2-dihydro-pyridine-3-carboxylic acid[3-fluoro-4-(6-piperidin-4-yl-pyrazolo[1,5-a]pyridin-4-yloxy)-phenyl]-amide (0.05 g, 0.09 mmol) in N,N-dimethylformamide (0.09 mL, 1.1 mmol)/methanol (4 mL)/acetic acid (0.02 mL, 0.37 mmol) under an atmosphere of nitrogen was added formaldehyde (0.01 mL, 0.46 mmol), followed by sodium cyanoborohydride (0.03 g, 0.46 mmol). The reaction was stirred at rt for 15 min and concentrated. The residue was dissolved in dichloromethane and washed with 1N sodium carbonate, water and brine, dried over sodium sulfate, and concentrated. The product was purified using Prep TLC plates (5% methanol/dichloromethane) and concentrated to give 0.02 g, 39%. mp=83-85° C.; LCMS m/z=556 (M+1); $^1$H NMR (DMSO-d$_6$) δ: 12.08 (s, 1H), 8.59 (m, 1H), 8.30 (s, 1H), 8.14

(m, 1H), 8.04 (m, 1H), 7.96 (m, 1H), 7.62 (m, 2H), 7.40-7.47 (m, 3H), 7.31 (m, 1H), 6.74 (m, 1H), 6.59 (m, 1H), 6.43 (s, 1H), 2.83 (m, 2H), 2.49 (m, 1H), 2.15 (s, 3H), 1.94 (m, 2H), 1.74 (m, 2H), 1.59 (m, 2H).

Example 47

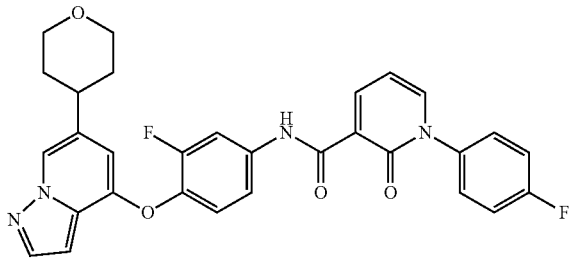 [SMILES: O=C(Nc1ccc(Oc2cc(C3CCOCC3)cn3nccc23)c(F)c1)c1cccn(-c2ccc(F)cc2)c1=O]

1-(4-Fluoro-phenyl)-2-oxo-1,2-dihydro-pyridine-3-carboxylic acid{3-fluoro-4-[6-(tetrahydro-pyran-4-yl)-pyrazolo[1,5-a]pyridin-4-yloxy]-phenyl}-amide. This compound was synthesized from 3-fluoro-4-[6-(tetrahydro-pyran-4-yl)-pyrazolo[1,5-a]pyridin-4-yloxy]-phenylamine and 1-(4-fluoro-phenyl)-2-oxo-1,2-dihydro-pyridine-3-carboxylic acid using the methods described in example 41. mp=90° C.; LCMS m/z=543 (M+1); $^1$H NMR (DMSO-d$_6$) δ: 12.08 (s, 1H), 8.59 (m, 1H), 8.31 (s, 1H), 8.12 (m, 1H), 8.00 (m, 1H), 7.96 (s, 1H), 7.63 (m, 2H), 7.49 (m, 3H), 7.31 (m, 1H), 6.77 (m, 1H), 6.54 (s, 1H), 6.43 (s, 1H), 3.95 (m, 2H), 3.37 (m, 2H), 2.79 (m, 1H), 1.69 (m, 4H).

Example 48

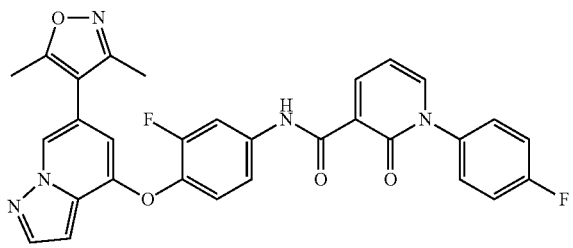 [SMILES: Cc1noc(C)c1-c1cc(Oc2ccc(NC(=O)c3cccn(-c4ccc(F)cc4)c3=O)cc2F)c2ccnn2c1]

1-(4-Fluoro-phenyl)-2-oxo-1,2-dihydro-pyridine-3-carboxylic acid{4-[6-(3,5-dimethyl-isoxazol-4-yl)-pyrazolo[1,5-a]pyridin-4-yloxy]-3-fluoro-phenyl}-amide. This compound was synthesized from 4-[6-(3,5-dimethyl-isoxazol-4-yl)-pyrazolo[1,5-a]pyridin-4-yloxy]-3-fluoro-phenylamine and 1-(4-fluoro-phenyl)-2-oxo-1,2-dihydro-pyridine-3-carboxylic acid using the methods described in example 41. mp=97-100° C.; LCMS m/z=554 (M+1); $^1$H NMR (DMSO-d$_6$) δ: 12.08 (s, 1H), 8.63 (s, 1H), 8.59 (dd, 1H, J=2.2 Hz), 8.14 (dd, 1H, J=2.2 Hz), 8.08 (s, 1H), 8.03 (m, 1H), 7.62 (m, 2H), 7.44 (m, 4H), 6.74 (m, 2H), 6.51 (s, 1H), 2.37 (s, 3H), 2.18 (s, 3H).

Example 49

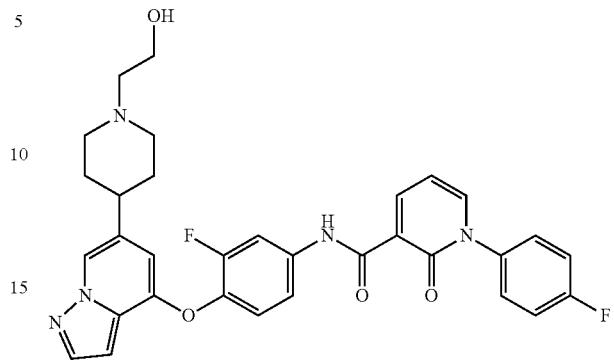

1-(4-Fluoro-phenyl)-2-oxo-1,2-dihydro-pyridine-3-carboxylic acid(3-fluoro-4-{6-[1-(2-hydroxy-ethyl)-piperidin-4-yl]-pyrazolo[1,5-a]pyridin-4-yloxy}-phenyl)-amide. This compound was synthesized using the methods described in example 45. To 1-(4-fluoro-phenyl)-2-oxo-1,2-dihydro-pyridine-3-carboxylic acid[3-fluoro-4-(6-piperidin-4-yl-pyrazolo[1,5-a]pyridin-4-yloxy)-phenyl]-amide (0.07 g, 0.12 mmol) in methanol (5 mL) was added ethylene oxide (0.03 mL, 0.6 mmol) (cooled at −78° C. as a liquid) (added excess) and the reaction was stirred at rt for 1 h and concentrated (monitored by LCMS). The product was purified using Prep TLC plates (5% methanol/DCM) and concentrated to give 0.04 g, 50%. mp=92-94° C.; LCMS m/z=586 (M+1); $^1$H NMR (DMSO-d$_6$) δ: 12.08 (s, 1H), 8.59 (m, 1H), 8.30 (s, 1H), 8.14 (m, 1H), 8.03 (m, 1H), 7.95 (s, 1H), 7.62 (m, 2H), 7.42 (m, 3H), 7.33 (m, 1H), 6.74 (m, 1H), 6.59 (s, 1H), 6.42 (s, 1H), 4.34 (m, 1H), 3.47 (m, 2H), 2.93 (d, 2H, J=11.5 Hz), 2.46 (m, 1H), 2.36 (m, 2H), 2.01 (t, 2H, J=11.5 Hz), 1.73 (m, 2H), 1.55 (m, 2H).

Example 50

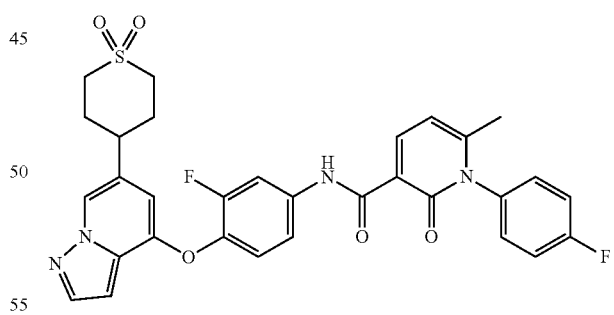

1-(4-Fluoro-phenyl)-6-methyl-2-oxo-1,2-dihydro-pyridine-3-carboxylic acid {4-[6-(1,1-dioxo-hexahydro-thiopyran-4-yl)-pyrazolo[1,5-a]pyridin-4-yloxy]-3-fluoro-phenyl}-amide. This compound was synthesized using the methods described in example 41. To 1-(fluoro-phenyl)-6-methyl-2-oxo-1,2-dihydro-pyridine-3-carboxylic acid{3-fluoro-4-[6-(tetrahydro-thiopyran-4-yl)-pyrazolo[1,5-a]pyridine-4-yloxy]-phenyl}-amide (0.12 g, 0.21 mmol) in dichloromethane (10 mL) at 0° C. under an atmosphere of nitrogen was added 77% mCPBA (m-chloroperbenzoic acid: (0.1 g, 0.44 mmol) and was warmed at rt for 30 min. The reaction was washed with 1N sodium carbonate solution, water and brine, dried over sodium sulfate, and concentrated. The product was purified using Prep TLC plates (5% methanol/dichloromethane) and concentrated to give 0.04 g, 28%. mp>280° C.; LCMS m/z=605 (M+1); $^1$H NMR (DMSO-d$_6$) δ: 12.05 (s, 1H), 8.50 (d, 1H, J=7.6 Hz), 8.35 (s, 1H), 7.98 (m, 2H), 7.48 (br m, 5H), 7.33 (m, 1H), 6.72 (m, 1H), 6.64 (m, 1H), 6.39 (s, 1H), 3.23 (m, 2H), 3.09 (m, 2H), 2.90 (m, 1H), 2.14 (m, 2H), 2.08 (s, 3H), 2.05 (m, 2H).

Example 51

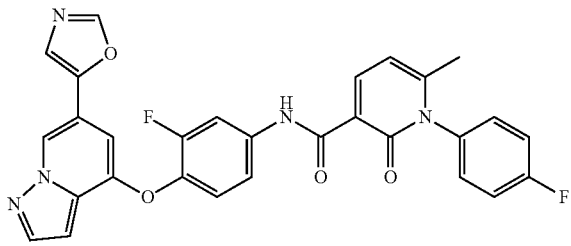 [SMILES: Cc1ccc(C(=O)Nc2ccc(Oc3cc(-c4cnco4)cn4nccc34)c(F)c2)c(=O)n1-c1ccc(F)cc1]

Step 1. 4-(2-Fluoro-4-nitro-phenoxy)-6-oxazol-5-yl-pyrazolo[1,5-a]pyridine. The compound was synthesized from 6-bromo-4-(2-fluoro-4-nitro-phenoxy)-pyrazolo[1,5-a]pyridine and 5-(4,4,5,5-tetramethyl-1,3,2-dioxaborolan-2-yl)-oxazole using the susuki method described in example 41 step 2. LCMS m/z=341 (M+1).

Step 2. 3-Fluoro-4-(6-oxazol-5-yl-pyrazolo[1,5-a]pyridin-4-yloxy)-phenylamine. To 4-(2-fluoro-4-nitro-phenoxy)-6-oxazol-5-yl-pyrazolo[1,5-a]pyridine (0.12 g, 0.34 mmol) in ethyl acetate (5 mL)/ethanol (1 mL) under an atmosphere of nitrogen was added tin (II) chloride dihydrate (0.69 g, 3.1 mmol) and was heated at 80° C. for 2 h, cooled at rt, and concentrated. The mixture was stirred with 1N sodium hydroxide solution, then extracted with dichloromethane, washed with water and brine, dried over sodium sulfate, and concentrated to give 0.09 g, 81%. LCMS m/z=311 (M+1).

Step 3. 1-(4-Fluoro-phenyl)-6-methyl-2-oxo-1,2-dihydro-pyridine-3-carboxylic acid [3-fluoro-4-(6-oxazol-5-yl-pyrazolo[1,5-a]pyridin-4-yloxy)-phenyl]-amide. This compound was synthesized from 3-fluoro-4-(6-oxazol-5-yl-pyrazolo[1,5-a]pyridin-4-yloxy)-phenylamine and 1-(4-fluoro-phenyl)-6-methyl-2-oxo-1,2-dihydro-pyridine-3-carboxylic acid using the amide coupling method described in example 41 step 4. mp=113° C.; LCMS m/z=540 (M+1); $^1$H NMR (DMSO-d$_6$) δ: 12.06 (s, 1H), 8.95 (s, 1H), 8.50 (d, 1H, J=7.6 Hz), 8.41 (s, 1H), 8.11 (d, 1H, J=2.3 Hz), 8.05 (m, 1H), 7.73 (s, 1H), 7.49 (br m, 6H), 6.78 (m, 3H), 2.08 (s, 3H).

Example 52

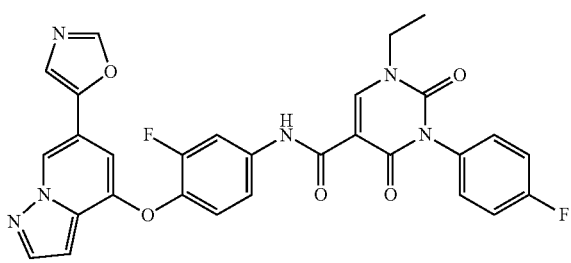 [SMILES: CCn1cc(C(=O)Nc2ccc(Oc3cc(-c4cnco4)cn4nccc34)c(F)c2)c(=O)n(-c2ccc(F)cc2)c1=O]

1-Ethyl-3-(4-fluoro-phenyl)-2,4-dioxo-1,2,3,4-tetrahydro-pyrimidine-5-carboxylic acid[3-fluoro-4-(6-oxazol-5-yl-pyrazolo[1,5-a]pyridin-4-yloxy)-phenyl]-amide. This compound was synthesized from 3-fluoro-4-(6-oxazol-5-yl-pyrazolo[1,5-a]pyridin-4-yloxy)-phenylamine and 1-ethyl-3-(4-fluoro-phenyl)-2,4-dioxo-1,2,3,4-tetrahydro-pyrimidine-5-carboxylic acid using the methods described in example 51. mp=276° C.; LCMS m/z=571 (M+1); $^1$H NMR (DMSO-d$_6$) δ: 11.01 (s, 1H), 8.95 (s, 1H), 8.88 (s, 1H), 8.42 (s, 1H), 8.11 (m, 1H), 8.01 (br m, 1H), 7.74 (s, 1H), 7.48 (m, 1H), 7.39 (br m, 5H), 6.79 (s, 1H) 6.75 (m, 1H), 4.04 (q, 2H), 1.29 (t, 3H, J=7.1 Hz).

Example 53

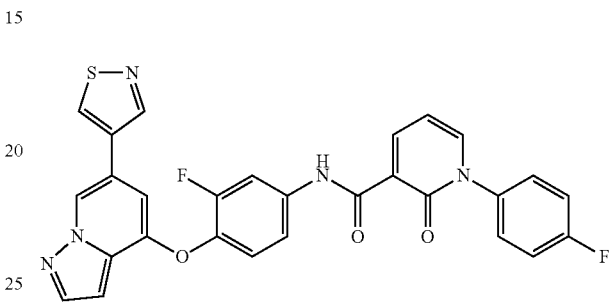

Step 1. 4-(4,4,5,5-Tetramethyl-1,3,2-dioxaborolan-2-yl)-isothiazole. To an oven dried schlenck flask charged with 6-bromo-isothiazole (0.5 g, 3.1 mmol), 4,4,5,5,4,4,5,5'-octamethyl-[2,2']bi[[1,3,2]dioxaborolanyl] (0.85 g, 3.4 mmol), tri(dibenyzlideneacetone)dipalladium(0) (0.28 g, 0.31 mmol), tricyclohexylphosphine (0.17 g, 0.61 mmol), potassium acetate (0.9 g, 9.14 mmol), followed by 1,4-dioxane (20 mL) was degassed for 5 min. under an atmosphere of nitrogen. The reaction was heated at 100° C. overnight, and cooled at rt. The reaction was diluted with dichloromethane, filtered through celite, washed with 1N sodium carbonate solution, water and brine, dried over sodium sulfate, and concentrated to give the product. LCMS m/z=212 (M+1).

Step 2. 1-(4-Fluoro-phenyl)-2-oxo-1,2-dihydro-pyridine-3-carboxylic acid[3-fluoro-4-(6-isothiazol-4-yl-pyrazolo[1,5-a]pyridin-4-yloxy)-phenyl]-amide. This compound was synthesized from 3-fluoro-4-(6-isothiazol-4-yl-pyazolo[1,5-a]pyridin-4-yloxy)-phenylamine and 1-(4-fluoro-phenyl)-2-oxo-1,2-dihydro-pyridine-3-carboxylic acid using the methods described in example 51. mp=213° C.; LCMS m/z=542 (M+1); $^1$H NMR (DMSO-d$_6$) δ: 12.08 (s, 1H), 9.39 (s, 1H), 9.18 (s, 1H), 9.13 (s, 1H), 8.59 (m, 1H), 8.14 (m, 1H), 8.01-8.07 (m, 2H), 7.62 (m, 2H), 7.32-7.45 (br m, 4H), 7.03 (s, 1H), 6.74 (m, 1H), 6.66 (m, 1H).

Example 54

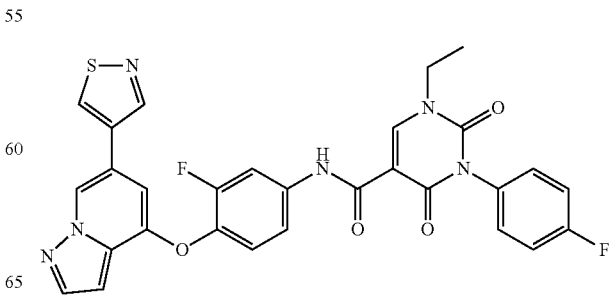

1-Ethyl-3-(4-fluoro-phenyl)-2,4-dioxo-1,2,3,4-tetrahydro-pyrimidine-5-carboxylic acid[3-fluoro-4-(6-isothiazol-4-yl-pyrazolo[1,5-a]pyridin-4-yloxy)-phenyl]-amide. This compound was synthesized from 3-fluoro-4-(6-isothiazol-4-yl-pyazolo[1,5-a]pyridin-4-yloxy)-phenylamine and 1-ethyl-3-(4-fluoro-phenyl)-2,4-dioxo-1,2,3,4-tetrahydro-pyrimidine-5-carboxylic acid using the methods described in example 53. mp=242° C.; LCMS m/z=587 (M+1); $^1$H NMR (DMSO-d$_6$) δ: 10.99 (s, 1H), 9.39 (s, 1H), 9.18 (s, 1H), 9.13 (s, 1H), 8.87 (s, 1H), 8.07 (m, 1H), 7.97 (m, 1H), 7.32-7.47 (br m, 6H), 7.02 (s, 1H), 6.65 (m, 1H), 4.02 (q, 2H), 1.31 (t, 3H, J=7.1 Hz).

Example 55

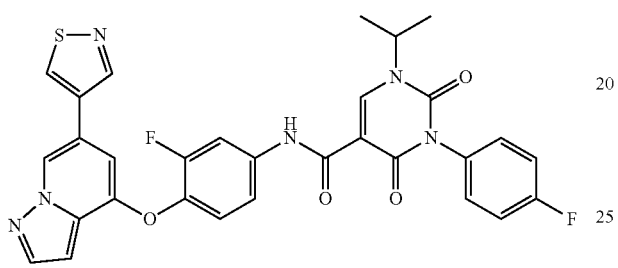

3-(4-Fluoro-phenyl)-1-isopropyl-2,4-dioxo-1,2,3,4-tetrahydro-pyrimidine-5-carboxylic acid[3-fluoro-4-(6-isothiazol-4-yl-pyrazolo[1,5-a]pyridin-4-yloxy)-phenyl]-amide. This compound was synthesized from 3-fluoro-4-(6-isothiazol-4-yl-pyazolo[1,5-a]pyridin-4-yloxy)-phenylamine and 3-(4-fluoro-phenyl)-1-isopropyl-2,4-dioxo-1,2,3,4-tetrahydro-pyrimidine-5-carboxylic acid using the methods described in example 53. mp=125-128° C.; LCMS m/z=601 (M+1); $^1$H NMR (DMSO-d$_6$) δ: 11.00 (s, 1H), 9.39 (s, 1H), 9.18 (s, 1H), 9.12 (s, 1H), 8.66 (s, 1H) 8.07 (m, 1H), 8.00 (m, 1H), 7.31-7.47 (br m, 6H), 7.04 (s, 1H), 6.65 (m, 1H), 4.77 (m, 1H), 1.43 (d, 6H, J=6.8 Hz).

Example 56

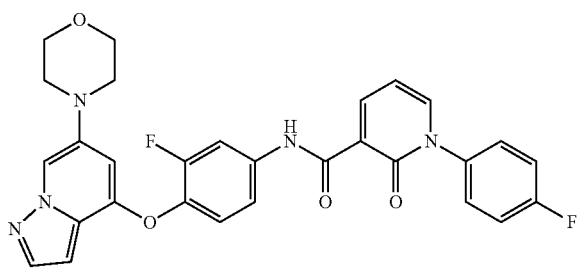

Step 1. 4-(2-Fluoro-4-nitro-phenoxy)-6-morpholin-4-yl-pyrazolo[1,5-a]pyridine. To an oven dried schlenck flask was added 6-bromo-4-(2-fluoro-4-nitro-phenoxy)-pyrazolo[1,5-a]pyridine (0.25 g, 0.72 mmol), morpholine (0.31 g, 3.61 mmol), palladium acetate (0.03 g, 0.14 mmol), (2'dicyclohexylphosphanyl-biphenyl-2-yl)-dimethyl-amine (0.11 g, 0.29 mmol), sodium tert-butoxide (0.21 g, 2.16 mmol), and xylenes (10 mL). The mixture was degassed for 5 min. under an atmosphere of nitrogen and heated at 138° C. overnight. The reaction was cooled at rt, diluted with dichloromethane, filtered through a pad of celite, washed with 1N sodium carbonate, water and brine, dried over sodium sulfate, and concentrated. The product was chromatographed on silica gel using a single step column (0.5-1% methanol/dichloromethane) and concentrated to give 0.07 g, 25%. LCMS m/z=359 (M+1).

Step 2. 3-Fluoro-4-(6-morpholin-4-yl-pyrazolo[1,5-a]pyridin-4-yloxy)-phenylamine. The compound was synthesized from 4-(2-fluoro-4-nitro-phenoxy)-6-morpholin-4-yl-pyrazolo[1,5-a]pyridine and 20% Pd(OH)$_2$/C, 50% wet (10:40:50, palladium hydroxide:carbon black:water) using the hydrogenation method described in example 41 step 3. LCMS m/z=329 (M+1);

Step 3. 1-(4-Fluoro-phenyl)-2-oxo-1,2-dihydro-pyridine-3-carboxylic acid[3-fluoro-4-(6-morpholin-4-yl-pyrazolo[1,5-a]pyridin-4-yloxy)-phenyl]-amide. This compound was synthesized from 3-fluoro-4-(6-morpholin-4-yl-pyrazolo[1,5-a]pyridin-4-yloxy)-phenylamine and 1-(4-fluoro-phenyl)-2-oxo-1,2-dihydro-pyridine-3-carboxylic acid using the amide coupling method described in example 41 step 4. mp=92-95° C.; LCMS m/z=544 (M+1); $^1$H NMR (DMSO-d$_6$) δ: 12.08 (s, 1H), 8.59 (m, 1H), 8.14 (m, 1H), 8.03 (m, 1H), 7.92 (s, 1H), 7.86 (m, 1H), 7.62 (m, 2H), 7.44 (m, 3H), 7.29 (m, 1H), 6.74 (m, 1H), 6.53 (m, 2H), 3.69 (m, 4H), 2.97 (m, 4H).

Example 57

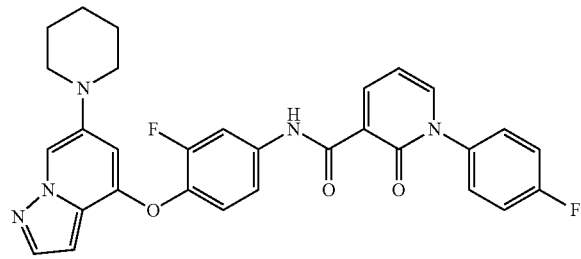 [SMILES: O=C(Nc1ccc(Oc2cc(N3CCCCC3)cn3nccc23)c(F)c1)c1cccn(-c2ccc(F)cc2)c1=O]

1-(4-Fluoro-phenyl)-2-oxo-1,2-dihydro-pyridine-3-carboxylic acid[3-fluoro-4-(6-piperidin-1-yl-pyrazolo[1,5-a]pyridin-4-yloxy)-phenyl]-amide. The following compound was synthesized from 3-fluoro-4-(6-piperidin-1-yl-pyrazolo[1,5-a]pyridin-4-yloxy)-phenylamine and 1-(4-fluoro-phenyl)-2-oxo-1,2-dihydro-pyridine-3-carboxylic acid using the methods described in example 56. mp=93° C.; LCMS m/z=542 (M+1); $^1$H NMR (DMSO-d$_6$) δ: 12.08 (s, 1H), 8.59 (m, 1H), 8.14 (m, 1H), 8.03 (m, 1H), 7.99 (m, 1H), 7.88 (m, 1H), 7.62 (m, 2H), 7.45 (m, 3H), 7.31 (m, 1H), 6.74 (m, 1H), 6.48 (m, 2H), 2.94 (m, 4H), 1.59 (m, 4H), 1.48 (m, 2H).

Example 58

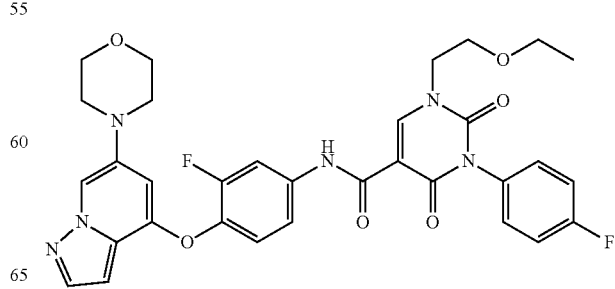

1-(2-Ethoxy-ethyl)-3-(4-fluoro-phenyl)-2,4-dioxo-1,2,3,4-tetrahydro-pyrimidine-5-carboxylic acid [3-fluoro-4-(6-morpholin-4-yl-pyrazolo[1,5-a]pyridin-4-yloxy)-phenyl]-amide. This compound was synthesized using methods described in example 56. 3-(4-Fluoro-phenyl)-1-ethoxy-ethyl-2,4-dioxo-1,2,3,4-tetrahydro-pyrimidine-5-carboxylic acid (0.04 g, 0.13 mmol) and N,N,N,N'-tetramethyl-O-(7-azabenzotriazol-1-yl)uronium hexafluorophosphate (0.05 g, 0.13 mmol) in N,N-dimethylformamide (4 mL) was added N,N-diisopropylethylamine (0.06 mL, 0.35 mmol) and stirred at rt. After 0.5 h, 3-fluoro-4-(6-morpholin-4-yl-pyrazolo[1,5-d]pyridin-4-yloxy)-phenylamine (0.04 g, 0.12 mmol) was added and was stirred at rt overnight. The reaction was diluted with ethyl acetate, washed with 1N sodium carbonate, water and brine, dried over sodium sulfate, and concentrated. The product was purified using Prep TLC plates (5% methanol/dichloromethane) and concentrated to give 0.02 g, 20%. mp=79-83° C.; LCMS m/z=633 (M+1); $^1$H NMR (DMSO-d$_6$) δ: 10.99 (s, 1H), 8.75 (s, 1H), 7.93 (m, 2H), 7.85 (m, 1H), 7.45 (m, 3H), 7.31 (br m, 3H), 6.49 (m, 2H), 4.15 (m, 2H), 3.68 (m, 6H), 3.52 (q, 2H, J=7.0 Hz), 2.96 (m, 4H), 1.14 (t, 3H, J=7.0 Hz).

Example 59

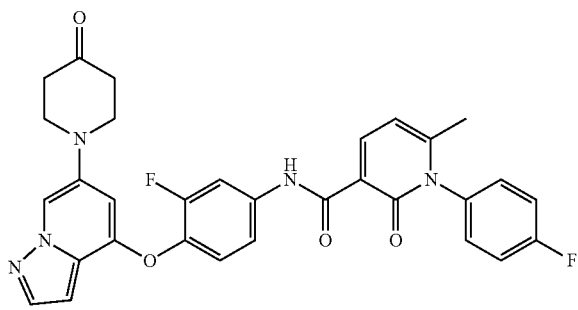

1-(4-Fluoro-phenyl)-6-methyl-2-oxo-1,2-dihydro-pyridine-3-carboxylic acid {3-fluoro-4-[6-(4-oxo-piperidin-1-yl)-pyrazolo[1,5-a]pyridin-4-yloxy]-phenyl}-amide. To 1-(4-fluoro-phenyl)-6-methyl-2-oxo-1,2-dihydro-pyridine-3-carboxylic acid{4-[6-(1,4-dioxa-8-aza-spiro[4,5]dec-8-yl)-pyrazolo[1,5-a]pyridin-4-yloxy]-3-fluoro-phenyl}-amide (0.04 g, 0.07 mmol) in 1,4-dioxane (20 mL) was added 2 M hydrochloric acid (1 mL) and was stirred at 65° C. for 1 h. The reaction was partitioned between dichloromethane and 1N sodium carbonate, washed with water and brine, dried over sodium sulfate, and concentrated. The product was purified using Prep TLC plates (5% methanol/dichloromethane) and concentrated to give 0.02 g, 16%. mp=90-94° C.; LCMS m/z=570 (M+1); $^1$H NMR (DMSO-d$_6$) δ: 12.04 (s, 1H), 8.50 (m, 1H), 8.06 (m, 1H), 7.99 (m, 1H), 7.86 (m, 1H), 7.44 (m, 5H), 7.28 (m, 1H), 6.72 (m, 1H), 6.62 (m, 1H), 6.49 (m, 1H), 3.36 (m, 4H), 2.43 (m, 4H), 2.07 (s, 3H).

Example 60

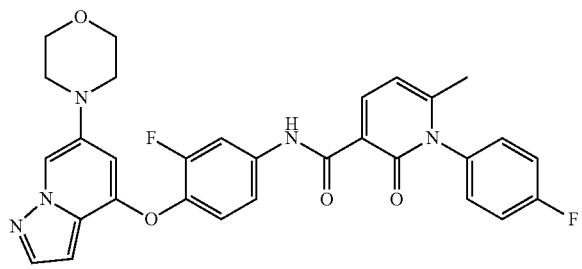

1-(4-Fluoro-phenyl)-6-methyl-2-oxo-1,2-dihydro-pyridine-3-carboxylic acid [3-fluoro-4-(6-morpholin-4-yl-pyrazolo[1,5-a]pyridin-4-yloxy)-phenyl]-amide. The compound was synthesized from 3-fluoro-4-(6-morpholin-4-yl-pyrazolo[1,5-d]pyridin-4-yloxy)-phenylamine and 1-(4-fluoro-phenyl)-6-methyl-2-oxo-1,2-dihydro-pyridine-3-carboxylic acid using method described in example 56 step 3. mp=209° C.; LCMS m/z=558 (M+1); $^1$H NMR (DMSO-d$_6$) δ: 12.01 (s, 1H), 8.50 (m, 1H), 8.05 (m, 1H), 7.91 (m, 1H), 7.86 (m, 1H), 7.45 (br m, 5H), 7.27 (m, 1H), 6.74 (m, 1H), 6.51 (m, 2H), 3.68 (m, 4H), 2.97 (m, 4H), 2.07 (s, 3H).

Example 61

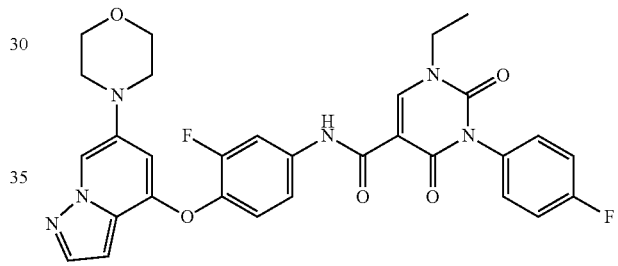

1-Ethyl-3-(4-fluoro-phenyl)-2,4-dioxo-1,2,3,4-tetrahydro-pyrimidine-5-carboxylic acid[3-fluoro-4-(6-morpholin-4-yl-pyrazolo[1,5-a]pyridin-4-yloxy)-phenyl]-amide. The compound was synthesized from 3-fluoro-4-(6-morpholin-4-yl-pyrazolo[1,5-a]pyridin-4-yloxy)-phenylamine and 1-ethyl-3-(4-fluoro-phenyl)-2,4-dioxo-1,2,3,4-tetrahydro-pyrimidine-5-carboxylic acid using the amide coupling method described in example 41 step 4 or example 56. mp=107° C.; LCMS m/z=589 (M+1); $^1$H NMR (DMSO-d$_6$) δ: 10.98 (s, 1H), 8.87 (s, 1H), 7.94 (m, 2H), 7.86 (m, 1H), 7.28-7.44 (br m, 6H), 6.52 (m, 2H), 4.02 (q, 2H), 3.69 (m, 4H), 2.97 (m, 4H), 1.30 (t, 3H, J=7.1 Hz).

Example 62

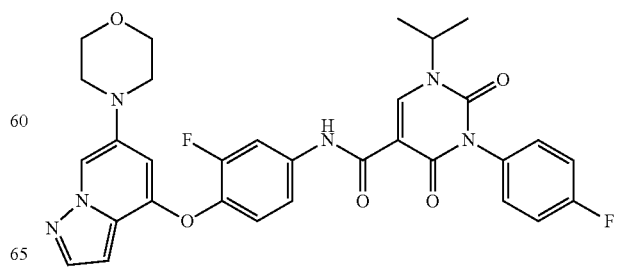

3-(4-Fluoro-phenyl)-1-isopropyl-2,4-dioxo-1,2,3,4-tetrahydro-pyrimidine-5-carboxylic acid[3-fluoro-4-(6-morpholin-4-yl-pyrazolo[1,5-a]pyridin-4-yloxy)-phenyl]-amide. This compound was synthesized from 3-fluoro-4-(6-morpholin-4-yl-pyrazolo[1,5-a]pyridin-4-yloxy)-phenylamine and 3-(4-fluoro-phenyl)-1-isopropyl-2,4-dioxo-1,2,3,4-tetrahydro-pyrimidine-5-carboxylic acid using the amide coupling method described in example 56. mp=125° C.; LCMS m/z=603 (M+1); $^1$H NMR (DMSO-$d_6$) δ: 10.99 (s, 1H), 8.66 (s, 1H), 7.98 (m, 2H), 7.86 (m, 1H), 7.25-7.45 (br m, 6H), 6.54 (m, 1H), 6.49 (m, 1H), 4.77 (m, 1H), 3.69 (m, 4H), 2.98 (m, 4H), 1.43 (d, 6H, J=6.8 Hz).

Example 63

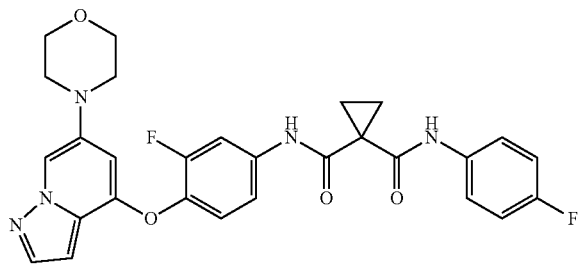 [SMILES: O=C(Nc1ccc(F)cc1)C1(C(=O)Nc2ccc(Oc3cc(N4CCOCC4)cn4nccc34)c(F)c2)CC1]

Cyclopropane-1,1-dicarboxylic acid[3-fluoro-4-(6-morpholin-4-yl-pyrazolo[1, 5-a]pyridin-4-yloxy)-phenyl]-amide(4-fluoro-phenyl)-amide. The compound was synthesized using the methods described in example 56. To 3-fluoro-4-(6-morpholin-4-yl-pyrazolo[1,5-a]pyridin-4-yloxy)-phenylamine (0.08 g, 0.24 mmol) in tetrahydrofuran (5 mL) and water (1.36 mL) was added potassium carbonate (0.10 g, 0.73 mmol) and the mixture was stirred at rt as 1-(4-fluoro-phenylcarbamoyl)-cyclopropanecarbonyl chloride (excess) was added drop wise. The reaction was stirred at rt for an additional 30 min., diluted with water, extracted with dichloromethane, dried over sodium sulfate, and concentrated. The product was purified using Prep TLC plates (5% methanol/dichloromethane) and concentrated to give 0.07 g, 54%. mp=85° C.; LCMS m/z=534 (M+1); $^1$H NMR (DMSO-$d_6$) δ: 10.31 (s, 1H), 9.97 (s, 1H), 7.92 (s, 1H), 7.86 (m, 2H), 7.63 (m, 2H), 7.44 (m, 1H), 7.28 (m, 1H), 7.16 (m, 2H), 6.49 (m, 2H), 3.69 (m, 4H), 2.97 (m, 4H), 1.47 (m, 4H).

Example 64

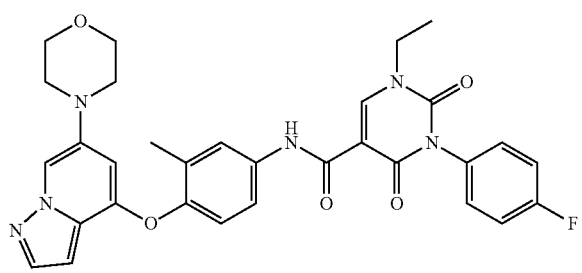 [SMILES: CCn1cc(C(=O)Nc2ccc(Oc3cc(N4CCOCC4)cn4nccc34)c(C)c2)c(=O)n(-c2ccc(F)cc2)c1=O]

Step 1. 6-Bromo-4-(2-methyl-4-nitro-phenoxy)-pyrazolo[1,5-a]pyridine. To 6-bromo-pyrazolo[1,5-a]pyridin-4-ol (1.5 g, 7 mmol) in N,N-dimethylformamide (30 mL) at 0° C. under an atmosphere of nitrogen was added sodium hydride, 60% dispersion in mineral oil (3:2, sodium hydride:mineral oil) (0.7 g, 18 mmol). After stirring 0.5 h at rt, 1-fluoro-2-methyl-4-nitro-benzene (3.3 g, 21.1 mmol) was added drop wise and stirred at 100° C. overnight. The reaction was diluted with ethyl acetate, washed with water and brine, dried over sodium sulfate, and concentrated. The product was chromatographed on silica gel using a single step column (5-10% ethyl acetate/hexanes) and concentrated to give 1.9 g, 77%. LCMS m/z=349 (M+1).

Step 2. 3-Methyl-4-(6-morpholin-4-yl-pyrazolo[1,5-a]pyridin-4-yloxy)-phenylamine. This compound was synthesized from 6-Bromo-4-(2-methyl-4-nitro-phenoxy)-pyrazolo[1,5-a]pyridine using the reduction procedure form example 56 step 2. LCMS m/z=325 (M+1).

Step 3. 1-Ethyl-3-(4-fluoro-phenyl)-2,4-dioxo-1,2,3,4-tetrahydro-pyrimidine-5-carboxylic acid[3-methyl-4-(6-morpholin-4-yl-pyrazolo[1,5-a]pyridin-4-yloxy)-phenyl]-amide. This compound was synthesized from 3-methyl-4-(6-morpholin-4-yl-pyrazolo[1,5-d]pyridin-4-yloxy)-phenylamine and 1-ethyl-3-(4-fluoro-phenyl)-2,4-dioxo-1,2,3,4-tetrahydro-pyrimidine-5-carboxylic acid using the methods described in example 41. mp=118° C.; LCMS m/z=585 (M+1); $^1$H NMR (DMSO-$d_6$) δ: 10.87 (s, 1H), 8.83 (s, 1H), 7.88 (s, 1H), 7.85 (m, 1H), 7.63 (m, 2H), 7.33-7.43 (m, 4H), 7.04 (m, 1H), 6.48 (m, 1H), 6.31 (s, 1H), 4.01 (q, 2H), 3.68 (m, 4H), 2.93 (m, 4H), 2.16 (s, 3H), 1.30 (t, 3H, J=7.1 Hz).

Example 65

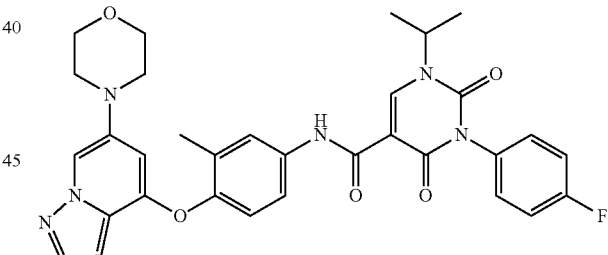

3-(4-Fluoro-phenyl)-1-isopropyl-2,4-dioxo-1,2,3,4-tetrahydro-pyrimidine-5-carboxylic acid[3-methyl-4-(6-morpholin-4-yl-pyrazolo[1,5-a]pyridin-4-yloxy)-phenyl]-amide. The compound was synthesized from 3-methyl-4-(6-morpholin-4-yl-pyrazolo[1,5-d]pyridin-4-yloxy)-phenylamine and 3-(4-fluoro-phenyl)-1-isopropyl-2,4-dioxo-1,2,3,4-tetrahydro-pyrimidine-5-carboxylic acid using the methods described in example 64. mp=121-124° C.; LCMS m/z=599 (M+1); $^1$H NMR (DMSO-$d_6$) δ: 10.87 (s, 1H), 8.64 (s, 1H), 7.89 (s, 1H), 7.84 (m, 1H), 7.65 (m, 2H), 7.33-7.44 (m, 4H), 7.03 (m, 1H), 6.47 (m, 1H), 6.33 (s, 1H), 4.77 (m, 1H), 3.68 (m, 4H), 2.94 (m, 4H), 2.16 (s, 3H), 1.42 (d, 6H, J=6.8 Hz).

Example 66

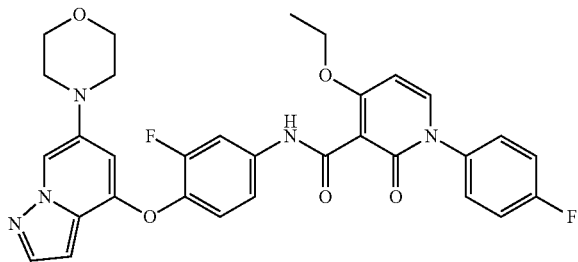 [SMILES: CCOc1ccn(-c2ccc(F)cc2)c(=O)c1C(=O)Nc1ccc(Oc2cc(N3CCOCC3)cn3nccc23)c(F)c1]

Step 1. 1-(4-Fluoro-phenyl)-4-iodo-2-oxo-1,2-dihydro-pyridine-3-carbonyl chloride. A suspension of 1-(4-fluoro-phenyl)-4-iodo-2-oxo-1,2-dihydro-pyridine-3-carboxylic acid (0.3 g, 0.84 mmol) in dichloromethane (4 mL) and N,N-dimethylformamide (0.2 mL) was cooled at ° C. under an atmosphere of nitrogen as 2M oxalyl chloride in dichloromethane (1.3 mL, 2.5 mmol) was added drop wise and stirred at rt for 1 h. The solvent was evaporated, dichloromethane was added and evaporated 3×, dried under vacuum, and taken directly on to the next step. LCMS m/z=378 (M+1).

Step 2. 1-(4-Fluoro-phenyl)-4-iodo-2-oxo-1,2-dihydro-pyridine-3-carboxylic acid [3-fluoro-4-(6-morpholin-4-yl-pyrazolo[1,5-a]pyridin-4-yloxy)-phenyl]-amide. 3-Fluoro-4-(6-morpholin-4-yl-pyrazolo[1,5-a]pyridin-4-yloxy)-phenylamine (0.07 g, 0.2 mmol) in N,N-dimethylformamide (1.1 mL) and tetrahydrofuran (3.3 mL) was stirred at 0° C. under an atmosphere of nitrogen as pyridine (0.04 mL, 0.45 mmol) was added drop wise. After 5 min., 1-(4-fluoro-phenyl)-4-iodo-2-oxo-1,2-dihydro-pyridine-3-carbonyl chloride (0.12 g, 0.31 mmol) in dichloromethane (5.2 mL) was added drop wise and was stirred at rt overnight and concentrated. The reaction was partitioned between ethyl acetate and water, washed with brine, dried over sodium sulfate, concentrated, and taken directly on to the next step. LCMS m/z=670 (M+1).

Step 3. 4-Ethoxy-1-(4-fluoro-phenyl)-2-oxo-1,2-dihydro-pyridine-3-carboxylic acid [3-fluoro-4-(6-morpholin-4-yl-pyrazolo[1,5-a]pyridin-4-yloxy)-phenyl]-amide. Sodium hydride, 60% dispersion in mineral oil (3:2, sodium hydride: mineral oil) (0.01 g, 0.23 mmol) in tetrahydrofuran (0.7 mL) under an atmosphere of nitrogen was stirred as ethanol (2.1 mL) was added slowly and stirred at rt for 10 min. To this sodium ethoxide solution was added a mixture of 1-(4-fluoro-phenyl)-4-iodo-2-oxo-1,2-dihydro-pyridine-3-carboxylic acid[3-fluoro-4-(6-morpholin-4-yl-pyrazolo[1,5-a]pyridin-4-yloxy)-phenyl]-amide (0.12 g, 0.18 mmol) in tetrahydrofuran (1.4 mL) and ethanol (0.82 mL) and stirred at rt for 1 h. The reaction was partitioned between dichloromethane and water, washed with brine, dried over sodium sulfate, and concentrated. The product was purified using Prep TLC plates (5% methanol/dichloromethane) and concentrated to give 0.05 g, 43%. mp=95-100° C.; LCMS m/z=588 (M+1); $^1$H NMR (DMSO-d$_6$) δ: 10.54 (s, 1H), 7.86 (m, 4H), 7.28-7.47 (br m, 6H), 6.53 (m, 2H), 6.46 (s, 1H), 4.26 (q, 2H), 3.69 (m, 4H), 2.95 (m, 4H), 1.31 (t, 3H, J=7.0 Hz).

Example 67

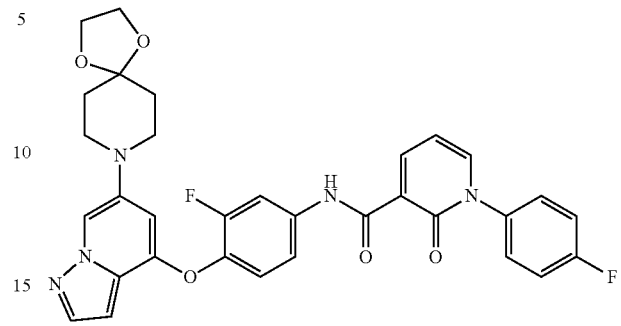

1-4-(Fluoro-phenyl)-2-oxo-1,2-dihydro-pyridine-3-carboxylic acid{4-[6-(1,4-dioxa-8-aza-spiro[4,5]dec-8-yl)-pyrazolo[1,5-a]pyridin-4-yloxy]-3-fluoro-phenyl}-amide. This compound was synthesized from 4-[6-(1,4-dioxa-8-aza-spiro[4,5]dec-8-yl)pyrazolo[1,5-a]pyridin-4-yloxy]-3-fluoro-phenylamine and 1-(4-fluoro-phenyl)-2-oxo-1,2-dihydro-pyridine-3-carboxylic acid using the method described in example 41 and 56. mp=86° C.; LCMS m/z=600 (M+1); $^1$H NMR (DMSO-d$_6$) δ: 12.07 (s, 1H), 8.59 (m, 1H), 8.14 (m, 1H), 8.03 (m, 1H), 7.95 (m, 1H), 7.85 (m, 1H), 7.62 (m, 2H), 7.45 (m, 2H), 7.29 (m, 2H), 6.72 (m, 1H), 6.51 (m, 2H), 3.88 (m, 4H), 3.08 (m, 4H), 1.71 (m, 4H).

Example 68

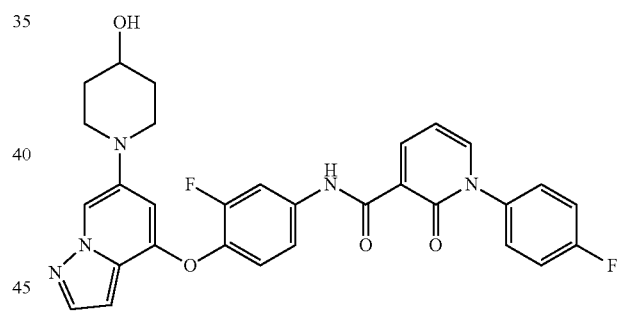

1-(4-Fluoro-phenyl)-2-oxo-1,2-dihydro-pyridine-3-carboxylic acid{3-fluoro-4-[6-(4-hydroxy-piperidin-1-yl)-pyrazolo[1,5-a]pyridin-4-yloxy]-phenyl}-amide. The compound was synthesized from example 67 using the methods described in example 59. To 1-(4-fluoro-phenyl)-2-oxo-1,2-dihydro-pyridine-3-carboxylic acid {3-fluoro-4-[6-(4-oxo-piperidin-1-yl)-pyrazolo[1,5-a]pyridin-4-yloxy]-phenyl}-amide (0.07 g, 0.12 mmol) in methanol (5 mL) at 0° C. under an atmosphere of nitrogen was added sodium borohydride (0.01 g, 0.24 mmol) and the reaction was stirred at this temp. for 15 min., quenched with water, separated with dichloromethane, dried over sodium sulfate, and concentrated. The product was purified using Prep TLC plates (5% methanol/dichloromethane) and concentrated to give 0.01 g, 15%. mp=100° C.; LCMS m/z=558 (M+1); $^1$H NMR (DMSO-d$_6$) δ: 12.07 (s, 1H), 8.60 (m, 1H), 8.14 (m, 1H), 8.03 (m, 1H), 7.89 (s, 1H), 7.83 (m, 1H), 7.62 (m, 2H), 7.42 (m, 3H), 7.31 (m, 1H), 6.74 (m, 1H), 6.48 (m, 1H), 4.67 (d, 1H, J=4.1 Hz), 3.58 (m, 1H), 3.28 (m, 2H), 2.73 (m, 2H), 1.80 (m, 2H), 1.48 (m, 2H).

Example 69

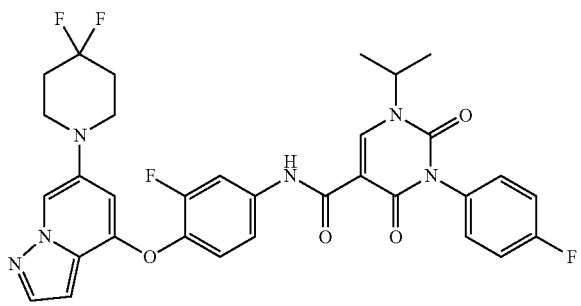 [SMILES: CC(C)n1cc(C(=O)Nc2ccc(Oc3cc(N4CCC(F)(F)CC4)cn4nccc34)c(F)c2)c(=O)n(-c2ccc(F)cc2)c1=O]

Step 1. 6-(4,4-Difluoro-piperidin-1-yl)-4-(2-fluoro-4-nitro-phenoxy)-pyrazolo[1,5-a]pyridine. The compound was synthesized from 6-bromo-4-(2-fluoro-4-nitro-phenoxy)-pyrazolo[1,5-a]pyridine and 4,4-difluoro-piperidine hydrochloride using the buchwald method described in example 62 step 1. LCMS m/z=393 (M+1).

Step 2. 4-[6-(4,4-Difluoro-piperidin-1-yl)-pyrazolo[1,5-a]pyridin-4-yloxy]-3-fluoro-phenylamine. 6-(4,4-Difluoro-piperidin-1-yl)-4-(2-fluoro-4-nitro-phenoxy)-pyrazolo[1,5-a]pyridine was hydrogenated with hydrogen and 20% Pd(OH)$_2$/C, 50% wet (10:40:50, palladium hydroxide:carbon black:water) using the method described in example 41 step 3.

Step 3. 3-(4-Fluoro-phenyl)-1-isopropyl-2,4-dioxo-1,2,3,4-tetrahydro-pyrimidine-5-carboxylic acid{4-[6-(4,4-difluoro-piperidin-1-yl)-pyrazolo[1,5-a]pyridin-4-yloxy]-3-fluoro-phenyl}-amide. This compound was synthesized from 4-[6-(4,4-difluoro-piperidin-1-yl)-pyrazolo[1,5-a]pyridin-4-yloxy]-3-fluoro-phenylamine and 3-(4-fluoro-phenyl)-1-isopropyl-2,4-dioxo-1,2,3,4-tetrahydro-pyrimidine-5-carboxylic acid using the method described in example 41 step 4. mp=115-119° C.; LCMS m/z=637 (M+1); $^1$H NMR (DMSO-d$_6$) δ: 10.99 (s, 1H), 8.66 (s, 1H), 8.03 (s, 1H), 7.98 (m, 1H), 7.87 (m, 1H), 7.27-7.46 (br m, 6H), 6.57 (m, 1H), 6.50 (m, 1H), 4.77 (m, 1H), 3.15 (m, 4H), 2.09 (m, 4H), 1.43 (d, 6H, J=6.8 Hz).

Example 70

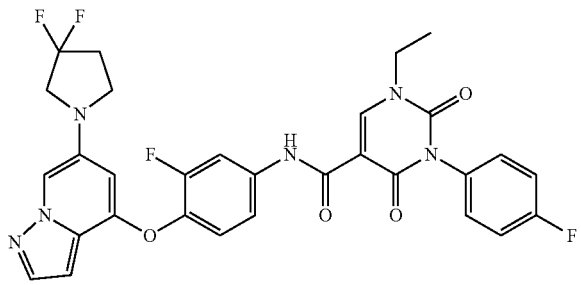 [SMILES: CCn1cc(C(=O)Nc2ccc(Oc3cc(N4CCC(F)(F)C4)cn4nccc34)c(F)c2)c(=O)n(-c2ccc(F)cc2)c1=O]

1-Ethyl-3-(4-fluoro-phenyl)-2,4-dioxo-1,2,3,4-tetrahydro-pyrimidine-5-carboxylic acid{4-[6-(3,3-difluoro-pyrrolidin-1-yl)-pyrazolo[1,5-a]pyridin-4-yloxy]-3-fluoro-phenyl}-amide. This compound was synthesized from 4-[6-3,3-difluoro-pyrrolidin-1-yl)-pyrazolo[1,5-a]pyridin-4-yloxy]-3-fluoro-phenylamine and 1-ethyl-3-(4-fluoro-phenyl)-2,4-dioxo-1,2,3,4-tetrahydro-pyrimidine-5-carboxylic acid using the methods described in example 69. mp=245° C.; LCMS m/z=609 (M+1); $^1$H NMR (DMSO-d$_6$) δ: 10.98 (s, 1H), 8.87 (s, 1H), 7.98 (m, 1H), 7.82 (m, 2H), 7.33-7.45 (br m, 5H), 7.26 (m, 1H), 6.43 (m, 2H), 4.02 (q, 2H), 3.62 (m, 2H), 3.38 (m, 2H), 2.46 (m, 2H), 1.31 (t, 3H, J=7.0 Hz).

Example 71

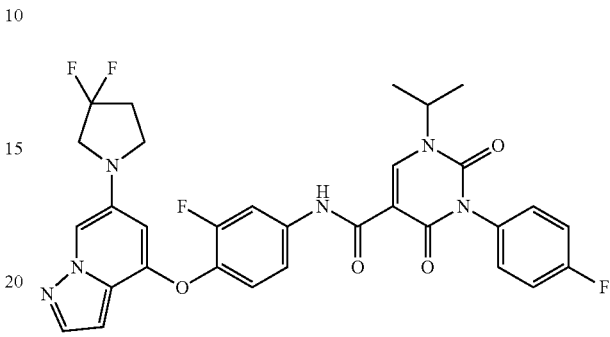

3-(4-Fluoro-phenyl)-1-isopropyl-2,4-dioxo-1,2,3,4-tetrahydro-pyrimidine-5-carboxylic acid{4-[6-(3,3-difluoro-pyrrolidin-1-yl)-pyrazolo[1,5-a]pyridin-4-yloxy]-3-fluoro-phenyl}-amide. This compound was synthesized from 4-[6-3,3-difluoro-pyrrolidin-1-yl)-pyrazolo[1,5-a]pyridin-4-yloxy]-3-fluoro-phenylamine and 3-(4-fluoro-phenyl)-1-isopropyl-2,4-dioxo-1,2,3,4-tetrahydro-pyrimidine-5-carboxylic acid using the methods described in example 69. mp=222-225° C.; LCMS m/z=623 (M+1); $^1$H NMR (DMSO-d$_6$) δ: 10.98 (s, 1H), 8.67 (s, 1H), 7.98 (m, 1H), 7.83 (m, 2H), 7.33-7.44 (br m, 5H), 7.28 (m, 1H), 6.45 (m, 2H), 4.77 (m, 1H), 3.65 (m, 2H), 3.40 (m, 2H), 2.46 (m, 2H), 1.42 (d, 6H, J=6.8 Hz).

Example 72

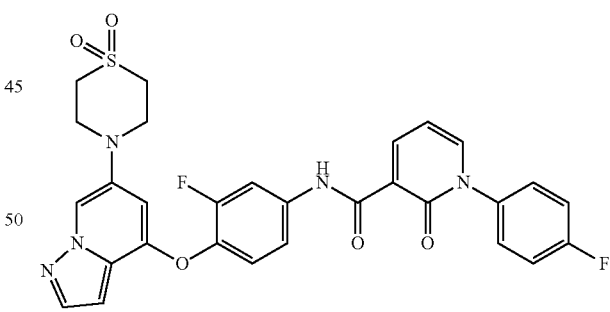

1-(4-Fluoro-phenyl)-2-oxo-1,2-dihydro-pyridine-3-carboxylic acid{4-[6-(1,1-dioxo-thiomorpholin-4-yl)-pyrazolo[1,5-a]pyridin-4-yloxy]-3-fluoro-phenyl}-amide. This compound was synthesized from 4-[6-(1,1-dioxo-thiomorpholin-4-yl)-pyrazolo[1,5-a]pyridin-4-yloxy]-3-fluoro-phenylamine and 1-(4-fluoro-phenyl)-2-oxo-1,2-dihydro-pyridine-3-carboxylic acid using the methods described in example 1 or 41. mp=125° C.; LCMS m/z=592 (M+1); $^1$H NMR (DMSO-d$_6$) δ: 12.07 (s, 1H), 8.59 (m, 1H), 8.16 (s, 1H), 8.14 (m, 1H), 8.03 (m, 1H), 7.88 (m, 1H), 7.60 (m, 2H), 7.44 (m, 3H), 7.32 (m, 1H), 6.74 (m, 1H), 6.62 (m, 1H), 6.50 (m, 1H), 3.55 (m, 4H), 3.20 (m, 4H).

Example 73

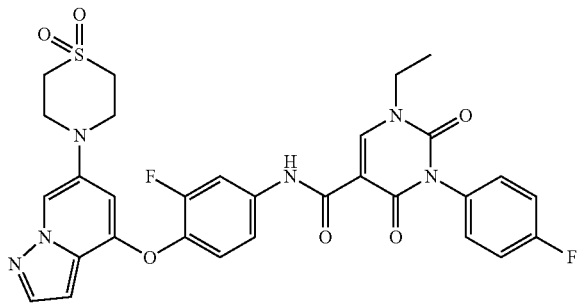 [SMILES: CCn1cc(C(=O)Nc2ccc(Oc3cc(N4CCS(=O)(=O)CC4)cn4nccc34)c(F)c2)c(=O)n(-c2ccc(F)cc2)c1=O]

1-Ethyl-3-(4-fluoro-phenyl)-2,4-dioxo-1,2,3,4-tetrahydro-pyrimidine-5-carboxylic acid{4-[6-(1,1-dioxo-thiomorpholin-4-yl)-pyrazolo[1,5-a]pyridin-4-yloxy]-3-fluoro-phenyl}-amide. This compound was synthesized from 4-[6-(1,1-dioxo-thiomorpholin-4-yl)-pyrazolo[1,5-a]pyridin-4-yloxy]-3-fluoro-phenylamine and 1-ethyl-3-(4-fluoro-phenyl)-2,4-dioxo-1,2,3,4-tetrahydro-pyrimidine-5-carboxylic acid using the methods described for example 69. mp=133° C.; LCMS m/z=637 (M+1); $^1$H NMR (DMSO-$d_6$) δ: 10.99 (s, 1H), 8.87 (s, 1H), 8.16 (s, 1H), 7.98 (m, 1H), 7.88 (m, 1H), 7.27-7.45 (br m, 6H), 6.61 (m, 1H), 6.51 (m, 1H), 4.02 (q, 2H), 3.56 (m, 4H), 3.19 (m, 4H), 1.29 (t, 3H, J=7.1 Hz).

Example 74

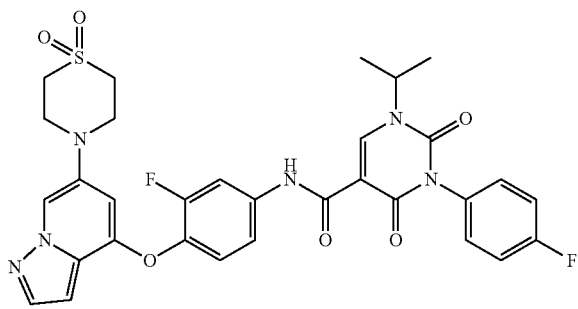 [SMILES: CC(C)n1cc(C(=O)Nc2ccc(Oc3cc(N4CCS(=O)(=O)CC4)cn4nccc34)c(F)c2)c(=O)n(-c2ccc(F)cc2)c1=O]

3-(4-Fluoro-phenyl)-1-isopropyl-2,4-dioxo-1,2,3,4-tetrahydro-pyrimidine-5-carboxylic acid{4-[6-(1,1-dioxo-thiomorpholin-4-yl)-pyrazolo[1, 5-a]pyridin-4-yloxy]-3-fluoro-phenyl}-amide. The compound was synthesized from 4-[6-(1,1-dioxo-thiomorpholin-4-yl)-pyrazolo[1,5-a]pyridin-4-yloxy]-3-fluoro-phenylamine and 3-(4-fluoro-phenyl)-1-isopropyl-2,4-dioxo-1,2,3,4-tetrahydro-pyrimidine-5-carboxylic acid using the methods described for example 69. mp=252° C.; LCMS m/z=651 (M+1); $^1$H NMR (DMSO-$d_6$) δ: 10.98 (s, 1H), 8.66 (s, 1H), 8.16 (s, 1H), 7.98 (m, 1H), 7.88 (m, 1H), 7.26-7.44 (br m, 6H), 6.63 (m, 1H), 6.50 (m, 1H), 4.75 (m, 1H), 3.56 (m, 4H), 3.18 (m, 4H), 1.43 (d, 6H, J=6.8 Hz).

Example 75

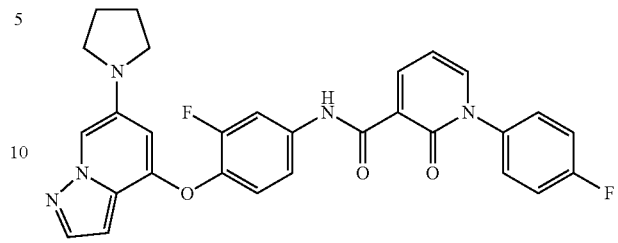

Step 1. 4-(2-Fluoro-4-nitro-phenoxy)-6-pyrrolidin-1-yl-pyrazolo[1,5-a]pyridine. To an oven dried schlenck flask was added 6-bromo-4-(2-fluoro-4-nitro-phenoxy)-pyrazolo[1,5-a]pyridine (0.2 g, 0.57 mmol), pyrrolidine (0.95 mL, 1.14 mmol), tris(dibenzylideneacetone)dipalladium(0) (0.1 g, 0.11 mmol), rac.-2,2'-bis(diphenylphosphino)-1,1'-binaphthyl (0.14 g, 0.4 mmol), sodium tert-butoxide (0.08 g, 0.85 mmol), followed by xylenes (10 mL) and was degassed 5 min. under an atmosphere of nitrogen and heated at 120° C. for 2 h. The reaction was cooled to rt, diluted with dichloromethane, filtered through a pad of celite, washed with 1N sodium carbonate, water/brine, dried over sodium sulfate, and concentrated. The product was chromatographed on silica gel using a single step column (0.5-1% methanol/dichloromethane) and concentrated to give 0.04 g, 20%. LCMS m/z=343 (M+1).

Step 2. 1-(4-Fluoro-phenyl)-2-oxo-1,2-dihydro-pyridine-3-carboxylic acid[3-fluoro-4-(6-pyrrolidin-1-yl-pyrazolo[1,5-a]pyridin-4-yloxy)-phenyl]-amide. This compound was synthesized from 3-fluoro-4-(6-pyrrolidin-1-ylpyrazolo[1,5-a]pyridin-4-yloxy)-phenylamine and 1-(4-fluoro-phenyl)-2-oxo-1,2-dihydro-pyridine-3-carboxylic acid using the methods described in example 41 step 3 and step 4. mp=190° C.; LCMS m/z=528 (M+1); $^1$H NMR (DMSO-$d_6$) δ: 12.07 (s, 1H), 8.59 (m, 1H), 8.16 (m, 1H), 8.03 (m, 1H), 7.74 (m, 1H), 7.62 (m, 3H), 7.42 (m, 3H), 7.29 (m, 1H), 6.74 (m, 1H), 6.40 (m, 1H), 6.31 (m, 1H), 3.13 (m, 4H), 1.91 (m, 4H).

Example 76

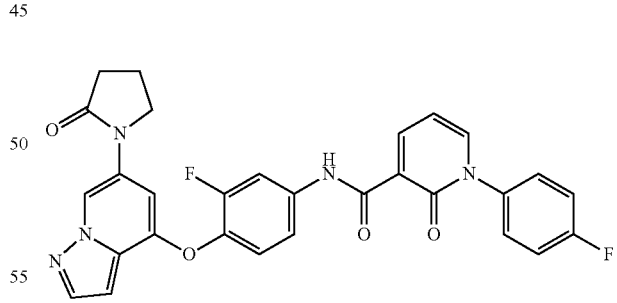

Step 1. 1-[4-(2-Fluoro-4-nitro-phenoxy)-pyrazolo[1,5-a]pyridin-6-yl]-pyrrolidin-2-one. To an oven dried schlenck flask was added 6-bromo-4-(2-fluoro-4-nitro-phenoxy)-pyrazolo[1,5-a]pyridine (0.2 g, 0.57 mmol), 2-pyrrolidinone (0.09 g, 1.14 mmol), tris(dibenzylideneacetone)dipalladium (0) (0.05 g, 0.06 mmol), 9,9-dimethyl-4,5-bis(diphenylphosphino)xanthene (0.07 g, 0.11 mmol), cesium carbonate (0.56 g, 1.7 mmol), and 1,4-dioxane (8 mL) and was degassed 5 min. under an atmosphere of nitrogen. The mixture was heated at 100° C. overnight. The reaction was cooled to rt, diluted with dichloromethane, filtered through celite, washed with water and brine, dried over sodium sulfate, and concentrated. The product was chromatographed on silica gel using a single step column (1-2% methanol/dichloromethane) and concentrated to give 0.12 g, 57%. LCMS m/z=357 (M+1).

Step 2. 1-(4-Fluoro-phenyl)-2-oxo-1,2-dihydro-pyridine-3-carboxylic acid{3-fluoro-4-[6-(2-oxo-pyrrolidin-1-yl)-pyrazolo[1,5-a]pyridin-4-yloxy]-phenyl}-amide. This compound was synthesized from 1-[4-(4-amino-2-fluoro-phenoxy)-pyrazolo[1,5-a]pyridin-6-yl]pyrrolidin-2-one and 1-(4-fluoro-phenyl)-2-oxo-1,2-dihydro-pyridine-3-carboxylic acid using the methods described in example 41 step 3 and step 4. mp=193° C.; LCMS m/z=542 (M+1); $^1$H NMR (DMSO-d$_6$) δ 12.09 (s, 1H), 8.63 (s, 1H), 8.59 (m, 1H), 8.14 (m, 1H), 8.01 (m, 2H), 7.60 (m, 2H), 7.33-7.48 (br m, 4H), 7.24 (s, 1H), 6.74 (m, 1H), 6.68 (m, 1H), 3.79 (m, 2H), 2.43 (m, 2H), 2.05 (m, 2H).

Example 77

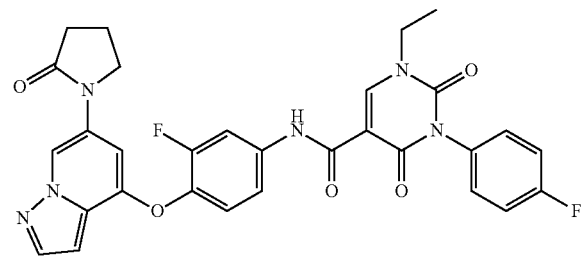 [SMILES: CCn1cc(C(=O)Nc2ccc(Oc3cc(N4CCCC4=O)cn4nccc34)c(F)c2)c(=O)n(-c2ccc(F)cc2)c1=O]

1-Ethyl-3-(4-fluoro-phenyl)-2,4-dioxo-1,2,3,4-tetrahydro-pyrimidine-5-carboxylic acid{3-fluoro-4-[6-(2-oxo-pyrrolidin-1-yl)-pyrazolo[1,5-a]pyridin-4-yloxy]-phenyl}-amide. This compound was synthesized from 1-[4-(4-amino-2-fluoro-phenoxy)-pyrazolo[1,5-a]pyridin-6-yl]pyrrolidin-2-one and 1-ethyl-3-(4-fluoro-phenyl)-2,4-dioxo-1,2,3,4-tetrahydro-pyrimidine-5-carboxylic acid using the methods described in example 76. mp=155-159° C.; LCMS m/z=587 (M+1); $^1$H NMR (DMSO-d$_6$) δ: 11.01 (s, 1H), 8.88 (s, 1H), 8.63 (s, 1H), 8.01 (m, 2H), 7.33-7.50 (br m, 6H), 7.23 (s, 1H), 6.68 (m, 1H), 4.00 (q, 2H), 3.81 (m, 2H), 2.43 (m, 2H), 2.05 (m, 2H), 1.29 (t, 3H, J=7.0 Hz).

Example 78

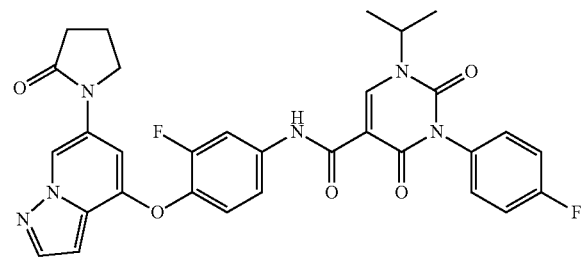 [SMILES: CC(C)n1cc(C(=O)Nc2ccc(Oc3cc(N4CCCC4=O)cn4nccc34)c(F)c2)c(=O)n(-c2ccc(F)cc2)c1=O]

3-(4-Fluoro-phenyl)-1-isopropyl-2,4-dioxo-1,2,3,4-tetrahydro-pyrimidine-5-carboxylic acid {3-fluoro-4-[6-(2-oxo-pyrrolidin-1-yl)-pyrazolo[1,5-a]pyridin-4-yloxy]-phenyl}-amide. The compound was synthesized from 1-[4-(4-amino-2-fluoro-phenoxy)-pyrazolo[1,5-a]pyridin-6-yl]pyrrolidin-2-one and 3-(4-fluoro-phenyl)-1-isopropyl-2,4-dioxo-1,2,3,4-tetrahydro-pyrimidine-5-carboxylic acid using the methods described in example 76. mp=119-122° C.; LCMS m/z=601 (M+1); $^1$H NMR (DMSO-d$_6$) δ 11.01 (s, 1H), 8.67 (s, 1H), 8.63 (s, 1H), 8.01 (m, 2H), 7.33-7.50 (br m, 6H), 7.25 (s, 1H), 6.67 (m, 1H), 4.79 (m, 1H), 3.81 (m, 2H), 2.43 (m, 2H), 2.05 (m, 2H), 1.43 (d, 6H, J=6.8 Hz).

Example 79

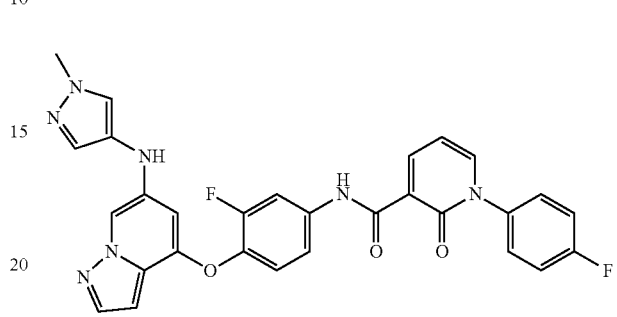

Step 1. [4-(2-Fluoro-4-nitro-phenoxy)-pyrazolo[1,5-a]pyridin-6-yl]-(1-methyl-1H-pyrazol-4-yl)-amine. To an oven dried schlenck flask was added 6-bromo-4-(2-fluoro-4-nitro-phenoxy)-pyrazolo[1,5-a]pyridine (0.2 g, 0.57 mmol), 1-methyl-1H-pyrazol-4-ylamine; hydrochloride (0.15 g, 1.14 mmol), tris(dibenzylideneacetone)dipalladium (0) (0.05 g, 0.06 mmol), 9,9-dimethyl-4,5-bis(diphenylphosphino)xanthene (0.07 g, 0.11 mmol), sodium tert-butoxide (0.16 g, 1.7 mmol), followed by 1,4-dioxane (10 mL) and was degassed for 5 min. under an atmosphere of nitrogen and heated at 100° C. for 2 h. The reaction was cooled to rt, diluted with dichloromethane, filtered through a pad of celite, washed with water, dried over sodium sulfate, and concentrated. The product was chromatographed on silica gel using a single step column (1-5% methanol/dichloromethane) and concentrated to give 0.09 g, 42%. LCMS m/z=369 (M+1).

Step 2. 1-(4-Fluoro-phenyl)-2-oxo-1,2-dihydro-pyridine-3-carboxylic acid {3-fluoro-4-[6-(1-methyl-1H-pyrazol-4-ylamino)-pyrazolo[1,5-a]pyridin-4-yloxy]-phenyl}-amide. This compound was synthesized from [4-(4-amino-2-fluoro-phenoxy)-pyrazolo[1,5-a]pyridin-6-yl]-(1-methyl-1H-pyrazol-4-yl)-amine and 1-(4-fluoro-phenyl)-2-oxo-1,2-dihydro-pyridine-3-carboxylic acid using the methods described in example 41 step 3 and step 4. mp=98-100° C.; LCMS m/z=554 (M+1); $^1$H NMR (DMSO-d$_6$) δ 12.08 (s, 1H), 8.60 (m, 1H), 8.14 (m, 1H), 8.06 (m, 1H), 7.58-7.76 (br m, 5H), 7.45 (m, 5H), 7.27 (m, 1H), 6.78 (m, 1H), 6.62 (m, 1H), 6.21 (s, 1H), 3.79 (s, 3H).

Example 80

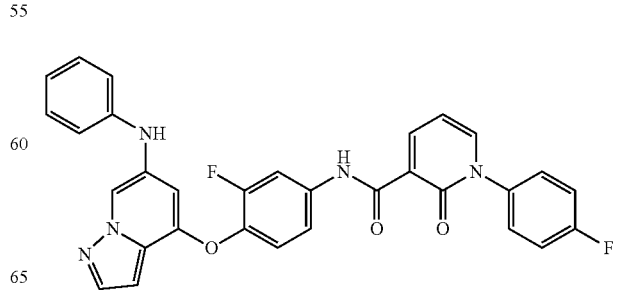

1-(4-Fluoro-phenyl)-2-oxo-1,2-dihydro-pyridine-3-carboxylic acid[3-fluoro-4-(6-phenylamino-pyrazolo[1,5-a]pyridin-4-yloxy)-phenyl]-amide. The compound was synthesized from [4-(4-amino-2-fluoro-phenoxy)-pyrazolo[1,5-a]pyridin-6-yl]-phenyl-amine and 1-(4-fluoro-phenyl)-2-oxo-1,2-dihydro-pyridine-3-carboxylic acid using the methods described in example 79. mp=93-95° C.; LCMS m/z=550 (M+1); $^1$H NMR (DMSO-$d_6$) δ: 12.08 (s, 1H), 8.59 (m, 1H), 8.16 (m, 2H), 8.05 (m, 2H), 7.87 (m, 1H), 7.62 (m, 2H), 7.40-7.51 (m, 4H), 7.29 (m, 2H), 7.00 (m, 2H), 6.83 (m, 1H), 6.74 (m, 1H), 6.65 (m, 1H), 6.34 (s, 1H).

Example 81

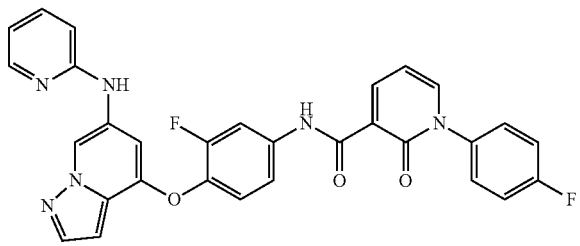 [SMILES: O=C(Nc1ccc(Oc2cc(Nc3ccccn3)cn3nccc23)c(F)c1)c1cccn(-c2ccc(F)cc2)c1=O]

1-(4-Fluoro-phenyl)-2-oxo-1,2-dihydro-pyridine-3-carboxylic acid{3-fluoro-4-[6-(pyridin-2-ylamino)-pyrazolo[1,5-a]pyridin-4-yloxy]-phenyl}-amide. This compound was synthesized from [4-(4-amino-2-fluoro-phenoxy)-pyrazolo[1,5-a]pyridin-6-yl]-pyridin-2-yl-amine and 1-(4-fluoro-phenyl)-2-oxo-1,2-dihydro-pyridine-3-carboxylic acid using the methods described in example 79. mp=176° C.; LCMS m/z=551 (M+1); $^1$H NMR (DMSO-$d_6$) δ: 12.10 (s, 1H), 9.58 (s, 1H), 9.05 (s, 1H), 8.60 (m, 1H), 8.25 (m, 1H), 8.15 (m, 1H), 8.08 (m, 1H), 7.88 (m, 1H), 7.40 (m, 3H), 7.60 (br m, 4H), 6.79 (m, 3H), 6.65 (m, 1H), 6.42 (s, 1H).

Example 82

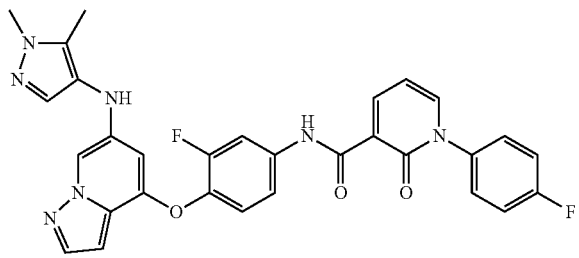 [SMILES: Cc1c(Nc2cc(Oc3ccc(NC(=O)c4cccn(-c5ccc(F)cc5)c4=O)cc3F)c3ccnn3c2)cnn1C]

1-(4-Fluoro-phenyl)-2-oxo-1,2-dihydro-pyridine-3-carboxylic acid{4-[6-(1,5-dimethyl-1H-pyrazol-4-ylamino)-pyrazolo[1,5-a]pyridin-4-yloxy]-3-fluoro-phenyl}-amide. This compound was synthesized from [4-(4-amino-2-fluoro-phenoxy)-pyrazolo[1,5-a]pyridin-6-yl]-(1,5-dimethyl-1H-pyrazol-4-yl)-amine and 1-(4-fluoro-phenyl)-2-oxo-1,2-dihydro-pyridine-3-carboxylic acid using the methods described in example 79. mp=105° C.; LCMS m/z=568 (M+1); $^1$H NMR (DMSO-$d_6$) δ: 12.08 (s, 1H), 8.60 (m, 1H), 8.14 (m, 1H), 8.06 (m, 1H), 7.72 (m, 1H), 7.62 (m, 2H), 7.52 (m, 1H), 7.37-7.45 (m, 3H), 7.28 (m, 2H), 6.98 (s, 1H), 6.80 (m, 1H), 6.62 (m, 1H), 6.27 (s, 1H), 3.71 (s, 3H), 2.08 (s, 3H).

Example 83

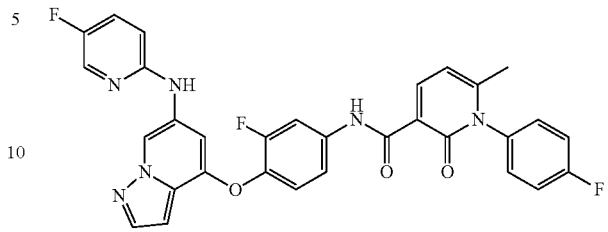

1-(4-Fluoro-phenyl)-6-methyl-2-oxo-1,2-dihydro-pyridine-3-carboxylic acid {3-fluoro-4-[6-(5-fluoro-pyridin-2-ylamino)-pyrazolo[1,5-a]pyridin-4-yloxy]-phenyl}-amide. This compound was synthesized from [4-(4-amino-2-fluoro-phenoxy)-pyrazolo[1,5-a]pyridin-6-yl]-(5-fluoro-pyridin-2-yl)-amine and 1-(4-fluoro-phenyl)-6-methyl-2-oxo-1,2-dihydro-pyridine-3-carboxylic acid using the buchwald method described in example 79 step 1 and the methods described in example 61 step 2 and step 3. mp=224° C.; LCMS m/z=583 (M+1); $^1$H NMR (DMSO-$d_6$) δ: 12.07 (s, 1H), 9.49 (s, 1H), 9.12 (s, 1H), 8.51 (d, 1H, J=7.5 Hz), 8.23 (m, 1H), 8.07 (m, 1H), 7.88 (m, 1H), 7.55 (br m, 7H), 6.81 (m, 1H), 6.73 (m, 1H), 6.65 (m, 1H), 6.36 (s, 1H), 2.03 (s, 3H).

Example 84

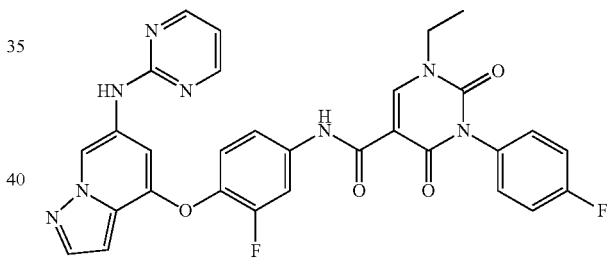

Step 1. [4-(2-Fluoro-4-nitro-phenoxy)-pyrazolo[1,5-a]pyridin-6-yl]-pyrimidin-2-yl-amine. To an oven dried schlenck flask was added 4-(2-fluoro-4-nitro-phenoxy)-pyrazolo[1,5-a]pyridin-6-ylamine (0.18 g, 0.61 mmol), 2-chloropyrimidine (0.08 g, 0.74 mmol), palladium acetate (0.01 g, 0.06 mmol), 2,2'-bis-dicyclohexylphosphanyl-biphenyl (0.07 g, 0.12 mmol), cesium carbonate (0.6 g, 1.84 mmol), followed by 1,4-dioxane (8 mL) and was degassed for 5 min. under an atmosphere of nitrogen and heated at 100° C. overnight. The reaction was cooled at rt, diluted with dichloromethane, filtered through a pad of celite, washed with water/brine, dried over sodium sulfate, and concentrated. The product was chromatographed on silica gel using a single step column (1-2% methanol/dichloromethane) and concentrated to give 0.16 g, 71%. LCMS m/z=367 (M+1).

Step 2. 1-Ethyl-3-(4-fluoro-phenyl)-2,4-dioxo-1,2,3,4-tetrahydro-pyrimidine-5-carboxylic acid{3-fluoro-4-[6-(pyrimidin-2-ylamino)-pyrazolo[1,5-a]pyridin-4-yloxy]-phenyl}-amide. The compound was synthesized from [4-(4-amino-2-fluoro-phenoxy)-pyrazolo[1,5-a]pyridin-6-yl]-pyrimidin-2-yl-amine and 1-ethyl-3-(4-fluoro-phenyl)-2,4-dioxo-1,2,3,4-tetrahydro-pyrimidine-5-carboxylic acid using the methods described in example 61 step 2 and step 3. mp=136-139° C.; LCMS m/z=597 (M+1); ¹H NMR (DMSO-d₆) δ 11.02 (s, 1H), 9.60 (s, 1H), 9.38 (s, 1H), 8.89 (s, 1H), 8.53 (m, 2H), 8.03 (m, 1H), 7.91 (m, 1H), 7.33-7.52 (br m, 6H), 6.89 (m, 1H), 6.77 (s, 1H), 6.63 (m, 1H), 4.02 (q, 2H), 1.31 (t, 3H, J=7.0 Hz).

Example 85

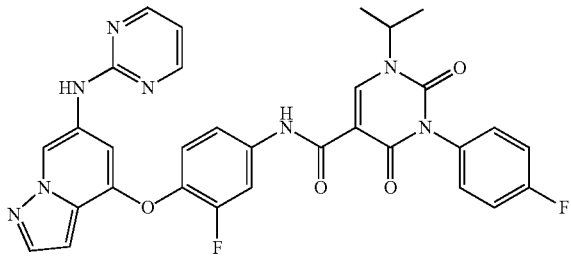 [SMILES: CC(C)n1cc(C(=O)Nc2ccc(Oc3cc(Nc4ncccn4)cn4nccc34)c(F)c2)c(=O)n(-c2ccc(F)cc2)c1=O]

3-(4-Fluoro-phenyl)-1-isopropyl-2,4-dioxo-1,2,3,4-tetrahydro-pyrimidine-5-carboxylic acid{3-fluoro-4-[6-(pyrimidin-2-ylamino)-pyrazolo[1,5-a]pyridin-4-yloxy]-phenyl}-amide. The compound was synthesized from [4-(4-amino-2-fluoro-phenoxy)-pyrazolo[1,5-a]pyridin-6-yl]-pyrimidin-2-yl-amine and 3-(4-fluoro-phenyl)-1-isopropyl-2,4-dioxo-1,2,3,4-tetrahydro-pyrimidine-5-carboxylic acid using the methods described in example 84. mp=207-210° C.; LCMS m/z=611 (M+1); ¹H NMR (DMSO-d₆) δ: 11.03 (s, 1H), 9.61 (s, 1H), 9.39 (s, 1H), 8.68 (s, 1H), 8.53 (m, 2H), 8.03 (m, 1H), 7.91 (m, 1H), 7.33-7.52 (br m, 6H), 6.88 (m, 1H), 6.78 (s, 1H), 6.63 (m, 1H), 4.79 (m, 1H), 1.43 (d, 6H, J=6.8 Hz).

Example 86

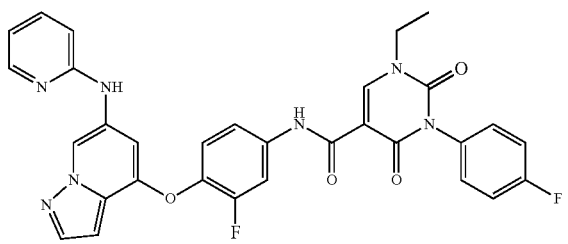 [SMILES: CCn1cc(C(=O)Nc2ccc(Oc3cc(Nc4ccccn4)cn4nccc34)c(F)c2)c(=O)n(-c2ccc(F)cc2)c1=O]

1-Ethyl-3-(4-fluoro-phenyl)-2,4-dioxo-1,2,3,4-tetrahydro-pyrimidine-5-carboxylic acid{3-fluoro-4-[6-(pyridin-2-ylamino)-pyrazolo[1,5-a]pyridin-4-yloxy]-phenyl}-amide. This compound was synthesized from [4-(4-amino-2-fluoro-phenoxy)-pyrazolo[1,5-a]pyridin-6-yl]-pyridin-2-yl-amine and 1-ethyl-3-(4-fluoro-phenyl)-2,4-dioxo-1,2,3,4-tetrahydro-pyrimidine-5-carboxylic acid using the methods described in example 84. mp=191° C.; LCMS m/z=596 (M+1); ¹H NMR (DMSO-d₆) δ 11.02 (s, 1H), 9.57 (s, 1H), 9.04 (s, 1H), 8.89 (s, 1H), 8.24 (m, 1H), 8.03 (m, 1H), 7.88 (m, 1H), 7.33-7.59 (br m, 7H), 6.79 (m, 2H), 6.65 (m, 1H), 6.41 (s, 1H), 4.02 (q, 2H), 1.31 (t, 3H, J=7.0 Hz).

Example 87

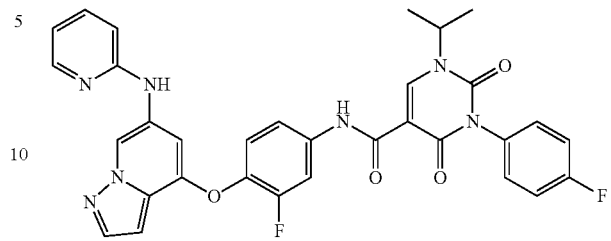

3-(4-Fluoro-phenyl)-1-isopropyl-2,4-dioxo-1,2,3,4-tetrahydro-pyrimidine-5-carboxylic acid{3-fluoro-4-[6-(pyridin-2-ylamino)-pyrazolo[1,5-a]pyridin-4-yloxy]-phenyl}-amide. This compound was synthesized from [4-(4-amino-2-fluoro-phenoxy)-pyrazolo[1,5-a]pyridin-6-yl]-pyridin-2-yl-amine and 3-(4-fluoro-phenyl)-1-isopropyl-2,4-dioxo-1,2,3,4-tetrahydro-pyrimidine-5-carboxylic acid using the methods described in example 84. mp=189° C.; LCMS m/z=610 (M+1); ¹H NMR (DMSO-d₆) δ 11.03 (s, 1H), 9.57 (s, 1H), 9.04 (s, 1H), 8.68 (s, 1H), 8.24 (m, 1H), 8.04 (m, 1H), 7.88 (m, 1H), 7.33-7.58 (br m, 7H), 6.79 (m, 2H), 6.65 (m, 1H), 6.42 (s, 1H), 4.79 (m, 1H), 1.43 (d, 6H, J=6.8 Hz).

Example 88

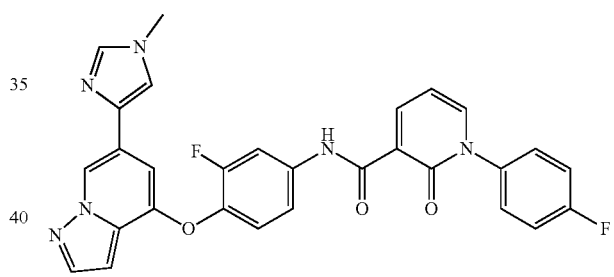

Step 1. 4-(2-Fluoro-4-nitro-phenoxy)-6-(1-methyl-1H-imidazol-4-yl)-pyrazolo[1,5-a]pyridine. To an oven dried schlenck flask was added 6-bromo-4-(2-fluoro-4-nitro-phenoxy)-pyrazolo[1,5-a]pyridine (0.15 g, 0.43 mmol), 1-methyl-4-tributylstannyl-1H-imidazole (0.79 g, 2.13 mmol), bis(triphenylphosphine)palladium(II) chloride (0.06 g, 0.09 mmol), followed by N,N-dimethylformamide (7 mL) and was degassed 3× under an atmosphere of nitrogen and heated at 130° C. for 1 h and cooled at rt. The reaction was partitioned between ethyl acetate/1N sodium carbonate, washed with water/brine, dried over sodium sulfate, and concentrated. The product was chromatographed on silica gel using a single step column (1-5% methanol/dichloromethane) and triturated with hexanes to give 0.1 g, 66%. LCMS m/z=354 (M+1). ¹H NMR (DMSO) δ: 8.90 (s, 1H), 8.42 (m, 1H), 8.10 (m, 1H), 8.01 (m, 1H), 7.72 (m, 1H), 7.66 (m, 1H), 7.43 (m, 1H), 7.34 (m, 1H), 6.58 (m, 1H), 3.67 (s, 3H).

Step 2. 3-Fluoro-4-[6-(1-methyl-1H-imidazol-4-yl)-pyrazolo[1,5-a]pyridin-4-yloxy]-phenylamine. 4-(2-Fluoro-4-nitro-phenoxy)-6-(1-methyl-1H-imidazol-4-yl)-pyrazolo[1,5-a]pyridine was reduced using the procedure for example 41 step 3. LCMS m/z=324 (M+1); ¹H NMR (DMSO) δ: 8.71 (s, 1H), 7.97 (m, 1H), 7.61 (m, 2H), 7.07 (m, 1H), 6.70 (m, 2H), 6.56 (m, 1H), 6.46 (m, 1H), 5.47 (br s, 2H), 3.65 (s, 3H).

Step 3. 1-(4-Fluoro-phenyl)-2-oxo-1,2-dihydro-pyridine-3-carboxylic acid {3-fluoro-4-[6-(1-methyl-1H-imidazol-4-yl)-pyrazolo[1,5-a]pyridin-4-yloxy]-phenyl}-amide. This compound was synthesized from 3-fluoro-4-[6-(1-methyl-1H-imidazol-4-yl)-pyrazolo[1,5-a]pyridin-4-yloxy]-phenylamine and 1-(4-fluoro-phenyl)-2-oxo-1,2-dihydro-pyridine-3-carboxylic acid using the methods described in example 41 step 4. mp=226° C.; LCMS m/z=539 (M+1); $^1$H NMR (DMSO-d$_6$) δ: 12.10 (s, 1H), 8.77 (s, 1H), 8.60 (m, 1H), 8.14 (m, 1H), 8.06 (m, 1H), 7.99 (m, 1H), 7.59-7.65 (m, 4H), 7.39-7.48 (m, 4H), 6.85 (s, 1H), 6.75 (m, 1H), 6.68 (m, 1H), 3.64 (s, 3H).

Example 89

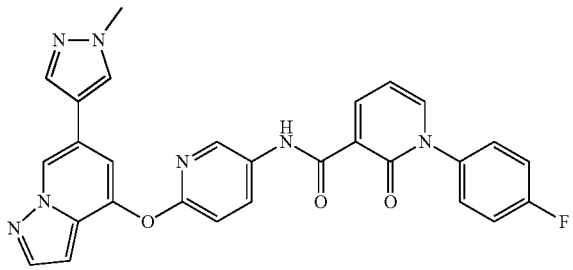 [SMILES: Cn1cc(-c2cc(Oc3ccc(NC(=O)c4cccn(-c5ccc(F)cc5)c4=O)cn3)c3ccnn3c2)cn1]

Step 1. 6-Bromo-4-(5-nitro-pyridin-2-yloxy)-pyrazolo[1,5-a]pyridine. To 6-bromo-pyrazolo[1,5-a]pyridin-4-ol (0.12 g, 0.56 mmol) in N,N-dimethylformamide (2 mL) under an atmosphere of nitrogen at 0° C. was added sodium hydride, 60% dispersion in mineral oil (3:2, sodium hydride:mineral oil) (0.06 g, 1.4 mmol). After stirring 0.5 h at rt, 2-fluoro-5-nitro-pyridine (0.09 g, 1.1 mmol) was added dropwise and stirred at rt for 4 h. The reaction was diluted with ethyl acetate, washed with water and brine, dried over sodium sulfate, and concentrated. The product was chromatographed on silica gel using a single step column (10-20% ethyl acetate/hexanes) and concentrated to give 0.08 g, 43%. LCMS m/z=336 (M+1).

Step 2. 6-(1-Methyl-1H-pyrazol-4-yl)-4-(5-nitro-pyridin-2-yloxy)-pyrazolo[1,5-a]pyridine. This compound was synthesized from 6-bromo-4-(5-nitro-pyridin-2-yloxy)-pyrazolo[1,5-a]pyridine and 1-methyl-4-(4,4,5,5-tetramethyl-[1,3,2]dioxaborolan-2-yl)-1H-pyrazole using the susuki method described in example 41 step 2. LCMS m/z=337 (M+1).

Step 3. 6-[6-(1-Methyl-1H-pyrazol-4-yl)-pyrazolo[1,5-a]pyridin-4-yloxy]-pyridin-3-ylamine. This compound was synthesized from 6-(1-methyl-1H-pyrazol-4-yl)-4-(5-nitro-pyridin-2-yloxy)-pyrazolo[1,5-a]pyridine and tin (II) chloride dihydrate using the reduction method described in example 61 step 2. LCMS m/z=307 (M+1).

Step 4. 1-(4-Fluoro-phenyl)-2-oxo-1,2-dihydro-pyridine-3-carboxylic acid{6-[6-(1-methyl-1H-pyrazol-4-yl)-pyrazolo[1,5-a]pyridin-4-yloxy]-pyridin-3-yl}-amide. The compound was synthesized from 6-[6-(1-methyl-1H-pyrazol-4-yl)-pyrazolo[1,5-a]pyridin-4-yloxy]-pyridin-3-ylamine and 1-(4-fluoro-phenyl)-2-oxo-1,2-dihydro-pyridine-3-carboxylic acid using the amide coupling method described in example 41 step 4. mp=213° C.; LCMS m/z=522 (M+1); $^1$H NMR (DMSO-d$_6$) δ 11.92 (s, 1H), 8.92 (s, 1H), 8.58 (m, 1H), 8.43 (m, 1H), 8.32 (m, 1H), 8.24 (s, 1H), 8.13 (m, 1H), 8.00 (m, 1H), 7.91 (m, 1H), 7.61 (m, 2H), 7.41 (m, 2H), 7.32 (m, 1H), 7.25 (m, 1H), 6.73 (m, 1H), 6.28 (m, 1H), 3.85 (s, 3H).

Example 90

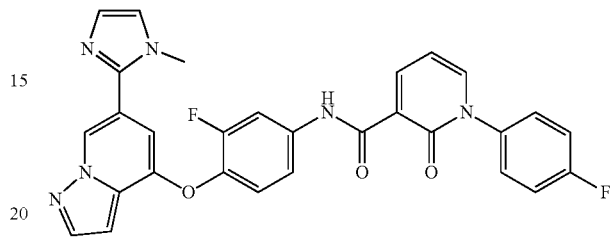

1-(4-Fluoro-phenyl)-2-oxo-1,2-dihydro-pyridine-3-carboxylic acid{3-fluoro-4-[6-(1-methyl-1H-imidazol-2-yl)-pyrazolo[1,5-a]pyridin-4-yloxy]-phenyl}-amide. This compound was synthesized from 3-fluoro-4-[6-(1-methyl-1H-imidazol-2-yl)-pyrazolo[1,5-a]pyridin-4-yloxy]-phenylamine and 1-(4-fluoro-phenyl)-2-oxo-1,2-dihydro-pyridine-3-carboxylic acid using the methods described in example 88. mp=205° C.; LCMS m/z=539 (M+1); $^1$H NMR (DMSO-d$_6$) δ: 12.10 (s, 1H), 8.82 (m, 1H), 8.60 (m, 1H), 8.14 (m, 2H), 8.05 (m, 1H), 7.62 (m, 2H), 7.51 (m, 1H), 7.42 (m, 3H), 7.25 (m, 1H), 6.92 (m, 1H), 6.81 (m, 1H), 6.74 (m, 2H) 3.81 (s, 3H).

Example 91

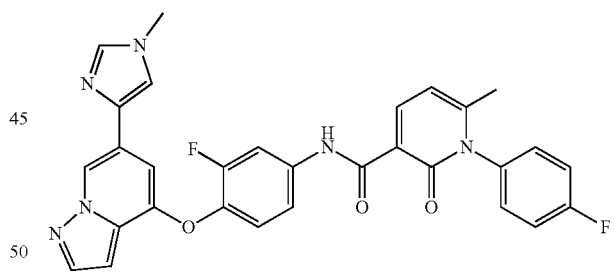

1-(4-Fluoro-phenyl)-6-methyl-2-oxo-1,2-dihydro-pyridine-3-carboxylic acid {3-fluoro-4-[6-(1-methyl-1H-imidazol-4-yl)-pyrazolo[1,5-a]pyridin-4-yloxy]-phenyl}-amide. This compound was synthesized from 3-fluoro-4-[6-(1-methyl-1H-imidazol-4-yl)-pyrazolo[1,5-a]pyridin-4-yloxy]-phenylamine and 1-(4-fluoro-phenyl)-6-methyl-2-oxo-1,2-dihydro-pyridine-3-carboxylic acid using the amide coupling method described in example 41 step 4. mp=245-250° C.; LCMS m/z=553 (M+1); $^1$H NMR (DMSO-d$_6$) δ: 12.06 (s, 1H), 8.77 (s, 1H), 8.51 (d, 1H, J=7.6 Hz), 8.05 (m, 2H), 7.65 (s, 1H), 7.59 (s, 1H), 7.44 (br m, 6H), 6.84 (s, 1H), 6.71 (m, 1H), 6.67 (m, 1H), 3.64 (s, 3H), 2.08 (s, 3H).

Example 92

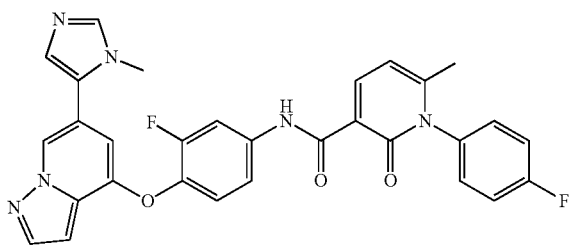 [SMILES: Cc1ccc(C(=O)Nc2ccc(Oc3cc(-c4cncn4C)cn4nccc34)c(F)c2)c(=O)n1-c1ccc(F)cc1]

1-(4-Fluoro-phenyl)-6-methyl-2-oxo-1,2-dihydro-pyridine-3-carboxylic acid {3-fluoro-4-[6-(3-methyl-3H-imidazol-4-yl)-pyrazolo[1,5-a]pyridin-4-yloxy]-phenyl}-amide. This compound was synthesized from 3-fluoro-4-[6-(3-methyl-3H-imidazol-4-yl)-pyrazolo[1,5-a]pyridin-4-yloxy]-phenylamine and 1-(4-fluoro-phenyl)-6-methyl-2-oxo-1,2-dihydro-pyridine-3-carboxylic acid using the methods described in example 88. mp=104-106° C.; LCMS m/z=553 (M+1); $^1$H NMR (DMSO-d$_6$) δ; 12.07 (s, 1H), 8.66 (s, 1H), 8.49 (d, 1H, J=7.6 Hz), 8.16 (m, 1H), 8.07 (m, 1H), 7.69 (s, 1H), 7.43 (br m, 5H), 7.36 (m, 1H), 7.06 (s, 1H), 6.70 (m, 2H), 6.60 (s, 1H), 3.63 (s, 3H), 2.07 (s, 3H).

Example 93

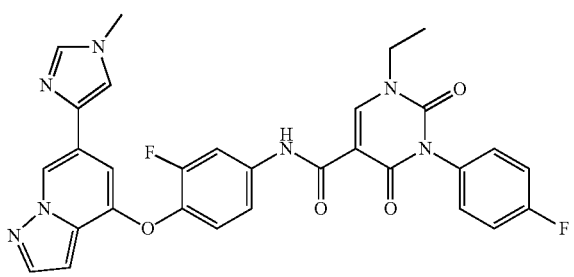

1-Ethyl-3-(4-fluoro-phenyl)-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide. This compound was synthesized from 3-fluoro-4-[6-(1-methyl-1H-imidazol-4-yl)-pyrazolo[1,5-a]pyridin-4-yloxy]-phenylamine and 1-ethyl-3-(4-fluoro-phenyl)-2,4-dioxo-1,2,3,4-tetrahydro-pyrimidine-5-carboxylic acid using the method described in example 88. mp=143° C.; LCMS m/z=584 (M+1); $^1$H NMR (DMSO-d$_6$) δ: 11.01 (s, 1H), 8.88 (s, 1H), 8.77 (s, 1H), 8.03 (m, 2H), 7.65 (s, 1H), 7.59 (s, 1H), 7.51 (m, 1H), 7.40 (br m, 5H), 6.84 (s, 1H), 6.68 (m, 1H), 4.04 (q, 2H), 3.64 (s, 3H), 1.31 (t, 3H, J=7.0 Hz).

Example 94

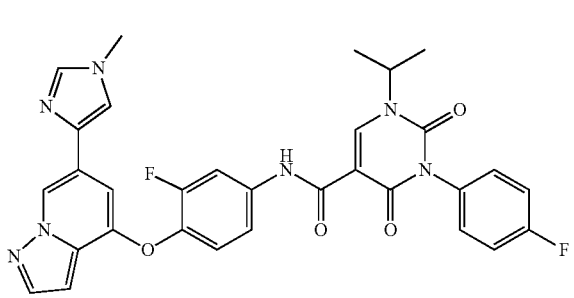 [SMILES: CC(C)n1cc(C(=O)Nc2ccc(Oc3cc(-c4cn(C)cn4)cn4nccc34)c(F)c2)c(=O)n(-c2ccc(F)cc2)c1=O]

3-(4-Fluoro-phenyl)-1-isopropyl-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide. This compound was synthesized from 3-fluoro-4-[6-(1-methyl-1H-imidazol-4-yl)-pyrazolo[1,5-a]pyridin-4-yloxy]-phenylamine and 3-(4-fluoro-phenyl)-1-isopropyl-2,4-dioxo-1,2,3,4-tetrahydro-pyrimidine-5-carboxylic acid using the methods described in example 88 step 4. mp=158° C.; LCMS m/z=598 (M+1); $^1$H NMR (DMSO-d$_6$) δ: 11.01 (s, 1H), 8.77 (s, 1H), 8.68 (s, 1H), 8.00 (m, 2H), 7.65 (s, 1H), 7.60 (s, 1H), 7.49 (m, 1H), 7.42 (br m, 5H), 6.86 (s, 1H), 6.67 (m, 1H), 4.79 (m, 1H), 3.65 (s, 3H), 1.43 (d, 6H, J=6.8 Hz).

3-(4-Fluoro-phenyl)-1-isopropyl-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide; hydrochloride. To 3-(4-fluoro-phenyl)-1-isopropyl-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide (0.25 g, 0.04 mmol) in ethyl acetate (2 mL) and methanol (2 mL) was added 2 M hydrochloric acid in ethanol (0.04 mL) and was concentrated. The HCl salt was crystallized from MeOH-ethyl acetate-ether to give 0.03 g, 94%. mp=180° C.

3-(4-Fluoro-phenyl)-1-isopropyl-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide; trifluoro-acetic acid salt. To 3-(4-fluoro-phenyl)-1-isopropyl-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide (0.03 g, 0.04 mmol) in ethyl acetate (2 mL) and methanol (2 mL) was added trifluoroacetic acid (0.01 mL, 0.08 mmol) and was concentrated. The TFA salt was crystallized from ethanol-ether. mp=195° C.

3-(4-Fluoro-phenyl)-1-isopropyl-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide; methanesulfonic acid salt. To 3-(4-fluoro-phenyl)-1-isopropyl-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide (0.03 g, 0.04 mmol) in ethyl acetate (2 mL) and methanol (2 mL) was added methanesulfonic acid (0.01 g, 0.08 mmol) and was concentrated. The salt was crystallized from MeOH-ethyl acetate-ether to give 0.02 g, 62%. mp=278° C.

Example 95

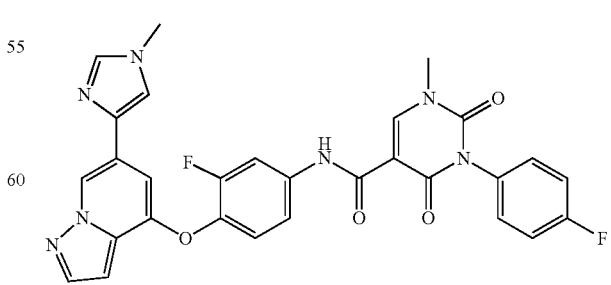

3-(4-Fluoro-phenyl)-1-methyl-2,4-dioxo-1,2,3,4-tetrahydro-pyrimidine-5-carboxylic acid{3-fluoro-4-[6-(1- methyl-1H-imidazol-4-yl)-pyrazolo[1,5-a]pyridin-4-yloxy]-phenyl}-amide. This compound was synthesized from 3-fluoro-4-[6-(1-methyl-1H-imidazol-4-yl)-pyrazolo[1,5-a]pyridin-4-yloxy]-phenylamine and 3-(4-fluoro-phenyl)-1-methyl-2,4-dioxo-1,2,3,4-tetrahydro-pyrimidine-5-carboxylic acid using the methods described in example 88. mp=153° C.; LCMS m/z=570 (M+1); $^1$H NMR (DMSO-d$_6$) δ: 11.01 (s, 1H), 8.89 (s, 1H), 8.77 (s, 1H), 8.01 (m, 2H), 7.65 (s, 1H), 7.59 (s, 1H), 7.51 (m, 1H), 7.42 (br m, 5H), 6.84 (s, 1H), 6.67 (m, 1H), 3.65 (s, 3H), 3.54 (s, 3H).

Example 96

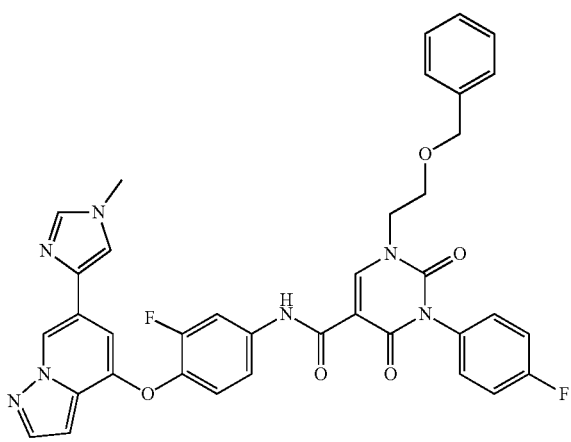 [SMILES: Cn1cnc(-c2cc(Oc3ccc(NC(=O)c4cn(CCOCc5ccccc5)c(=O)n(-c5ccc(F)cc5)c4=O)cc3F)c3ccnn3c2)c1]

1-(2-Benzyloxy-ethyl)-3-(4-fluoro-phenyl-)-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide. This compound was synthesized from 3-fluoro-4-[6-(1-methyl-1H-imidazol-4-yl)-pyrazolo[1,5-a]pyridin-4-yloxy]-phenylamine and 1-(2-benzyloxy-ethyl)-3-(4-fluoro-phenyl)-2,4-dioxo-1,2,3,4-tetrahydro-pyrimidine-5-carboxylic acid using the methods described in example 88. mp=213-215° C.; LCMS m/z=690 (M+1); $^1$H NMR (DMSO-d$_6$) δ: 10.98 (s, 1H), 8.84 (s, 1H), 8.77 (m, 1H), 8.01 (m, 2H), 7.65 (m, 2H), 7.53 (m, 1H), 7.33-7.42 (br m, 10H), 6.85 (s, 1H), 6.68 (m, 1H), 4.55 (m, 2H), 4.23 (m, 2H), 3.73 (m, 2H), 3.65 (s, 3H).

Example 97

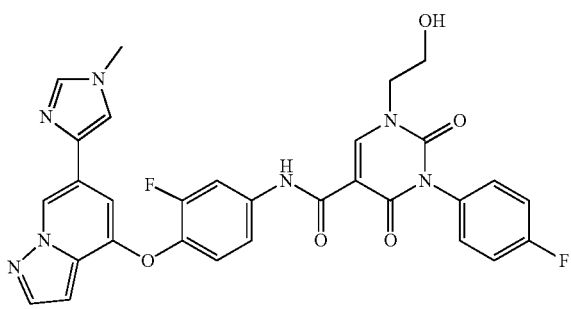 [SMILES: Cn1cnc(-c2cc(Oc3ccc(NC(=O)c4cn(CCO)c(=O)n(-c5ccc(F)cc5)c4=O)cc3F)c3ccnn3c2)c1]

3-(4-Fluoro-phenyl)-1-(2-hydroxy-ethyl)-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide. To example 96 (0.11 g, 15 mmol) in ethyl acetate (5 mL) and methanol (1 mL) was added 20% Pd(OH)$_2$/C, 50% wet (10:40:50, palladium hydroxide: carbon black:water) (0.02 g, 0.03 mmol), followed by 4 drops of conc. hydrochloric acid and was hydrogenated at 40 psi on a Parr overnight. The reaction was filtered through a pad of celite, washed with dichloromethane/methanol, concentrated, partitioned between dichloromethane and 1N sodium carbonate solution, washed with water and brine, dried over sodium sulfate, and concentrated. The product was purified using Prep TLC plates (8% methanol/dichloromethane) and concentrated to give 0.02 g, 12%. mp=237° C.; LCMS m/z=600 (M+1); $^1$H NMR (DMSO-d$_6$) δ; 11.00 (s, 1H), 8.82 (m, 2H), 8.01 (m, 2H), 7.63 (br m, 2H), 7.49 (m, 1H), 7.38 (br m, 5H), 6.84 (s, 1H) 6.68 (m, 1H), 5.07 (m, 1H), 4.05 (m, 2H), 3.69 (m, 2H), 3.64 (s, 3H).

Example 98

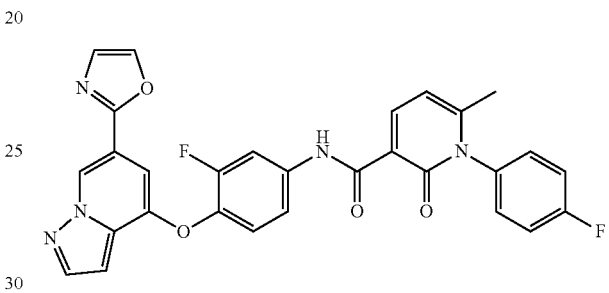

1-(4-Fluoro-phenyl)-6-methyl-2-oxo-1,2-dihydro-pyridine-3-carboxylic acid [3-fluoro-4-(6-oxazol-2-yl-pyrazolo[1,5-a]pyridin-4-yloxy)-phenyl]-amide. This compound was synthesized from 3-fluoro-4-(6-oxazol-2-yl-pyrazolo[1,5-a]pyridin-4-yloxy)-phenylamine and 1-(4-fluoro-phenyl)-6-methyl-2-oxo-1,2-dihydro-pyridine-3-carboxylic acid using the methods described in example 88. mp=118-120° C.; LCMS m/z=540 (M+1); $^1$H NMR (DMSO-d$_6$) δ: 12.14 (s, 1H), 9.03 (s, 1H), 8.51 (d, 1H, J=7.5 Hz), 8.20 (m, 2H), 8.08 (m, 1H), 7.50 (br m, 6H), 7.32 (s, 1H), 6.89 (m, 1H), 6.78 (s, 1H), 6.73 (m, 1H), 2.08 (s, 3H).

Example 99

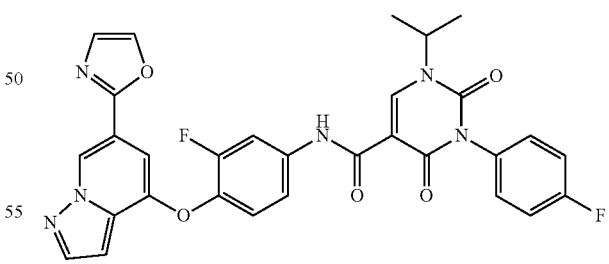

3-(4-Fluoro-phenyl)-1-isopropyl-2,4-dioxo-1,2,3,4-tetrahydro-pyrimidine-5-carboxylic acid[3-fluoro-4-(6-oxazol-2-yl-pyrazolo[1,5-a]pyridin-4-yloxy)-phenyl]-amide. This compound was synthesized from 3-fluoro-4-(6-oxazol-2-yl-pyrazolo[1,5-a]pyridin-4-yloxy)-phenylamine and 3-(4-fluoro-phenyl)-1-isopropyl-2,4-dioxo-1,2,3,4-tetrahydro-pyrimidine-5-carboxylic acid using the methods described in example 88 and 93. mp=255° C.; LCMS m/z=585 (M+1); $^1$H NMR (DMSO-d$_6$) δ: 11.04 (s, 1H), 9.03 (s, 1H), 8.68 (s, 1H), 8.21 (m, 2H), 8.04 (m, 1H), 7.32-7.53 (br m, 7H), 6.89 (m, 1H), 6.79 (s, 1H), 4.78 (m, 1H), 1.43 (d, 6H, J=6.8 Hz).

Example 100

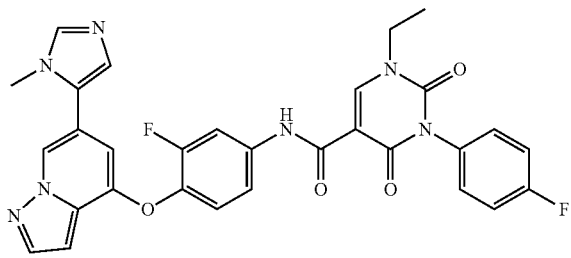

1-Ethyl-3-(4-fluoro-phenyl)-2,4-dioxo-1,2,3,4-tetra-hydro-pyrimidine-5-carboxylic acid{3-fluoro-4-[6-(3-methyl-3H-imidazol-4-yl)-pyrazolo[1,5-a]pyridin-4-yloxy]-phenyl}-amide. This compound was synthesized from 3-fluoro-4-[6-(3-methyl-3H-imidazol-4-yl)-pyrazolo[1,5-a]pyridin-4-yloxy]-phenylamine and 1-ethyl-3-(4-fluoro-phenyl)-2,4-dioxo-1,2,3,4-tetrahydro-pyrimidine-5-carboxylic acid using the methods described in example 88. mp=151° C.; LCMS m/z=584 (M+1); $^1$H NMR (DMSO-d$_6$) δ: 11.03 (s, 1H), 8.87 (s, 1H), 8.67 (s, 1H), 8.08 (m, 1H), 7.98 (m, 1H), 7.69 (s, 1H), 7.40 (br m, 6H), 7.06 (s, 1H), 6.70 (m, 1H), 6.61 (s, 1H), 4.01 (m, 2H), 3.63 (s, 3H), 1.30 (t, 3H, J=7.0 Hz).

Example 101

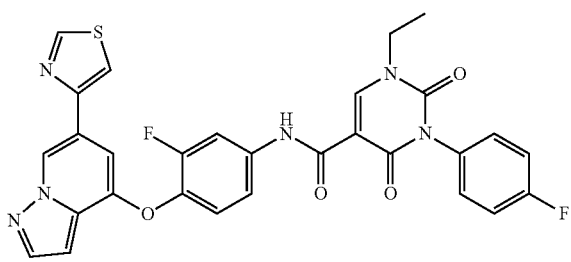 [SMILES: CCn1cc(C(=O)Nc2ccc(Oc3cc(-c4cscn4)cn4nccc34)c(F)c2)c(=O)n(-c2ccc(F)cc2)c1=O]

1-Ethyl-3-(4-fluoro-phenyl)-2,4-dioxo-1,2,3,4-tetra-hydro-pyrimidine-5-carboxylic acid[3-fluoro-4-(6-thiazol-4-yl-pyrazolo[1,5-a]pyridin-4-yloxy)-phenyl]-amide. This compound was synthesized from 3-fluoro-4-(6-thiazol-4-yl-pyrazolo[1,5-a]pyridin-4-yloxy)-phenylamine and 1-ethyl-3-(4-fluoro-phenyl)-2,4-dioxo-1,2,3,4-tetrahydro-pyrimidine-5-carboxylic acid using the methods described in example 93. mp=147° C.; LCMS m/z=587 (M+1); $^1$H NMR (DMSO-d$_6$) δ: 11.01 (s, 1H), 9.16 (m, 2H), 8.89 (s, 1H), 8.27 (m, 1H), 8.08 (m, 1H), 8.01 (m, 1H), 7.30-7.51 (br m, 6H), 7.09 (s, 1H), 6.74 (m, 1H), 4.02 (q, 2H), 1.29 (t, 3H, J=7.0 Hz).

Example 102

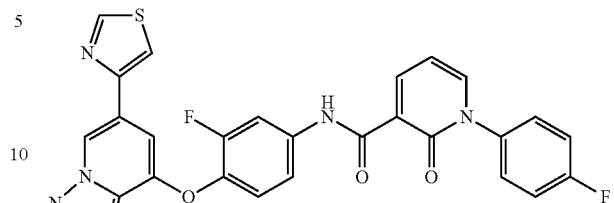

1-(4-Fluoro-phenyl)-2-oxo-1,2-dihydro-pyridine-3-carboxylic acid[3-fluoro-4-(6-thiazol-4-yl-pyrazolo[1,5-a]pyridin-4-yloxy)-phenyl]-amide. The compound was synthesized from 3-fluoro-4-(6-thiazol-4-yl-pyrazolo[1,5-a]pyridin-4-yloxy)-phenylamine and 1-(4-fluoro-phenyl)-2-oxo-1,2-dihydro-pyridine-3-carboxylic acid using the methods described in example 93. mp=258° C.; LCMS m/z=542 (M+1); $^1$H NMR (DMSO-d$_6$) δ: 12.10 (s, 1H), 9.12 (m, 2H), 8.60 (m, 1H), 8.27 (m, 1H), 8.03-8.14 (br m, 3H), 7.63 (m, 2H), 7.39-7.50 (br m, 4H), 7.10 (s, 1H), 6.75 (m, 2H).

Example 103

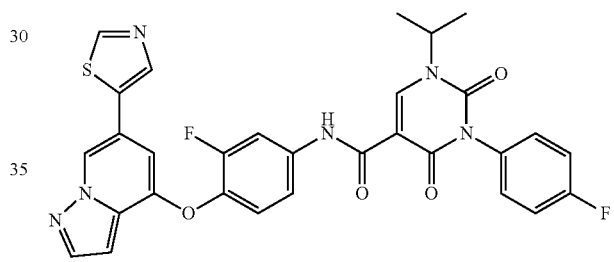

3-(4-Fluoro-phenyl)-1-isopropyl-2,4-dioxo-1,2,3,4-tetra-hydro-pyrimidine-5-carboxylic acid[3-fluoro-4-(6-thiazol-5-yl-pyrazolo[1,5-a]pyridin-4-yloxy)-phenyl]-amide. This compound was synthesized from 3-fluoro-4-(6-thiazol-5-yl-pyrazolo[1,5-a]pyridin-4-yloxy)-phenylamine and 3-(4-fluoro-phenyl)-1-isopropyl-2,4-dioxo-1,2,3,4-tetrahydro-pyrimidine-5-carboxylic acid using the methods described in example 93. mp=110° C.; LCMS m/z=601 (M+1); $^1$H NMR (DMSO-d$_6$) δ: 11.00 (s, 1H), 9.08 (s, 1H), 8.97 (s, 1H), 8.67 (s, 1H), 8.33 (s, 1H), 8.09 (m, 1H), 8.00 (m, 1H), 7.33-7.48 (br m, 6H), 6.84 (s, 1H), 6.69 (m, 1H), 4.78 (m, 1H), 1.43 (d, 6H, J=6.8 Hz).

Example 104

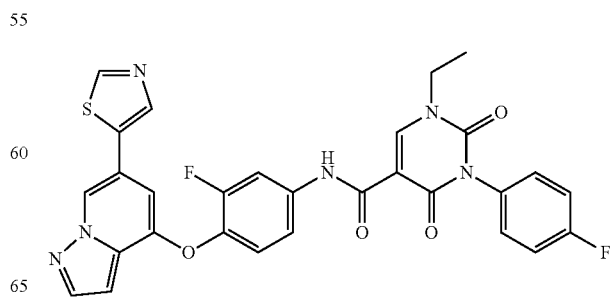

1-Ethyl-3-(4-fluoro-phenyl)-2,4-dioxo-1,2,3,4-tetrahydro-pyrimidine-5-carboxylic acid[3-fluoro-4-(6-thiazol-5-yl-pyrazolo[1,5-a]pyridin-4-yloxy)-phenyl]-amide. The compound was synthesized from 3-fluoro-4-(6-thiazol-5-yl-pyrazolo[1,5-a]pyridin-4-yloxy)-phenylamine and 1-ethyl-3-(4-fluoro-phenyl)-2,4-dioxo-1,2,3,4-tetrahydro-pyrimidine-5-carboxylic acid using the methods described in example 93. mp=246° C.; LCMS m/z=587 (M+1); $^1$H NMR (DMSO-$d_6$) δ: 11.00 (s, 1H), 9.08 (s, 1H), 8.97 (s, 1H), 8.88 (s, 1H), 8.33 (s, 1H), 8.09 (m, 1H), 8.00 (m, 1H), 7.33-7.48 (br m, 6H), 6.82 (s, 1H), 6.70 (m, 1H), 4.02 (q, 2H), 1.31 (t, 3H, J=7.0 Hz).

Example 105

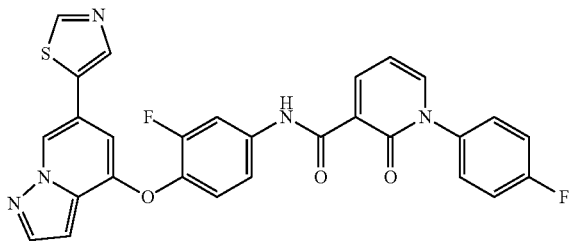 [SMILES: O=C(Nc1ccc(Oc2cc(-c3cncs3)cn3nccc23)c(F)c1)c1cccn(-c2ccc(F)cc2)c1=O]

1-(4-Fluoro-phenyl)-2-oxo-1,2-dihydro-pyridine-3-carboxylic acid[3-fluoro-4-(6-thiazol-5-yl-pyrazolo[1,5-a]pyridin-4-yloxy)-phenyl]-amide. The compound was synthesized from 3-fluoro-4-(6-thiazol-5-yl-pyrazolo[1,5-a]pyridin-4-yloxy)-phenylamine and 1-(4-fluoro-phenyl)-2-oxo-1,2-dihydro-pyridine-3-carboxylic acid using the methods described in example 93. mp=212-215° C.; LCMS m/z=542 (M+1); $^1$H NMR (DMSO-$d_6$) δ: 12.09 (s, 1H), 9.08 (s, 1H), 8.97 (s, 1H), 8.59 (m, 1H), 8.33 (s, 1H), 8.02-8.14 (br m, 3H), 7.60 (m, 2H), 7.35-7.48 (br m, 4H), 6.83 (s, 1H), 6.71 (m, 2H).

Example 106

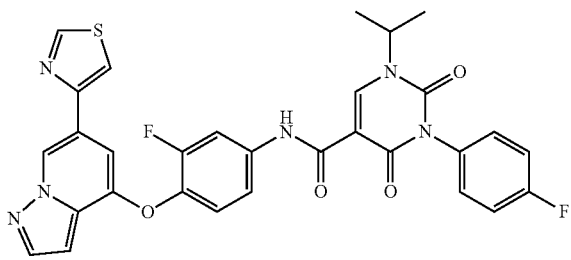 [SMILES: CC(C)n1cc(C(=O)Nc2ccc(Oc3cc(-c4cscn4)cn4nccc34)c(F)c2)c(=O)n(-c2ccc(F)cc2)c1=O]

3-(4-Fluoro-phenyl)-1-isopropyl-2,4-dioxo-1,2,3,4-tetrahydro-pyrimidine-5-carboxylic acid[3-fluoro-4-(6-thiazol-4-yl-pyrazolo[1,5-a]pyridin-4-yloxy)-phenyl]-amide. This compound was synthesized from 3-fluoro-4-(6-thiazol-4-yl-pyrazolo[1,5-a]pyridin-4-yloxy)-phenylamine and 3-(4-fluoro-phenyl)-1-isopropyl-2,4-dioxo-1,2,3,4-tetrahydro-pyrimidine-5-carboxylic acid using the methods described in example 93. mp=150-155° C.; LCMS m/z=601 (M+1); $^1$H NMR (DMSO-$d_6$) δ: 11.01 (s, 1H), 9.16 (m, 1H), 9.13 (s, 1H), 8.67 (s, 1H), 8.28 (m, 1H), 8.08 (m, 1H), 8.01 (m, 1H), 7.33-7.51 (br m, 6H), 7.10 (s, 1H), 6.74 (m, 1H), 4.77 (m, 1H), 1.43 (d, 6H, J=6.8 Hz).

Example 107

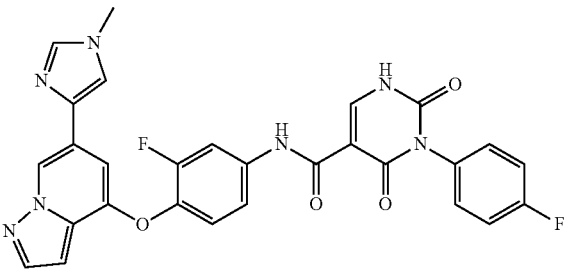 [SMILES: Cn1cnc(-c2cc(Oc3ccc(NC(=O)c4c[nH]c(=O)n(-c5ccc(F)cc5)c4=O)cc3F)c3ccnn3c2)c1]

3-(4-Fluoro-phenyl)-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide. The compound was synthesized using the methods described in example 93. 3-(4-Fluoro-phenyl)-2,4-dioxo-1,2,3,4-tetrahydro-pyrimidine-5-carboxylic acid (0.04 g, 0.15 mmol) and N,N,N',N'-tetramethyl-O-(7-azabenzotriazol-1-yl)uronium hexafluorophosphate (0.06 g, 0.15 mmol) in N,N-dimethylformamide (3 ml) was added N,N-diisopropylethylamine (0.07 mL, 0.40 mmol) and stirred at rt. After 0.5 h, 3-fluoro-4-[6-(1-methyl-1H-imidazol-4-yl)-pyrazolo[1,5-a]pyridine-4-yloxy]phenylamine (0.04 g, 0.13 mmol) was added and was stirred at 65° C. for 1 h and cooled at rt. The reaction was diluted with dichloromethane, washed with 1N sodium carbonate solution, water, and the precipitate in the water layer was collected and dried to give 0.02 g, 27%. mp=225° C.; LCMS m/z=556 (M+1); $^1$H NMR (DMSO-$d_6$) δ: 11.59 (s, 1H), 8.74 (s, 1H), 8.59 (s, 1H), 8.00 (m, 2H), 7.60 (m, 2H), 7.18-7.32 (br m, 6H), 6.79 (s, 1H), 6.69 (s, 1H), 3.64 (s, 3H).

Example 108

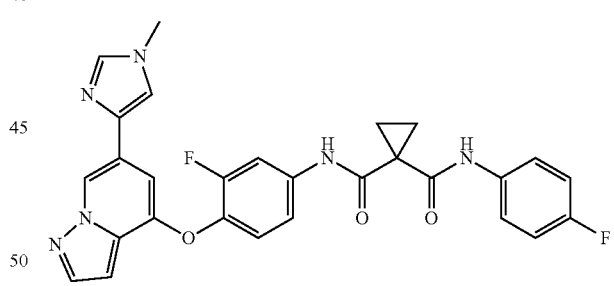

Cyclopropane-1,1-dicarboxylic acid{3-fluoro-4-[6-(1-methyl-1H-imidazol-4-yl)-pyrazolo[1,5-a]pyridin-4-yloxy]-phenyl}-amide(4-fluoro-phenyl)-amide. To 3-fluoro-4-[6-(1-methyl-1H-imidazol-4-yl)-pyrazolo[1,5-a]pyridin-4-yloxy]-phenylamine (0.06 g, 0.19 mmol) in tetrahydrofuran (4 mL) and water (1 mL) was added potassium carbonate (0.08 g, 0.58 mmol) at rt as 1-(4-fluoro-phenylcarbamoyl)-cyclopropanecarbonyl chloride (0.06 g, 0.25 mmol) was added drop wise. The reaction was stirred for 15 min., diluted with water, extracted with dichloromethane, dried over sodium sulfate, and concentrated. The product was purified using Prep TLC plates (5% methanol/dichloromethane) to give 0.05 g, 49%. mp=95° C.; LCMS m/z=529 (M+1); $^1$H NMR (DMSO-$d_6$) δ: 10.34 (s, 1H), 10.01 (s, 1H), 8.77 (s, 1H), 7.99 (m, 1H), 7.90 (m, 1H), 7.64 (m, 4H), 7.60 (m, 1H), 7.40 (m, 1H), 7.17 (m, 2H), 6.82 (s, 1H), 6.69 (m, 1H), 3.65 (s, 3H), 1.46 (s, 4H).

Example 109

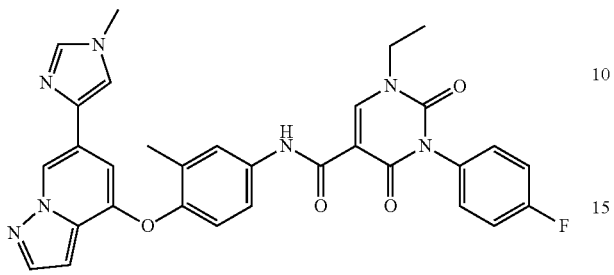

Step 1. 6-Bromo-4-(2-methyl-4-nitro-phenoxy)-pyrazolo[1,5-a]pyridine. This compound was synthesized from 6-bromo-pyrazolo[1,5-a]pyridin-4-ol and 1-fluoro-2-methyl-4-nitro-benzene using the method described for example 41 step 1. LCMS m/z=349 (M+1).

Step 2. 6-(1-Methyl-1H-imidazol-4-yl)-4-(2-methyl-4-nitro-phenoxy)-pyrazolo[1,5-a]pyridine. This intermediate was synthesized from 6-Bromo-4-(2-methyl-4-nitro-phenoxy)-pyrazolo[1,5-a]pyridine and 1-methyl-4-tributylstannyl-1H-imidazole using the methods for example 88 step 1. LCMS m/z=350 (M+1).

Step 3. 3-Methyl-4-[6-(1-methyl-1H-imidazol-4-yl)-pyrazolo[1,5-a]pyridin-4-yloxy]-phenylamine. Reduction of 6-(1-methyl-1H-imidazol-4-yl)-4-(2-methyl-4-nitro-phenoxy)-pyrazolo[1,5-a]pyridine using the methods for example 88 step 2 gave the target compound. LCMS m/z=320 (M+1).

Step 4. 1-Ethyl-3-(4-fluoro-phenyl)-2,4-dioxo-1,2,3,4-tetrahydro-pyrimidine-5-carboxylic acid{3-methyl-4-[6-(1-methyl-1H-imidazol-4-yl)-pyrazolo[1,5-a]pyridin-4-yloxy]-phenyl}-amide. These compound was synthesized from 3-methyl-4-[6-(1-methyl-1H-imidazol-4-yl)-pyrazolo[1,5-a]pyridin-4-yloxy]-phenylamine and 1-ethyl-3-(4-fluoro-phenyl)-2,4-dioxo-1,2,3,4-tetrahydro-pyrimidine-5-carboxylic acid using the methods described in example 88. mp=160-164° C.; LCMS m/z=580 (M+1); $^1$H NMR (DMSO-$d_6$) δ: 10.90 (s, 1H), 8.85 (s, 1H), 8.73 (s, 1H), 7.97 (m, 1H), 7.58-7.68 (m, 4H), 7.33-7.44 (m, 4H), 7.13 (m, 1H), 6.70 (s, 1H), 6.66 (m, 1H), 4.02 (q, 2H), 3.64 (s, 3H), 2.16 (s, 3H), 1.31 (t, 3H, J=7.0 Hz).

Example 110

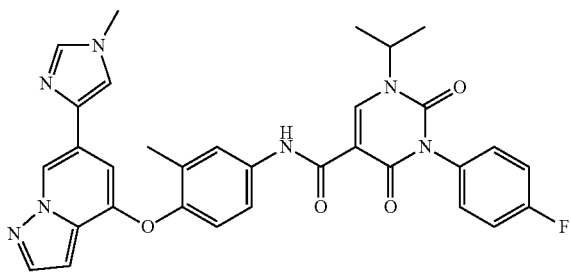 [SMILES: Cc1cc(NC(=O)c2cn(C(C)C)c(=O)n(-c3ccc(F)cc3)c2=O)ccc1Oc1cc(-c2cn(C)cn2)cn2nccc12]

3-(4-Fluoro-phenyl)-1-isopropyl-2,4-dioxo-1,2,3,4-tetrahydro-pyrimidine-5-carboxylic acid{3-methyl-4-[6-(1-methyl-1H-imidazol-4-yl)-pyrazolo[1,5-a]pyridin-4-yloxy]-phenyl}-amide. This compound was synthesized from 3-methyl-4-[6-(1-methyl-1H-imidazol-4-yl)-pyrazolo[1,5-a]pyridin-4-yloxy]-phenylamine and 3-(4-fluoro-phenyl)-1-isopropyl-2,4-dioxo-1,2,3,4-tetrahydro-pyrimidine-5-carboxylic acid using the methods described for example 109. mp=136-140° C.; LCMS m/z=594 (M+1); $^1$H NMR (DMSO-$d_6$) δ: 10.89 (s, 1H), 8.73 (s, 1H), 8.66 (s, 1H), 7.97 (m, 1H), 7.58-7.67 (m, 4H), 7.33-7.45 (m, 4H), 7.13 (m, 1H), 6.71 (s, 1H), 6.66 (m, 1H), 4.79 (m, 1H), 3.63 (s, 3H), 2.16 (s, 3H), 1.43 (d, 6H, J=6.8 Hz).

Example 111

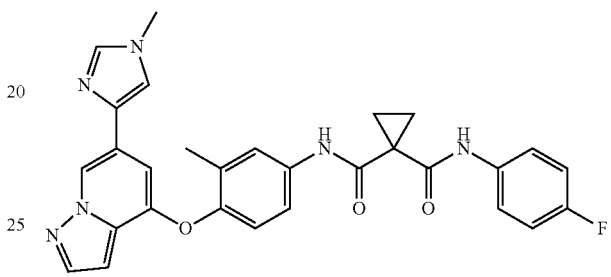

Cyclopropane-1,1-dicarboxylic acid(4-fluoro-phenyl)-amide {3-methyl-4-[6-(1-methyl-1H-imidazol-4-yl)-pyrazolo[1,5-a]pyridin-4-yloxy]-phenyl}-amide. This compound was synthesized from 3-methyl-4-[6-(1-methyl-1H-imidazol-4-yl)-pyrazolo[1,5-a]pyridin-4-yloxy]-phenylamine and 1-(4-fluoro-phenylcarbamoyl)-cyclopropanecarbonyl chloride using the methods described for example 108. mp=85-90° C.; LCMS m/z=525 (M+1); $^1$H NMR (DMSO-$d_6$) δ: 10.11 (br m, 2H), 8.73 (s, 1H), 7.97 (m, 1H), 7.53-7.67 (m, 6H), 7.16 (m, 3H), 6.68 (m, 2H), 3.64 (s, 3H), 2.15 (s, 3H), 1.46 (s, 4H).

Example 112

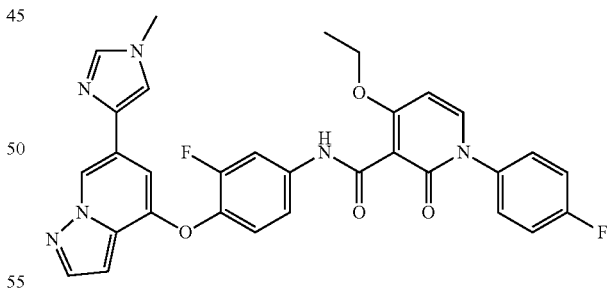

Step 1. 1-(4-Fluoro-phenyl)-4-iodo-2-oxo-1,2-dihydro-pyridine-3-carbonyl chloride. A suspension of 1-(4-fluoro-phenyl)-4-iodo-2-oxo-1,2-dihydro-pyridine-3-carboxylic acid (0.3 g, 0.84 mmol) in dichloromethane (4 mL) and N,N-dimethylformamide (0.2 mL) was cooled at ° C. under an atmosphere of nitrogen as 2M oxalyl chloride in dichloromethane (1.3 mL, 2.5 mmol) was added drop wise and stirred at rt for 1 h. The solvent was evaporated, dichloromethane was added and evaporated 3×. The acid chloride was then dried under vacuum, and used directly in the next step. LCMS m/z=378 (M+1).

Step 2. 1-(4-Fluoro-phenyl)-4-iodo-2-oxo-1,2-dihydro-pyridine-3-carboxylic acid {3-fluoro-4-[6-(1-methyl-1H-imidazol-4-yl)-pyrazolo[1,5-a]pyridin-4-yloxy]-phenyl}-amide. 3-Fluoro-4-[6-(1-methyl-1H-imidazol-4-yl)-pyrazolo[1,5-a]pyridine-4-yloxy]phenylamine (0.14 g, 0.43 mmol) in N,N-dimethylformamide (2.3 mL) and tetrahydrofuran (9 mL) was stirred at ° C. under an atmosphere of nitrogen as pyridine (0.08 mL, 0.95 mmol) was added drop wise. After 5 min., 1-(4-fluoro-phenyl)-4-iodo-2-oxo-1,2-dihydro-pyridine-3-carbonyl chloride (0.21 g, 0.56 mmol) in dichloromethane (11 mL) was added drop wise, stirred at rt for 2 h and concentrated. The reaction was partitioned between ethyl acetate and water, washed with brine, dried over sodium sulfate, and concentrated. The product was chromatographed on silica gel using a single step column (1-3% methanol/dichloromethane) and concentrated. LCMS m/z=665 (M+1).

Step 3. 4-Ethoxy-1-(4-fluoro-phenyl)-2-oxo-1,2-dihydro-pyridine-3-carboxylic acid {3-fluoro-4-[6-(1-methyl-1H-imidazol-4-yl)-pyrazolo[1,5-a]pyridin-4-yloxy]-phenyl}-amide. Sodium hydride (60% dispersion mineral oil; 3:2, sodium hydride:mineral oil) (0.01 g, 0.24 mmol) under an atmosphere of nitrogen was stirred as ethanol (2.1 mL) was added slowly and stirred at rt for 10 min. To this sodium ethoxide solution was added a mixture of 1-(4-fluoro-phenyl)-4-iodo-2-oxo-1,2-dihydro-pyridine-3-carboxylic acid{3-fluoro-4-[6-(1-methyl-1H-imidazol-4-yl)-pyrazolo[1,5-a]pyridine-4-yloxy]-phenyl}-amide (0.12 g, 0.18 mmol) in tetrahydrofuran (1.5 mL) and ethanol (0.9 mL) and stirred at rt for 1 h. The reaction was partitioned between dichloromethane and water, washed with brine, dried over sodium sulfate, and concentrated. The product was purified using Prep TLC plates (5% methanol/dichloromethane) and concentrated to give 0.07 g, 65%. mp=128-131° C.; LCMS m/z=583 (M+1); $^1$H NMR (DMSO-$d_6$) δ 10.57 (s, 1H), 8.76 (s, 1H), 7.99 (m, 1H), 7.90 (m, 2H), 7.65 (m, 2H), 7.35-7.48 (br m, 6H), 6.80 (s, 1H), 6.71 (m, 1H), 6.53 (m, 1H), 4.27 (q, 2H), 3.64 (s, 3H), 1.31 (t, 3H, J=7.0 Hz).

Example 113

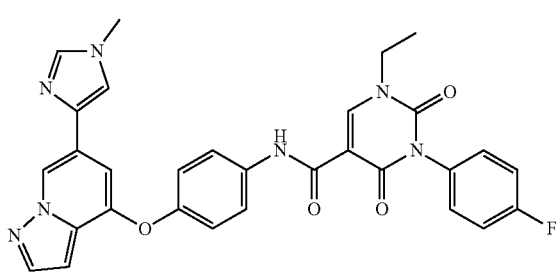 [SMILES: CCn1cc(C(=O)Nc2ccc(Oc3cc(-c4cn(C)cn4)cn4nccc34)cc2)c(=O)n(-c2ccc(F)cc2)c1=O]

Step 1. 6-Bromo-4-(4-nitro-phenoxy)-pyrazolo[1,5-a]pyridine. To 6-bromo-pyrazolo[1,5-a]pyridin-4-ol (0.5 g, 2.35 mmol) in N,N-dimethylformamide (10 mL) under an atmosphere of nitrogen at 0° C. was added sodium hydride (60% dispersion in mineral oil; 3:2, sodium hydride:mineral oil) (0.24 g, 5.9 mmol). After stirring 0.5 h at rt, 4-fluoronitrobenzene (0.4 g, 2.82 mmol) was added drop wise and stirred at 100° C. overnight. The reaction was cooled at rt, diluted with ethyl acetate, washed with water and brine, dried over sodium sulfate, and concentrated. The product was chromatographed on silica gel using a single step column (10% ethyl acetate/hexanes) and concentrated to give 0.43 g, 55%. LCMS m/z=335 (M+1).

Step 2. 6-(1-Methyl-1H-imidazol-4-yl)-4-(4-nitro-phenoxy)-pyrazolo[1,5-a]pyridine. The compound was synthesized from 6-bromo-4-(4-nitro-phenoxy)-pyrazolo[1,5-a]pyridine and 1-methyl-4-tributylstannanyl-1H-imidazole using the still method described in example 88 step 1. LCMS m/z=336 (M+1).

Step 3. 4-[6-(1-Methyl-1H-imidazol-4-yl)-pyrazolo[1,5-a]pyridin-4-yloxy]-phenylamine. The compound was synthesized from 6-(1-methyl-1H-imidazol-4-yl)-4-(4-nitro-phenoxy)-pyrazolo[1,5-a]pyridine and tin (II) chloride dihydrate using the reduction method described in example 51 step 2. LCMS m/z=306 (M+1).

Step 4. 1-Ethyl-3-(4-fluoro-phenyl)-2,4-dioxo-1,2,3,4-tetrahydro-pyrimidine-5-carboxylic acid {4-[6-(1-methyl-1H-imidazol-4-yl)-pyrazolo[1,5-a]pyridin-4-yloxy]-phenyl}-amide. The compound was synthesized from 3-methyl-4-[6-(1-methyl-1H-imidazol-4-yl)-pyrazolo[1,5-a]pyridin-4-yloxy]-phenylamine and 1-ethyl-3-(4-fluoro-phenyl)-2,4-dioxo-1,2,3,4-tetrahydro-pyrimidine-5-carboxylic acid using the amide coupling method described in example 41 step 4. mp=152-156° C.; LCMS m/z=566 (M+1); $^1$H NMR (DMSO-$d_6$) δ: 10.89 (s, 1H), 8.85 (s, 1H), 8.77 (s, 1H), 7.96 (m, 1H), 7.76 (m, 2H), 7.65 (m, 2H), 7.33-7.44 (br m, 4H), 7.21 (m, 2H), 6.97 (m, 1H), 6.56 (m, 1H), 4.01 (q, 2H), 3.65 (s, 3H), 1.30 (t, 3H, J=7.0 Hz).

Example 114

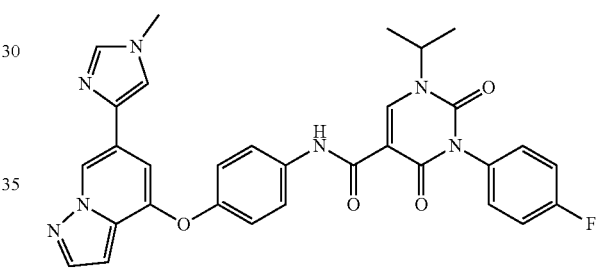

3-(4-Fluoro-phenyl)-1-isopropyl-2,4-dioxo-1,2,3,4-tetrahydro-pyrimidine-5-carboxylic acid{4-[6-(1-methyl-1H-imidazol-4-yl)-pyrazolo[1,5-a]pyridin-4-yloxy]-phenyl}-amide. This compound was synthesized from 3-methyl-4-[6-(1-methyl-1H-imidazol-4-yl)-pyrazolo[1,5-a]pyridin-4-yloxy]-phenylamine and 3-(4-fluoro-phenyl)-1-isopropyl-2,4-dioxo-1,2,3,4-tetrahydro-pyrimidine-5-carboxylic acid using the methods described in example 113. mp=148-152° C.; LCMS m/z=580 (M+1); $^1$H NMR (DMSO-$d_6$) δ: 10.88 (s, 1H), 8.77 (s, 1H), 8.65 (s, 1H), 7.96 (m, 1H), 7.76 (m, 2H), 7.65 (m, 2H), 7.33-7.44 (br m, 4H), 7.20 (m, 2H), 6.98 (m, 1H), 6.56 (m, 1H), 4.79 (m, 1H), 3.65 (s, 3H), 1.43 (d, 6H, J=6.8 Hz).

Example 115

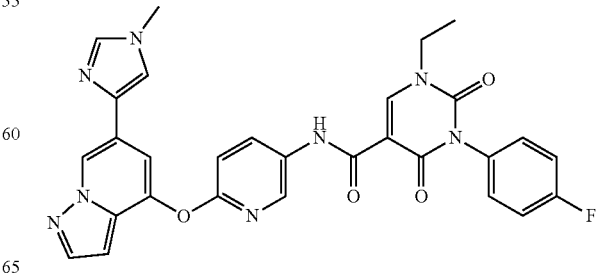

Step 1. 6-(1-Methyl-1H-pyrazol-4-yl)-4-(5-nitro-pyridin-2-yloxy)-pyrazolo[1,5-a]pyridine. This compound was synthesized from 6-bromo-4-(5-nitro-pyridin-2-yloxy)-pyrazolo[1,5-a]pyridine (example 89 step 2) and 1-methyl-4-(4,4,5,5-tetramethyl-[1,3,2]dioxaborolan-2-yl)-1H-pyrazole using the susuki method described in example 41 step 2. LCMS m/z=337 (M+1).

Step 2. 6-[6-(1-Methyl-1H-imidazol-4-yl)-pyrazolo[1,5-a]pyridin-4-yloxy]-pyridin-3-ylamine. 6-(1-Methyl-1H-pyrazol-4-yl)-4-(5-nitro-pyridin-2-yloxy)-pyrazolo[1,5-a]pyridine was reduced using the method for example 51 step 2. LCMS m/z=307 (M+1).

Step 3. 1-Ethyl-3-(4-fluoro-phenyl)-2,4-dioxo-1,2,3,4-tetrahydro-pyrimidine-5-carboxylic acid{6-[6-(1-methyl-1H-imidazol-4-yl)-pyrazolo[1,5-a]pyridin-4-yloxy]-pyridin-3-yl}-amide. This compound was synthesized from 6-[6-(1-methyl-1H-imidazol-4-yl)-pyrazolo[1,5-a]pyridin-4-yloxy]-pyridin-3-ylamine and 1-ethyl-3-(4-fluoro-phenyl)-2,4-dioxo-1,2,3,4-tetrahydro-pyrimidine-5-carboxylic acid using the methods described in example 93. mp=217-220° C.; LCMS m/z=567 (M+1); $^1$H NMR (DMSO-d$_6$) δ: 10.85 (s, 1H), 8.87 (m, 2H), 8.45 (m, 1H), 8.27 (m, 1H), 7.92 (m, 1H), 7.72 (m, 1H), 7.66 (s, 1H), 7.32-7.43 (br m, 5H), 7.26 (m, 1H), 6.32 (m, 1H), 4.00 (q, 2H), 3.67 (s, 3H), 1.28 (t, 3H, J=7.0H).

Example 116

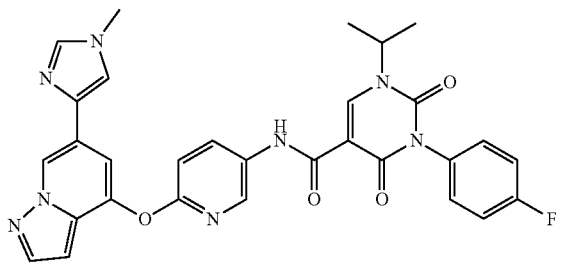 [SMILES: CC(C)n1cc(C(=O)Nc2ccc(Oc3cc(-c4cn(C)cn4)cn4nccc34)nc2)c(=O)n(-c2ccc(F)cc2)c1=O]

3-(4-Fluoro-phenyl)-1-isopropyl-2,4-dioxo-1,2,3,4-tetrahydro-pyrimidine-5-carboxylic acid{6-[6-(1-methyl-1H-imidazol-4-yl)-pyrazolo[1,5-a]pyridin-4-yloxy]-pyridin-3-yl}-amide. This compound was synthesized from 6-[6-(1-methyl-1H-imidazol-4-yl)-pyrazolo[1,5-a]pyridin-4-yloxy]-pyridin-3-ylamine and 3-(4-fluoro-phenyl)-1-isopropyl-2,4-dioxo-1,2,3,4-tetrahydro-pyrimidine-5-carboxylic acid using the methods described for example 115. mp=134-135° C.; LCMS m/z=581 (M+1); $^1$H NMR (DMSO-d$_6$) δ: 10.86 (s, 1H), 8.84 (s, 1H), 8.66 (s, 1H), 8.46 (m, 1H), 8.27 (m, 1H), 7.92 (m, 1H), 7.72 (m, 1H), 7.66 (s, 1H), 7.32-7.43 (br m, 5H), 7.26 (m, 1H), 6.33 (m, 1H), 4.76 (m, 1H), 3.67 (s, 3H), 1.42 (d, 6H, J=6.8 Hz).

Example 117

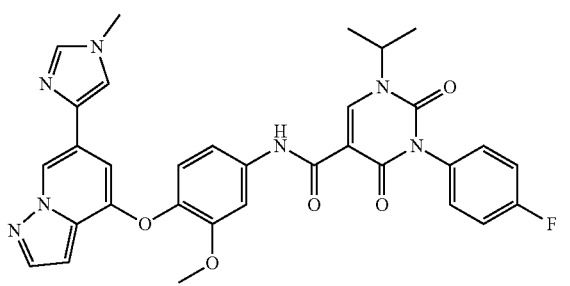 [SMILES: COc1cc(NC(=O)c2cn(C(C)C)c(=O)n(-c3ccc(F)cc3)c2=O)ccc1Oc1cc(-c2cn(C)cn2)cn2nccc12]

Step 1. 6-Bromo-4-(2-methoxy-4-nitro-phenoxy)-pyrazolo[1,5-a]pyridine. To 6-bromo-pyrazolo[1,5-a]pyridin-4-ol (0.35 g, 1.64 mmol) in N,N-dimethylformamide (7 mL) under an atmosphere of nitrogen at 0° C. was added sodium hydride, (60% dispersion in mineral oil; 3:2, sodium hydride:mineral oil) (0.16 g, 4.11 mmol). After stirring 0.5 h at rt, 1-fluoro-2-methoxy-4-nitro-benzene (0.34 g, 1.97 mmol) was added dropwise and stirred at 100° C. overnight. The reaction was diluted with ethyl acetate, washed with water and brine, dried over sodium sulfate, and concentrated. The product was chromatographed on silica gel using a single step column (5-10% ethyl acetate/hexanes) and concentrated to give 0.33 g, 55%. LCMS m/z=365 (M+1).

Step 2. 4-(2-Methoxy-4-nitro-phenoxy)-6-(1-methyl-1H-imidazol-4-yl)-pyrazolo[1,5-a]pyridine. This compound was synthesized from 6-bromo-4-(2-methoxy-4-nitro-phenoxy)-pyrazolo[1,5-a]pyridine and 1-methyl-4-tributylstannanyl-1H-imidazole using the stille method described in example 88 step 1. LCMS m/z=366 (M+1).

Step 3. 3-Methoxy-4-[6-(1-methyl-1H-imidazol-4-yl)-pyrazolo[1,5-a]pyridin-4-yloxy]-phenylamine. This compound was synthesized from 4-(2-methoxy-4-nitro-phenoxy)-6-(1-methyl-1H-imidazol-4-yl)-pyrazolo[1,5-a]pyridine and tin (II) chloride dihydrate using the reduction method described in example 51 step 2. LCMS m/z=336 (M+1).

Step 4. 3-(4-Fluoro-phenyl)-1-isopropyl-2,4-dioxo-1,2,3,4-tetrahydro-pyrimidine-5-carboxylic acid {3-methoxy-4-[6-(1-methyl-1H-imidazol-4-yl)-pyrazolo[1, 5-a]pyridin-4-yloxy]-phenyl}-amide. This compound was synthesized from 3-methoxy-4-[6-(1-methyl-1H-imidazol-4-yl)-pyrazolo[1,5-a]pyridin-4-yloxy]-phenylamine and 3-(4-fluoro-phenyl)-1-isopropyl-2,4-dioxo-1,2,3,4-tetrahydro-pyrimidine-5-carboxylic acid using the amide coupling method described in example 41 step 4. mp=155-158° C.; LCMS m/z=610 (M+1); $^1$H NMR (DMSO-d$_6$) δ: 10.95 (s, 1H), 8.69 (m, 2H), 7.96 (m, 1H), 7.62 (m, 1H), 7.59 (m, 2H), 7.33-7.46 (br m, 5H), 7.22 (m, 1H), 6.64 (m, 2H), 4.78 (m, 1H), 3.73 (s, 3H), 3.64 (s, 3H), 1.43 (d, 6H, J=6.8 Hz).

Example 118

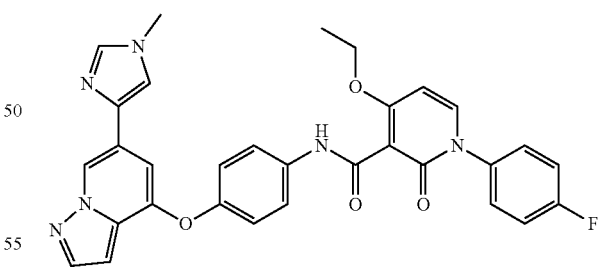

4-Ethoxy-1-(4-fluoro-phenyl)-2-oxo-1,2-dihydro-pyridine-3-carboxylic acid {4-[6-(1-methyl-1H-imidazol-4-yl)-pyrazolo[1,5-a]pyridin-4-yloxy]-phenyl}-amide. This compound was synthesized from 1-(4-fluoro-phenyl)-4-iodo-2-oxo-1,2-dihydro-pyridine-3-carboxylic acid {4-[6-(1-methyl-1H-imidazol-4-yl)-pyrazolo[1,5-a]pyridin-4-yloxy]-phenyl}-amide using the methods described for example 112 steps 2-3. mp=189-193° C.; LCMS m/z=565 (M+1); $^1$H NMR (DMSO-d$_6$) δ: 10.33 (s, 1H), 8.74 (s, 1H), 7.96 (m, 1H), 7.84 (m, 1H), 7.76 (m, 2H), 7.63 (m, 2H), 7.47 (m, 2H), 7.38 (m, 2H), 7.20 (m, 2H), 6.90 (m, 1H), 6.60 (m, 1H), 6.51 (m, 1H), 4.26 (q, 2H), 3.64 (s, 3H), 1.32 (t, 3H, J=7.0 Hz).

Example 119

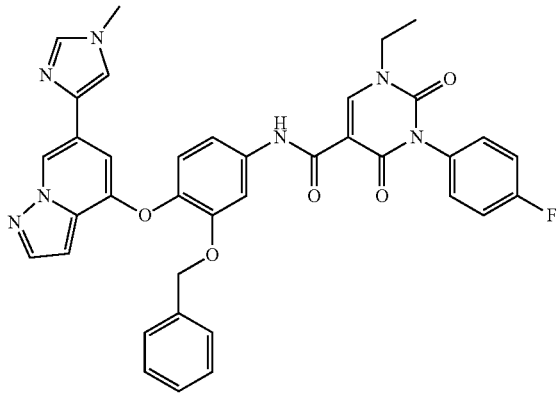 [SMILES: CCn1cc(C(=O)Nc2ccc(Oc3cc(-c4cn(C)cn4)cn4nccc34)c(OCc3ccccc3)c2)c(=O)n(-c2ccc(F)cc2)c1=O]

Step 1. 4-(2-Benzyloxy-4-nitro-phenoxy)-6-bromo-pyrazolo[1,5-a]pyridine. This compound was synthesized from 6-bromo-pyrazolo[1,5-a]pyridin-4-ol and 2-benzyloxy-1-fluoro-4-nitro-benzene using the method described in example 117 step 1. LCMS m/z=441 (M+1).

Step 2. 4-(2-Benzyloxy-4-nitro-phenoxy)-6-(1-methyl-1H-imidazol-4-yl)-pyrazolo[1,5-a]pyridine. This compound was synthesized from 4-(2-benzyloxy-4-nitro-phenoxy)-6-bromo-pyrazolo[1,5-a]pyridine and 1-methyl-4-tributylstannanyl-1H-imidazole using the stille method described in example 88 step 1. LCMS m/z=442 (M+1).

Step 3. 3-Benzyloxy-4-[6-(1-methyl-1H-imidazol-4-yl)-pyrazolo[1,5-a]pyridin-4-yloxy]-phenylamine. Reduction of 4-(2-benzyloxy-4-nitro-phenoxy)-6-(1-methyl-1H-imidazol-4-yl)-pyrazolo[1,5-a]pyridine with tin (II) chloride dihydrate using the method described in example 51 step 2 gave the target compound. LCMS m/z=412 (M+1).

Step 4. 1-Ethyl-3-(4-fluoro-phenyl)-2,4-dioxo-1,2,3,4-tetrahydro-pyrimidine-5-carboxylic acid{3-benzyloxy-4-[6-(1-methyl-1H-imidazol-4-yl)-pyrazolo[1,5-a]pyridin-4-yloxy-phenyl}-amide. The compound was synthesized from 3-benzyloxy-4-[6-(1-methyl-1H-imidazol-4-yl)-pyrazolo[1,5-a]pyridin-4-yloxy]-phenylamine and 1-ethyl-3-(4-fluoro-phenyl)-2,4-dioxo-1,2,3,4-tetrahydro-pyrimidine-5-carboxylic acid using the amide coupling method described in example 41 step 4. mp=240° C.; LCMS m/z=672 (M+1); $^1$H NMR (DMSO-d$_6$) δ: 10.03 (s, 1H), 8.87 (s, 1H), 8.71 (s, 1H), 7.95 (m, 1H), 7.61 (m, 3H), 7.26-7.50 (br m, 6H), 7.13 (m, 5H), 6.74 (m, 1H), 6.65 (m, 1H), 5.08 (s, 2H), 4.02 (q, 2H), 3.64 (s, 3H), 1.29 (t, 3H, J=7.1 Hz).

Example 120

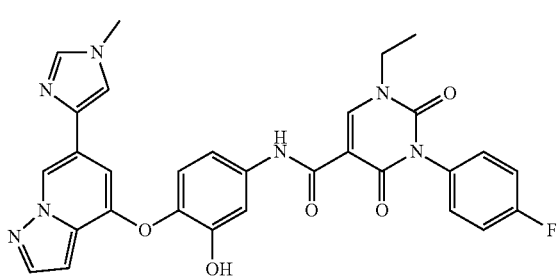 [SMILES: CCn1cc(C(=O)Nc2ccc(Oc3cc(-c4cn(C)cn4)cn4nccc34)c(O)c2)c(=O)n(-c2ccc(F)cc2)c1=O]

1-Ethyl-3-(4-fluoro-phenyl)-2,4-dioxo-1,2,3,4-tetrahydro-pyrimidine-5-carboxylic acid{3-hydroxy-4-[6-(1-methyl-1H-imidazol-4-yl)-pyrazolo[1,5-a]pyridin-4-yloxy]-phenyl}-amide. To 1-ethyl-3-(4-fluoro-phenyl)-2,4-dioxo-1,2,3,4-tetrahydro-pyrimidine-5-carboxylic acid{3-benzyloxy-4-[6-(1-methyl-1H-imidazol-4-yl)-pyrazolo[1,5-a]pyridin-4-yloxy-phenyl}-amide (example 119) (0.11 g, 0.16 mmol) in ethanol (15 mL) and dichloromethane (5 mL) under an atmosphere of nitrogen was added 5 drops of conc. hydrochloric acid and 20% Pd(OH)$_2$/C, 50% wet (10:40:50, palladium hydroxide:carbon black:water) (0.03 g, 0.04 mmol) and hydrogenated on a Parr appratus at 50 psi overnight. The reaction was filtered through a pad of celite, washed with dichloromethane and methanol and concentrated. The residue was partitioned between dichloromethane and water, washed with brine, dried over sodium sulfate, and concentrated. The product was chromatographed on silica gel using a single step column (1-5% methanol/dichloromethane) and concentrated to give 0.03 g, 33%. mp=278° C.; LCMS m/z=582 (M+1); $^1$H NMR (DMSO-d$_6$) δ: 10.82 (s, 1H), 9.91 (s, 1H), 8.85 (s, 1H), 8.68 (s, 1H), 7.95 (m, 1H), 7.58 (m, 3H), 7.33-7.44 (br m, 4H), 7.13 (m, 1H), 7.03 (m, 1H), 6.66 (m, 2H), 4.02 (q, 2H), 3.63 (s, 3H), 1.31 (t, 3H, J=7.0 Hz).

Example 121

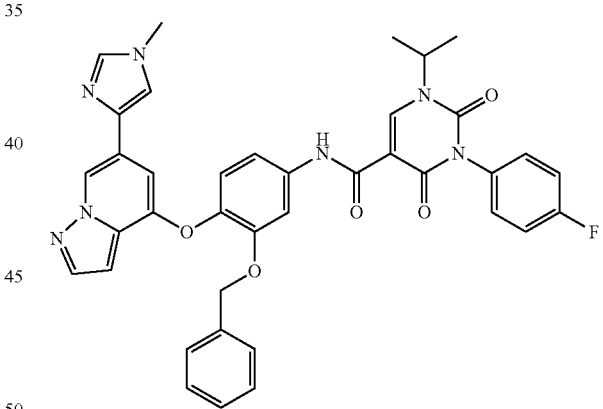

3-(4-Fluoro-phenyl)-1-isopropyl-2,4-dioxo-1,2,3,4-tetrahydro-pyrimidine-5-carboxylic acid {3-benzyloxy-4-[6-(1-methyl-1H-imidazol-4-yl)-pyrazolo[1,5-a]pyridine-4-yloxy]-phenyl}-amide. The compound was synthesized from 3-benzyloxy-4-[6-(1-methyl-1H-imidazol-4-yl)-pyrazolo[1,5-a]pyridin-4-yloxy]phenylamine and 3-(4-fluoro-phenyl)-1-isopropyl-2,4-dioxo-1,2,3,4-tetrahydro-pyrimidine-5-carboxylic acid using the methods described in example 119. mp=118-121° C.; LCMS m/z=686 (M+1); $^1$H NMR (DMSO-d$_6$) δ: 10.94 (s, 1H), 8.72 (m, 2H), 7.95 (m, 1H), 7.67 (m, 1H), 7.58 (m, 2H), 7.27-7.47 (br m, 6H), 7.13 (m, 5H), 6.75 (m, 1H), 6.65 (m, 1H), 5.08 (s, 2H), 4.81 (m, 1H), 3.64 (s, 3H), 1.43 (d, 6H, J=6.8 Hz).

Example 122

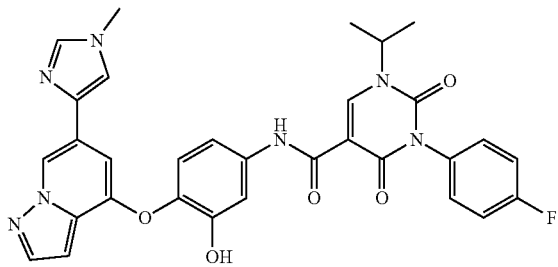 [SMILES: CC(C)n1cc(C(=O)Nc2ccc(Oc3cc(-c4cn(C)cn4)cn4nccc34)c(O)c2)c(=O)n(-c2ccc(F)cc2)c1=O]

3-(4-Fluoro-phenyl)-1-isopropyl-2,4-dioxo-1,2,3,4-tetrahydro-pyrimidine-5-carboxylic acid{3-hydroxy-4-[6-(1-methyl-1H-imidazol-4-yl)-pyrazolo[1,5-a]pyridin-4-yloxy]-phenyl}-amide. This compound was synthesized from 3-(4-fluoro-phenyl)-1-isopropyl-2,4-dioxo-1,2,3,4-tetrahydro-pyrimidine-5-carboxylic acid {3-benzyloxy-4-[6-(1-methyl-1H-imidazol-4-yl)-pyrazolo[1,5-a]pyridin-4-yloxy]-phenyl}-amide (example 121) and 20% Pd(OH)$_2$/C (50% wet; 10:40:50, palladium hydroxide:carbon black: water) using the methods described in example 120. mp=275° C.; LCMS m/z=596 (M+1); $^1$H NMR (DMSO-d$_6$) δ: 10.82 (s, 1H), 9.91 (s, 1H), 8.69 (s, 1H), 8.65 (s, 1H), 7.95 (m, 1H), 7.58 (m, 3H), 7.33-7.44 (m, 4H), 7.12 (m, 1H), 7.05 (m, 1H), 6.67 (m, 2H), 4.79 (m, 1H), 3.63 (s, 3H), 1.43 (d, 6H, J=6.8 Hz).

Example 123

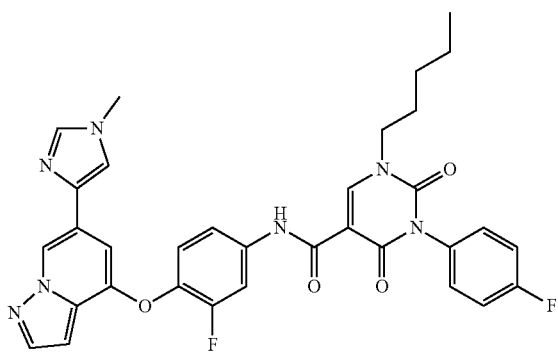 [SMILES: CCCCCn1cc(C(=O)Nc2ccc(Oc3cc(-c4cn(C)cn4)cn4nccc34)c(F)c2)c(=O)n(-c2ccc(F)cc2)c1=O]

3-(4-Fluoro-phenyl)-2,4-dioxo-1-pentyl-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide. This compound was synthesized from 3-fluoro-4-[6-(1-methyl-1H-imidazol-4-yl)-pyrazolo[1,5-a]pyridin-4-yloxy]-phenylamine and 1-pentyl-3-(4-fluoro-phenyl)-2,4-dioxo-1,2,3,4-tetrahydro-pyrimidine-5-carboxylic acid using the methods described in example 88. mp=181° C.; LCMS m/z=626 (M+1); $^1$H NMR (DMSO-d$_6$) δ: 11.02 (s, 1H), 8.85 (s, 1H), 8.77 (s, 1H), 8.01 (m, 2H), 7.65 (m, 1H), 7.59 (m, 1H), 7.33-7.51 (br m, 6H), 6.84 (s, 1H), 6.68 (m, 1H), 3.96 (m, 2H), 3.64 (s, 3H), 1.71 (m, 2H), 1.32 (m, 4H), 0.91 (m, 3H).

Example 124

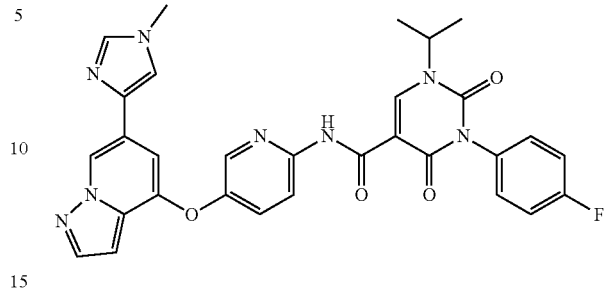

Step 1. 6-Bromo-4-(6-nitro-pyridin-3-yloxy)-pyrazolo[1,5-a]pyridine. To an oven dried schlenck flask was added 6-bromo-pyrazolo[1,5-a]pyridine-4-ol (0.3 g, 1.41 mmol), 5-bromo-2-nitro-pyridine (0.43 g, 2.11 mmol), copper(I) iodide (0.03 g, 0.14 mmol), potassium phosphate (0.9 g, 4.22 mmol), picolinic acid (0.04 g, 0.28 mmol), followed by DMSO (8 mL) and was degassed for 5 min. under an atmosphere of nitrogen, then heated at 100° C. overnight. The reaction was cooled at rt, diluted with dichloromethane, washed with 1N sodium carbonate solution, water and brine, dried over sodium sulfate, and concentrated. The product was chromatographed on silica gel using a single step column (10-20% ethyl acetate/hexanes) and concentrated to give 0.21 g, 43%. LCMS m/z=336 (M+1).

Step 2. 6-(1-Methyl-1H-imidazol-4-yl)-4-(6-nitro-pyridin-3-yloxy)-pyrazolo[1,5-a]pyridine. The compound was synthesized from 6-bromo-4-(6-nitro-pyridin-3-yloxy)-pyrazolo[1,5-a]pyridine and 1-methyl-4-tributylstannanyl-1H-imidazole using the stille method described in example 88 step 1. LCMS m/z=337 (M+1).

Step 3. 5-[6-(1-Methyl-1H-imidazol-4-yl)-pyrazolo[1,5-a]pyridin-4-yloxy]-pyridin-2-ylamine. 6-(1-Methyl-1H-imidazol-4-yl)-4-(6-nitro-pyridin-3-yloxy)-pyrazolo[1,5-a]pyridine was reduced with tin (II) chloride dihydrate using the method described in example 51 step 2. LCMS m/z=307 (M+1).

Step 4. 3-(4-Fluoro-phenyl)-1-isopropyl-2,4-dioxo-1,2,3,4-tetrahydro-pyrimidine-5-carboxylic acid {5-[6-(1-methyl-1H-imidazol-4-yl)-pyrazolo[1,5-a]pyridin-4-yloxy]-pyridin-2-yl}-amide. This compound was synthesized from 5-[6-(1-methyl-1H-imidazol-4-yl)-pyrazolo[1,5-a]pyridin-4-yloxy]-pyridin-2-ylamine and 3-(4-fluoro-phenyl)-1-isopropyl-2,4-dioxo-1,2,3,4-tetrahydro-pyrimidine-5-carboxylic acid using the amide coupling method described in example 41 step 4. mp=120-124° C.; LCMS m/z=581 (M+1); $^1$H NMR (DMSO-d$_6$) δ: 11.35 (s, 1H), 8.79 (s, 1H), 8.71 (s, 1H), 8.33 (m, 2H), 7.98 (m, 1H), 7.80 (m, 1H), 7.68 (m, 1H), 7.62 (m, 1H), 7.33-7.44 (m, 4H), 7.00 (m, 1H), 6.61 (m, 1H), 4.77 (m, 1H), 3.65 (s, 3H), 1.43 (d, 6H, J=6.8 Hz).

Example 125

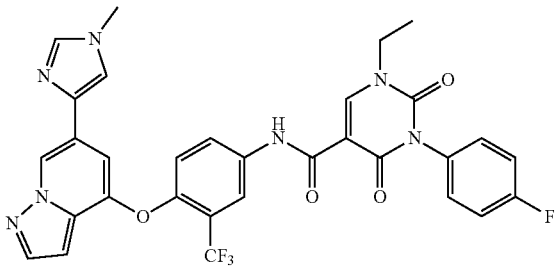 [SMILES: CC(C)n1cc(C(=O)Nc2ccc(Oc3cc(-c4cn(C)cn4)cn4nccc34)c(C(F)(F)F)c2)c(=O)n(-c2ccc(F)cc2)c1=O]

Step 1. 6-Bromo-4-(4-nitro-2-trifluoromethyl-phenoxy)-pyrazolo[1,5-a]pyridine. This compound was synthesized from 6-bromo-pyrazolo[1,5-a]pyridine-4-ol and 1-fluoro-4-nitro-2-trifluoromethyl-benzene using the method described in example 41 step 1. LCMS m/z=403 (M+1).

Step 2. 6-(1-Methyl-1H-imidazol-4-yl)-4-(4-nitro-2-trifluoromethyl-phenoxy)-pyrazolo[1,5-a]pyridine. This compounds was synthesized from 6-Bromo-4-(4-nitro-2-trifluoromethyl-phenoxy)-pyrazolo[1,5-a]pyridine and 1-methyl-4-tributylstannanyl-1H-imidazole using the stille method described in example 88 step 1. LCMS m/z=404 (M+1).

Step 3. 4-[6-(1-Methyl-1H-imidazol-4-yl)-pyrazolo[1,5-a]pyridin-4-yloxy]-3-trifluoromethyl-phenylamine. 6-(1-Methyl-1H-imidazol-4-yl)-4-(4-nitro-2-trifluoromethyl-phenoxy)-pyrazolo[1,5-a]pyridine was reduced using the method for example 41 step 3. LCMS m/z=374 (M+1).

Step 4. 1-Ethyl-3-(4-fluoro-phenyl)-2,4-dioxo-1,2,3,4-tetrahydro-pyrimidine-5-carboxylic acid {4-[6-(1-methyl-1H-imidazol-4-yl)-pyrazolo[1,5-a]pyridin-4-yloxy]-3-trifluoromethyl-phenyl}-amide. This compound was synthesized from 4-[6-(1-methyl-1H-imidazol-4-yl)-pyrazolo[1,5-a]pyridine-4-yloxy]-3-trifluoromethyl-phenylamine and 1-ethyl-3-(4-fluoro-phenyl)-2,4-dioxo-1,2,3,4-tetrahydro-pyrimidine-5-carboxylic acid using the methods described in example 88 or 93. mp=263° C.; LCMS m/z=634 (M+1); $^1$H NMR (DMSO-d$_6$) δ: 11.04 (s, 1H), 8.88 (s, 1H), 8.82 (s, 1H), 8.36 (m, 1H), 7.97 (m, 1H), 7.89 (m, 1H), 7.70 (m, 1H), 7.62 (m, 1H), 7.28-7.44 (br m, 5H), 7.07 (m, 1H), 6.49 (m, 1H), 4.02 (q, 2H), 3.66 (s, 3H), 1.31 (t, 3H, J=7.1 Hz).

Example 126

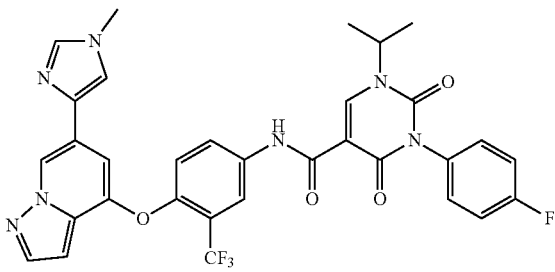

3-(4-Fluoro-phenyl)-1-isopropyl-2,4-dioxo-1,2,3,4-tetrahydro-pyrimidine-5-carboxylic acid{4-[6-(1-methyl-1H-imidazol-4-yl)-pyrazolo[1,5-a]pyridin-4-yloxy]-3-trifluoromethyl-phenyl}-amide. This compound was synthesized from 4-[6-(1-methyl-1H-imidazol-4-yl)-pyrazolo[1,5-a]pyridine-4-yloxy]-3-trifluoromethyl-phenylamine and 3-(4-fluoro-phenyl)-1-isopropyl-2,4-dioxo-1,2,3,4-tetrahydro-pyrimidine-5-carboxylic acid using the methods described in example 126. mp=149-151° C.; LCMS m/z=648 (M+1); $^1$H NMR (DMSO-d$_6$) δ: 11.04 (s, 1H), 8.82 (s, 1H), 8.68 (s, 1H), 8.41 (m, 1H), 7.97 (m, 1H), 7.87 (m, 1H), 7.70 (m, 1H), 7.63 (m, 1H), 7.28-7.44 (br m, 5H), 7.09 (m, 1H), 6.48 (m, 1H), 4.78 (m, 1H), 3.65 (s, 3H), 1.43 (d, 6H, J=6.8 Hz).

Example 127

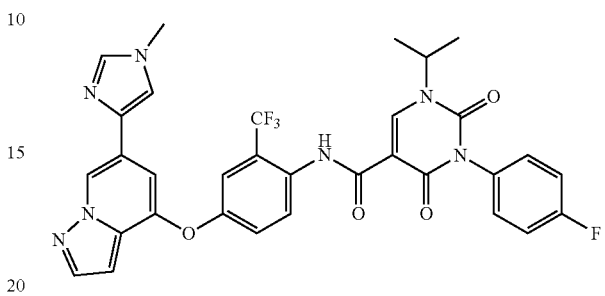

Step 1. 6-Bromo-4-(4-nitro-3-trifluoromethyl-phenoxy)-pyrazolo[1,5-a]pyridine. This compound was synthesized from 6-bromo-pyrazolo[1,5-a]pyridine-4-ol and 4-fluoro-1-nitro-2-trifluoromethyl-benzene using the method described in example 41 step 1. LCMS m/z=403 (M+1).

Step 2. 6-(1-Methyl-1H-imidazol-4-yl)-4-(4-nitro-3-trifluoromethyl-phenoxy)-pyrazolo[1,5-a]pyridine. This compound was synthesized using 6-bromo-4-(4-nitro-3-trifluoromethyl-phenoxy)-pyrazolo[1,5-a]pyridine and 1-methyl-4-tributylstannanyl-1H-imidazole using the stille method described in example 88 step 1. LCMS m/z=404 (M+1).

Step 3. 4-[6-(1-Methyl-1H-imidazol-4-yl)-pyrazolo[1,5-a]pyridin-4-yloxy]-3-trifluoromethyl-phenylamine. 6-(1-Methyl-1H-imidazol-4-yl)-4-(4-nitro-3-trifluoromethyl-phenoxy)-pyrazolo[1,5-a]pyridine was reduced using the method for example 41 step 3. LCMS m/z=374 (M+1).

Step 4. 3-(4-Fluoro-phenyl)-1-isopropyl-2,4-dioxo-1,2,3,4-tetrahydro-pyrimidine-5-carboxylic acid{4-[6-(1-methyl-1H-imidazol-4-yl)-pyrazolo[1,5-a]pyridin-4-yloxy]-2-trifluoromethyl-phenyl}-amide. This compound was synthesized from 4-[6-(1-methyl-1H-imidazol-4-yl)-pyrazolo[1,5-a]pyridine-4-yloxy]-2-trifluoromethyl-phenylamine and 3-(4-fluoro-phenyl)-1-isopropyl-2,4-dioxo-1,2,3,4-tetrahydro-pyrimidine-5-carboxylic acid using the methods described in example 88 or 93. mp=113-115° C.; LCMS m/z=648 (M+1); $^1$H NMR (DMSO-d$_6$) δ: 11.13 (s, 1H), 8.84 (s, 1H), 8.68 (s, 1H), 8.26 (m, 1H), 7.98 (m, 1H), 7.70 (m, 1H), 7.64 (s, 1H), 7.58 (m, 1H), 7.33-7.52 (br m, 5H), 7.16 (m, 1H), 6.55 (m, 1H), 4.76 (m, 1H), 3.71 (s, 3H), 1.42 (d, 6H, J=6.8 Hz).

Example 128

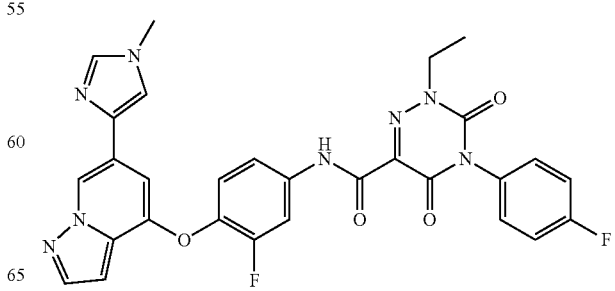

2-Ethyl-4-(4-fluoro-phenyl)-3,5-dioxo-2,3,4,5-tetrahydro-1,2,4-triazine-6-carboxylic acid {3-fluoro-4-[6-(1-methyl-1H-imidazol-4-yl)-pyrazolo[1,5-a]pyridin-4-yloxy]-phenyl}-amide. To 2-ethyl-4-(4-fluoro-phenyl)-3,5-dioxo-2,3,4,5-tetrahydro-1,2,4-triazine-6-carboxylic acid (0.04 g, 0.16 mmol) and N,N,N',N'-tetramethyl-O-(7-azabenzotriazol-1-yl)uronium hexafluorophosphate (0.07 g, 0.17 mmol) in N,N-dimethylformamide (5 mL) was added N,N-diisopropylethylamine (0.03 mL, 0.16 mmol). After 0.5 h stirring at rt, 3-fluoro-4-[6-(1-methyl-1H-imidazol-4-yl)-pyrazolo[1,5-a]pyridin-4-yloxy]phenylamine (0.05 g, 0.15 mmol) was added and stirred at 80° C. for 2 h. The reaction was diluted with ethyl acetate, washed with 1N sodium carbonate solution, water and brine, dried over sodium sulfate, and concentrated. The product was purified using Prep TLC plates (5% methanol/dichloromethane) and concentrated to give 0.05 g, 55%. mp=147-150° C.; LCMS m/z=585 (M+1); $^1$H NMR (DMSO-d$_6$) δ: 10.86 (s, 1H), 8.78 (s, 1H), 7.99 (m, 2H), 7.66 (m, 1H), 7.60 (m, 1H), 7.55 (m, 1H), 7.36-7.46 (br m, 5H), 6.86 (s, 1H), 6.69 (m, 1H), 4.09 (q, 2H), 3.64 (s, 3H), 1.36 (t, 3H, J=7.0 Hz).

Example 129

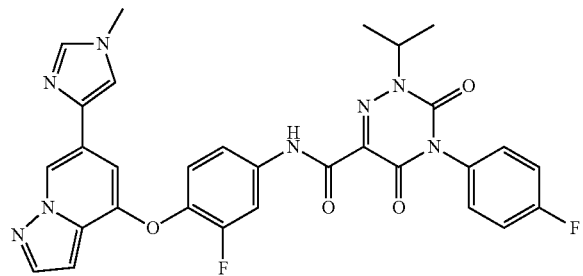 [SMILES: CC(C)n1nc(C(=O)Nc2ccc(Oc3cc(-c4cn(C)cn4)cn4nccc34)c(F)c2)c(=O)n(-c2ccc(F)cc2)c1=O]

4-(4-Fluoro-phenyl)-2-isopropyl-3,5-dioxo-2,3,4,5-tetrahydro-1,2,4-triazine-6-carboxylic acid{3-fluoro-4-[6-(1-methyl-1H-imidazol-4-yl)-pyrazolo[1, 5-a]pyridin-4-yloxy]-phenyl}-amide. This compound was synthesized from 3-fluoro-4-[6-(1-methyl-1H-imidazol-4-yl)-pyrazolo[1,5-a]pyridin-4-yloxy]-phenylamine and 4-(4-fluoro-phenyl)-2-isopropyl-3,5-dioxo-2,3,4,5-tetrahydro-1,2,4-triazine-6-carboxylic acid using the methods described in example 128. mp=171-173° C.; LCMS m/z=599 (M+1); $^1$H NMR (DMSO-d$_6$) δ: 10.84 (s, 1H), 8.78 (s, 1H), 8.00 (m, 2H), 7.66 (m, 1H), 7.60 (m, 1H), 7.54 (m, 1H), 7.36-7.45 (br m, 5H), 6.87 (s, 1H), 6.69 (m, 1H), 4.91 (m, 1H), 3.65 (s, 3H), 1.38 (d, 6H, J=6.6 Hz).

Example 130

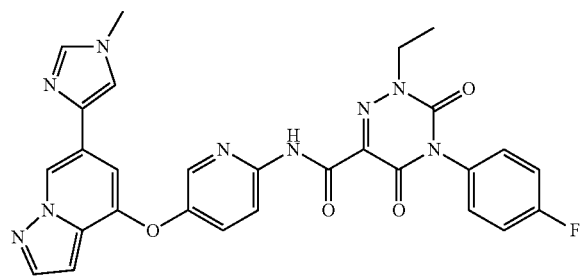 [SMILES: CCn1nc(C(=O)Nc2ccc(Oc3cc(-c4cn(C)cn4)cn4nccc34)cn2)c(=O)n(-c2ccc(F)cc2)c1=O]

2-Ethyl-4-(4-fluoro-phenyl)-3,5-dioxo-2,3,4,5-tetrahydro-1,2,4-triazine-6-carboxylic acid{5-[6-(1-methyl-1H-imidazol-4-yl)-pyrazolo[1,5-a]pyridin-4-yloxy]-pyridin-2-yl}-amide. The compound was synthesized from 5-[6-(1-methyl-1H-imidazol-4-yl)-pyrazolo[1,5-a]pyridin-4-yloxy]-pyridin-2-ylamine and 2-ethyl-4-(4-fluoro-phenyl)-3,5-dioxo-2,3,4,5-tetrahydro-1,2,4-triazine-6-carboxylic acid using the amide coupling method described in example 128. mp=100° C.; LCMS m/z=568 (M+1); $^1$H NMR (DMSO-d$_6$) δ: 11.19 (s, 1H), 8.80 (s, 1H), 8.38 (m, 1H), 8.27 (m, 1H), 7.99 (m, 1H), 7.83 (m, 1H), 7.68 (s, 1H), 7.62 (s, 1H), 7.43 (m, 4H), 7.02 (s, 1H), 6.62 (m, 1H), 4.10 (q, 2H), 3.65 (s, 3H), 1.36 (t, 3H, J=7.2 Hz).

Example 131

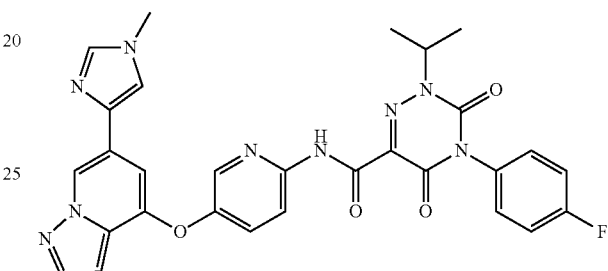

4-(4-Fluoro-phenyl)-2-isopropyl-3,5-dioxo-2,3,4,5-tetrahydro-1,2,4-triazine-6-carboxylic acid{5-[6-(1-methyl-1H-imidazol-4-yl)-pyrazolo[1,5-a]pyridin-4-yloxy]-pyridin-2-yl}-amide. This compound was synthesized from 5-[6-(1-methyl-1H-imidazol-4-yl)-pyrazolo[1,5-a]pyridin-4-yloxy]-pyridin-2-ylamine and 4-(4-fluoro-phenyl)-2-isopropyl-3,5-dioxo-2,3,4,5-tetrahydro-1,2,4-triazine-6-carboxylic acid using the methods described in example 128 and 130. mp=113° C.; LCMS m/z=582 (M+1); $^1$H NMR (DMSO-d$_6$) δ: 11.18 (s, 1H), 8.80 (s, 1H), 8.38 (m, 1H), 8.29 (m, 1H), 7.99 (m, 1H), 7.83 (m, 1H), 7.68 (m, 1H), 7.62 (m, 1H), 7.36-7.45 (m, 4H), 7.03 (m, 1H), 6.62 (m, 1H), 4.92 (m, 1H), 3.65 (s, 3H), 1.37 (d, 6H, J=6.6 Hz).

Example 132

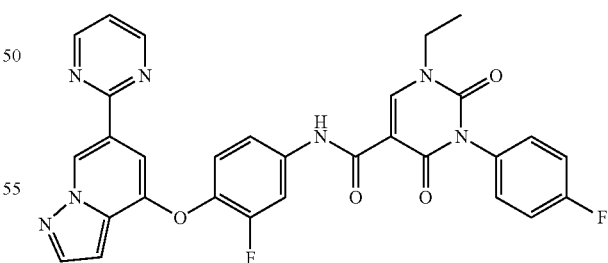

Step 1. 4-(2-Fluoro-4-nitro-phenoxy)-6-pyrimidin-2-yl-pyrazolo[1,5-a]pyridine. To an oven dried schlenck flask was added 6-bromo-4-(2-fluoro-4-nitro-phenoxy)-pyrazolo[1,5-a]pyridine (0.25 g, 0.71 mmol), 2-tributylstannanyl-pyrimidine (0.52 mL, 1.42 mmol), bis(triphenylphosphine) palladium(II) chloride (0.1 g, 0.14 mmol), followed by N,N-dimethylformamide (8 mL) was degassed 3× under an atmosphere of nitrogen and then heated at 130° C. for 1 h and cooled at rt. The reaction was partitioned between dichloromethane and 1N sodium carbonate, washed with water and brine, dried over sodium sulfate, and concentrated. The product was chromatographed on silica gel using a single step column (20-50% ethyl acetate/hexanes) and concentrated to give 0.14 g, 56%. LCMS m/z=352 (M+1).

Step 2. 3-Fluoro-4-(6-pyrimidin-2-yl-pyrazolo[1,5-a]pyridin-4-yloxy)-phenylamine. This compound was synthesized from 4-(2-fluoro-4-nitro-phenoxy)-6-pyrimidin-2-yl-pyrazolo[1,5-a]pyridine and tin (II) chloride dihydrate using the reduction method described in example 51 step 2. LCMS m/z=322 (M+1).

Step 3. 1-Ethyl-3-(4-fluoro-phenyl)-2,4-dioxo-1,2,3,4-tetrahydro-pyrimidine-5-carboxylic acid [3-fluoro-4-(6-pyrimidin-2-yl-pyrazolo[1,5-a]pyridin-4-yloxy)-phenyl]-amide. The compound was synthesized from 3-fluoro-4-(6-pyrimidin-2-yl-pyrazolo[1,5-a]pyridin-4-yloxy)-phenylamine and 1-ethyl-3-(4-fluoro-phenyl)-2,4-dioxo-1,2,3,4-tetrahydro-pyrimidine-5-carboxylic acid using the amide coupling method described in example 41 step 4. mp=290° C.; LCMS m/z=582 (M+1); $^1$H NMR (DMSO-$d_6$) δ: 11.04 (s, 1H), 9.31 (s, 1H), 8.89 (s, 1H), 8.86 (m, 2H), 8.18 (m, 1H), 8.04 (m, 1H), 7.33-7.57 (br m, 7H), 7.25 (s, 1H), 6.88 (m, 1H), 4.03 (q, 2H), 1.31 (t, 3H, J=7.0 Hz).

Example 133

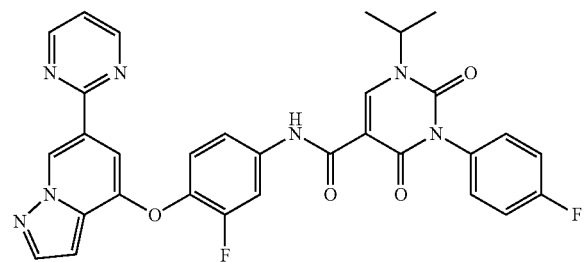 [SMILES: CC(C)n1cc(C(=O)Nc2ccc(Oc3cc(-c4ncccn4)cn4nccc34)c(F)c2)c(=O)n(-c2ccc(F)cc2)c1=O]

3-(4-Fluoro-phenyl)-1-isopropyl-2,4-dioxo-1,2,3,4-tetrahydro-pyrimidine-5-carboxylic acid[3-fluoro-4-(6-pyrimidin-2-yl-pyrazolo[1,5-a]pyridin-4-yloxy)-phenyl]-amide. This compound was synthesized from 3-fluoro-4-(6-pyrimidin-2-yl-pyrazolo[1,5-a]pyridin-4-yloxy)-phenylamine and 3-(4-fluoro-phenyl)-1-isopropyl-2,4-dioxo-1,2,3,4-tetrahydro-pyrimidine-5-carboxylic acid using the methods described in example 132. mp=248-250° C.; LCMS m/z=596 (M+1); $^1$H NMR (DMSO-$d_6$) δ: 11.04 (s, 1H), 9.31 (s, 1H), 8.86 (m, 2H), 8.68 (s, 1H), 8.18 (m, 1H), 8.04 (m, 1H), 7.34-7.56 (br m, 7H), 7.25 (s, 1H), 6.88 (m, 1H), 4.80 (m, 1H), 1.44 (d, 6H, J=6.8 Hz).

Example 134

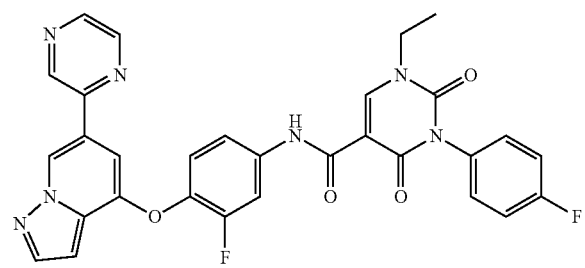 [SMILES: CCn1cc(C(=O)Nc2ccc(Oc3cc(-c4cnccn4)cn4nccc34)c(F)c2)c(=O)n(-c2ccc(F)cc2)c1=O]

1-Ethyl-3-(4-fluoro-phenyl)-2,4-dioxo-1,2,3,4-tetrahydro-pyrimidine-5-carboxylic acid[3-fluoro-4-(6-pyrazin-2-yl-pyrazolo[1,5-a]pyridin-4-yloxy)-phenyl]-amide. The compound was synthesized from 3-fluoro-4-(6-pyazin-2-yl-pyrazolo[1,5-a]pyridin-4-yloxy)-phenylamine and 1-ethyl-3-(4-fluoro-phenyl)-2,4-dioxo-1,2,3,4-tetrahydro-pyrimidine-5-carboxylic acid using the methods described in example 132. mp=263° C.; LCMS m/z=582 (M+1); $^1$H NMR (DMSO-$d_6$) δ: 11.03 (s, 1H), 9.45 (s, 1H), 9.40 (m, 1H), 8.89 (s, 1H), 8.63 (m, 1H), 8.58 (m, 1H), 8.17 (m, 1H), 8.02 (m, 1H), 7.33-7.54 (br m, 6H), 7.16 (s, 1H), 6.84 (m, 1H), 4.02 (q, 2H), 1.31 (t, 3H, J=7.0 Hz).

Example 135

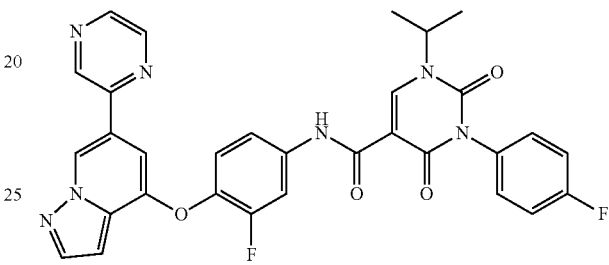

3-(4-Fluoro-phenyl)-1-isopropyl-2,4-dioxo-1,2,3,4-tetrahydro-pyrimidine-5-carboxylic acid[3-fluoro-4-(6-pyrazin-2-yl-pyrazolo[1,5-a]pyridin-4-yloxy)-phenyl]-amide. This compound was synthesized from 3-fluoro-4-(6-pyazin-2-yl-pyrazolo[1,5-a]pyridin-4-yloxy)-phenylamine and 3-(4-fluoro-phenyl)-1-isopropyl-2,4-dioxo-1,2,3,4-tetrahydro-pyrimidine-5-carboxylic acid using the methods described in example 135. mp=242° C.; LCMS m/z=596 (M+1); $^1$H NMR (DMSO-$d_6$) δ: 11.03 (s, 1H), 9.45 (s, 1H), 9.40 (m, 1H), 8.68 (s, 1H), 8.63 (m, 1H), 8.58 (m, 1H), 8.17 (m, 1H), 8.03 (m, 1H), 7.33-7.54 (br m, 6H), 7.17 (s, 1H), 6.83 (m, 1H), 4.79 (m, 1H), 1.43 (d, 6H, J=6.8 Hz).

Example 136

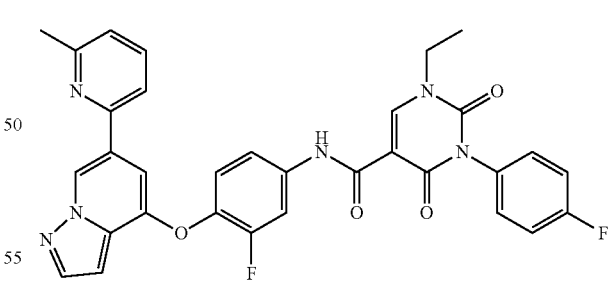

1-Ethyl-3-(4-fluoro-phenyl)-2,4-dioxo-1,2,3,4-tetrahydro-pyrimidine-5-carboxylic acid{3-fluoro-4-[6-(6-methyl-pyridin-2-yl)-pyrazolo[1,5-a]pyridin-4-yloxy]-phenyl}-amide. The compound was synthesized from 3-fluoro-4-[6-(6-methyl-pyridin-2-yl)-pyrazolo[1,5-a]pyridin-4-yloxy]phenylamine and 1-ethyl-3-(4-fluoro-phenyl)-2,4-dioxo-1,2,3,4-tetrahydro-pyrimidine-5-carboxylic acid using the methods described in example 132. mp=266-267° C.; LCMS m/z=595 (M+1); $^1$H NMR (DMSO-$d_6$) δ: 11.02 (s, 1H), 9.23 (s, 1H), 8.88 (s, 1H), 8.10 (s, 1H), 8.01 (m, 1H), 7.84 (m, 1H), 7.76 (m, 1H), 7.33-7.50 (br m, 6H), 7.26 (s, 1H), 7.21 (m, 1H), 6.72 (m, 1H), 4.02 (q, 2H), 2.46 (s, 3H), 1.31 (t, 3H, J=7.0 Hz).

Example 137

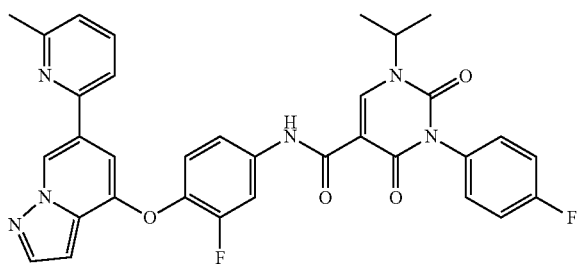 [SMILES: Cc1cccc(-c2cc(Oc3ccc(NC(=O)c4cn(C(C)C)c(=O)n(-c5ccc(F)cc5)c4=O)cc3F)c3ccnn3c2)n1]

3-(4-Fluoro-phenyl)-1-isopropyl-2,4-dioxo-1,2,3,4-tetrahydro-pyrimidine-5-carboxylic acid{3-fluoro-4-[6-(6-methyl-pyridin-2-yl)-pyrazolo[1,5-a]pyridin-4-yloxy]-phenyl}-amide. The compound was synthesized from 3-fluoro-4-[6-(6-methyl-pyridin-2-yl)-pyrazolo[1,5-a]pyridin-4-yloxy]phenylamine and 3-(4-fluoro-phenyl)-1-isopropyl-2,4-dioxo-1,2,3,4-tetrahydro-pyrimidine-5-carboxylic acid using the methods described in example 132. mp=222° C.; LCMS m/z=609 (M+1); $^1$H NMR (DMSO-d$_6$) δ: 11.02 (s, 1H), 9.23 (s, 1H), 8.67 (s, 1H), 8.10 (m, 1H), 8.02 (m, 1H), 7.85 (m, 1H), 7.73 (m, 1H), 7.33-7.50 (br m, 6H), 7.27 (s, 1H), 7.21 (m, 1H), 6.72 (m, 1H), 4.79 (m, 1H), 2.46 (s, 3H), 1.43 (d, 6H, J=6.8 Hz).

Example 138

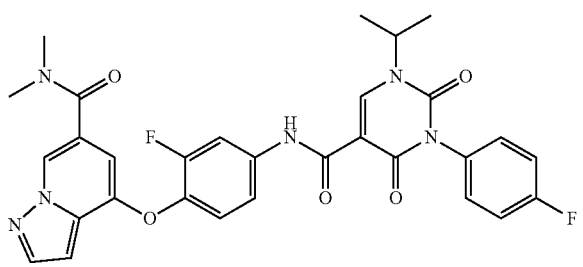 [SMILES: CC(C)n1cc(C(=O)Nc2ccc(Oc3cc(C(=O)N(C)C)cn4nccc34)c(F)c2)c(=O)n(-c2ccc(F)cc2)c1=O]

Step 1. 4-Benzyloxy-pyrazolo[1,5-a]pyridine-6-carbonitrile. To an oven dried schlenck flask was added 4-benzyloxy-6-bromo-pyrazolo[1,5-a]pyridine (0.5 g, 1.65 mmol), zinc cyanide (0.39 g, 3.3 mmol), tetrakis(triphenylphosphine)palladium(0) (0.19 g, 0.17 mmol), followed by in N-methylpyrrolidinone (40 mL) and was degassed 3× under an atmosphere of nitrogen, heated at 140° C. for 2 h, and cooled at rt. The reaction was partitioned between ethyl acetate and water, washed with brine, dried over sodium sulfate, and concentrated. The product was chromatographed on silica gel using a single step column (5-20% ethyl acetate/hexanes) and concentrated to give 0.3 g, 72%. LCMS m/z=250 (M+1).

Step 2. 4-Benzyloxy-pyrazolo[1,5-a]pyridine-6-carboxylic acid. To 4-benzyloxy-pyrazolo[1,5-a]pyridine-6-carbonitrile (0.28 g, 1.12 mmol) in ethanol (3 mL) and 5 M sodium hydroxide (3 mL) was heated at 100° C. for 2 h and concentrated to remove organics. 1N HCl was added dropwise to acid pH and extracted with dichloromethane, washed with water and brine, dried over sodium sulfate, and concentrated to give the title compound 0.23 g, 75%. LCMS m/z=269 (M+1).

Step 3. 4-Hydroxy-pyrazolo[1,5-a]pyridine-6-carboxylic acid dimethylamide. To 4-benzyloxy-pyrazolo[1,5-a]pyridine-6-carboxylic acid (0.21 g, 0.78 mmol) in N,N-dimethylformamide (7 mL) was added N-(3-dimethylaminopropyl)-N'-ethylcarbodiimide hydrochloride (0.16 g, 0.85 mmol), 1-hydroxybenzotriazole (0.12 g, 0.85 mmol), N,N-diisopropylethylamine (0.41 mL, 2.33 mmol), followed by 2 M dimethylamine in tetrahydrofuran (0.43 mL, 0.85 mmol) and was heated at 70° C. for 4 h and cooled at rt. The reaction was diluted with ethyl acetate, washed with water and brine, dried over sodium sulfate, and concentrated to give 4-benzyloxy-pyrazolo[1,5-a]pyridine-6-carboxylic acid dimethylamide 0.21 g, 93%; LCMS m/z=296 (M+1). To 4-benzyloxy-pyrazolo[1,5-a]pyridine-6-carboxylic acid dimethylamide (0.21 g, 0.73 mmol) in ethanol (10 mL) under an atmosphere of nitrogen was added 20% Pd(OH)$_2$/C (50% wet; 10:40:50, palladium hydroxide:carbon black:water) (0.11 g, 0.16 mmol), 1 drop of HCl and hydrogenated on a Parr at 40 psi overnight. The reaction was filtered through a pad of celite, washed with dichloromethane and methanol and concentrated. The product was chromatographed on silica gel using a single step column (5% methanol/dichloromethane) and concentrated to give 0.12 g, 79%. LCMS m/z=206 (M+1).

Step 4. 4-(2-fluoro-4-nitro-phenoxy)-pyrazolo[1,5-a]pyridine-6-carboxylic acid dimethylamide. This compound was synthesized from 4-hydroxy-pyrazolo[1,5-a]pyridine-6-carboxylic acid dimethylamide and 1,2-difluoro-4-nitro-benzene using the method described in example 41 step 1. LCMS m/z=345 (M+1).

Step 5. 4-(4-Amino-2-fluoro-phenoxy)-pyrazolo[1,5-a]pyridine-6-carboxylic acid dimethylamide. The compound was synthesized from 4-(2-fluoro-4-nitro-phenoxy)-pyrazolo[1,5-a]pyridine-6-carboxylic acid dimethylamide and 20% Pd(OH)$_2$/C (50% wet; 10:40:50, palladium hydroxide:carbon black:water) using the reduction method described in example 41 step 3. LCMS m/z=315 (M+1).

Step 6. 4-(2-Fluoro-4-{[3-(4-fluoro-phenyl)-1-isopropyl-2,4-dioxo-1,2,3,4-tetrahydro-pyrimidine-5-carbonyl]-amino}-phenoxy)-pyrazolo[1,5-a]pyridine-6-carboxylic acid dimethylamide. This compound was synthesized from 4-(4-amino-2-fluoro-phenoxy)-pyrazolo[1,5-a]pyridine-6-carboxylic acid dimethylamide and 3-(4-fluoro-phenyl)-1-isopropyl-2,4-dioxo-1,2,3,4-tetrahydro-pyrimidine-5-carboxylic acid using the amide coupling method described in example 41 step 4. mp=109° C.; LCMS m/z=589 (M+1); $^1$H NMR (DMSO-d$_6$) δ: 11.01 (s, 1H), 8.67 (s, 2H), 8.12 (m, 1H), 8.00 (m, 1H), 7.33-7.50 (br m, 6H), 6.78 (m, 1H), 6.40 (s, 1H), 4.77 (m, 1H), 2.95 (s, 6H), 1.43 (d, 6H, J=6.8 Hz).

Example 139

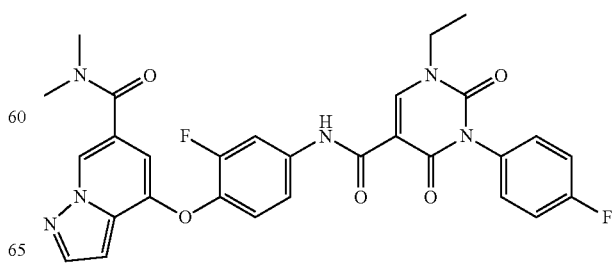

4-(4-{[1-Ethyl-3-(4-fluoro-phenyl)-2,4-dioxo-1,2,3,4-tetrahydro-pyrimidine-5-carbonyl]-amino}-2-fluoro-phenoxy)-pyrazolo[1,5-a]pyridine-6-carboxylic acid dimethylamide. This compound was synthesized from 4-(4-amino-2-fluoro-phenoxy)-pyrazolo[1,5-a]pyridine-6-carboxylic acid dimethylamide and 1-ethyl-3-(4-fluoro-phenyl)-2,4-dioxo-1,2,3,4-tetrahydro-pyrimidine-5-carboxylic acid using the methods described in example 138. mp=99-102° C.; LCMS m/z=575 (M+1); $^1$H NMR (DMSO-d$_6$) δ: 11.01 (s, 1H), 8.88 (s, 1H), 8.66 (s, 1H), 8.12 (m, 1H), 8.00 (m, 1H), 7.33-7.51 (br m, 6H), 6.78 (m, 1H), 6.39 (s, 1H), 4.02 (q, 2H), 2.95 (s, 6H), 1.31 (t, 3H, J=7.0 Hz).

Example 140

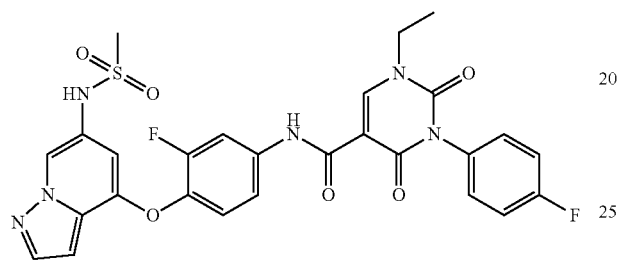

Step 1. 4-(2-Fluoro-4-nitro-phenoxy)-pyrazolo[1,5-a]pyridin-6-ylamine. To an oven dried schlenck flask was added 6-bromo-4-(2-fluoro-4-nitro-phenoxy)-pyrazolo[1,5-a]pyridine (0.32 g, 0.9 mmol), palladium acetate (0.02 g, 0.09 mmol), rac.-2,2'-bis(diphenylphosphino)-1,1'-binaphthyl (0.11 g, 0.18 mmol), cesium carbonate (0.88 g, 2.7 mmol), and benzophenone imine (0.18 mL, 1.1 mmol). Toluene (10 mL) was added and degassed 3× under an atmosphere of nitrogen then heated at 100° C. overnight. The reaction was cooled at rt, diluted with dichloromethane, filtered through a pad of celite, washed with water and brine, dried over sodium sulfate, and concentrated. The product was chromatographed on silica gel using a single step column (10% ethyl acetate/hexanes) and concentrated to give benzhydrylidene-[4-(2-fluoro-4-nitro-phenoxy)-pyrazolo[1,5-a]pyridine-6-yl]-amine 0.37 g, 91%; LCMS m/z=453 (M+1). Benzhydrylidene-[4-(2-fluoro-4-nitro-phenoxy)-pyrazolo[1,5-a]pyridine-6-yl]-amine was dissolved in tetrohydrofuran (10 mL) and 2M hydrogen chloride (5 mL) was added and was stirred at rt overnight. The solvent was evaporated, 2N sodium hydroxide was added to adjust pH ~9-10, extracted with dichloromethane, washed with water and brine, dried over sodium sulfate, and concentrated. The product was chromatographed on silica gel using a single step column (1% methanol/dichloromethane) and concentrated to give 0.18 g, 71%. LCMS m/z=289 (M+1).

Step 2. N-[4-(2-Fluoro-4-nitro-phenoxy)-pyrazolo[1,5-a]pyridin-6yl]-methanesulfonamide. To 4-(2-fluoro-4-nitro-phenoxy)-pyrazolo[1,5-a]pyridin-6-ylamine (0.08 g, 0.29 mmol) in pyridine (3 mL) under an atmosphere of nitrogen was added methanesulfonyl chloride (0.04 mL, 0.58 mmol) and the reaction was stirred at rt for 15 min. The reaction was diluted with dichloromethane, washed with aq. citric acid 3×, 1N sodium carbonate solution, water and brine, then dried over sodium sulfate, and concentrated to give product 0.100 g, 95%. LCMS m/z=367 (M+1).

Step 3. N-[4-(4-Amino-2-fluoro-phenoxy)-pyrazolo[1,5-a]pyridin-6-yl]-methanesulfonamide. This compound was synthesized from N-[4-(2-fluoro-4-nitro-phenoxy)-pyrazolo[1,5-a]pyridin-6yl]-methanesulfonamide and 20% Pd(OH)$_2$/C (50% wet; 10:40:50, palladium hydroxide:carbon black:water) using the reduction method described in example 41 step 3. LCMS m/z=337 (M+1).

Step 4. 1-Ethyl-3-(4-fluoro-phenyl)-2,4-dioxo-1,2,3,4-tetrahydro-pyrimidine-5-carboxylic acid[3-fluoro-4-(6-methanesulfonylamino-pyrazolo[1,5-a]pyridin-4-yloxy)-phenyl]-amide. The compound was synthesized from N-[4-(4-amino-2-fluoro-phenoxy)-pyrazolo[1,5-a]pyridin-6-yl]-methanesulfonamide and 1-ethyl-3-(4-fluoro-phenyl)-2,4-dioxo-1,2,3,4-tetrahydro-pyrimidine-5-carboxylic acid using the amide coupling method described in example 41 step 4. mp=127° C.; LCMS m/z=597 (M+1); $^1$H NMR (DMSO-d$_6$) δ: 11.01 (s, 1H), 9.58 (br s, 1H), 8.88 (s, 1H), 8.22 (s, 1H), 8.00 (m, 2H), 7.33-7.51 (br m, 6H), 6.65 (m, 1H), 6.32 (s, 1H), 4.02 (q, 2H), 2.91 (s, 3H), 1.30 (t, 3H, J=7.1 Hz).

Example 141

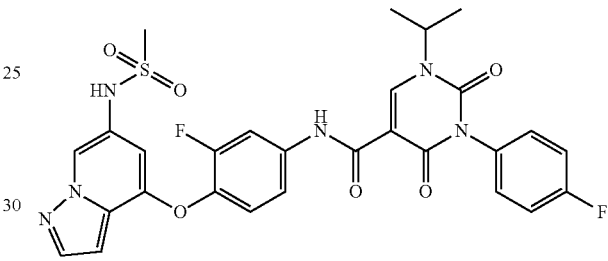

3-(4-Fluoro-phenyl)-1-isopropyl-2,4-dioxo-1,2,3,4-tetrahydro-pyrimidine-5-carboxylic acid[3-fluoro-4-(6-methanesulfonylamino-pyrazolo[1,5-a]pyridin-4-yloxy)-phenyl]-amide. This compound was synthesized from N-[4-(4-amino-2-fluoro-phenoxy)-pyrazolo[1,5-a]pyridin-6-yl]-methanesulfonamide and 3-(4-fluoro-phenyl)-1-isopropyl-2,4-dioxo-1,2,3,4-tetrahydro-pyrimidine-5-carboxylic acid using the methods described in example 140. mp=125° C.; LCMS m/z=611 (M+1); $^1$H NMR (DMSO-d$_6$) δ: 11.01 (s, 1H), 9.58 (br s, 1H), 8.68 (s, 1H), 8.28 (s, 1H), 8.00 (m, 2H), 7.33-7.52 (br m, 6H), 6.68 (m, 1H), 6.38 (s, 1H), 4.78 (m, 1H), 2.96 (s, 3H), 1.43 (d, 6H, J=6.8 Hz).

Example 142

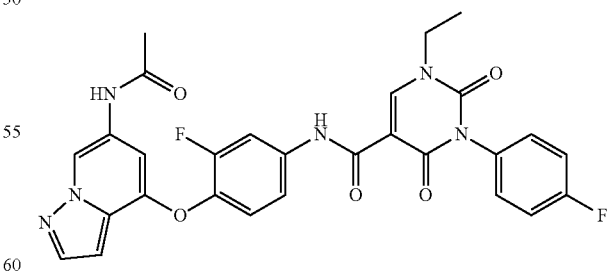

Step 1. N-[4-(2-fluoro-4-nitro-phenoxy)-pyrazolo[1,5-a]pyridin-6-yl]-acetamide. To 4-(2-fluoro-4-nitro-phenoxy)-pyrazolo[1,5-a]pyridin-6-ylamine (0.09 g, 0.29 mmol) in dichloromethane (5 mL) at 0° C. under an atmosphere of nitrogen was added triethylamine (0.08 mL, 0.59 mmol), followed by acetyl chloride (0.04 mL, 0.59 mmol) and warmed at rt for 1 h. The reaction was washed with 1N sodium carbonate solution, water and brine, dried over sodium sulfate, and concentrated to give product 0.1 g (100%). LCMS m/z=331 (M+1).

Step 2. N-[4-(4-Amino-2-fluoro-phenoxy)-pyrazolo[1,5-a]pyridin-6-yl]-acetamide. The compound was synthesized from N-[4-(2-fluoro-4-nitro-phenoxy)-pyrazolo[1,5-a]pyridin-6-yl]-acetamide and 20% Pd(OH)$_2$/C (50% wet, 10:40:50, palladium hydroxide:carbon black:water) using the reduction method described in example 41 step 3. LCMS m/z=301 (M+1).

Step 3. 1-Ethyl-3-(4-fluoro-phenyl)-2,4-dioxo-1,2,3,4-tetrahydro-pyrimidine-5-carboxylic acid[4-(6-acetylamino-pyrazolo[1,5-a]pyridin-4-yloxy)-3-fluoro-phenyl]-amide.
The compound was synthesized from N-[4-(4-amino-2-fluoro-phenoxy)-pyrazolo[1,5-a]pyridin-6-yl]-acetamide and 1-ethyl-3-(4-fluoro-phenyl)-2,4-dioxo-1,2,3,4-tetrahydro-pyrimidine-5-carboxylic acid using the amide coupling method described in example 41 step 4. mp=290° C.; LCMS m/z=561 (M+1); $^1$H NMR (DMSO-d$_6$) δ: 11.03 (s, 1H), 9.94 (s, 1H), 9.11 (s, 1H), 8.89 (s, 1H), 8.03 (m, 1H), 7.95 (m, 1H), 7.55 (m, 1H), 7.33-7.45 (br m, 5H), 6.71 (m, 1H), 6.38 (s, 1H), 4.02 (q, 2H), 2.00 (s, 3H), 1.31 (t, 3H, J=7.1 Hz).

Example 143

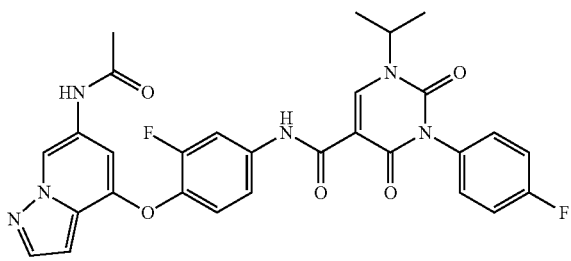 [SMILES: CC(=O)Nc1cc(Oc2ccc(NC(=O)c3cn(C(C)C)c(=O)n(-c4ccc(F)cc4)c3=O)cc2F)c2ccnn2c1]

3-(4-Fluoro-phenyl)-1-isopropyl-2,4-dioxo-1,2,3,4-tetrahydro-pyrimidine-5-carboxylic acid[4-(6-acetylamino-pyrazolo[1,5-a]pyridin-4-yloxy)-3-fluoro-phenyl]-amide. This compound was synthesized from N-[4-(4-amino-2-fluoro-phenoxy)-pyrazolo[1,5-a]pyridin-6-yl]-acetamide and 3-(4-fluoro-phenyl)-1-isopropyl-2,4-dioxo-1,2,3,4-tetrahydro-pyrimidine-5-carboxylic acid using the methods described in example 142. mp=>290° C.; LCMS m/z=575 (M+1); $^1$H NMR (DMSO-d$_6$) δ: 11.03 (s, 1H), 9.94 (s, 1H), 9.12 (s, 1H), 8.68 (s, 1H), 8.04 (m, 1H), 7.95 (m, 1H), 7.53 (m, 1H), 7.33-7.45 (br m, 5H), 6.71 (m, 1H), 6.39 (s, 1H), 4.78 (m, 1H), 1.99 (s, 3H), 1.43 (d, 6H, J=6.8 Hz).

Example 144

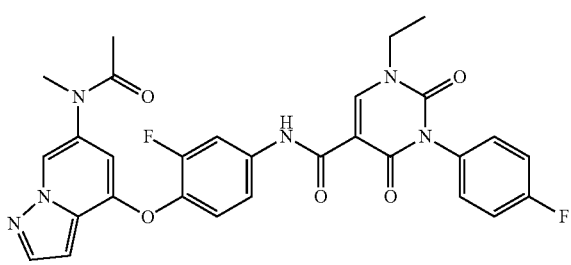 [SMILES: CCn1cc(C(=O)Nc2ccc(Oc3cc(N(C)C(C)=O)cn4nccc34)c(F)c2)c(=O)n(-c2ccc(F)cc2)c1=O]

Step 1. N-[4-(2-fluoro-nitro-phenoxy)-pyrazolo[1,5-a]pyridin-6-yl]-N-methyl-acetamide. To N-[4-(2-fluoro-4-nitro-phenoxy)-pyrazolo[1,5-a]pyridin-6-yl]-acetamide (0.08 g, 0.23 mmol) in N,N-dimethylformamide (5 mL) at 0° C. under an atmosphere of nitrogen was added sodium hydride (60% dispersion in mineral oil, 3:2, sodium hydride:mineral oil) (0.01 g, 0.28 mmol), followed by methyl iodide (0.03 mL, 0.46 mmol) and stirred at this temp for 30 min. The reaction was partitioned between ethyl acetate and 1N sodium carbonate, washed with water and brine, dried over sodium sulfate, and concentrated. The product was chromatographed on silica gel using a single step column (1% methanol/dichloromethane) and concentrated to give 0.08 g, 97%. LCMS m/z=345 (M+1).

Step 2. N-[4-(4-Amino-2-fluoro-phenoxy)-pyrazolo[1,5-a]pyridin-6-yl]-N-methyl-acetamide. The compound was synthesized from N-[4-(2-fluoro-nitro-phenoxy)-pyrazolo[1,5-a]pyridin-6-yl]-N-methyl-acetamide and 20% Pd(OH)$_2$/C (50% wet, 10:40:50, palladium hydroxide:carbon black:water) using the reduction method described in example 41 step 3. LCMS m/z=315 (M+1).

Step 3. 1-Ethyl-3-(4-fluoro-phenyl)-2,4-dioxo-1,2,3,4-tetrahydro-pyrimidine-5-carboxylic acid{4-[6-(acetyl-methyl-amino)-pyrazolo[1,5-a]pyridin-4-yloxy]-3-fluoro-phenyl}-amide. This compound was synthesized from N-[4-(4-amino-2-fluoro-phenoxy)-pyrazolo[1,5-a]pyridin-6-yl]-N-methyl-acetamide and 1-ethyl-3-(4-fluoro-phenyl)-2,4-dioxo-1,2,3,4-tetrahydro-pyrimidine-5-carboxylic acid using the amide coupling method described in example 41 step 4. mp=205-208° C.; LCMS m/z=575 (M+1); $^1$H NMR (DMSO-d$_6$) δ: 11.00 (s, 1H), 8.88 (s, 1H), 8.75 (s, 1H), 8.08 (s, 1H), 7.99 (m, 1H), 7.33-7.49 (br m, 6H), 6.72 (s, 1H), 6.62 (s, 1H), 4.02 (q, 2H), 3.08 (s, 3H), 1.81 (s, 3H), 1.30 (t, 3H, J=7.0 Hz).

Example 145

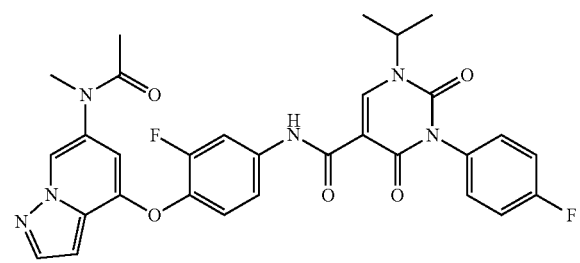 [SMILES: CC(=O)N(C)c1cc(Oc2ccc(NC(=O)c3cn(C(C)C)c(=O)n(-c4ccc(F)cc4)c3=O)cc2F)c2ccnn2c1]

3-(4-Fluoro-phenyl)-1-isopropyl-2,4-dioxo-1,2,3,4-tetrahydro-pyrimidine-5-carboxylic acid{4-[6-(acetyl-methyl-amino)-pyrazolo[1,5-a]pyridin-4-yloxy]-3-fluoro-phenyl}-amide. The compound was synthesized from N-[4-(4-amino-2-fluoro-phenoxy)-pyrazolo[1,5-a]pyridin-6-yl]-N-methyl-acetamide and 3-(4-fluoro-phenyl)-1-isopropyl-2,4-dioxo-1,2,3,4-tetrahydro-pyrimidine-5-carboxylic acid using the methods described in example 144. mp=233-236° C.; LCMS m/z=589 (M+1); $^1$H NMR (DMSO-d$_6$) δ: 11.00 (s, 1H), 8.75 (s, 1H), 8.67 (s, 1H), 8.08 (s, 1H), 7.99 (m, 1H), 7.33-7.48 (br m, 6H), 6.72 (m, 1H), 6.63 (s, 1H), 4.77 (m, 1H), 3.08 (s, 3H), 1.82 (s, 3H), 1.43 (d, 6H, J=6.8 Hz).

Example 146

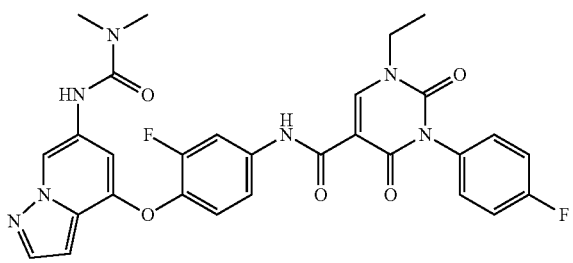 [SMILES: CCn1cc(C(=O)Nc2ccc(Oc3cc(NC(=O)N(C)C)cn4nccc34)c(F)c2)c(=O)n(-c2ccc(F)cc2)c1=O]

Step 1. 3-[4-(2-Fluoro-4-nitro-phenoxy)-pyrazolo[1,5-a]pyridin-6-yl]-1,1-dimethyl-urea. To 4-(2-fluoro-4-nitro-phenoxy)-pyrazolo[1,5-a]pyridin-6-ylamine (example 140 step 1) (0.09 g, 0.31 mmol) in pyridine (3 mL) under an atmosphere of nitrogen was added N, N-dimethylcarbamoyl chloride (0.06 mL, 0.62 mmol) and stirred at 50° C. overnight. The reaction was cooled at rt, diluted with dichloromethane, washed with aq. citric acid 3×, 1N sodium carbonate solution and water, dried over sodium sulfate, and concentrated. The product was chromatographed on silica gel using a single step column (1-2% methanol/dichloromethane) and concentrated to give 0.09 g, 79%. LCMS m/z=360 (M+1).

Step 2. 3-[4-(4-Amino-2-fluoro-phenoxy)-pyrazolo[1,5-a]pyridin-6-yl]-1,1-dimethyl-urea. 3-[4-(2-Fluoro-4-nitro-phenoxy)-pyrazolo[1,5-a]pyridin-6-yl]-1,1-dimethyl-urea was reduced with 20% Pd(OH)$_2$/C (50% wet; 10:40:50, palladium hydroxide:carbon black:water) using the method described in example 41 step 3. LCMS m/z=330 (M+1).

Step 3. 1-Ethyl-3-(4-fluoro-phenyl)-2,4-dioxo-1,2,3,4-tetrahydro-pyrimidine-5-carboxylic acid {4-[6-(3,3-dimethyl-urea)-pyrazolo[1,5-a]pyridin-4-yloxy]-3-fluoro-phenyl}-amide. The compound was synthesized from 3-[4-(4-amino-2-fluoro-phenoxy)-pyrazolo[1,5-a]pyridin-6-yl]-1,1-dimethyl-urea and 1-ethyl-3-(4-fluoro-phenyl)-2,4-dioxo-1,2,3,4-tetrahydro-pyrimidine-5-carboxylic acid using the amide coupling method described in example 41 step 4. mp=165-170° C.; LCMS m/z=590 (M+1); $^1$H NMR (DMSO-d$_6$) δ: 11.02 (s, 1H), 8.88 (d, 2H, J=5.6 Hz), 8.23 (s, 1H), 8.02 (m, 1H), 7.89 (m, 1H), 7.53 (m, 1H), 7.33-7.44 (br m, 5H), 6.66 (m, 2H), 4.02 (q, 2H), 2.88 (s, 6H), 1.31 (t, 3H, J=7.0 Hz).

Example 147

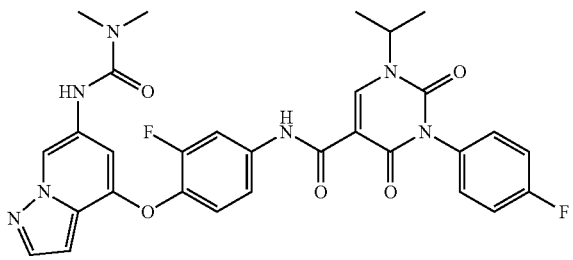 [SMILES: CC(C)n1cc(C(=O)Nc2ccc(Oc3cc(NC(=O)N(C)C)cn4nccc34)c(F)c2)c(=O)n(-c2ccc(F)cc2)c1=O]

3-(4-Fluoro-phenyl)-1-isopropyl-2,4-dioxo-1,2,3,4-tetrahydro-pyrimidine-5-carboxylic acid{4-[6-(3,3-dimethyl-ureido)-pyrazolo[1,5-a]pyridin-4-yloxy]-3-fluoro-phenyl}-amide. This compound was synthesized from 3-[4-(4-amino-2-fluoro-phenoxy)-pyrazolo[1,5-a]pyridin-6-yl]-1,1-dimethyl-urea and 3-(4-fluoro-phenyl)-1-isopropyl-2,4-dioxo-1,2,3,4-tetrahydro-pyrimidine-5-carboxylic acid using the methods described in example 146. mp=174-178° C.; LCMS m/z=604 (M+1); $^1$H NMR (DMSO-d$_6$) δ: 11.02 (s, 1H), 8.87 (s, 1H), 8.68 (s, 1H), 8.24 (s, 1H), 8.02 (m, 1H), 7.89 (m, 1H), 7.53 (m, 1H), 7.33-7.44 (br m, 5H), 6.67 (s, 1H), 6.63 (s, 1H), 4.77 (m, 1H), 2.88 (s, 6H), 1.43 (d, 6H, J=6.8 Hz).

Example 148

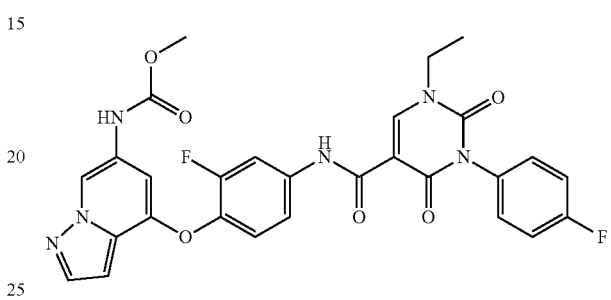

Step 1. [4-(2-Fluoro-4-nitro-phenoxy)-pyrazolo[1,5-a]pyridin-6-yl]-carbamic acid methyl ester. To 4-(2-fluoro-4-nitro-phenoxy)-pyrazolo[1,5-a]pyridin-6-ylamine (example 140 step 1)(0.21 g, 0.71 mmol) in dichloromethane (10 mL) under an atmosphere of nitrogen was added triethylamine (0.2 mL, 1.42 mmol) and was cooled at 0° C. Methyl chloroformate (0.11 mL, 1.42 mmol) was added and the reaction was warmed at rt for 1 h, washed with 1N sodium carbonate solution and water, dried over sodium sulfate, and concentrated. The product was chromatographed on silica gel using a single step column (0.5-1% methanol/dichloromethane) and concentrated to give 0.14 g, 58%. LCMS m/z=347 (M+1).

Step 2. [4-(4-Amino-2-fluoro-phenoxy)-pyrazolo[1,5-a]pyridin-6-yl]-carbamic acid methyl ester. [4-(2-fluoro-4-nitro-phenoxy)-pyrazolo[1,5-a]pyridin-6-yl]-carbamic acid methyl ester was hydrogenated with 20% Pd(OH)$_2$/C, 50% wet (10:40:50, palladium hydroxide:carbon black:water) using the reduction method described in example 41 step 3. LCMS m/z=317 (M+1).

Step 3. [4-(4-{[1-Ethyl-3-(4-fluoro-phenyl)-2,4-dioxo-1,2,3,4-tetrahydro-pyrimidine-5-carbonyl]-amino}-2-fluoro-phenoxy)-pyrazolo[1,5-a]pyridin-6-yl]-carbamic acid methyl ester. This compound was synthesized from [4-(4-amino-2-fluoro-phenoxy)-pyrazolo[1,5-a]pyridin-6-yl]-carbamic acid methyl ester and 1-ethyl-3-(4-fluoro-phenyl)-2,4-dioxo-1,2,3,4-tetrahydro-pyrimidine-5-carboxylic acid using the amide coupling method described in example 41 step 4. mp=143-146° C.; LCMS m/z=577 (M+1); $^1$H NMR (DMSO-d$_6$) δ: 11.02 (s, 1H), 9.60 (br s, 1H), 8.88 (s, 1H), 8.72 (s, 1H), 8.01 (m, 1H), 7.93 (m, 1H), 7.52 (m, 1H), 7.33-7.44 (br m, 5H), 6.67 (m, 1H), 6.53 (s, 1H), 4.02 (q, 2H), 3.65 (s, 3H), 1.31 (t, 3H, J=7.1 Hz).

Example 149

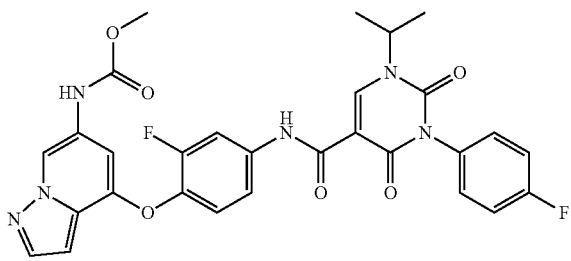 [SMILES: COC(=O)Nc1cc(Oc2ccc(NC(=O)c3cn(C(C)C)c(=O)n(-c4ccc(F)cc4)c3=O)cc2F)c2ccnn2c1]

[4-(2-Fluoro-4-{[3-(4-fluoro-phenyl)-1-isopropyl-2,4-dioxo-1,2,3,4-tetrahydro-pyrimidine-5-carbonyl]-amino}-phenoxy)-pyrazolo[1,5-a]pyridin-6-yl]-carbamic acid methyl ester. This compound was synthesized from [4-(4-amino-2-fluoro-phenoxy)-pyrazolo[1,5-a]pyridin-6-yl]-carbamic acid methyl ester and 3-(4-fluoro-phenyl)-1-isopropyl-2,4-dioxo-1,2,3,4-tetrahydro-pyrimidine-5-carboxylic acid using the methods described in example 148. mp=234° C.; LCMS m/z=591 (M+1); $^1$H NMR (DMSO-$d_6$) δ: 11.02 (s, 1H), 9.61 (br s, 1H), 8.73 (s, 1H), 8.68 (s, 1H), 8.02 (m, 1H), 7.93 (m, 1H), 7.52 (m, 1H), 7.33-7.44 (br m, 5H), 6.67 (m, 1H), 6.54 (s, 1H), 4.79 (m, 1H), 3.65 (s, 3H), 1.43 (d, 6H, J=6.8 Hz).

Example 150

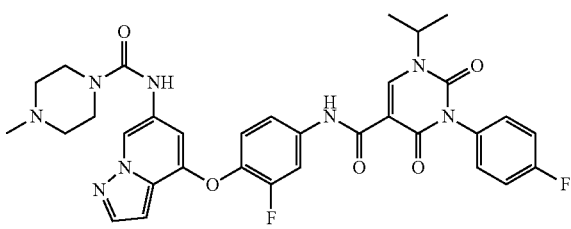 [SMILES: CC(C)n1cc(C(=O)Nc2ccc(Oc3cc(NC(=O)N4CCN(C)CC4)cn4nccc34)c(F)c2)c(=O)n(-c2ccc(F)cc2)c1=O]

Step 1. 4-Methyl-piperazine-1-carboxylic acid [4-(2-fluoro-4-nitro-phenoxy)-pyrazolo[1,5-a]pyridin-6-yl]-amide. To 4-(2-fluoro-4-nitro-phenoxy)-pyrazolo[1,5-a]pyridin-6-ylamine (0.25 g, 0.87 mmol) in tetrahydrofuran (10 mL)/acetonitrile (5 mL) under an atmosphere of nitrogen was added triethylamine (0.73 mL, 5.2 mmol) and was stirred for 5 minutes. 4-Methyl-piperazine-1-carbonyl chloride hydrochloride (0.52 g, 2.6 mmol) and 4-dimethylaminopyridine (0.02 g, 0.17 mmol) were added and heated at 70° C. overnight. The reaction was cooled at rt, diluted with dichloromethane, washed with 1N sodium carbonate solution, water and brine, dried over sodium sulfate, and concentrated. The product was chromatrograhed on silica gel using a single step column (10% methanol/dichloromethane) and concentrated to give 0.17 g, 47%. LCMS m/z=415 (M+1).

Step 2. 4-Methyl-piperazine-1-carboxylic acid [4-(4-amino-2-fluoro-phenoxy)-pyrazolo[1,5-a]pyridin-6-yl]-amide. 4-Methyl-piperazine-1-carboxylic acid [4-(2-fluoro-4-nitro-phenoxy)-pyrazolo[1,5-a]pyridin-6-yl]-amide was hydrogenated with 20% Pd(OH)$_2$/C (50% wet; 10:40:50, palladium hydroxide:carbon black:water) using the reduction method described in example 41 step 3. LCMS m/z=385 (M+1).

Step 3. 3-(4-Fluoro-phenyl)-1-isopropyl-2,4-dioxo-1,2,3,4-tetrahydro-pyrimidine-5-carboxylic acid(3-fluoro-4-{6-[(4-methyl-piperazine-1-carbonyl)-amino]-pyrazolo[1,5-a]pyridin-4-yloxy}-phenyl)-amide. This compound was synthesized from 4-methyl-piperazine-1-carboxylic acid [4-(4-amino-2-fluoro-phenoxy)-pyrazolo[1,5-a]pyridin-6-yl]-amide and 3-(4-fluoro-phenyl)-1-isopropyl-2,4-dioxo-1,2,3,4-tetrahydro-pyrimidine-5-carboxylic acid using the amide coupling method described in example 41 step 4. mp=137° C.; LCMS m/z=659 (M+1); $^1$H NMR (DMSO-$d_6$) δ: 11.03 (s, 1H), 8.88 (s, 1H), 8.68 (s, 1H), 8.42 (s, 1H), 8.02 (m, 1H), 7.89 (m, 1H), 7.33-7.53 (br m, 6H), 6.65 (m, 2H), 4.81 (m, 1H), 3.39 (m, 4H), 2.29 (m, 4H), 2.17 (s, 3H), 1.43 (d, 6H, J=6.8 Hz).

Example 151

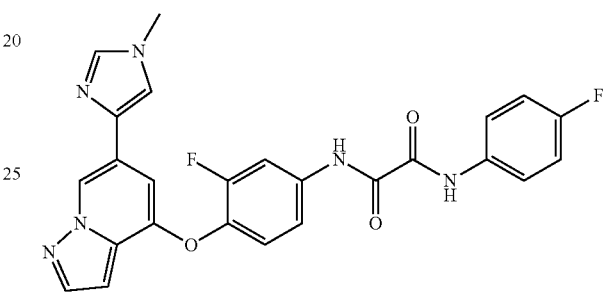

N-{3-fluoro-4-[6-(1-methyl-1H-imidazole-4-yl)-pyrazolo[1,5-a]pyridine-4-yloxy]-phenyl}-N'-(4-fluoro-phenyl)-oxalamide. N-4(fluoro-phenyl)-oxalamic acid (0.08 g, 0.44 mmol) and N,N,N,N'-tetramethyl-O-(7-azabenzotriazol-1-yl)uronium hexafluorophosphate (0.16 g, 0.44 mmol) in N,N-dimethylformamide (5 mL) was added N,N-diisopropylethylamine (0.1 mL, 0.6 mmol) and stirred at rt. After 0.5 h, 3-fluoro-4-[6-(1-methyl-1H-imidazol-4-yl)-pyrazolo[1,5-a]pyridin-4-yloxy]-phenylamine (0.06 g, 0.2 mmol) was added and was stirred at 80° C. for 2 h and cooled at rt. The reaction was diluted with ethyl acetate, washed with 1N sodium carbonate solution, water and brine, dried over sodium sulfate, and concentrated. The product was purified using Prep TLC plates (5% methanol/dichloromethane) and concentrated to give 0.02 g, 21%. mp=262-265° C.; LCMS m/z=489 (M+1); $^1$H NMR (DMSO-$d_6$) δ: 11.21 (s, 1H), 11.00 (s, 1H), 8.78 (s, 1H), 8.08 (m, 1H), 8.00 (m, 1H), 7.92 (m, 2H), 7.85 (m, 1H), 7.67 (m, 1H), 7.61 (s, 1H), 7.47 (m, 1H), 7.24 (m, 2H), 6.85 (s, 1H), 6.70 (m, 1H), 3.65 (s, 3H).

Example 152

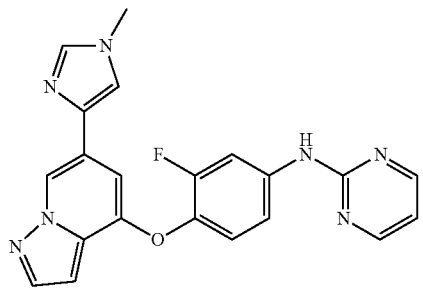 [SMILES: Cn1cnc(-c2cc(Oc3ccc(Nc4ncccn4)cc3F)c3ccnn3c2)c1]

{3-Fluoro-4-[6-(1-methyl-1H-imidazol-4-yl)-pyrazolo[1,5-a]pyridin-4-yloxy]-phenyl}-pyrimidin-2-yl-amine. This compound was synthesized from 3-fluoro-4-[6-(1-methyl-1H-imidazol-4-yl)-pyrazolo[1,5-a]pyridin-4-yloxy]-phenylamine and 2-chloropyrimidine using the buchwald method described in example 84 step 1. mp=228-230° C.; LCMS m/z=402 (M+1); $^1$H NMR (DMSO-d$_6$) δ: 10.01 (s, 1H), 8.75 (s, 1H), 8.55 (m, 2H), 8.10 (m, 1H), 7.99 (m, 1H), 7.60 (m, 3H), 7.38 (m, 1H), 6.92 (m, 1H), 6.78 (s, 1H), 6.72 (m, 1H), 3.64 (s, 3H).

Example 153

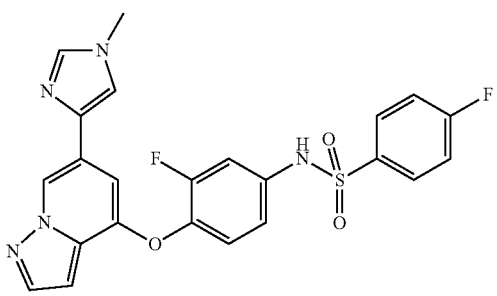 [SMILES: Cn1cnc(-c2cc(Oc3ccc(NS(=O)(=O)c4ccc(F)cc4)cc3F)c3ccnn3c2)c1]

4-Fluoro-N-{3-fluoro-4-[6-(1-methyl-1H-imidazol-4-yl)-pyrazolo[1,5-a]pyridin-4-yloxy]-phenyl}-benzenesulfonamide. To 3-fluoro-4-[6-(1-methyl-1H-imidazol-4-yl)-pyrazolo[1,5-a]pyridin-4-yloxy]-phenylamine (0.05 g, 0.15 mmol) in pyridine (3 mL) under an atmosphere of nitrogen was added 4-fluoro-benzenesulfonyl chloride (0.06 g, 0.31 mmol) and was stirred at rt for 15 min. The reaction was diluted with dichloromethane, washed with aq. citric acid 3×, 1N sodium carbonate solution, water and brine, dried over sodium sulfate, and concentrated. The product was chromatographed on silica gel using a single step column (3-5% methanol/dichloromethane) and concentrated to give 0.03 g, 40%. mp=229-231° C.; LCMS m/z=482 (M+1); $^1$H NMR (DMSO-d$_6$) δ: 10.59 (s, 1H), 8.77 (s, 1H), 7.97 (m, 1H), 7.86 (m, 2H), 7.64 (m, 2H), 7.45 (m, 2H), 7.33 (m, 1H), 7.16 (m, 1H), 6.96 (m, 1H), 6.78 (s, 1H), 6.58 (m, 1H), 3.66 (s, 3H).

Example 154

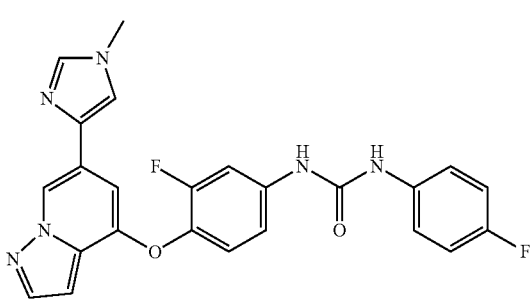 [SMILES: Cn1cnc(-c2cc(Oc3ccc(NC(=O)Nc4ccc(F)cc4)cc3F)c3ccnn3c2)c1]

1-{3-Fluoro-4-[6-(1-methyl-1H-imidazol-4-yl)-pyrazolo[1,5-a]pyridin-4-yloxy]-phenyl}-3-(4-fluoro-phenyl)-urea. To 3-fluoro-4-[6-(1-methyl-1H-imidazol-4-yl)-pyrazolo[1,5-a]pyridine-4-yloxy]-phenylamine (0.02 g, 0.06 mmol) in tetrahydrofuran (2 mL) under an atmosphere of nitrogen was added 4-fluorophenyl isocyanate (0.01 mL, 0.11 mmol) and was stirred at rt overnight. The reaction was diluted with dichloromethane, washed with 1N sodium carbonate solution and brine, dried over sodium sulfate, and concentrated. The product was purified using Prep TLC plates (5% methanol/dichloromethane) and concentrated to give 0.004 g, 20%. mp=200-203° C.; LCMS m/z=461 (M+1); $^1$H NMR (DMSO-d$_6$) δ: 9.09 (s, 1H), 8.90 (s, 1H), 8.76 (s, 1H), 7.99 (m, 1H), 7.74 (m, 1H), 7.63 (br m, 2H), 7.48 (m, 2H), 7.35 (m, 1H), 7.23 (m, 1H), 7.13 (m, 2H), 6.80 (s, 1H), 6.70 (m, 1H), 3.65 (s, 3H).

Example 155

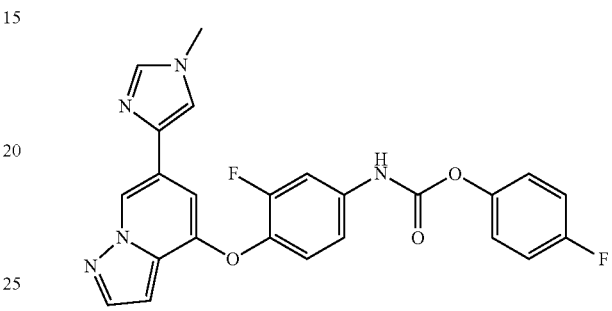

{3-Fluoro-4-[6-(1-methyl-1H-imidazol-4-yl)-pyrazolo[1,5-a]pyridin-4-yloxy]-phenyl}-carbamic acid 4-fluoro-phenyl ester. To 3-fluoro-4-[6-(1-methyl-1H-imidazol-4-yl)-pyrazolo[1,5-a]pyridine-4-yloxy]-phenylamine (0.04 g, 0.12 mmol) in dichloromethane (3 mL) under an atmosphere of nitrogen was added triethylamine (0.05 mL, 0.35 mmol) and was cooled at 0° C. 4-Fluorophenyl chloroformate (0.03 mL, 0.24 mmol) was added and stirred at rt for 1 h. The reaction was diluted with dichloromethane, washed with 1N sodium carbonate solution and brine, dried over sodium sulfate, and concentrated. The product was purified using Prep TLC plates (5% methanol/dichloromethane) and concentrated to give 0.01 g, 18%. mp=154-157° C.; LCMS m/z=462 (M+1); $^1$H NMR (DMSO-d$_6$) δ 10.60 (s, 1H), 8.77 (s, 1H), 7.99 (m, 1H), 7.67 (m, 3H), 7.25-7.45 (br m, 6H), 6.81 (s, 1H), 6.69 (m, 1H), 3.65 (s, 3H).

Example 156

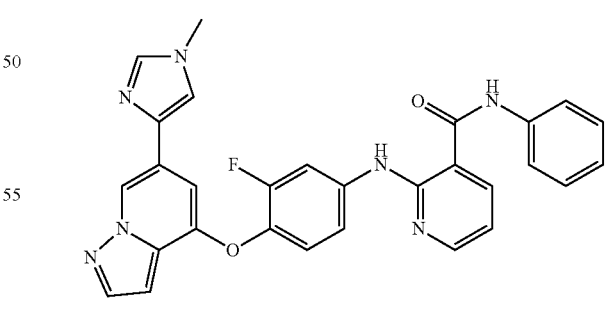

Step 1. 2-{3-Fluoro-4-[6-(1-methyl-1H-imidazol-4-yl)-pyrazolo[1,5-a]pyridin-4-yloxy]-phenylamino}-nicotinic acid. To an oven dried schlenck flask was added 3-fluoro-4-[6-(1-methyl-1H-imidazol-4-yl)-pyrazolo[1,5-a]pyridin-4-yloxy]-phenylamine (0.15 g, 0.46 mmol), 2-chloro-nicotinic acid ethyl ester (0.13 g, 0.7 mmol), palladium acetate (0.01 g, 0.05 mmol), 2,2'-bis-dicyclohexylphosphanyl-biphenyl (0.05 g, 0.09 mmol), cesium carbonate (0.45 g, 1.4 mmol), followed by 1,4-dioxane (8 mL) and was degassed under an atmosphere of nitrogen for 5 min. and heated at 100° C. overnight. The reaction was cooled at rt, diluted with dichloromethane, filtered through a pad of celite, washed with 1N sodium carbonate solution, washed with water and brine, dried over sodium sulfate, and concentrated. The product was chromatographed on silica gel using a single step column (1-3% methanol/dichloromethane) and concentrated to give 2-{3-fluoro-4-[6-(1-methyl-1H-imiazol-4-yl)-pyrazolo[1,5-a]pyridin-4-yloxy]-phenylamino}-nicotinic acid ethyl ester 0.1 g, 47%; LCMS m/z=473 (M+1). 2-{3-Fluoro-4-[6-(1-methyl-1H-imiazol-4-yl)-pyrazolo[1,5-a]pyridin-4-yloxy]-phenylamino}-nicotinic acid ethyl ester was slurried in ethanol (5 mL) and 1N sodium hydroxide (1 mL), stirred at rt for 1 h, and concentrated. The aqueous layer was acidified with 2N hydrochloric acid, extracted with dichloromethane, washed with water and brine, dried over sodium sulfate, and concentrated to give 0.08 g, 85%. LCMS m/z=445 (M+1).

Step 2. 2-{3-Fluoro-4-[6-(1-methyl-1H-imidazol-4-yl)-pyrazolo[1,5-a]pyridin-4-yloxy]-phenylamino}-N-phenyl-nicotinamide. To 2-{3-fluoro-4-[6-(1-methyl-1H-imidazol-4-yl)-pyrazolo[1,5-a]pyridin-4-yloxy]-phenylamino}-nicotinic acid (0.08 g, 0.18 mmol) in N,N-dimethylformamide (4 mL) was added N-(3-dimethylaminopropyl)-N'-ethylcarbodiimide hydrochloride (0.04 g, 0.2 mmol), 1-hydroxybenzotriazole (0.03 g, 0.2 mmol), N,N-diisopropylethylamine (0.06 mL, 0.37 mmol), followed by aniline (0.02 mL, 0.2 mmol) and stirred at 50° C. for 2 h. The reaction was diluted with ethyl acetate, washed with 1N sodium carbonate solution, water and brine, dried over sodium sulfate, and concentrated. The product was purified using Prep TLC plates (5% methanol/dichloromethane) and concentrated to give 0.04 g, 38%. mp=132-135° C.; LCMS m/z=520 (M+1); $^1$H NMR (DMSO-$d_6$) δ: 10.51 (s, 2H), 8.76 (s, 1H), 8.43 (m, 1H), 8.30 (m, 1H), 8.18 (m, 1H), 7.99 (m, 1H), 7.74 (m, 2H), 7.66 (m, 1H), 7.59 (m, 1H), 7.36-7.47 (br m, 4H), 7.16 (m, 1H), 7.04 (m, 1H), 6.81 (s, 1H), 6.72 (m, 1H), 3.64 (s, 3H).

Example 157

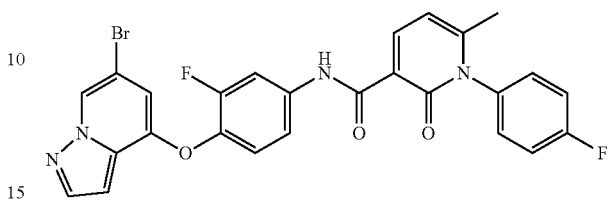

1-(4-Fluoro-phenyl)-6-methyl-2-oxo-1,2-dihydro-pyridine-3-carboxylic acid [4-(6-bromo-pyrazolo[1,5-a]pyridin-4-yloxy)-3-fluoro-phenyl]-amide. This example was synthesized using 4-(6-bromo-pyrazolo[1,5-a]pyridin-4-yloxy)-3-fluoro-phenylamine and 1-(4-fluoro-phenyl)-6-methyl-2-oxo-1,2-dihydro-pyridine-3-carboxylic acid by the methods for example 1. mp=92° C.; LCMS m/z=552 (M+1); $^1$H NMR (DMSO) δ: 12.07 (s, 1H), 8.87 (s, 1H), 8.50 (d, 1H, J=7.5 Hz), 8.05 (m, 2H), 7.45 (br m, 6H), 6.78 (m, 1H), 6.71 (m, 1H), 6.51 (s, 1H), 2.08 (s, 3H).

Biological data for certain compounds of the invention is presented in the following Table 1. Unless otherwise specified in Table 1, $IC_{50}$ nanomolar value ranges designated as A, B, or C indicate the following ranges:

$IC_{50}$ <10 nM A;
$IC_{50}$ 10 nM to 100 nM B;
$IC_{50}$ 101 nM to 1,000 nM C; and
$IC_{50}$ 1,001 nM to 10,000 nM.
"NT" denotes not tested.
Unless otherwise specified, all values are an average of two or more determinations.

| Compound Structure | Ex. No. | AXL $IC_{50}$ (nM) | c-MET $IC_{50}$ (nM) |
|---|---|---|---|
| 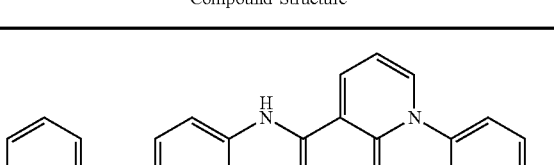 | 1 | C | A |
| 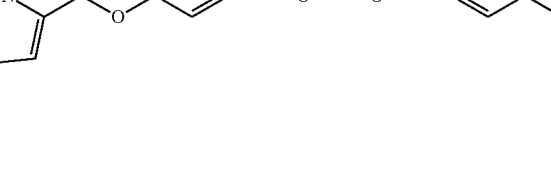 | 2 | D | NT |

| Compound Structure | Ex. No. | AXL IC$_{50}$ (nM) | c-MET IC$_{50}$ (nM) |
|---|---|---|---|
| (pyrazolo[1,5-a]pyridin-4-yloxy-3-fluorophenyl)-NH-C(O)-pyridazinone-N-(4-fluorophenyl) | 3 | C | NT |
| (pyrazolo[1,5-a]pyridin-4-yloxy-3-fluorophenyl)-NH-C(O)-pyridinone-N-(4-fluorophenyl) | 4 | B | A |
| (pyrazolo[1,5-a]pyridin-4-yloxy-3-fluorophenyl)-NH-C(O)-cyclopropyl-C(O)-NH-(4-fluorophenyl) | 5 | D | A |
| (pyrazolo[1,5-a]pyridin-4-yloxy-3-fluorophenyl)-NH-C(S)-NH-C(O)-CH$_2$-(4-fluorophenyl) | 6 | D | B |
| (pyrazolo[1,5-a]pyridin-4-yloxy-3-fluorophenyl)-NH-C(O)-CH$_2$-(4-fluorophenyl) | 7 | D | NT |
| (pyrazolo[1,5-a]pyridin-4-yloxy-3-fluorophenyl)-NH-C(O)-pyridinone-N-CH$_2$-(4-fluorophenyl) | 8 | D | C |
| (pyrazolo[1,5-a]pyridin-4-yloxy-3-fluorophenyl)-NH-C(O)-pyridinone-N-CH$_2$-(3-fluorophenyl) | 9 | D | C |

-continued

| Compound Structure | Ex. No. | AXL IC$_{50}$ (nM) | c-MET IC$_{50}$ (nM) |
|---|---|---|---|
| 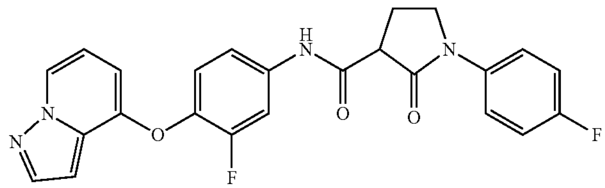 [SMILES: O=C(Nc1ccc(Oc2cccn3nccc23)c(F)c1)C1CCN(c2ccc(F)cc2)C1=O] | 10 | D | B |
| 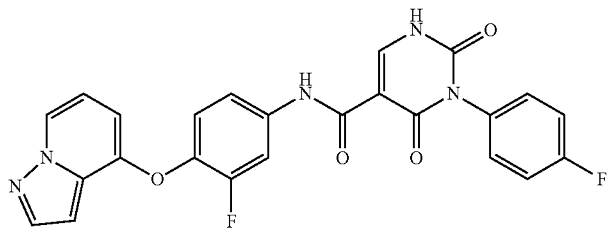 [SMILES: O=C(Nc1ccc(Oc2cccn3nccc23)c(F)c1)c1c[nH]c(=O)n(-c2ccc(F)cc2)c1=O] | 11 | C | B |
| 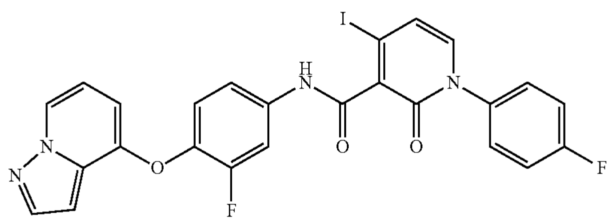 [SMILES: O=C(Nc1ccc(Oc2cccn3nccc23)c(F)c1)c1c(I)ccn(-c2ccc(F)cc2)c1=O] | 12 | C | B |
| 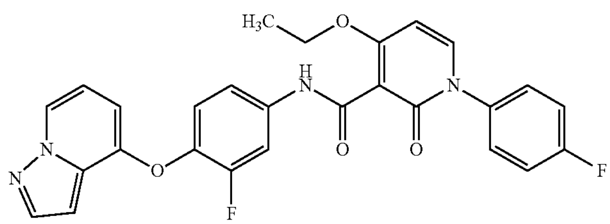 [SMILES: CCOc1ccn(-c2ccc(F)cc2)c(=O)c1C(=O)Nc1ccc(Oc2cccn3nccc23)c(F)c1] | 13 | C | A |
| 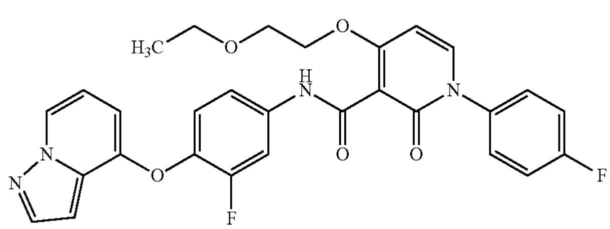 [SMILES: CCOCCOc1ccn(-c2ccc(F)cc2)c(=O)c1C(=O)Nc1ccc(Oc2cccn3nccc23)c(F)c1] | 14 | C | B |
| 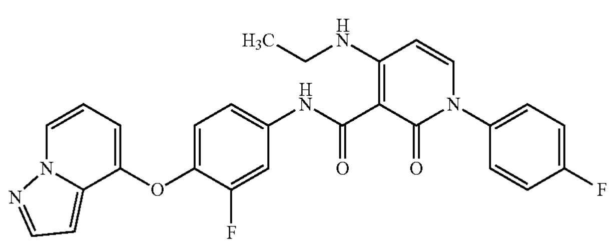 [SMILES: CCNc1ccn(-c2ccc(F)cc2)c(=O)c1C(=O)Nc1ccc(Oc2cccn3nccc23)c(F)c1] | 15 | C | B |
| 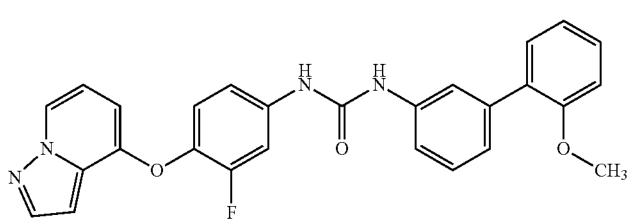 [SMILES: COc1ccccc1-c1cccc(NC(=O)Nc2ccc(Oc3cccn4nccc34)c(F)c2)c1] | 16 | D | NT |

-continued

| Compound Structure | Ex. No. | AXL IC$_{50}$ (nM) | c-MET IC$_{50}$ (nM) |
|---|---|---|---|
| 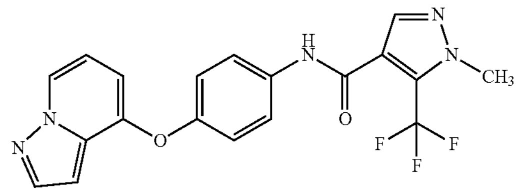 [SMILES: Cn1ncc(C(=O)Nc2ccc(Oc3cccn4nccc34)cc2)c1C(F)(F)F] | 17 | D | D |
| 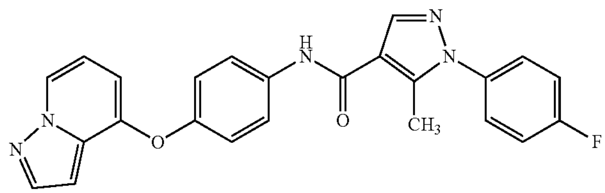 [SMILES: Cc1c(C(=O)Nc2ccc(Oc3cccn4nccc34)cc2)cnn1-c1ccc(F)cc1] | 18 | D | D |
| 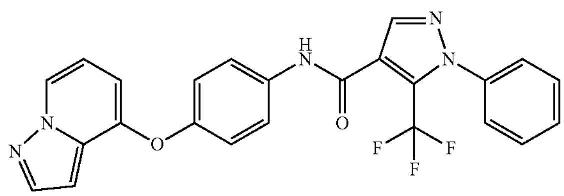 [SMILES: O=C(Nc1ccc(Oc2cccn3nccc23)cc1)c1cnn(-c2ccccc2)c1C(F)(F)F] | 19 | D | D |
| 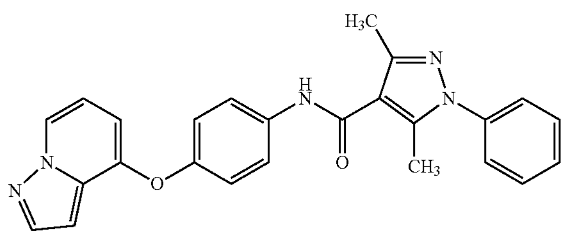 [SMILES: Cc1nn(-c2ccccc2)c(C)c1C(=O)Nc1ccc(Oc2cccn3nccc23)cc1] | 20 | D | D |
| 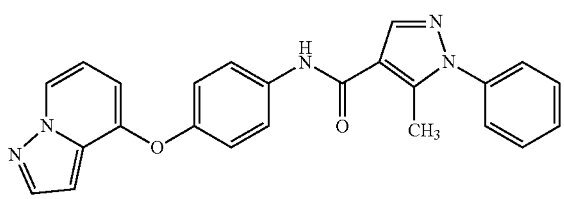 [SMILES: Cc1c(C(=O)Nc2ccc(Oc3cccn4nccc34)cc2)cnn1-c1ccccc1] | 21 | D | D |
| 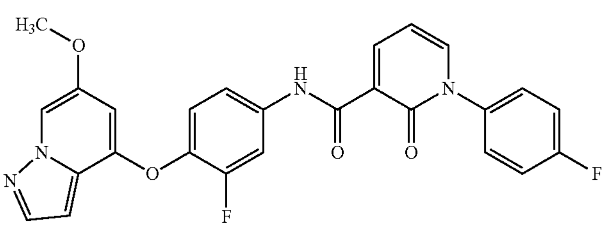 [SMILES: COc1cc(Oc2ccc(NC(=O)c3cccn(-c4ccc(F)cc4)c3=O)cc2F)c2ccnn2c1] | 22 | D | C |
| 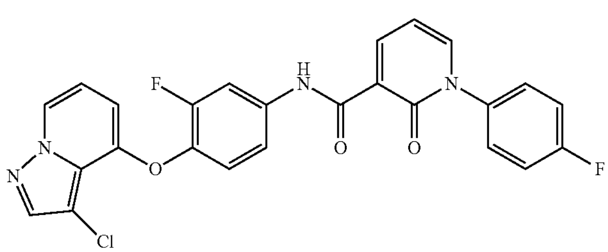 [SMILES: O=C(Nc1ccc(Oc2cccn3ncc(Cl)c23)c(F)c1)c1cccn(-c2ccc(F)cc2)c1=O] | 23 | D | C |

-continued

| Compound Structure | Ex. No. | AXL IC$_{50}$ (nM) | c-MET IC$_{50}$ (nM) |
|---|---|---|---|
| (structure) | 24 | B | A |
| (structure) | 25 | A | A |
| (structure) | 26 | A | A |
| (structure) | 27 | A | A |
| (structure) | 28 | B | A |

-continued

| Compound Structure | Ex. No. | AXL IC$_{50}$ (nM) | c-MET IC$_{50}$ (nM) |
|---|---|---|---|
| 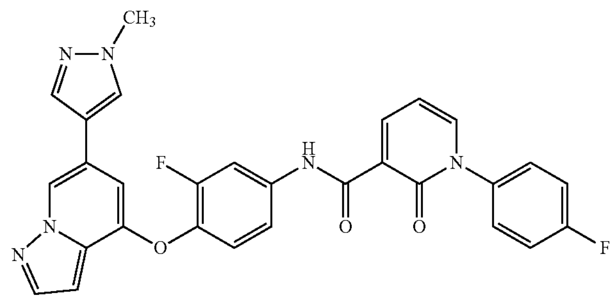 [SMILES: Cn1cc(-c2cc(Oc3ccc(NC(=O)c4cccn(-c5ccc(F)cc5)c4=O)cc3F)c3ccnn3c2)cn1] | 29 | A | A |
| 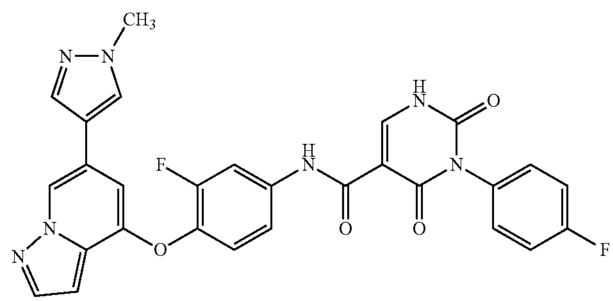 [SMILES: Cn1cc(-c2cc(Oc3ccc(NC(=O)c4c[nH]c(=O)n(-c5ccc(F)cc5)c4=O)cc3F)c3ccnn3c2)cn1] | 30 | A | A |
| 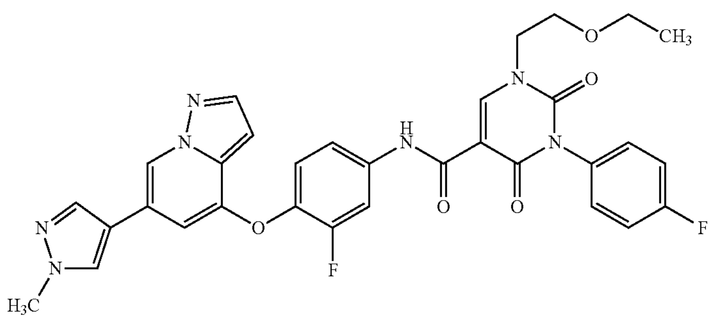 [SMILES: CCOCCn1cc(C(=O)Nc2ccc(Oc3cc(-c4cnn(C)c4)cn4nccc34)c(F)c2)c(=O)n(-c2ccc(F)cc2)c1=O] | 31 | A | A |
| 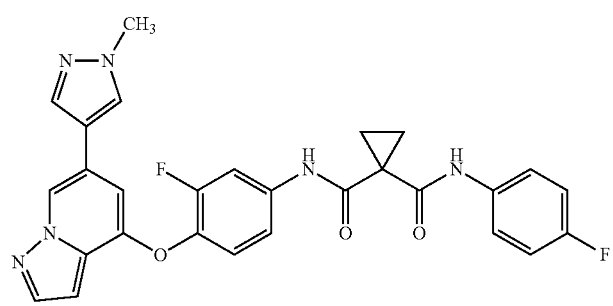 [SMILES: Cn1cc(-c2cc(Oc3ccc(NC(=O)C4(C(=O)Nc5ccc(F)cc5)CC4)cc3F)c3ccnn3c2)cn1] | 32 | B | A |
| 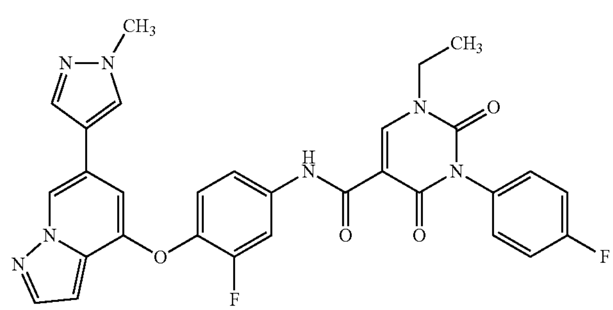 [SMILES: CCn1cc(C(=O)Nc2ccc(Oc3cc(-c4cnn(C)c4)cn4nccc34)c(F)c2)c(=O)n(-c2ccc(F)cc2)c1=O] | 33 | A | A |

-continued

| Compound Structure | Ex. No. | AXL IC$_{50}$ (nM) | c-MET IC$_{50}$ (nM) |
|---|---|---|---|
| 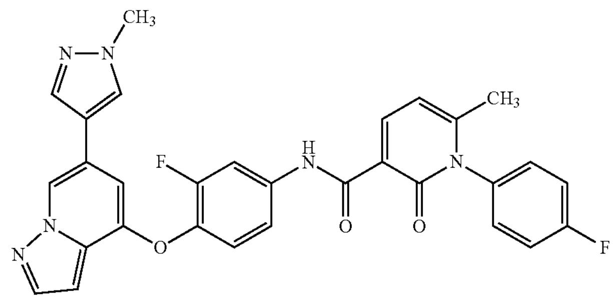 [SMILES: Cc1ccc(C(=O)Nc2ccc(Oc3cc(-c4cnn(C)c4)cn4nccc34)c(F)c2)c(=O)n1-c1ccc(F)cc1] | 34 | A | A |
| 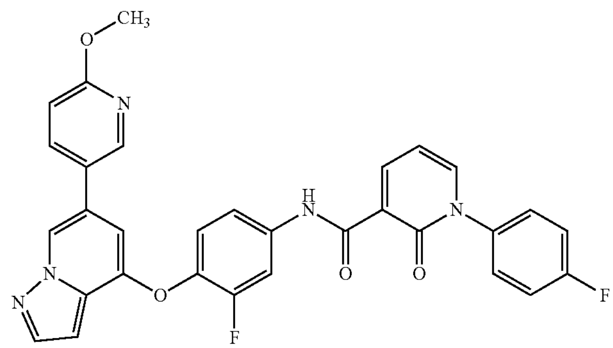 [SMILES: COc1ccc(-c2cc(Oc3ccc(NC(=O)c4cccn(-c5ccc(F)cc5)c4=O)cc3F)c3ccnn3c2)cn1] | 35 | B | A |
| 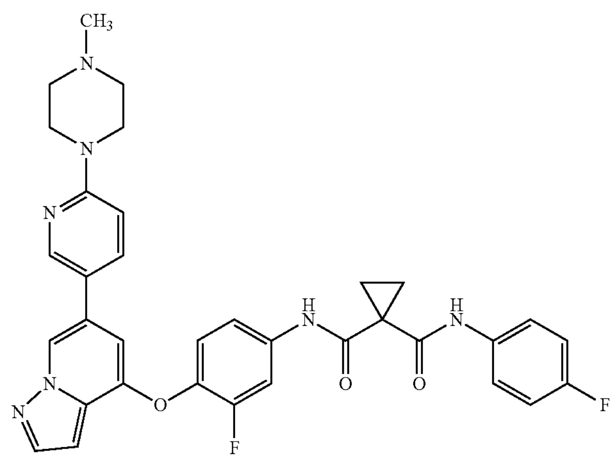 [SMILES: CN1CCN(c2ccc(-c3cc(Oc4ccc(NC(=O)C5(C(=O)Nc6ccc(F)cc6)CC5)cc4F)c4ccnn4c3)cn2)CC1] | 36 | B | A |
| 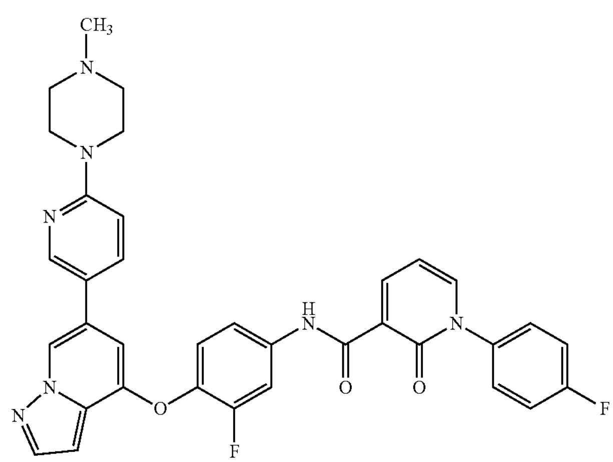 [SMILES: CN1CCN(c2ccc(-c3cc(Oc4ccc(NC(=O)c5cccn(-c6ccc(F)cc6)c5=O)cc4F)c4ccnn4c3)cn2)CC1] | 37 | B | A |

| Compound Structure | Ex. No. | AXL IC$_{50}$ (nM) | c-MET IC$_{50}$ (nM) |
|---|---|---|---|
| 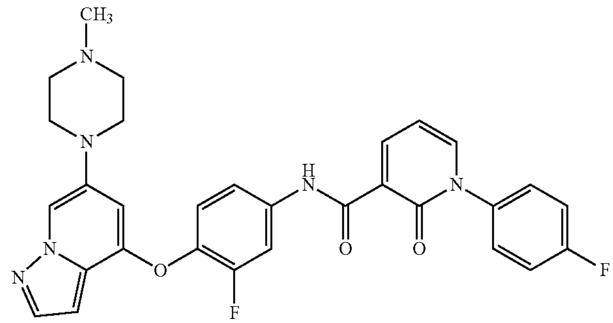 [SMILES: CN1CCN(c2cc(Oc3ccc(NC(=O)c4cccn(-c5ccc(F)cc5)c4=O)cc3F)c3ccnn3c2)CC1] | 38 | B | A |
| 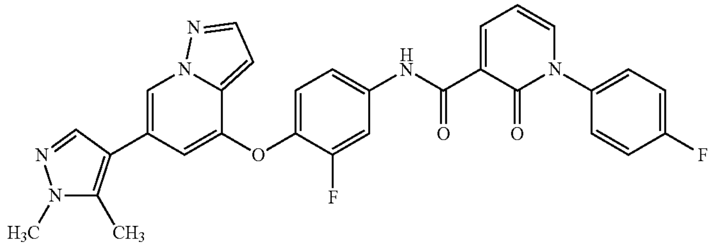 [SMILES: Cc1c(-c2cc(Oc3ccc(NC(=O)c4cccn(-c5ccc(F)cc5)c4=O)cc3F)c3ccnn3c2)cnn1C] | 39 | A | A |
| 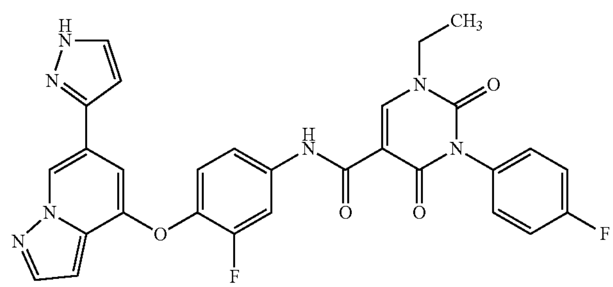 [SMILES: CCn1cc(C(=O)Nc2ccc(Oc3cc(-c4cc[nH]n4)cn4nccc34)c(F)c2)c(=O)n(-c2ccc(F)cc2)c1=O] | 40 | A | A |
| 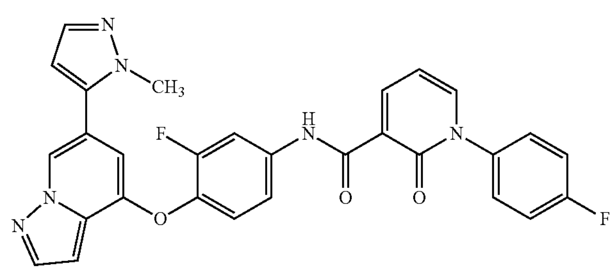 [SMILES: Cn1nccc1-c1cc(Oc2ccc(NC(=O)c3cccn(-c4ccc(F)cc4)c3=O)cc2F)c2ccnn2c1] | 41 | B | A |
| 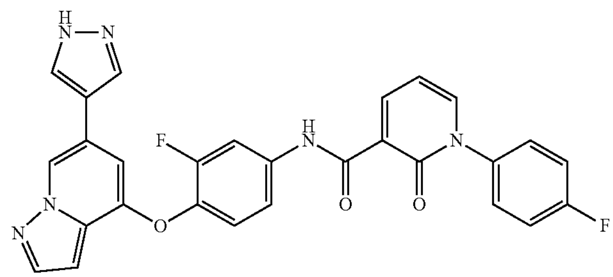 [SMILES: O=C(Nc1ccc(Oc2cc(-c3cn[nH]c3)cn3nccc23)c(F)c1)c1cccn(-c2ccc(F)cc2)c1=O] | 42 | A | A |

-continued

| Compound Structure | Ex. No. | AXL IC$_{50}$ (nM) | c-MET IC$_{50}$ (nM) |
|---|---|---|---|
| 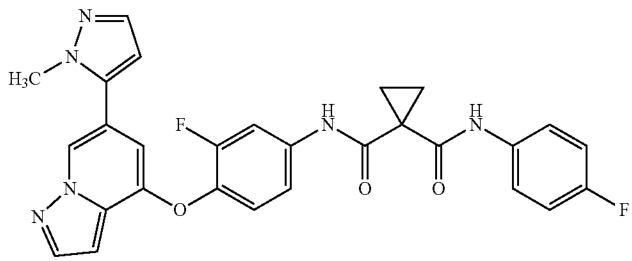 [SMILES: Cn1nccc1-c1cc(Oc2ccc(NC(=O)C3(C(=O)Nc4ccc(F)cc4)CC3)cc2F)c2ccnn2c1] | 43 | C | NT |
| 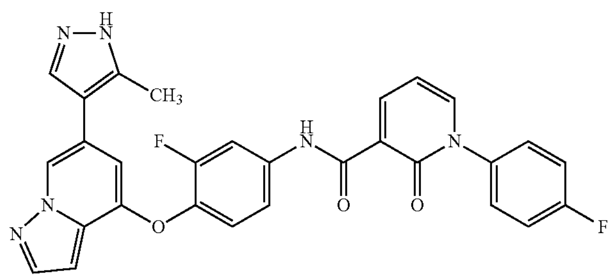 [SMILES: Cc1[nH]ncc1-c1cc(Oc2ccc(NC(=O)c3cccn(-c4ccc(F)cc4)c3=O)cc2F)c2ccnn2c1] | 44 | A | A |
| 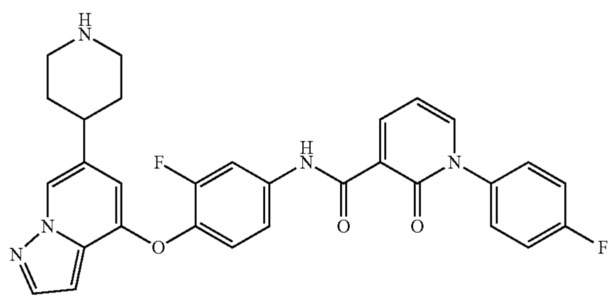 [SMILES: O=C(Nc1ccc(Oc2cc(C3CCNCC3)cn3nccc23)c(F)c1)c1cccn(-c2ccc(F)cc2)c1=O] | 45 | C | NT |
| 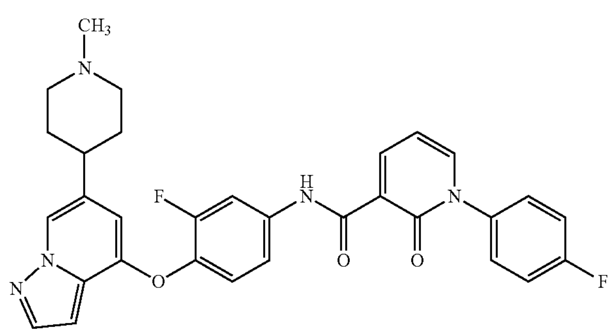 [SMILES: CN1CCC(c2cc(Oc3ccc(NC(=O)c4cccn(-c5ccc(F)cc5)c4=O)cc3F)c3ccnn3c2)CC1] | 46 | C | NT |
| 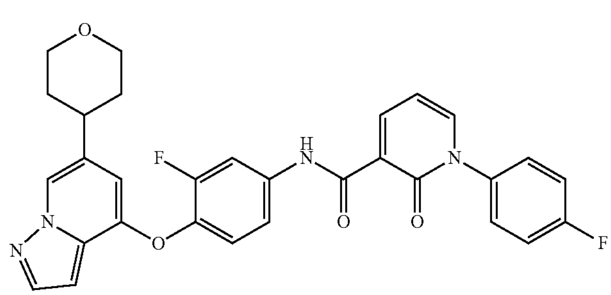 [SMILES: O=C(Nc1ccc(Oc2cc(C3CCOCC3)cn3nccc23)c(F)c1)c1cccn(-c2ccc(F)cc2)c1=O] | 47 | B | A |

| Compound Structure | Ex. No. | AXL IC$_{50}$ (nM) | c-MET IC$_{50}$ (nM) |
|---|---|---|---|
| 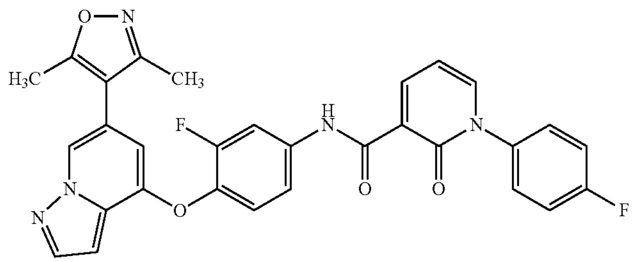 [SMILES: Cc1noc(C)c1-c1cc(Oc2ccc(NC(=O)c3cccn(-c4ccc(F)cc4)c3=O)cc2F)c2ccnn2c1] | 48 | C | A |
| 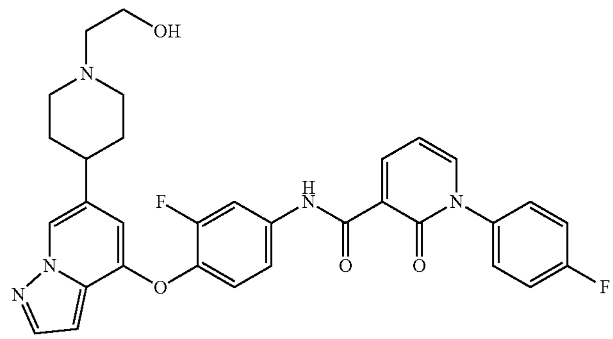 [SMILES: O=C(Nc1ccc(Oc2cc(C3CCN(CCO)CC3)cn3nccc23)c(F)c1)c1cccn(-c2ccc(F)cc2)c1=O] | 49 | C | NT |
| 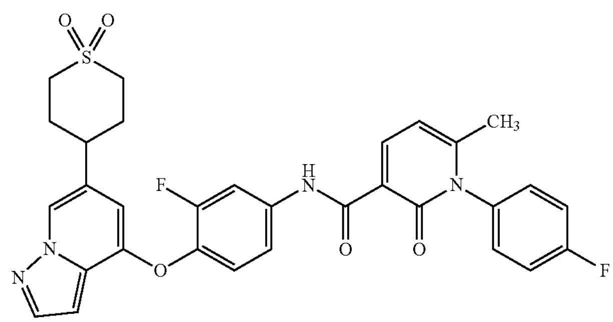 [SMILES: Cc1ccc(C(=O)Nc2ccc(Oc3cc(C4CCS(=O)(=O)CC4)cn4nccc34)c(F)c2)c(=O)n1-c1ccc(F)cc1] | 50 | B | A |
| 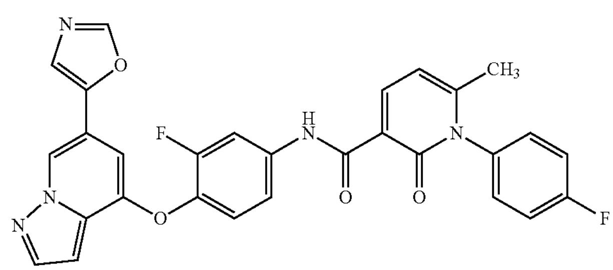 [SMILES: Cc1ccc(C(=O)Nc2ccc(Oc3cc(-c4cnco4)cn4nccc34)c(F)c2)c(=O)n1-c1ccc(F)cc1] | 51 | A | A |
| 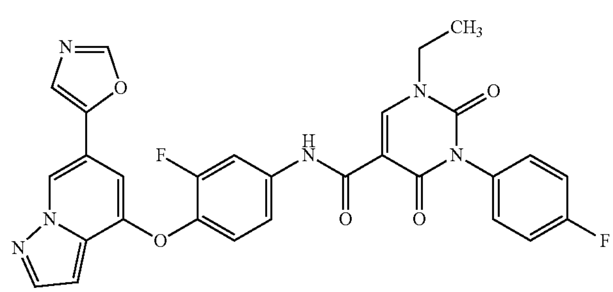 | 52 | B | A |

-continued

| Compound Structure | Ex. No. | AXL IC$_{50}$ (nM) | c-MET IC$_{50}$ (nM) |
|---|---|---|---|
| 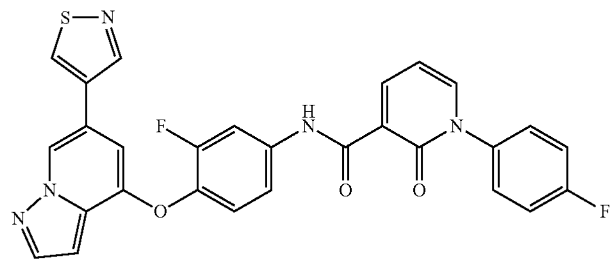 [SMILES: O=C(Nc1ccc(Oc2cc(-c3cnsc3)cn3nccc23)c(F)c1)c1cccn(-c2ccc(F)cc2)c1=O] | 53 | B | A |
| 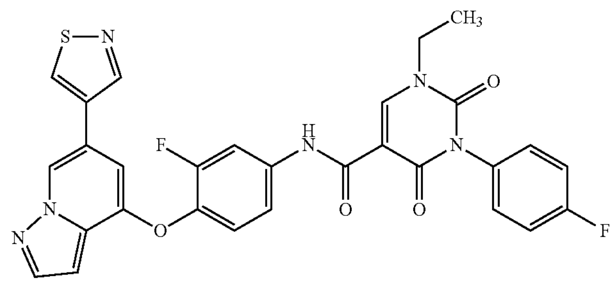 | 54 | A | A |
| 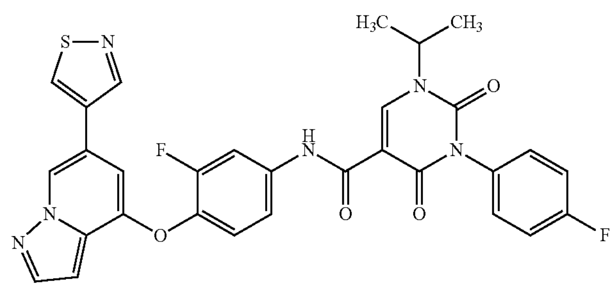 | 55 | A | A |
| 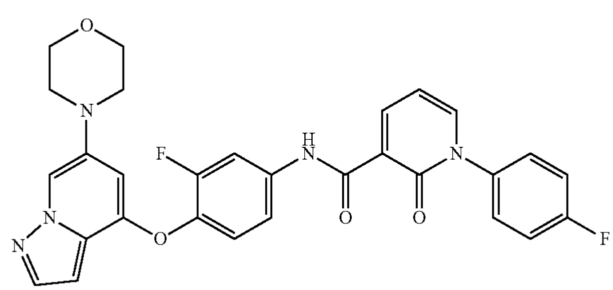 [SMILES: O=C(Nc1ccc(Oc2cc(N3CCOCC3)cn3nccc23)c(F)c1)c1cccn(-c2ccc(F)cc2)c1=O] | 56 | A | A |
| 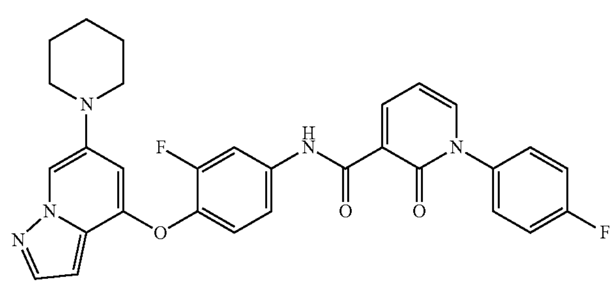 [SMILES: O=C(Nc1ccc(Oc2cc(N3CCCCC3)cn3nccc23)c(F)c1)c1cccn(-c2ccc(F)cc2)c1=O] | 57 | B | A |

-continued

| Compound Structure | Ex. No. | AXL IC$_{50}$ (nM) | c-MET IC$_{50}$ (nM) |
|---|---|---|---|
| 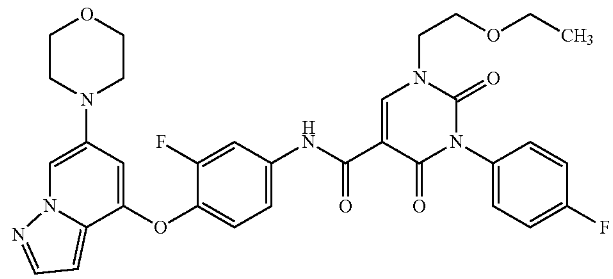 [SMILES: CCOCCn1cc(C(=O)Nc2ccc(Oc3cc(N4CCOCC4)cn4nccc34)c(F)c2)c(=O)n(-c2ccc(F)cc2)c1=O] | 58 | B | B |
| 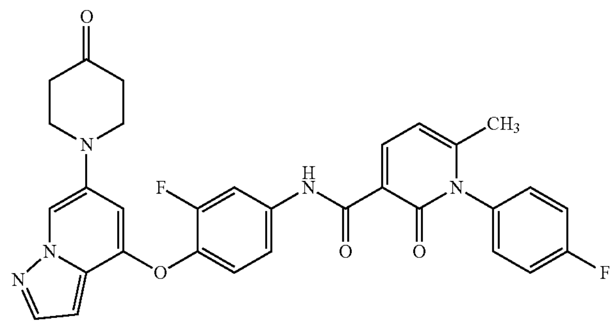 [SMILES: Cc1ccc(C(=O)Nc2ccc(Oc3cc(N4CCC(=O)CC4)cn4nccc34)c(F)c2)c(=O)n1-c1ccc(F)cc1] | 59 | A | B |
| 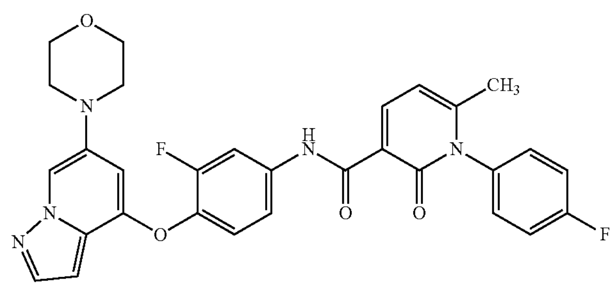 [SMILES: Cc1ccc(C(=O)Nc2ccc(Oc3cc(N4CCOCC4)cn4nccc34)c(F)c2)c(=O)n1-c1ccc(F)cc1] | 60 | B | A |
| 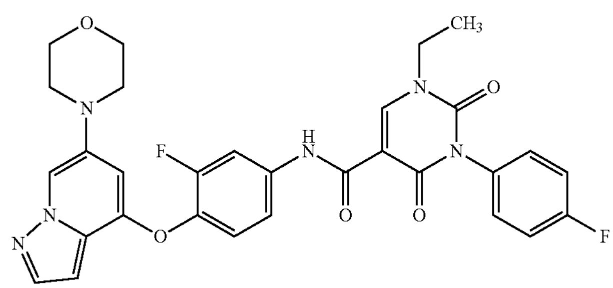 [SMILES: CCn1cc(C(=O)Nc2ccc(Oc3cc(N4CCOCC4)cn4nccc34)c(F)c2)c(=O)n(-c2ccc(F)cc2)c1=O] | 61 | B | A |
| 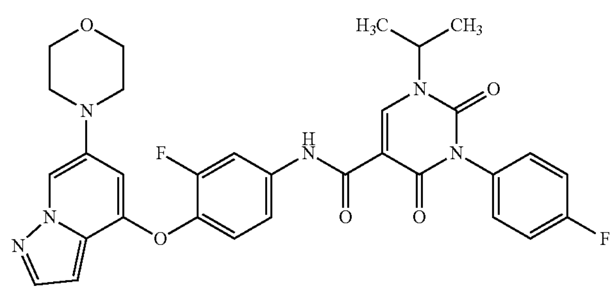 [SMILES: CC(C)n1cc(C(=O)Nc2ccc(Oc3cc(N4CCOCC4)cn4nccc34)c(F)c2)c(=O)n(-c2ccc(F)cc2)c1=O] | 62 | A | A |

-continued

| Compound Structure | Ex. No. | AXL IC$_{50}$ (nM) | c-MET IC$_{50}$ (nM) |
|---|---|---|---|
| 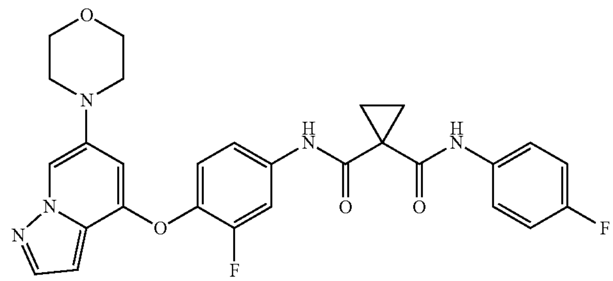 [SMILES: O=C(Nc1ccc(F)cc1)C1(C(=O)Nc2ccc(Oc3cc(N4CCOCC4)cn4nccc34)c(F)c2)CC1] | 63 | C | B |
| 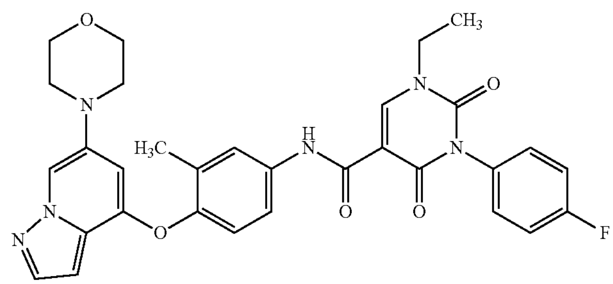 [SMILES: CCn1cc(C(=O)Nc2ccc(Oc3cc(N4CCOCC4)cn4nccc34)c(C)c2)c(=O)n(-c2ccc(F)cc2)c1=O] | 64 | C | NT |
| 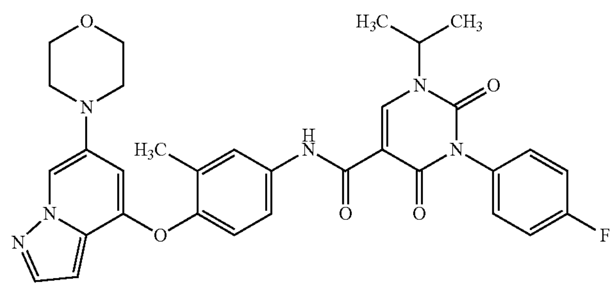 [SMILES: Cc1cc(NC(=O)c2cn(C(C)C)c(=O)n(-c3ccc(F)cc3)c2=O)ccc1Oc1cc(N2CCOCC2)cn2nccc12] | 65 | C | NT |
| 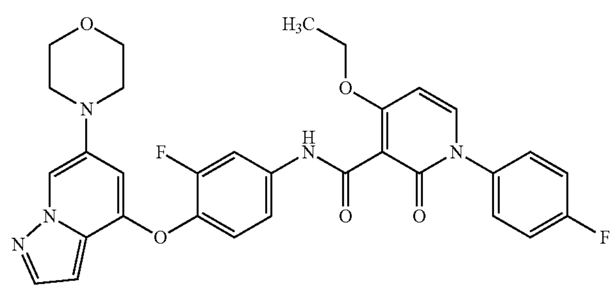 [SMILES: CCOc1ccn(-c2ccc(F)cc2)c(=O)c1C(=O)Nc1ccc(Oc2cc(N3CCOCC3)cn3nccc23)c(F)c1] | 66 | B | A |
| 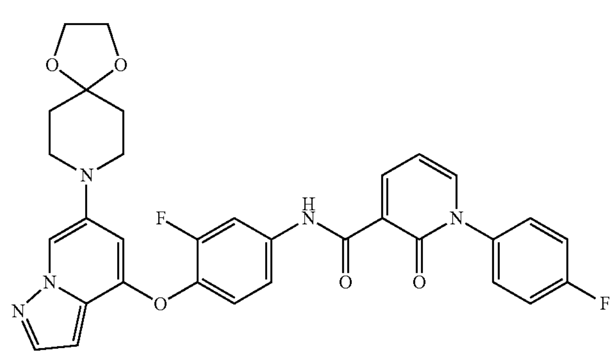 [SMILES: O=C(Nc1ccc(Oc2cc(N3CCC4(CC3)OCCO4)cn3nccc23)c(F)c1)c1cccn(-c2ccc(F)cc2)c1=O] | 67 | B | B |

-continued

| Compound Structure | Ex. No. | AXL IC$_{50}$ (nM) | c-MET IC$_{50}$ (nM) |
|---|---|---|---|
| 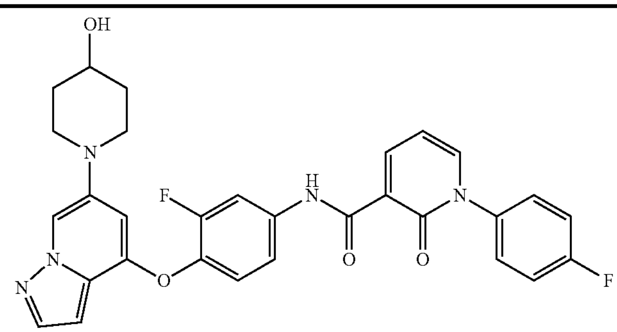 | 68 | A | A |
| 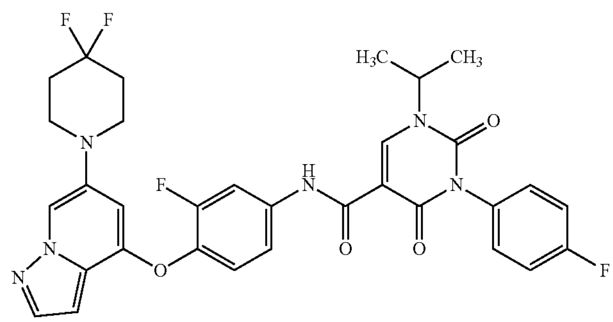 [SMILES: CC(C)n1cc(C(=O)Nc2ccc(Oc3cc(N4CCC(F)(F)CC4)cn4nccc34)c(F)c2)c(=O)n(-c2ccc(F)cc2)c1=O] | 69 | B | B |
| 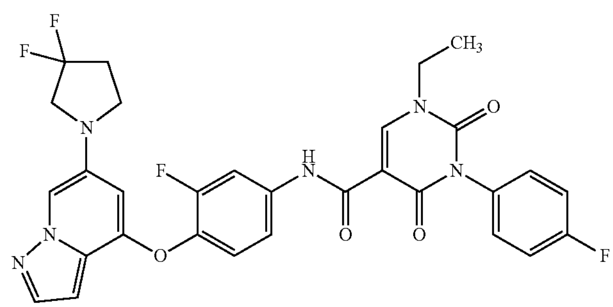 [SMILES: CCn1cc(C(=O)Nc2ccc(Oc3cc(N4CCC(F)(F)C4)cn4nccc34)c(F)c2)c(=O)n(-c2ccc(F)cc2)c1=O] | 70 | B | B |
| 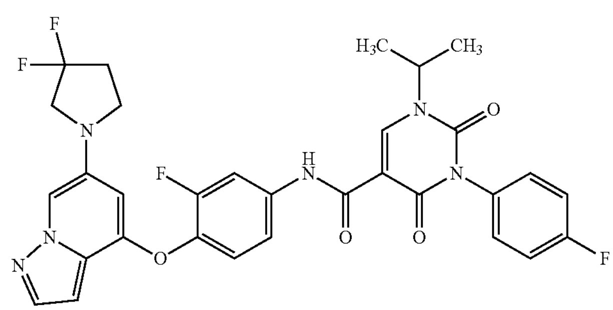 [SMILES: CC(C)n1cc(C(=O)Nc2ccc(Oc3cc(N4CCC(F)(F)C4)cn4nccc34)c(F)c2)c(=O)n(-c2ccc(F)cc2)c1=O] | 71 | B | B |
| 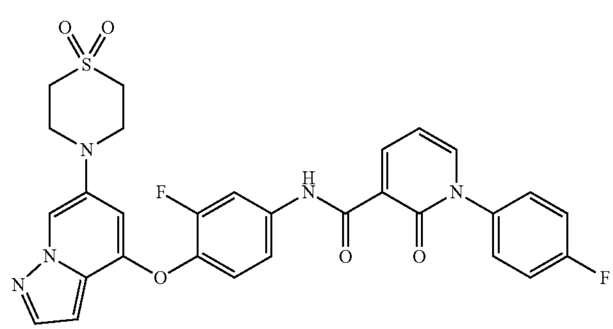 [SMILES: O=C(Nc1ccc(Oc2cc(N3CCS(=O)(=O)CC3)cn3nccc23)c(F)c1)c1cccn(-c2ccc(F)cc2)c1=O] | 72 | B | B |

-continued

| Compound Structure | Ex. No. | AXL IC$_{50}$ (nM) | c-MET IC$_{50}$ (nM) |
|---|---|---|---|
| (structure) | 73 | B | A |
| (structure) | 74 | B | A |
| (structure) | 75 | B | A |
| (structure) | 76 | B | A |
| (structure) | 77 | B | NT |

-continued

| Compound Structure | Ex. No. | AXL IC$_{50}$ (nM) | c-MET IC$_{50}$ (nM) |
|---|---|---|---|
| 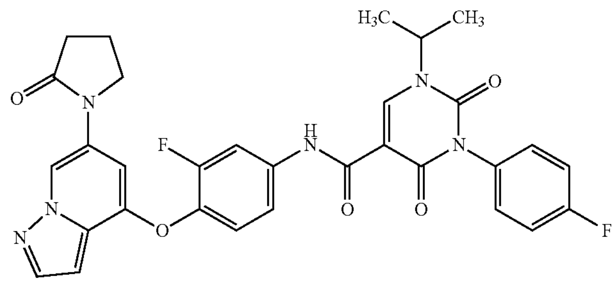 [SMILES: CC(C)n1cc(C(=O)Nc2ccc(Oc3cc(N4CCCC4=O)cn4nccc34)c(F)c2)c(=O)n(-c2ccc(F)cc2)c1=O] | 78 | B | A |
| 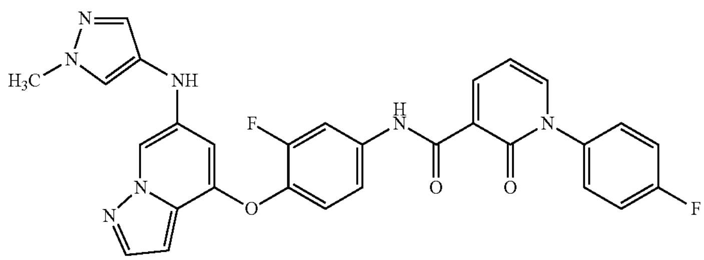 [SMILES: Cn1cc(Nc2cc(Oc3ccc(NC(=O)c4cccn(-c5ccc(F)cc5)c4=O)cc3F)c3ccnn3c2)cn1] | 79 | A | A |
| 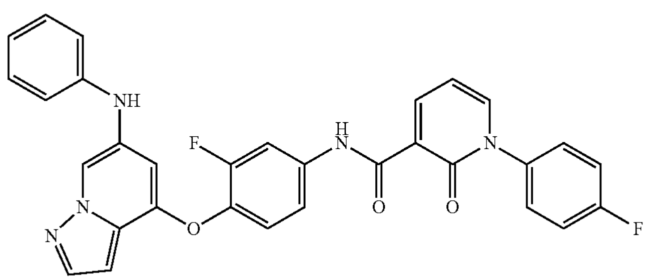 [SMILES: O=C(Nc1ccc(Oc2cc(Nc3ccccc3)cn3nccc23)c(F)c1)c1cccn(-c2ccc(F)cc2)c1=O] | 80 | B | A |
| 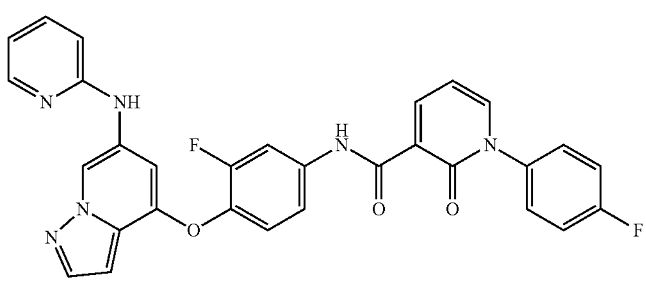 [SMILES: O=C(Nc1ccc(Oc2cc(Nc3ccccn3)cn3nccc23)c(F)c1)c1cccn(-c2ccc(F)cc2)c1=O] | 81 | B | A |
| 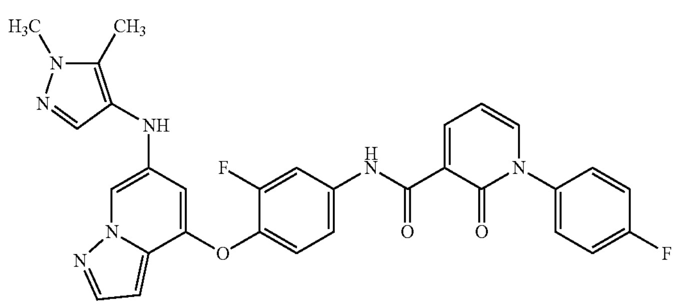 [SMILES: Cc1c(Nc2cc(Oc3ccc(NC(=O)c4cccn(-c5ccc(F)cc5)c4=O)cc3F)c3ccnn3c2)cnn1C] | 82 | B | A |

-continued

| Compound Structure | Ex. No. | AXL IC$_{50}$ (nM) | c-MET IC$_{50}$ (nM) |
|---|---|---|---|
| 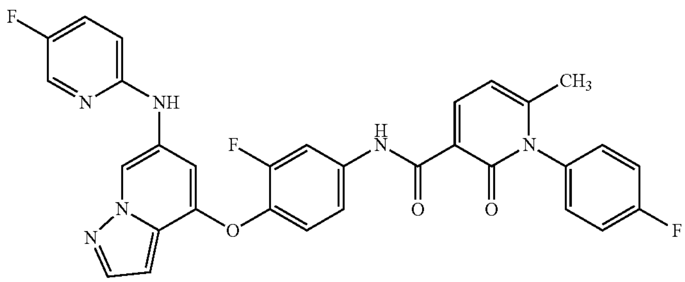 [SMILES: Cc1ccc(C(=O)Nc2ccc(Oc3cc(Nc4ccc(F)cn4)cn4nccc34)c(F)c2)c(=O)n1-c1ccc(F)cc1] | 83 | B | A |
| 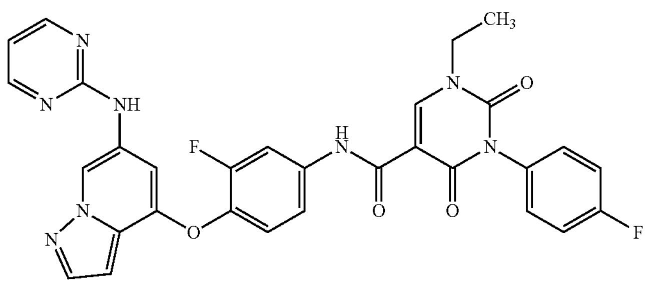 [SMILES: CCn1cc(C(=O)Nc2ccc(Oc3cc(Nc4ncccn4)cn4nccc34)c(F)c2)c(=O)n(-c2ccc(F)cc2)c1=O] | 84 | B | B |
| 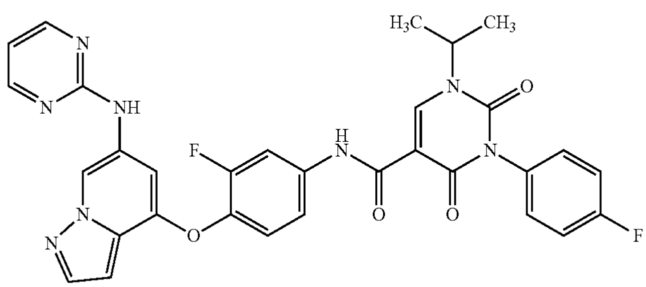 [SMILES: CC(C)n1cc(C(=O)Nc2ccc(Oc3cc(Nc4ncccn4)cn4nccc34)c(F)c2)c(=O)n(-c2ccc(F)cc2)c1=O] | 85 | B | A |
| 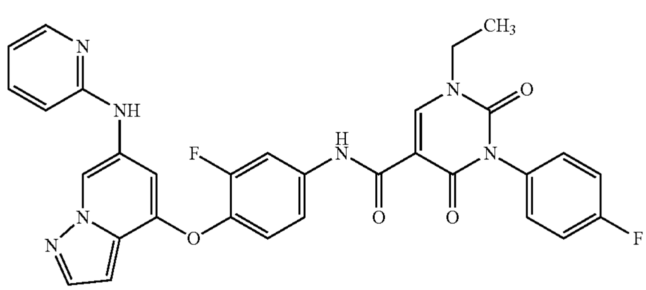 [SMILES: CCn1cc(C(=O)Nc2ccc(Oc3cc(Nc4ccccn4)cn4nccc34)c(F)c2)c(=O)n(-c2ccc(F)cc2)c1=O] | 86 | B | B |
| 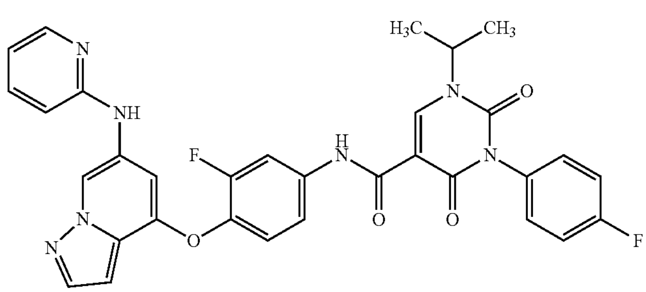 [SMILES: CC(C)n1cc(C(=O)Nc2ccc(Oc3cc(Nc4ccccn4)cn4nccc34)c(F)c2)c(=O)n(-c2ccc(F)cc2)c1=O] | 87 | B | B |

-continued

| Compound Structure | Ex. No. | AXL IC$_{50}$ (nM) | c-MET IC$_{50}$ (nM) |
|---|---|---|---|
| (structure) | 88 | A | A |
| (structure) | 89 | B | A |
| (structure) | 90 | B | A |
| (structure) | 91 | A | A |
| (structure) | 92 | B | A |

-continued
| Compound Structure | Ex. No. | AXL IC$_{50}$ (nM) | c-MET IC$_{50}$ (nM) |
|---|---|---|---|
| 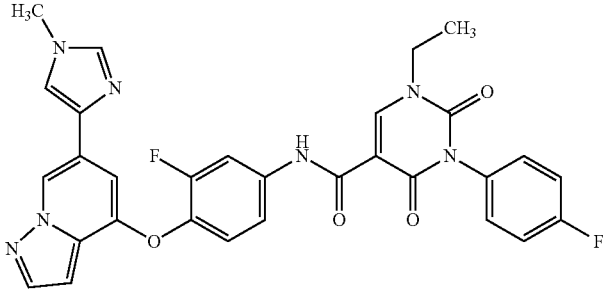 [SMILES: CCn1cc(C(=O)Nc2ccc(Oc3cc(-c4cn(C)cn4)cn4nccc34)c(F)c2)c(=O)n(-c2ccc(F)cc2)c1=O] | 93 | A | A |
| 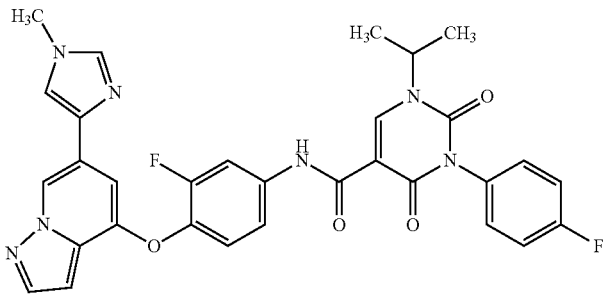 [SMILES: CC(C)n1cc(C(=O)Nc2ccc(Oc3cc(-c4cn(C)cn4)cn4nccc34)c(F)c2)c(=O)n(-c2ccc(F)cc2)c1=O] | 94 | A | A |
| 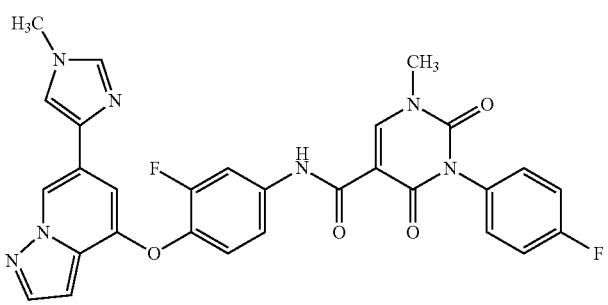 [SMILES: Cn1cnc(-c2cc(Oc3ccc(NC(=O)c4cn(C)c(=O)n(-c5ccc(F)cc5)c4=O)cc3F)c3ccnn3c2)c1] | 95 | A | A |
| 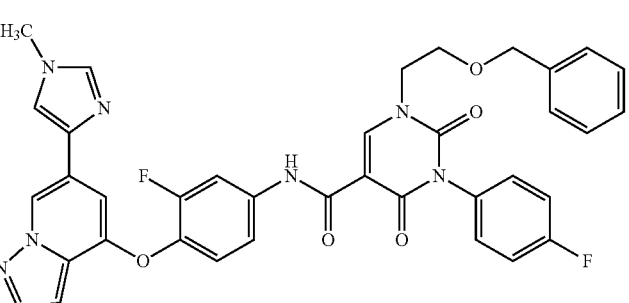 | 96 | A | B |
| 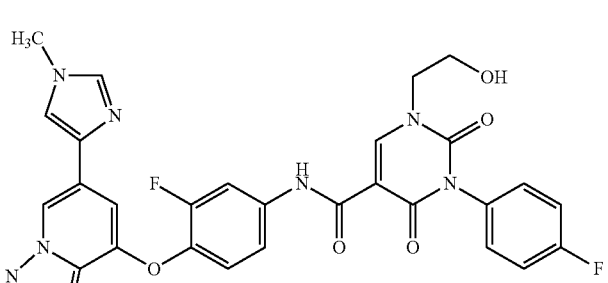 | 97 | B | A |

-continued

| Compound Structure | Ex. No. | AXL IC$_{50}$ (nM) | c-MET IC$_{50}$ (nM) |
| --- | --- | --- | --- |
| 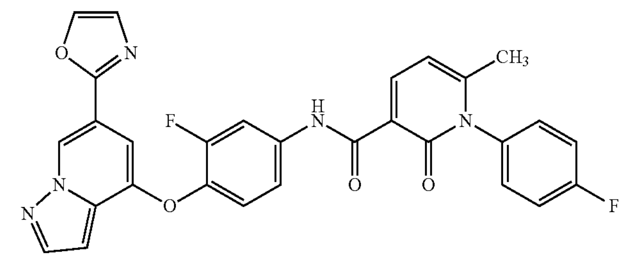 [SMILES: Cc1ccc(C(=O)Nc2ccc(Oc3cc(-c4ncco4)cn4nccc34)c(F)c2)c(=O)n1-c1ccc(F)cc1] | 98 | B | A |
| 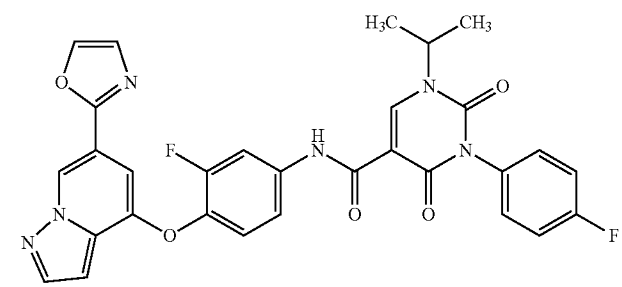 [SMILES: CC(C)n1cc(C(=O)Nc2ccc(Oc3cc(-c4ncco4)cn4nccc34)c(F)c2)c(=O)n(-c2ccc(F)cc2)c1=O] | 99 | A | A |
| 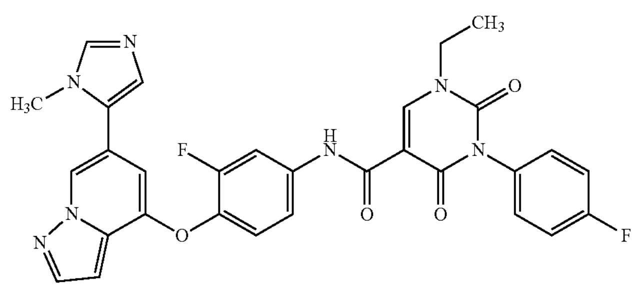 [SMILES: CCn1cc(C(=O)Nc2ccc(Oc3cc(-c4cncn4C)cn4nccc34)c(F)c2)c(=O)n(-c2ccc(F)cc2)c1=O] | 100 | B | A |
| 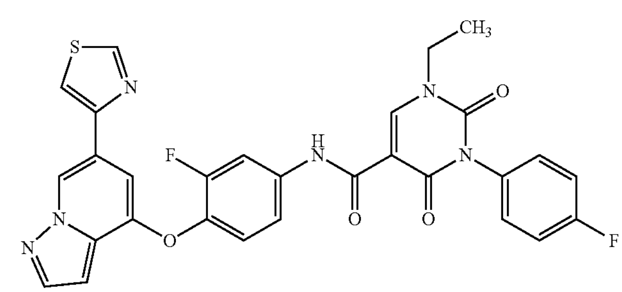 [SMILES: CCn1cc(C(=O)Nc2ccc(Oc3cc(-c4cscn4)cn4nccc34)c(F)c2)c(=O)n(-c2ccc(F)cc2)c1=O] | 101 | A | A |
| 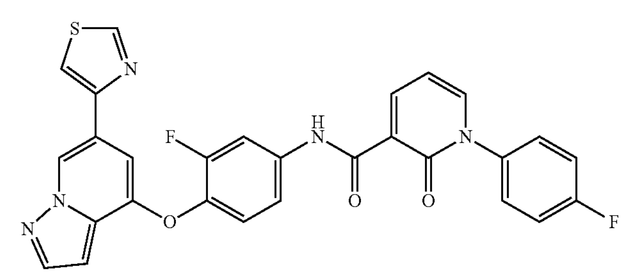 [SMILES: O=C(Nc1ccc(Oc2cc(-c3cscn3)cn3nccc23)c(F)c1)c1cccn(-c2ccc(F)cc2)c1=O] | 102 | A | A |

-continued
| Compound Structure | Ex. No. | AXL IC$_{50}$ (nM) | c-MET IC$_{50}$ (nM) |
|---|---|---|---|
| 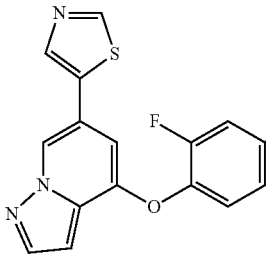 | 103 | A | A |
| 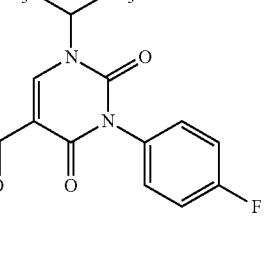 | 104 | A | A |
| 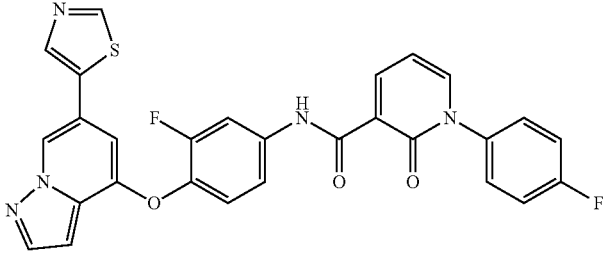 [SMILES: O=C(Nc1ccc(Oc2cc(-c3cncs3)cn3nccc23)c(F)c1)c1cccn(-c2ccc(F)cc2)c1=O] | 105 | B | A |
| 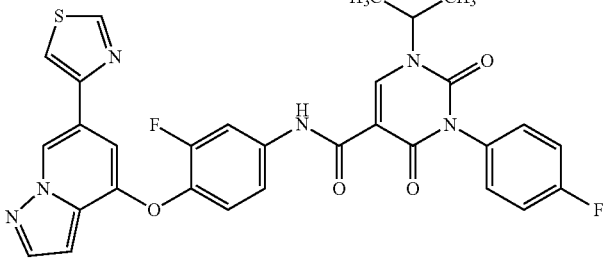 | 106 | B | A |
| 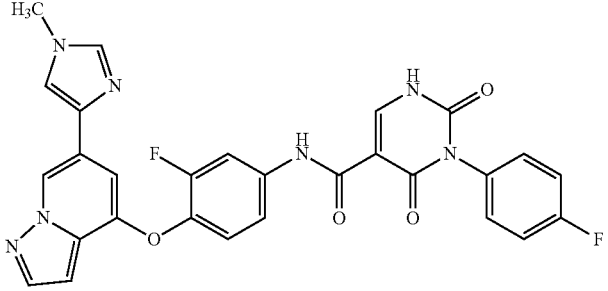 [SMILES: Cn1cnc(-c2cc(Oc3ccc(NC(=O)c4c[nH]c(=O)n(-c5ccc(F)cc5)c4=O)cc3F)c3ccnn3c2)c1] | 107 | A | A |

-continued
| Compound Structure | Ex. No. | AXL IC$_{50}$ (nM) | c-MET IC$_{50}$ (nM) |
|---|---|---|---|
| 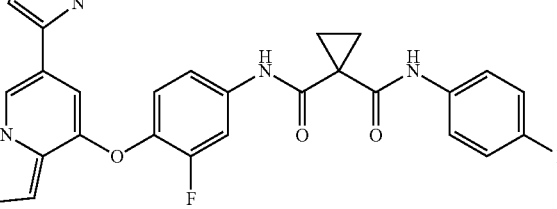 | 108 | B | A |
| 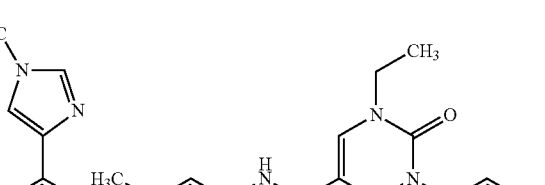 | 109 | B | A |
| 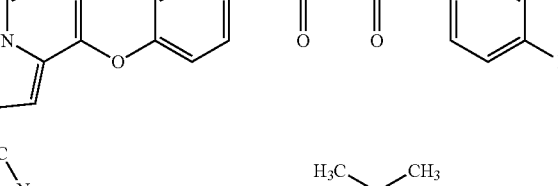 | 110 | A | B |
| 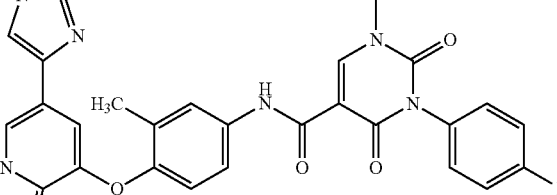 | 111 | C | NT |
| 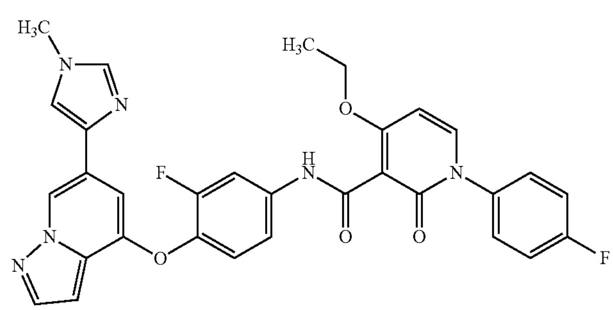 [SMILES: CCOc1ccn(-c2ccc(F)cc2)c(=O)c1C(=O)Nc1ccc(Oc2cc(-c3cn(C)cn3)cn3nccc23)c(F)c1] | 112 | A | A |

-continued

| Compound Structure | Ex. No. | AXL IC$_{50}$ (nM) | c-MET IC$_{50}$ (nM) |
|---|---|---|---|
| 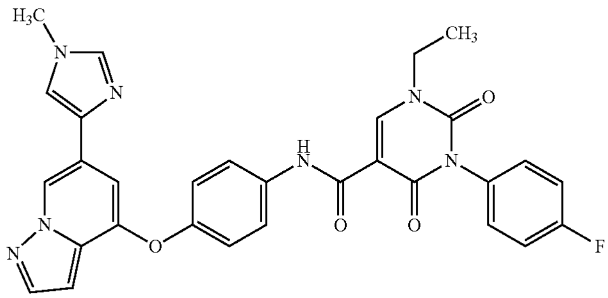 [SMILES: CCn1cc(C(=O)Nc2ccc(Oc3cc(-c4cn(C)cn4)cn4nccc34)cc2)c(=O)n(-c2ccc(F)cc2)c1=O] | 113 | A | A |
| 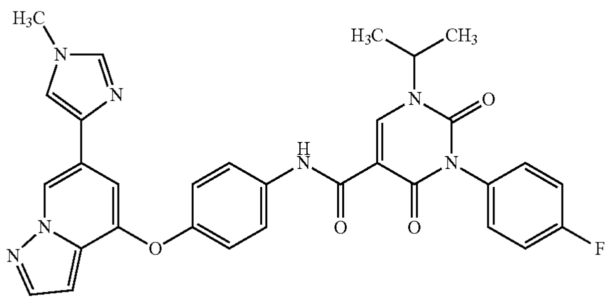 [SMILES: CC(C)n1cc(C(=O)Nc2ccc(Oc3cc(-c4cn(C)cn4)cn4nccc34)cc2)c(=O)n(-c2ccc(F)cc2)c1=O] | 114 | A | A |
| 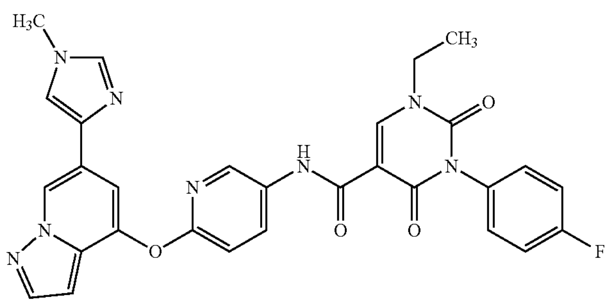 [SMILES: CCn1cc(C(=O)Nc2ccc(Oc3cc(-c4cn(C)cn4)cn4nccc34)nc2)c(=O)n(-c2ccc(F)cc2)c1=O] | 115 | B | A |
| 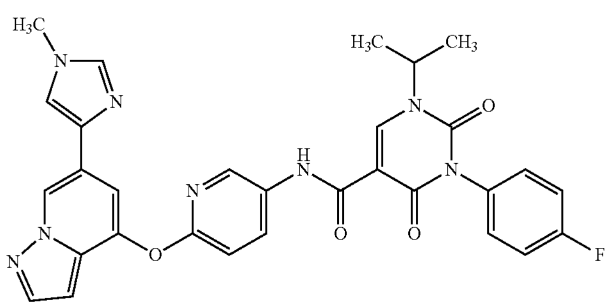 [SMILES: CC(C)n1cc(C(=O)Nc2ccc(Oc3cc(-c4cn(C)cn4)cn4nccc34)nc2)c(=O)n(-c2ccc(F)cc2)c1=O] | 116 | B | A |
| 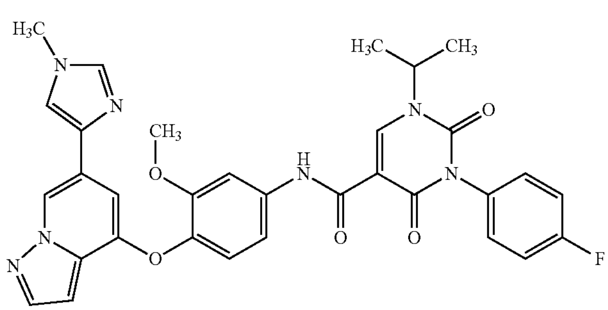 [SMILES: COc1cc(NC(=O)c2cn(C(C)C)c(=O)n(-c3ccc(F)cc3)c2=O)ccc1Oc1cc(-c2cn(C)cn2)cn2nccc12] | 117 | C | NT |

-continued

| Compound Structure | Ex. No. | AXL IC$_{50}$ (nM) | c-MET IC$_{50}$ (nM) |
|---|---|---|---|
| 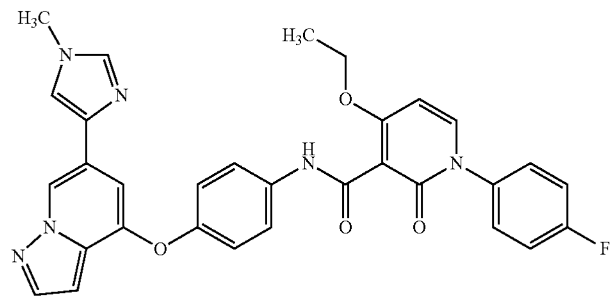 [SMILES: CCOc1ccn(-c2ccc(F)cc2)c(=O)c1C(=O)Nc1ccc(Oc2cc(-c3cn(C)cn3)cn3nccc23)cc1] | 118 | B | A |
| 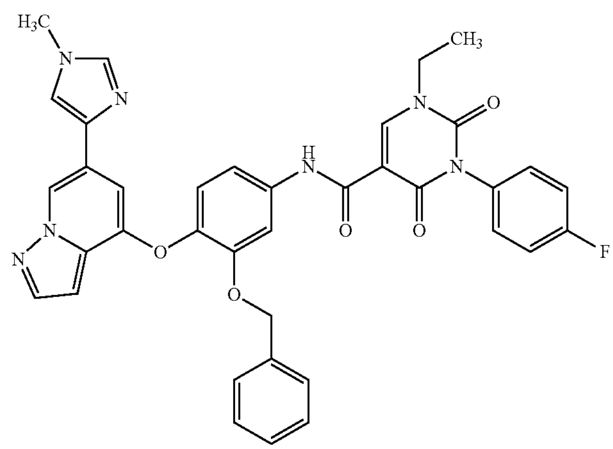 [SMILES: CCn1cc(C(=O)Nc2ccc(Oc3cc(-c4cn(C)cn4)cn4nccc34)c(OCc3ccccc3)c2)c(=O)n(-c2ccc(F)cc2)c1=O] | 119 | D | B |
| 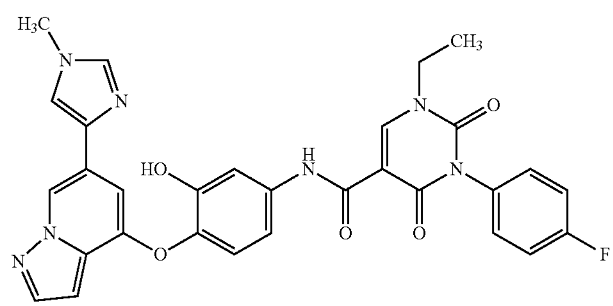 [SMILES: CCn1cc(C(=O)Nc2ccc(Oc3cc(-c4cn(C)cn4)cn4nccc34)c(O)c2)c(=O)n(-c2ccc(F)cc2)c1=O] | 120 | B | B |
| 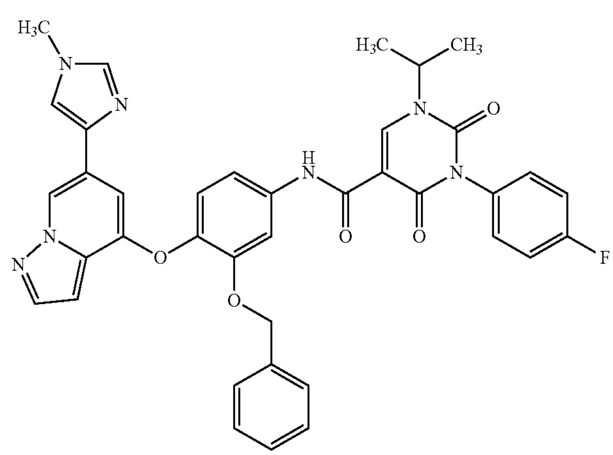 [SMILES: CC(C)n1cc(C(=O)Nc2ccc(Oc3cc(-c4cn(C)cn4)cn4nccc34)c(OCc3ccccc3)c2)c(=O)n(-c2ccc(F)cc2)c1=O] | 121 | D | B |

-continued

| Compound Structure | Ex. No. | AXL IC$_{50}$ (nM) | c-MET IC$_{50}$ (nM) |
|---|---|---|---|
| 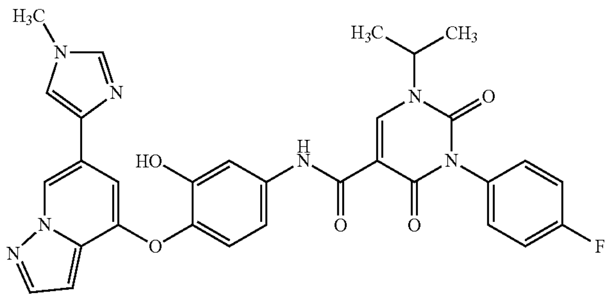 | 122 | B | B |
| 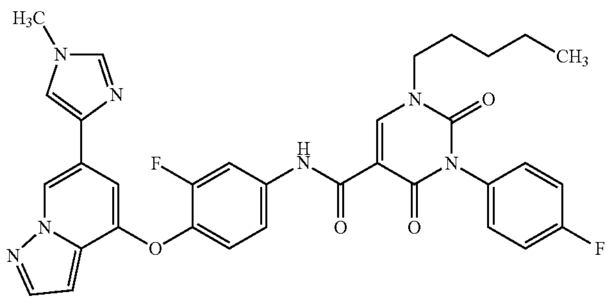 [SMILES: CCCCCn1cc(C(=O)Nc2ccc(Oc3cc(-c4cn(C)cn4)cn4nccc34)c(F)c2)c(=O)n(-c2ccc(F)cc2)c1=O] | 123 | B | A |
| 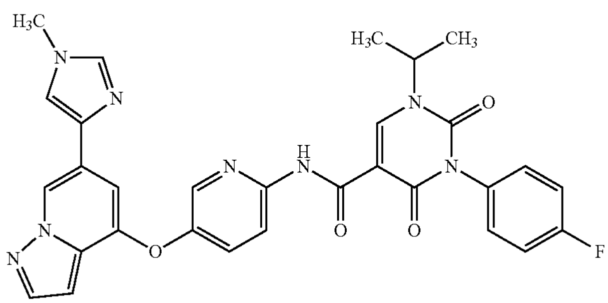 | 124 | A | A |
| 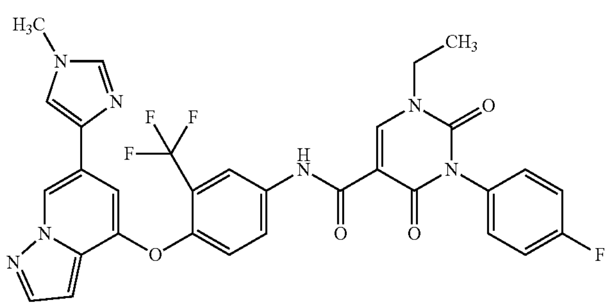 [SMILES: CCn1cc(C(=O)Nc2ccc(Oc3cc(-c4cn(C)cn4)cn4nccc34)c(C(F)(F)F)c2)c(=O)n(-c2ccc(F)cc2)c1=O] | 125 | C | A |
| 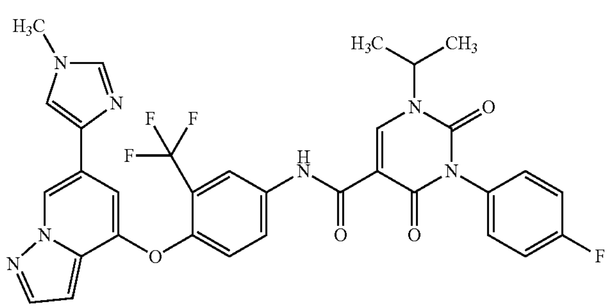 [SMILES: CC(C)n1cc(C(=O)Nc2ccc(Oc3cc(-c4cn(C)cn4)cn4nccc34)c(C(F)(F)F)c2)c(=O)n(-c2ccc(F)cc2)c1=O] | 126 | B | B |

-continued

| Compound Structure | Ex. No. | AXL IC$_{50}$ (nM) | c-MET IC$_{50}$ (nM) |
|---|---|---|---|
| 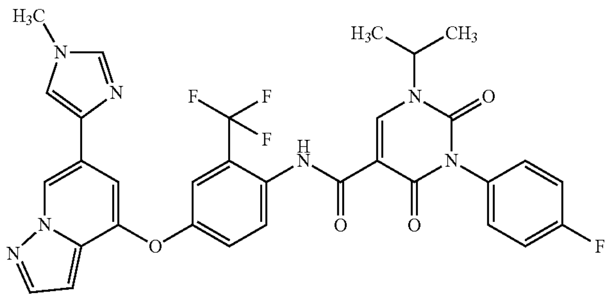 [SMILES: CC(C)n1cc(C(=O)Nc2ccc(Oc3cc(-c4cn(C)cn4)cn4nccc34)cc2C(F)(F)F)c(=O)n(-c2ccc(F)cc2)c1=O] | 127 | C | NT |
| 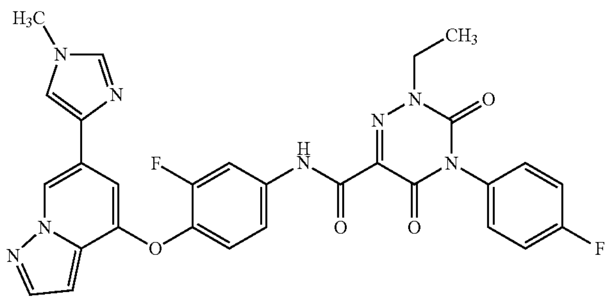 | 128 | A | A |
| 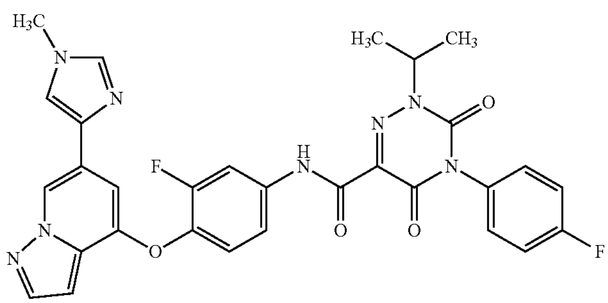 | 129 | A | A |
| 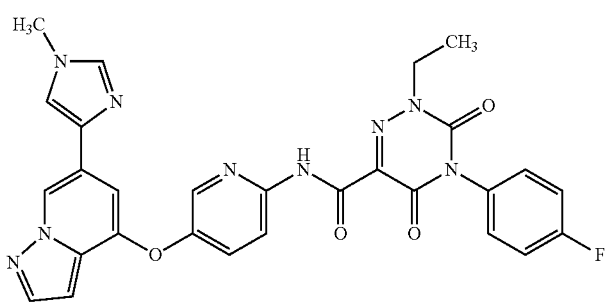 [SMILES: CCn1nc(C(=O)Nc2ccc(Oc3cc(-c4cn(C)cn4)cn4nccc34)cn2)c(=O)n(-c2ccc(F)cc2)c1=O] | 130 | B | A |
| 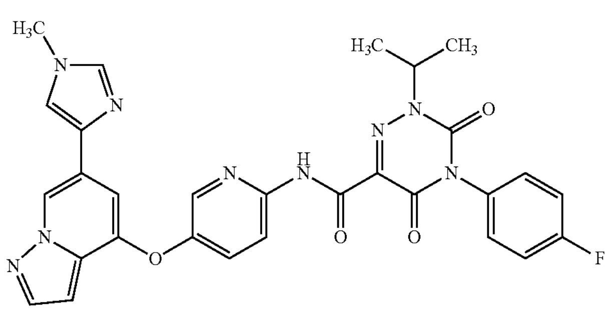 | 131 | B | A |

| Compound Structure | Ex. No. | AXL IC$_{50}$ (nM) | c-MET IC$_{50}$ (nM) |
|---|---|---|---|
| 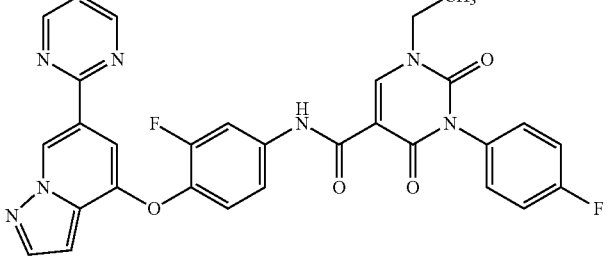 | 132 | B | B |
| 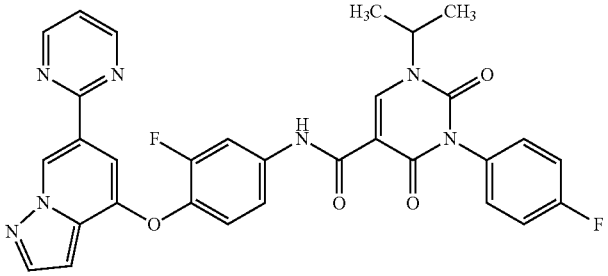 [SMILES: CC(C)n1cc(C(=O)Nc2ccc(Oc3cc(-c4ncccn4)cn4nccc34)c(F)c2)c(=O)n(-c2ccc(F)cc2)c1=O] | 133 | B | B |
| 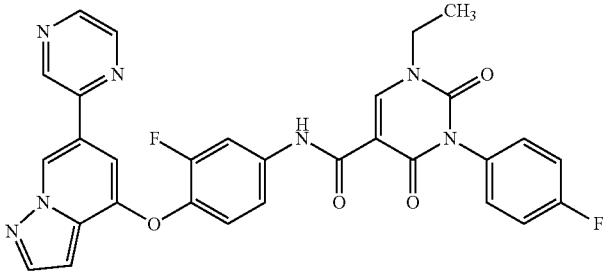 [SMILES: CCn1cc(C(=O)Nc2ccc(Oc3cc(-c4cnccn4)cn4nccc34)c(F)c2)c(=O)n(-c2ccc(F)cc2)c1=O] | 134 | B | B |
| 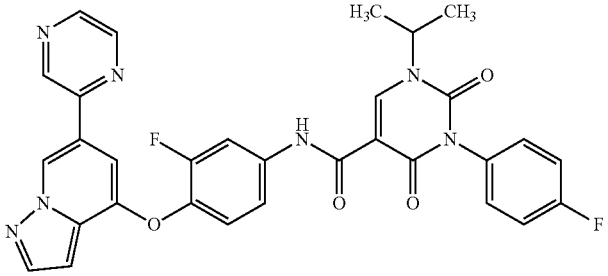 [SMILES: CC(C)n1cc(C(=O)Nc2ccc(Oc3cc(-c4cnccn4)cn4nccc34)c(F)c2)c(=O)n(-c2ccc(F)cc2)c1=O] | 135 | B | B |
| 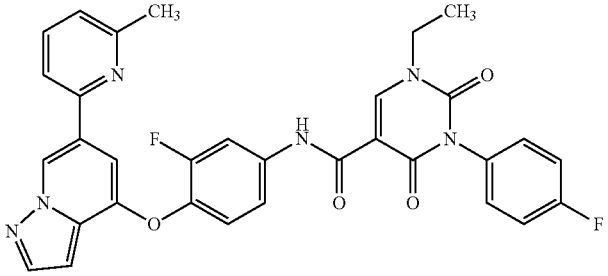 [SMILES: CCn1cc(C(=O)Nc2ccc(Oc3cc(-c4cccc(C)n4)cn4nccc34)c(F)c2)c(=O)n(-c2ccc(F)cc2)c1=O] | 136 | B | B |

-continued

| Compound Structure | Ex. No. | AXL IC$_{50}$ (nM) | c-MET IC$_{50}$ (nM) |
|---|---|---|---|
| (structure) | 137 | B | B |
| (structure) | 138 | B | A |
| (structure) | 139 | C | A |
| (structure) | 140 | C | B |
| (structure) | 141 | B | B |

-continued

| Compound Structure | Ex. No. | AXL IC$_{50}$ (nM) | c-MET IC$_{50}$ (nM) |
|---|---|---|---|
| 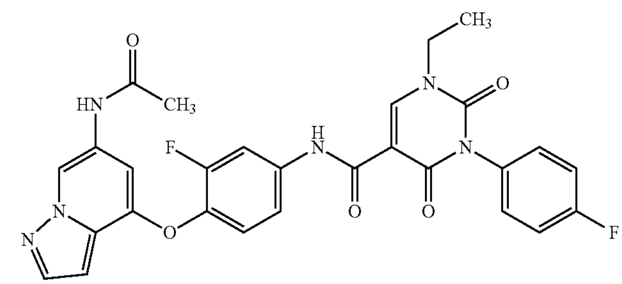 [SMILES: CCn1cc(C(=O)Nc2ccc(Oc3cc(NC(C)=O)cn4nccc34)c(F)c2)c(=O)n(-c2ccc(F)cc2)c1=O] | 142 | A | A |
| 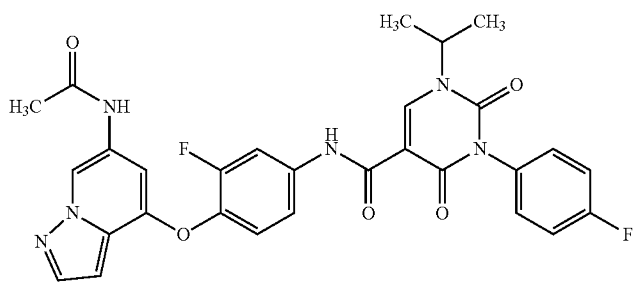 [SMILES: CC(=O)Nc1cc(Oc2ccc(NC(=O)c3cn(C(C)C)c(=O)n(-c4ccc(F)cc4)c3=O)cc2F)c2ccnn2c1] | 143 | B | A |
| 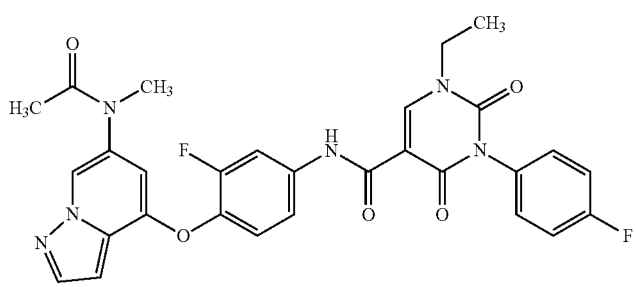 [SMILES: CCn1cc(C(=O)Nc2ccc(Oc3cc(N(C)C(C)=O)cn4nccc34)c(F)c2)c(=O)n(-c2ccc(F)cc2)c1=O] | 144 | C | NT |
| 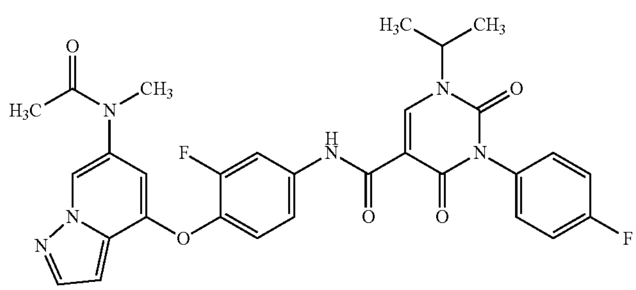 [SMILES: CC(=O)N(C)c1cc(Oc2ccc(NC(=O)c3cn(C(C)C)c(=O)n(-c4ccc(F)cc4)c3=O)cc2F)c2ccnn2c1] | 145 | C | NT |
| 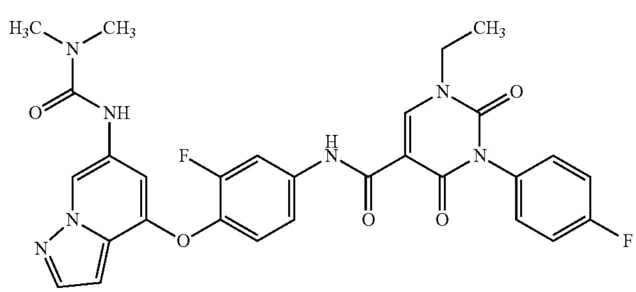 [SMILES: CCn1cc(C(=O)Nc2ccc(Oc3cc(NC(=O)N(C)C)cn4nccc34)c(F)c2)c(=O)n(-c2ccc(F)cc2)c1=O] | 146 | B | A |

-continued

| Compound Structure | Ex. No. | AXL IC$_{50}$ (nM) | c-MET IC$_{50}$ (nM) |
|---|---|---|---|
| 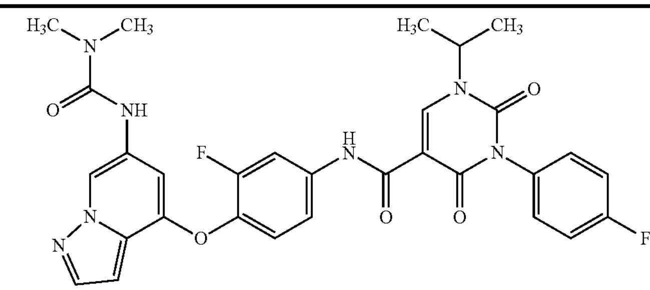 | 147 | A | A |
| 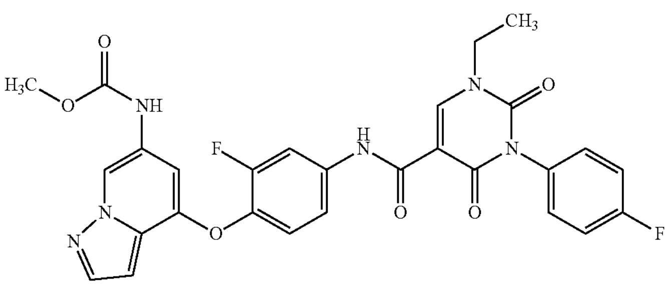 [SMILES: CCn1cc(C(=O)Nc2ccc(Oc3cc(NC(=O)OC)cn4nccc34)c(F)c2)c(=O)n(-c2ccc(F)cc2)c1=O] | 148 | A | B |
| 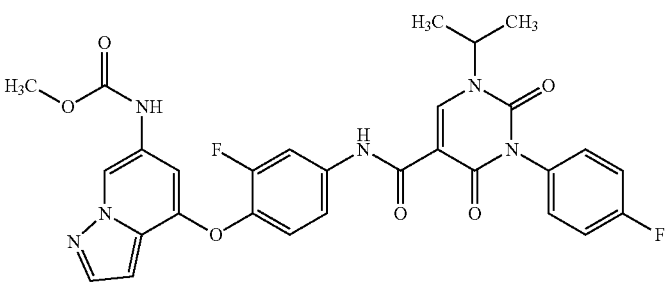 [SMILES: COC(=O)Nc1cc(Oc2ccc(NC(=O)c3cn(C(C)C)c(=O)n(-c4ccc(F)cc4)c3=O)cc2F)c2ccnn2c1] | 149 | A | B |
| 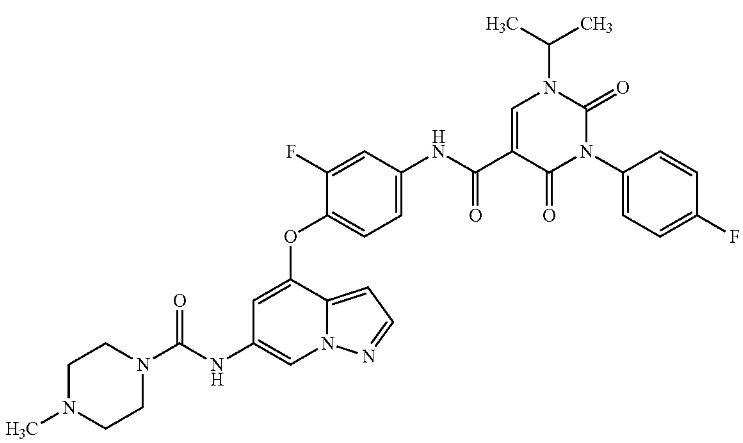 [SMILES: CC(C)n1cc(C(=O)Nc2ccc(Oc3cc(NC(=O)N4CCN(C)CC4)cn4nccc34)c(F)c2)c(=O)n(-c2ccc(F)cc2)c1=O] | 150 | B | B |
| 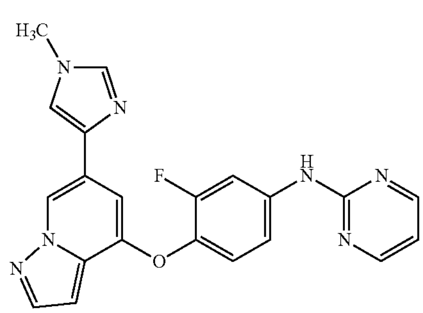 [SMILES: Cn1cnc(-c2cc(Oc3ccc(Nc4ncccn4)cc3F)c3ccnn3c2)c1] | 152 | D | D |

-continued

| Compound Structure | Ex. No. | AXL IC$_{50}$ (nM) | c-MET IC$_{50}$ (nM) |
|---|---|---|---|
| 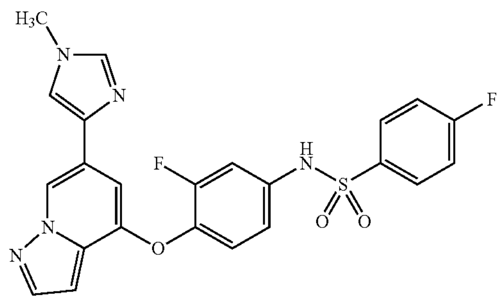 [SMILES: Cn1cnc(-c2cc(Oc3ccc(NS(=O)(=O)c4ccc(F)cc4)cc3F)c3ccnn3c2)c1] | 153 | D | D |
| 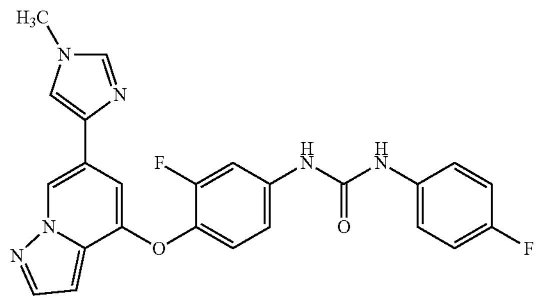 [SMILES: Cn1cnc(-c2cc(Oc3ccc(NC(=O)Nc4ccc(F)cc4)cc3F)c3ccnn3c2)c1] | 154 | D | NT |
| 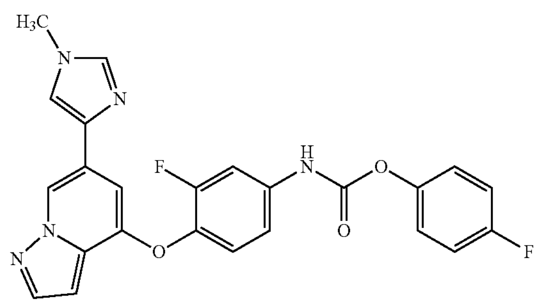 [SMILES: Cn1cnc(-c2cc(Oc3ccc(NC(=O)Oc4ccc(F)cc4)cc3F)c3ccnn3c2)c1] | 155 | D | NT |
| 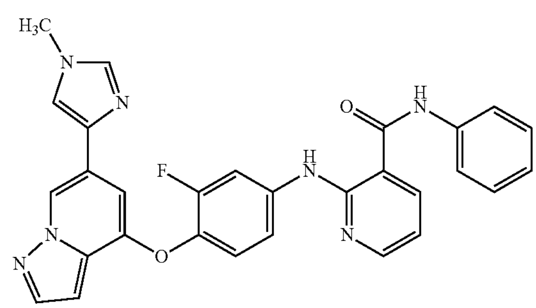 [SMILES: Cn1cnc(-c2cc(Oc3ccc(Nc4ncccc4C(=O)Nc4ccccc4)cc3F)c3ccnn3c2)c1] | 156 | B | NT |
| 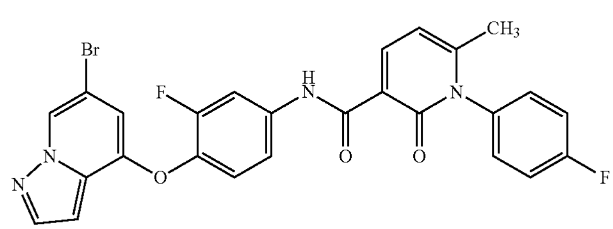 [SMILES: Cc1ccc(C(=O)Nc2ccc(Oc3cc(Br)cn4nccc34)c(F)c2)c(=O)n1-c1ccc(F)cc1] | 157 | C | B |

What is claimed:
1. A compound of Formula I:

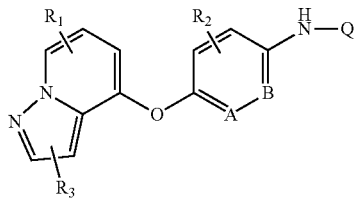

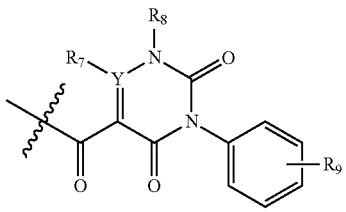

wherein
R$_1$ is H; halo; —C$_{1-6}$alkyl; —C$_{1-6}$alkoxy; optionally substituted pyridyl; optionally substituted pyrimidinyl; optionally substituted pyrazinyl; optionally substituted pyrazolyl; optionally substituted imidazolyl; optionally substituted isoxazolyl; optionally substituted oxazolyl; optionally substituted thiazolyl; optionally substituted isothiazolyl; optionally substituted morpholinyl; optionally substituted piperazinyl; optionally substituted piperidinyl; optionally substituted tetrahydropyranyl; optionally substituted pyrrolidinyl; tetrahydrothiopyranyl 1,1-dioxide; thiomorpholinyl 1,1-dioxide; pyrrolidinyl-one; piperidinyl-one; optionally substituted —NH-aryl; optionally substituted —NH-pyridyl; optionally substituted —NH-pyrimidinyl; —C(O)NHC$_{1-6}$alkyl; —C(O)N(C$_{1-6}$alkyl)$_2$; —NHS(O)$_2$C$_{1-6}$alkyl; —N(C$_{1-6}$alkyl)S(O)$_2$C$_{1-6}$alkyl; —NHC(O)C$_{1-6}$alkyl; —NC$_{1-6}$alkylC(O)C$_{1-6}$alkyl; —NHC(O)OC$_{1-6}$alkyl; —NC$_{1-6}$alkylC(O)OC$_{1-6}$alkyl; —NHC(O)NHC$_{1-6}$alkyl; —NC$_{1-6}$alkylC(O)N(C$_{1-6}$alkyl)$_2$; optionally substituted —NHC(O)— piperazinyl; or optionally substituted —NC$_{1-6}$alkylC(O)-piperazinyl;
each R$_2$ is independently H, halo, —C$_{1-6}$alkyl, —C$_{1-6}$alkoxy, —OH, —O-alkaryl, or trihaloalkyl;
R$_3$ is H or halo;
A is CR$_2$ or N;
B is CR$_2$ or N;
Q is —S(O)$_2$aryl optionally substituted with halo or C$_{1-6}$alkyl; pyridyl optionally substituted with halo or —C(O)NHphenyl; pyrimidinyl; pyrazinyl;
—C(O)—NHC(O)-alkaryl optionally substituted with halo or C$_{1-6}$alkyl;
—C(S)—NHC(O)-alkaryl optionally substituted with halo or C$_{1-6}$alkyl;
—C(O)-alkaryl optionally substituted with halo or C$_{1-6}$alkyl; —C(O)NH-aryl optionally substituted with halo, C$_{1-6}$alkyl or C$_{1-6}$alkoxy; —C(O)—O-aryl optionally substituted with halo, C$_{1-6}$alkyl or C$_{1-6}$alkoxy; or

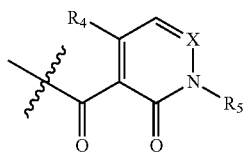

wherein X is CR$_6$, wherein R$_6$ is H or C$_{1-6}$alkyl; or N;
R$_4$ is H; C$_{1-6}$alkoxy; halo; —OC$_{1-6}$alkylene-O—C$_{1-6}$alkyl; —NHC$_{1-6}$alkyl; or —N(C$_{1-6}$alkyl)$_2$;
R$_5$ is aryl optionally substituted with halo or C$_{1-6}$alkyl; or alkaryl optionally substituted with halo or C$_{1-6}$alkyl;

or wherein Y is C or N;
R$_7$ is H or C$_{1-6}$alkyl;
R$_8$ is H; C$_{1-6}$alkylene-O—C$_{1-6}$alkyl; C$_{1-6}$alkyl; C$_{1-6}$alkylene-O—C$_{1-6}$alkaryl; or C$_{1-6}$alkylene-OH;
R$_9$ is H; C$_{1-6}$alkyl; or halo;
or

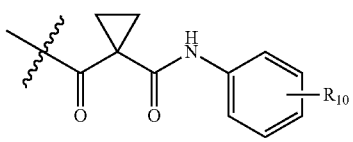

wherein
R$_{10}$ is H; halo; or C$_{1-6}$alkyl;
or

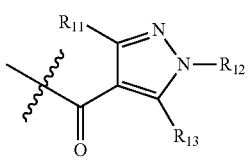

wherein
R$_{11}$ is H or C$_{1-6}$alkyl;
R$_{12}$ is H; C$_{1-6}$alkyl; or aryl optionally substituted with halo;
R$_{13}$ is H; C$_{1-6}$alkyl; or trihaloC$_{1-6}$alkyl;
or

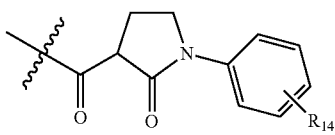

wherein
R$_{14}$ is H; C$_{1-6}$alkyl; or halo;
or a pharmaceutically acceptable salt thereof.
2. The compound of claim 1, wherein A is CR$_2$, or a pharmaceutically acceptable salt thereof.
3. The compound of claim 1, wherein B is CR$_2$, or a pharmaceutically acceptable salt thereof.
4. The compound of claim 1, wherein each R$_2$ is independently H or halo, or a pharmaceutically acceptable salt thereof.
5. The compound of claim 4, wherein halo is F, or a pharmaceutically acceptable salt thereof.
6. The compound claim 1, wherein R$_3$ is H, or a pharmaceutically acceptable salt thereof.

7. The compound of claim 1, wherein Q is

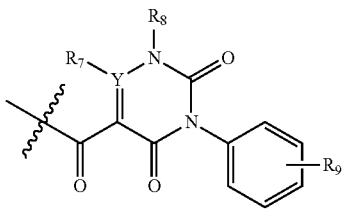

or a pharmaceutically acceptable salt thereof.

8. The compound of claim 7, wherein Y is C, or a pharmaceutically acceptable salt thereof.

9. The compound of claim 7, wherein $R_7$ is H, or a pharmaceutically acceptable salt thereof.

10. The compound of claim 7, wherein $R_8$ is H; $C_{1-6}$alkylene—O—$C_{1-6}$alkyl; or $C_{1-6}$alkyl, or a pharmaceutically acceptable salt thereof.

11. The compound of claim 7, wherein $R_8$ is $C_{1-6}$alkyl, or a pharmaceutically acceptable salt thereof.

12. The compound of claim 7, wherein $R_9$ is halo, or a pharmaceutically acceptable salt thereof.

13. The compound of claim 1, wherein $R_1$ is optionally substituted imidazolyl, or a pharmaceutically acceptable salt thereof.

14. The compound of claim 1, wherein said compound is selected from 3-(4-Fluoro-phenyl)-2,4-dioxo-1,2,3,4-tetrahydro-pyrimidine-5-carboxylic acid[3-fluoro-4-(pyrazolo[1,5-a]pyridin-4-yloxy)-phenyl]-amide; 3-(4-Fluoro-phenyl)-2,4-dioxo-1,2,3,4-tetrahydro-pyrimidine-5-carboxylic acid [3-fluoro-4-(6-pyridin-4-yl-pyrazolo[1,5-a]pyridin-4-yloxy)-phenyl]-amide; 3-(4-Fluoro-phenyl)-2,4-dioxo-1,2,3,4-tetrahydro-pyrimidine-5-carboxylic acid {3-fluoro-4-[6-(1-methyl-1H-pyrazol-4-yl)-pyrazolo[1,5-a]pyridin-4-yloxy]-phenyl}-amide; 1-(2-Ethoxy-ethyl)-3-(4-fluoro-phenyl)-2,4-dioxo-1,2,3,4-tetrahydro-pyrimidine-5-carboxylic acid {3-fluoro-4-[6-(1-methyl-1H-pyrazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid {3-fluoro-4-[6-(1-methyl-H-pyrazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid {3-fluoro-4-[6-(1H-pyrazol-3-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid[3-fluoro-4-(6-oxazol-5-yl-pyrazolo[1,5-a]pyridin-4-yloxy)-phenyl]-amide; 1-Ethyl-3-(4-fluoro-phenyl)-2,4-dioxo-1,2,3,4-tetrahydro-pyrimidine-5-carboxylic acid[3-fluoro-4-(6-isothiazol-4-yl-pyrazolo[1,5-a]pyridin-4-yloxy)-phenyl]-amide; 3-(4-Fluoro-phenyl)-1-isopropyl-2,4-dioxo-1,2,3,4-tetrahydro-pyrimidine-5-carboxylic acid[3-fluoro-4-(6-isothiazol-4-yl-pyrazolo[1,5-a]pyridin-4-yloxy)-phenyl]-amide; 1-(2-Ethoxy-ethyl)-3-(4-fluoro-phenyl)-2,4-dioxo-1,2,3,4-tetrahydro-pyrimidine-5-carboxylic acid[3-fluoro-4-(6-morpholin-4-yl-pyrazolo[1,5-a]pyridin-4-yloxy)-phenyl]-amide; 1-Ethyl-3-(4-fluoro-phenyl)-2,4-dioxo-1,2,3,4-tetrahydro-pyrimidine-5-carboxylic acid[3-fluoro-4-(6-morpholin-4-yl-pyrazolo[1,5-a]pyridin-4-yloxy)-phenyl]-amide; 3-(4-Fluoro-phenyl)-1-isopropyl-2,4-dioxo-1,2,3,4-tetrahydro-pyrimidine-5-carboxylic acid[3-fluoro-4-(6-morpholin-4-yl-pyrazolo[1,5-a]pyridin-4-yloxy)-phenyl]-amide; 1-Ethyl-3-(4-fluoro-phenyl)-2,4-dioxo-1,2,3,4-tetrahydro-pyrimidine-5-carboxylic acid[3-methyl-4-(6-morpholin-4-yl-pyrazolo[1,5-a]pyridin-4-yloxy)-phenyl]amide; 3-(4-Fluoro-phenyl)-1-isopropyl-2,4-dioxo-1,2,3,4-tetrahydro-pyrimidine-5-carboxylic acid[3-methyl-4-(6-morpholin-4-yl-pyrazolo[1,5-a]pyridin-4-yloxy)-phenyl]-amide; 3-(4-Fluoro-phenyl)-1-isopropyl-2,4-dioxo-1,2,3,4-tetrahydro-pyrimidine-5-carboxylic acid{4-[6-(4,4-difluoro-piperidin-1-yl)-pyrazolo[1,5-a]pyridin-4-yloxy]-3-fluoro-phenyl}-amide; 1-Ethyl-3-(4-fluoro-phenyl)-2,4-dioxo-1,2,3,4-tetrahydro-pyrimidine-5-carboxylic acid {4-[6-(3,3-difluoro-pyrrolidin-1-yl)-pyrazolo[1,5-a]pyridin-4-yloxy]-3-fluoro-phenyl}-amide; 3-(4-Fluoro-phenyl)-1-isopropyl-2,4-dioxo-1,2,3,4-tetrahydro-pyrimidine-5-carboxylic acid{4-[6-(3,3-difluoro-pyrrolidin-1-yl)-pyrazolo[1,5-a]pyridin-4-yloxy]-3-fluoro-phenyl}-amide; -Ethyl-3-(4-fluoro-phenyl)-2,4-dioxo-1,2,3,4-tetrahydro-pyrimidine-5-carboxylic acid{4-[6-(1,1-dioxo-thiomorpholin-4-yl)-pyrazolo[1,5-a]pyridin-4-yloxy]-3-fluoro-phenyl}-amide; 3-(4-Fluoro-phenyl)-1-isopropyl-2,4-dioxo-1,2,3,4-tetrahydro-pyrimidine-5-carboxylic acid{4-[6-(1,1-dioxo-thiomorpholin-4-yl)-pyrazolo[1,5-a]pyridin-4-yloxy]-3-fluoro-phenyl}-amide; 1-Ethyl-3-(4-fluoro-phenyl)-2,4-dioxo-1,2,3,4-tetrahydro-pyrimidine-5-carboxylic acid{3-fluoro-4-[6-(2-oxo-pyrrolidin-1-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid {3-fluoro-4-[6-(2-oxo-pyrrolidin-1-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid{3-fluoro-4-[6-(pyrimidin-2-ylamino)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid{3-fluoro-4-[6-(pyrimidin-2-ylamino)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid{3-fluoro-4-[6-(pyridin-2-ylamino)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid{3-fluoro-4-[6-(pyridin-2-ylamino)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide; 3-(4-Fluoro-phenyl)-1-methyl-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide; 1-(2-Benzyloxy-ethyl)-3-(4-fluoro-phenyl-)-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide; 3-(4-Fluoro-phenyl)-1-(2-hydroxy-ethyl)-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid[3-fluoro-4-(6-oxazol-2-yl-pyrazolo[1,5-a]pyridin-4-yloxy)-phenyl]-amide; 1-Ethyl-3-(4-fluoro-phenyl)-2,4-dioxo-1,2,3,4-tetrahydro-pyrimidine-5-carboxylic acid{3-fluoro-4-[6-(3-methyl-3H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid[3-fluoro-4-(6-thiazol-4-yl-pyrazolo[1,5-a]pyridin-4-yloxy)-phenyl]-amide; 3-(4-Fluoro-phenyl)-1-isopropyl-2,4-dioxo-1,2,3,4-tetrahydro-pyrimidine-5-carboxylic acid[3-fluoro-4-(6-thiazol-5-yl-pyrazolo[1,5-a]pyridin-4-yloxy)-phenyl]-amide; 1-Ethyl-3-

(4-fluoro-phenyl)-2,4-dioxo-1,2,3,4-tetrahydro-pyrimidine-5-carboxylic acid[3-fluoro-4-(6-thiazol-5-yl-pyrazolo[1,5-a]pyridin-4-yloxy)-phenyl]-amide; 3-(4-Fluoro-phenyl)-1-isopropyl-2,4-dioxo-1,2,3,4-tetrahydro-pyrimidine-5-carboxylic acid[3-fluoro-4-(6-thiazol-4-yl-pyrazolo[1,5-a]pyridin-4-yloxy)-phenyl]-amide; 3-(4-Fluoro-phenyl)-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid{3-methyl-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid{3-methyl-4-[6-(1-methyl-1H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid{4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid{4-[6-(1-methyl-1H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid{6-[6-(1-methyl-1H-imidazol-4-yl)-pyrazolo[1,5-a]pyridin-4-yloxy]-pyridin-3-yl}-amide; 3-(4-Fluoro-phenyl)-1-isopropyl-2,4-dioxo-1,2,3,4-tetrahydro-pyrimidine-5-carboxylic acid{6-[6-(1-methyl-1H-imidazol-4-yl)-pyrazolo[1,5-a]pyridin-4-yloxy]-pyridin-3-yl}-amide; 3-(4-Fluoro-phenyl)-1-isopropyl-2,4-dioxo-1,2,3,4-tetrahydro-pyrimidine-5-carboxylic acid {3-methoxy-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid {3-methoxy-4-[6-(1-methyl-1H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid{3-hydroxy-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid{3-benzyloxy-4-[6-(1-methyl-1H-imidazol-4-yl)-pyrazolo[1,5-a]pyridine-4-yloxy]-phenyl}-amide; 3-(4-Fluoro-phenyl)-1-isopropyl-2,4-dioxo-1,2,3,4-tetrahydro-pyrimidine-5-carboxylic acid{3-hydroxy-4-[6-(1-methyl-1H-imidazol-4-yl)-pyrazolo[1,5-a]pyridin-4-yloxy]-phenyl}-amide; 3-(4-Fluoro-phenyl)-2,4-dioxo-1-pentyl-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid {5-[6-(1-methyl-1H-imidazol-4-yl)-pyrazolo[1,5-a]pyridin-4-yloxy]-pyridin-2-yl}-amide; 1-Ethyl-3-(4-fluoro-phenyl)-2,4-dioxo-1,2,3,4-tetrahydro-pyrimidine-5-carboxylic acid {4-[6-(1-methyl-1H-imidazol-4-yl)-pyrazolo[1,5-a]pyridin-4-yloxy]-3-trifluoromethyl-phenyl}-amide; 3-(4-Fluoro-phenyl)-1-isopropyl-2,4-dioxo-1,2,3,4-tetrahydro-pyrimidine-5-carboxylic acid{4-[6-(1-methyl-1H-imidazol-4-yl)-pyrazolo[1,5-a]pyridin-4-yloxy]-3-trifluoromethyl-phenyl}-amide; 3-(4-Fluoro-phenyl)-1-isopropyl-2,4-dioxo-1,2,3,4-tetrahydro-pyrimidine-5-carboxylic acid {4-[6-(1-methyl-1H-imidazol-4-yl)-pyrazolo[1,5-a]pyridin-4-yloxy]-2-trifluoromethyl-phenyl}-amide; 1-Ethyl-3-(4-fluoro-phenyl)-2,4-dioxo-1,2,3,4-tetrahydro-pyrimidine-5-carboxylic acid[3-fluoro-4-(6-pyrimidin-2-yl-pyrazolo[1,5-a]pyridin-4-yloxy)-phenyl]-amide; 3-(4-Fluoro-phenyl)-1-isopropyl-2,4-dioxo-1,2,3,4-tetrahydro-pyrimidine-5-carboxylic acid[3-fluoro-4-(6-pyrimidin-2-yl-pyrazolo[1,5-a]pyridin-4-yloxy)-phenyl]-amide; 1-Ethyl-3-(4-fluoro-phenyl)-2,4-dioxo-1,2,3,4-tetrahydro-pyrimidine-5-carboxylic acid[3-fluoro-4-(6-pyrazin-2-yl-pyrazolo[1,5-a]pyridin-4-yloxy)-phenyl]-amide; 3-(4-Fluoro-phenyl)-1-isopropyl-2,4-dioxo-1,2,3,4-tetrahydro-pyrimidine-5-carboxylic acid [3-fluoro-4-(6-pyrazin-2-yl-pyrazolo[1,5-a]pyridin-4-yloxy)-phenyl]-amide; 1-Ethyl-3-(4-fluoro-phenyl)-2,4-dioxo-1,2,3,4-tetrahydro-pyrimidine-5-carboxylic acid{3-fluoro-4-[6-(6-methyl-pyridin-2-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid {3-fluoro-4-[6-(6-methyl-pyridin-2-yl)-pyrazolo[1,5-a]pyridin-4-yloxy]-phenyl}-amide; 4-(2-Fluoro-4-{[3-(4-fluoro-phenyl)-1-isopropyl-2,4-dioxo-1,2,3,4-tetrahydro-pyrimidine-5-carbonyl]-amino}-phenoxy)-pyrazolo[1,5-a]pyridine-6-carboxylic acid dimethylamide; 4-(4-{[1-Ethyl-3-(4-fluoro-phenyl)-2,4-dioxo-1,2,3,4-tetrahydro-pyrimidine-5-carbonyl]-amino}-2-fluoro-phenoxy)-pyrazolo[1,5-a]pyridine-6-carboxylic acid dimethylamide; 1-Ethyl-3-(4-fluoro-phenyl)-2,4-dioxo-1,2,3,4-tetrahydro-pyrimidine-5-carboxylic acid[3-fluoro-4-(6-methanesulfonylamino-pyrazolo[1,5-a]pyridin-4-yloxy)-phenyl]-amide; 3-(4-Fluoro-phenyl)-1-isopropyl-2,4-dioxo-1,2,3,4-tetrahydro-pyrimidine-5-carboxylic acid[3-fluoro-4-(6-methanesulfonylamino-pyrazolo[1,5-a]pyridin-4-yloxy)-phenyl]-amide; 1-Ethyl-3-(4-fluoro-phenyl)-2,4-dioxo-1,2,3,4-tetrahydro-pyrimidine-5-carboxylic acid[4-(6-acetylamino-pyrazolo[1,5-a]pyridin-4-yloxy)-3-fluoro-phenyl]-amide; 3-(4-Fluoro-phenyl)-1-isopropyl-2,4-dioxo-1,2,3,4-tetrahydro-pyrimidine-5-carboxylic acid[4-(6-acetylamino-pyrazolo[1,5-a]pyridin-4-yloxy)-3-fluoro-phenyl]-amide; 1-Ethyl-3-(4-fluoro-phenyl)-2,4-dioxo-1,2,3,4-tetrahydro-pyrimidine-5-carboxylic acid{4-[6-(acetyl-methyl-amino)-pyrazolo[1,5-a]pyridin-4-yloxy]-3-fluoro-phenyl}-amide; 3-(4-Fluoro-phenyl)-1-isopropyl-2,4-dioxo-1,2,3,4-tetrahydro-pyrimidine-5-carboxylic acid{4-[6-(acetyl-methyl-amino)-pyrazolo[1,5-a]pyridin-4-yloxy]-3-fluoro-phenyl}-amide; 1-Ethyl-3-(4-fluoro-phenyl)-2,4-dioxo-1,2,3,4-tetrahydro-pyrimidine-5-carboxylic acid{4-[6-(3,3-dimethyl-urea)-pyrazolo[1,5-a]pyridin-4-yloxy]-3-fluoro-phenyl})-amide; 3-(4-Fluoro-phenyl)-1-isopropyl-2,4-dioxo-1,2,3,4-tetrahydro-pyrimidine-5-carboxylic acid{4-[6-(3,3-dimethyl-ureido)-pyrazolo[1,5-a]pyridin-4-yloxy]-3-fluoro-phenyl}-amide; [4-(4-{[1-Ethyl-3-(4-fluoro-phenyl)-2,4-dioxo-1,2,3,4-tetrahydro-pyrimidine-5-carbonyl]-amino}-2-fluoro-phenoxy)-pyrazolo[1,5-a]pyridin-6-yl]-carbamic acid methyl ester; [4-(2-Fluoro-4-{[3-(4-fluoro-phenyl)-1-isopropyl-2,4-dioxo-1,2,3,4-tetrahydro-pyrimidine-5-carbonyl]-amino}-phenoxy)-pyrazolo[1,5-a]pyridin-6-yl]-carbamic acid methyl ester; and 3-(4-Fluoro-phenyl)-1-isopropyl-2,4-dioxo-1,2,3,4-tetrahydro-pyrimidine-5-carboxylic acid(3-fluoro-4-{6-[(4-methyl-piperazine-1-carbonyl)-amino]-pyrazolo[1,5-a]pyridin-4-yloxy}-phenyl)-amide; or a pharmaceutically acceptable salt thereof.

15. The compound of claim 1, wherein said compound is selected from 1-Ethyl-3-(4-fluoro-phenyl)-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide; 3-(4-Fluoro-phenyl)-1-methyl-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide; 1-(2-Benzyloxy-ethyl)-3-(4-fluoro-phenyl-)-2,4-dioxo-1,2,3,4-tetrahydro-pyrimidine-5-carboxylic acid {3-fluoro-4-[6-(1- methyl-1H-imidazol-4-yl)-pyrazolo[1,5-a]pyridin-4-yloxy]-phenyl}-amide; 3-(4-Fluoro-phenyl)-1-(2-hydroxy-ethyl)-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid {3-fluoro-4-[6-(3-methyl-3H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid{3-methyl-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid{3-methyl-4-[6-(1-methyl-1H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid{4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid{4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid {3-methoxy-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid {3-methoxy-4-[6-(1-methyl-1H-imidazol-4-yl)-pyrazolo[1,5-yloxy]-phenyl}-amide; 1-Ethyl-3-(4-fluoro-phenyl)-2,4-dioxo-1,2,3,4-tetrahydro-pyrimidine-5-carboxylic acid{3-hydroxy-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid{3-benzyloxy-4-[6-(1-methyl-1H-imidazol-4-yl)-pyrazolo[1,5-a]pyridine-4-yloxy]-phenyl}-amide; 3-(4-Fluoro-phenyl)-1-isopropyl-2,4-dioxo-1,2,3,4-tetrahydro-pyrimidine-5-carboxylic acid{3-hydroxy-4-[6-(1-methyl-1H-imidazol-4-yl)-pyrazolo[1,5-a]pyridin-4-yloxy]-phenyl}-amide; 3-(4-Fluoro-phenyl)-2,4-dioxo-1-pentyl-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid {4-[6-(1-methyl-1H-imidazol-4-yl)-pyrazolo[1,5-a]pyridin-4-yloxy]-3-trifluoromethyl-phenyl}-amide; 3-(4-Fluoro-phenyl)-1-isopropyl-2,4-dioxo-1,2,3,4-tetrahydro-pyrimidine-5-carboxylic acid{4-[6-(i-methyl-1H-imidazol-4-yl)-pyrazolo[1,5-a]pyridin-4-yloxy]-3-trifluoromethyl-phenyl}-amide; and 3-(4-Fluoro-phenyl)-1-isopropyl-2,4-dioxo-1,2,3,4-tetrahydro-pyrimidine-5-carboxylic acid{4-[6-(1-methyl-1H-imidazol-4-yl)-pyrazolo[1,5-a]pyridin-4-yloxy]-2-trifluoromethyl-phenyl}-amide; or a pharmaceutically acceptable salt thereof.

16. The compound of claim 1, wherein said compound is selected from 1-Ethyl-3-(4-fluoro-phenyl)-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl)}-amide; 3-(4-Fluoro-phenyl)-1-isopropyl-2,4-dioxo-1,2,3,4-tetrahydro-pyrimidine-5-carboxylic acid {3-fluoro-4-[6-(1-methyl-1H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid{3-fluoro-4-[6-(3-methyl-3H-imidazol-4-yl)-pyrazolo[1,5-a]pyridin-4-yloxy]-phenyl}-amide; 3-(4-Fluoro-phenyl)-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide; 3-(4-Fluoro-phenyl)-1-isopropyl-2,4-dioxo-1,2,3,4-tetrahydro-pyrimidine-5-carboxylic acid{3-methyl-4-[6-(1-methyl-1H-imidazol-4-yl)-pyrazolo[1,5-a]pyridin-4-yloxy]-phenyl}-amide; 3-(4-Fluoro-phenyl)-2,4-dioxo-1-pentyl-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide; 1-Ethyl-3-(4-fluoro-phenyl)-2,4-dioxo-1,2,3,4-tetrahydro-pyrimidine-5-carboxylic acid {4-[6-(1-methyl-H-imidazol-4-yl)-pyrazolo[1,5-a]pyridin-4-yloxy]-3-trifluoromethyl-phenyl}-amide; 3-(4-Fluoro-phenyl)-1-isopropyl-2,4-dioxo-1,2,3,4-tetrahydro-pyrimidine-5-carboxylic acid{4-[6-(1-methyl-1H-imidazol-4-yl)-pyrazolo[1,5-a]pyridin-4-yloxy]-3-trifluoromethyl-phenyl}-amide; and 3-(4-Fluoro-phenyl)-1-isopropyl-2,4-dioxo-1,2,3,4-tetrahydro-pyrimidine-5-carboxylic acid {4-[6-(1-methyl-1H-imidazol-4-yl)-pyrazolo[1,5-a]pyridin-4-yloxy]-2-trifluoromethyl-phenyl}-amide; or a pharmaceutically acceptable salt thereof.

17. A compound which is 3-(4-Fluoro-phenyl)-1-isopropyl-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide, or a pharmaceutically acceptable salt thereof.

18. A pharmaceutical composition, comprising a therapeutically effective amount of 3-(4-Fluoro-phenyl)-1-isopropyl-2,4-dioxo-1,2,3,4-tetrahydro-pyrimidine-5-carboxylic acid{3-fluoro-4-[6-(1-methyl-1H-imidazol-4-yl)-pyrazolo[1,5-a]pyridin-4-yloxy]-phenyl}-amide, or a pharmaceutically acceptable salt thereof, and one or more pharmaceutically acceptable carriers.

* * * * *